（12) United States Patent
Mazzulli et al.

(10) Patent No.: US 12,226,410 B2
(45) Date of Patent: *Feb. 18, 2025

(54) METHODS FOR ENHANCING CELLULAR CLEARANCE OF PATHOLOGICAL MOLECULES VIA ACTIVATION OF THE CELLULAR PROTEIN YKT6

(71) Applicant: NORTHWESTERN UNIVERSITY, Evanston, IL (US)

(72) Inventors: Joseph R. Mazzulli, Chicago, IL (US); Leah K. Cuddy, Chicago, IL (US)

(73) Assignee: Northwestern University, Evanston, IL (US)

( * ) Notice: Subject to any disclaimer, the term of this patent is extended or adjusted under 35 U.S.C. 154(b) by 870 days.

This patent is subject to a terminal disclaimer.

(21) Appl. No.: 17/073,603

(22) Filed: Oct. 19, 2020

(65) Prior Publication Data

US 2021/0113552 A1 Apr. 22, 2021

Related U.S. Application Data

(60) Provisional application No. 62/923,159, filed on Oct. 18, 2019.

(51) Int. Cl.
*A61K 31/4709* (2006.01)
*A61K 31/454* (2006.01)
*A61P 25/16* (2006.01)
*G01N 33/68* (2006.01)

(52) U.S. Cl.
CPC ........ *A61K 31/4709* (2013.01); *A61K 31/454* (2013.01); *A61P 25/16* (2018.01); *G01N 33/6896* (2013.01)

(58) Field of Classification Search
None
See application file for complete search history.

(56) References Cited

U.S. PATENT DOCUMENTS

| | | | |
|---|---|---|---|
| 4,496,538 A | 1/1985 | Gordon | |
| 4,727,136 A | 2/1988 | Jennings | |
| 5,478,730 A | 12/1995 | Alakhov et al. | |
| 5,556,769 A | 9/1996 | Wu et al. | |
| 5,623,057 A | 4/1997 | Kniskern | |
| 5,665,563 A | 9/1997 | Beckler | |
| 5,679,352 A | 10/1997 | Chong | |
| 6,168,931 B1 | 1/2001 | Swartz et al. | |
| 6,248,334 B1 | 6/2001 | Lees | |
| 6,531,131 B1 | 3/2003 | Gu | |
| 6,869,774 B2 | 3/2005 | Endo et al. | |
| 6,994,986 B2 | 2/2006 | Swartz et al. | |
| 7,118,883 B2 | 10/2006 | Inoue et al. | |
| 7,189,528 B2 | 3/2007 | Higashide et al. | |
| 7,338,789 B2 | 3/2008 | Swartz et al. | |
| 7,387,884 B2 | 6/2008 | Suzuki et al. | |
| 7,399,610 B2 | 7/2008 | Shikata et al. | |
| 8,399,241 B2 | 3/2013 | Lindquist | |
| 8,703,471 B2 | 4/2014 | Aebi | |
| 8,999,668 B2 | 4/2015 | Delisa | |
| 2004/0209321 A1 | 10/2004 | Swartz et al. | |
| 2005/0054044 A1 | 3/2005 | Swartz et al. | |
| 2005/0170452 A1 | 8/2005 | Wildt | |
| 2005/0277629 A1 | 12/2005 | Lansbury | |
| 2006/0106060 A1 | 5/2006 | Lansbury | |
| 2006/0211085 A1 | 9/2006 | Bobrowicz | |
| 2006/0234345 A1 | 10/2006 | Schwartz | |
| 2006/0252672 A1 | 11/2006 | Betenbaugh | |
| 2006/0257399 A1 | 11/2006 | Gerngross | |
| 2006/0286637 A1 | 12/2006 | Hamilton | |
| 2007/0026485 A1 | 2/2007 | Defrees | |
| 2007/0154983 A1 | 7/2007 | Calhoun et al. | |
| 2007/0178551 A1 | 8/2007 | Gerngross | |
| 2008/0138857 A1 | 6/2008 | Swartz et al. | |
| 2012/0171720 A1 | 7/2012 | Church et al. | |
| 2014/0045267 A1 | 2/2014 | Lajoie | |
| 2014/0255987 A1 | 9/2014 | Delisa | |
| 2014/0295492 A1 | 10/2014 | Jewett et al. | |
| 2015/0259757 A1 | 9/2015 | Jewett | |
| 2016/0060301 A1 | 3/2016 | Jewett | |
| 2017/0349928 A1 | 12/2017 | Jewett | |
| 2018/0016612 A1 | 1/2018 | Jewett | |
| 2018/0016614 A1 | 1/2018 | Jewett | |
| 2018/0298416 A1 | 10/2018 | Jewett | |
| 2019/0284600 A1 | 9/2019 | Jewett | |

FOREIGN PATENT DOCUMENTS

| | | |
|---|---|---|
| WO | 2003056914 A1 | 7/2003 |
| WO | 2004013151 | 2/2004 |
| WO | 2004035605 | 4/2004 |
| WO | 2006073734 A2 | 7/2006 |
| WO | 2006102652 | 9/2006 |
| WO | 2006119987 | 11/2006 |
| WO | 2007120932 | 10/2007 |
| WO | 2009151683 A2 | 12/2009 |

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Cuddy, L. K., et al. "Stress-induced cellular clearance is mediated by the SNARE protein ykt6 and disrupted by a-Synuclein." Neuron 104.5 (Oct. 21, 2019): 869-884.
Fukasawa, M., et al. (2004). Localization and activity of the SNARE Ykt6 determined by its regulatory domain and palmitoylation. Proceedings of the National Academy of Sciences of the United States of America 101, 4815-4820.

(Continued)

*Primary Examiner* — Po-Chih Chen
(74) *Attorney, Agent, or Firm* — Quarles & Brady LLP

(57) ABSTRACT

Disclosed are methods and compositions for enhancing cellular clearance of pathological molecules. Particularly disclosed are methods and compositions enhancing cellular clearance of pathological molecules via activating the cellular protein ykt6. The disclosed methods and compositions may be utilized in order to treat a subject having or at risk for developing a proteinopathy or other cellular storage disorder.

10 Claims, 123 Drawing Sheets

(56) References Cited

OTHER PUBLICATIONS

Hasegawa, H., et al. (2003). Mammalian ykt6 is a neuronal SNARE targeted to a specialized compartment by its profilin-like amino terminal domain. Molecular biology of the cell 14, 698-720.

Matsui, T., et al. (2018). Autophagosomal YKT6 is required for fusion with lysosomes independently of syntaxin 17. J Cell Biol 217, 2633-2645.

McNew, J.A., et al. (1997). Ykt6p, a prenylated SNARE essential for endoplasmic reticulum-Golgi transport. J Biol Chem 272, 17776-17783.

Pylypenko, O., el al. (2008). Farnesylation of the SNARE protein Ykt6 increases its stability and helical folding. J Mol Biol 377, 1334-1345.

Tai, G., et al. (2004). Participation of the syntaxin 5/Ykt6/GS28/GS15 SNARE complex in transport from the early/recycling endosome to the trans-Golgi network. Mol Biol Cell 15, 4011-4022.

Takats, S., et al. (2018). Noncanonical role of the SNARE protein Ykt6 in autophagosome-lysosome fusion. PLoS Genet 14, e1007359.

Thayanidhi, N., et al. (2012). R-SNARE ykt6 resides in membrane-associated protease-resistant protein particles and modulates cell cycle progression when over-expressed. Biology of the Cell 104, 397-417.

Tochio, H., et al. (2001). An autoinhibitory mechanism for nonsyntaxin SNARE proteins revealed by the structure of Ykt6p. Science 293, 698-702.

Wen, W., et al. (2010). Lipid-Induced conformational switch controls fusion activity of longin domain SNARE Ykt6. Molecular cell 37, 383-395.

Xu, Y., et al. (2002). GS15 forms a SNARE complex with syntaxin 5, 6828, and Ykt6 and is implicated in traffic in the early cisternae of the Golgi apparatus. Mol Biol Cell 13, 3493-3507.

Zhang, T., et al. (2001). Ykt6 forms a SNARE complex with syntaxin 5, GS28, and Bet1 and participates in a late stage in endoplasmic reticulum-Golgi transport. J Biol Chem 276, 27480-27487.

\* cited by examiner

Figure 2D

METHODS FOR ENHANCING CELLULAR CLEARANCE OF PATHOLOGICAL MOLECULES VIA ACTIVATION OF THE CELLULAR PROTEIN YKT6

CROSS-REFERENCE TO RELATED PATENT APPLICATIONS

The present application claims the benefit of priority under 35 U.S.C. § 119(e) to U.S. Provisional Application No. 62/923,159, filed on Oct. 18, 2019, the content of which is incorporated herein by reference in its entirety.

STATEMENT REGARDING FEDERALLY SPONSORED RESEARCH OR DEVELOPMENT

This invention was made with government support under NS092823 awarded by the National Institutes of Health. The government has certain rights in the invention.

BACKGROUND

The invention relates to methods and compositions for enhancing cellular clearance of pathological molecules. In particular, the invention relates to methods and compositions enhancing cellular clearance of pathological molecules via activating the cellular protein ykt6. The disclosed methods and compositions may be utilized in order to treat a subject having or at risk for developing a disease or disorder associated with proteinopathy or other cellular storage.

Proteinopathies and other storage disorders result from the inability to degrade and clear waste material from the cell, leading to pathological accumulation and toxicity. Cellular storage material also builds up in a chronic manner during the normal aging process, reflecting compromised clearance and cellular self-renewal. The toxicity of protein accumulation is best exemplified by age-related neurodegenerative disorders, including Parkinson's disease (PD), Lewy body Dementia (LBD), and Alzheimer's disease (AD), which are all characterized by the accumulation of insoluble protein and lipid aggregates within the nervous system. Although cells can elicit physiological responses to enhance cellular clearance and counteract accumulation, it is unclear how pathogenic proteins evade this process in disease.

In studying Parkinson's disease as an exemplary neurodegenerative disorders, we have found that Parkinson's disease a-synuclein perturbs the physiological response to lysosomal stress by impeding the SNARE protein ykt6. SNARE proteins form a large protein complex that mediates vesicle fusion and degradation of cellular components and clearance through autophagy, and other pathways that utilize lysosomes for degrading macromolecules.

Cytosolic ykt6 is normally auto-inhibited by a unique farnesyl-mediated regulatory mechanism however during lysosomal stress, it activates and redistributes into membranes to preferentially promote hydrolase trafficking and enhance cellular clearance. a-Synuclein aberrantly binds and deactivates ykt6 in patient-derived neurons, thereby disabling the lysosomal stress response and facilitating protein accumulation. Activating ykt6 by small-molecule farnesyl-transferase inhibitors restores lysosomal activity and reduces a-synuclein in patient-derived neurons and mice. Our findings indicate that a-synuclein creates a permissive environment for aggregate persistence by inhibiting regulated cellular clearance, and provide a therapeutic strategy to restore protein homeostasis by harnessing SNARE activity.

SUMMARY

Disclosed are methods and compositions for enhancing cellular clearance of pathological molecules. Particularly disclosed are methods and compositions enhancing cellular clearance of pathological molecules via activating the cellular protein ykt6. The disclosed methods and compositions may be utilized in order to treat a subject having or at risk for developing a disease or disorder associated with a proteinopathy and/or cellular storage.

BRIEF DESCRIPTION OF THE FIGURES

FIGS. 2A, 2B, 2C, 2D, 2E, 2F, 2G, 2H, and 2I. Ykt6 is required for lysosomal function in human midbrain neurons. 2A) Lentiviral mediated knockdown (KD) of ykt6 by shRNA (MOI3, dpi7) in control iPSn (scrb, scrambled). b-iii-tubulin (biiiTub) and GAPDH are loading controls (n=8 lysate, n=3 media). 2B) Immunofluorescence of LAMP1 in control iPSn infected with lentiykt6 shRNA. GFP indicates infected neurons (n=3). 2C) mRNA quantification by Q-RT-PCT (n=4). 2D) Analysis of GCase maturity by endoglycosidase H (endo H) digestion of iPSn lysates. 2E) Quantification of total and endo H resistant GCase by western blot (from panel 2D), GCase activity from whole cell lysates, and GBA1 mRNA levels by Q-RT-PCR (n=4). 2F) Western blot of media from iPSn after ykt6 KD (n=3). *, band detected in media alone. 2G) GCase activity in media from scrb of ykt6 KD iPSn. 2H) Proteolysis quantification in living iPSn by measuring soluble (sol.) amino acids released into the media over time. The shaded area shows the response to lysosomal inhibitors, leupeptin (Leu) and NH4Cl (quantified on the right (n=4)). 2I) GCase activity was measured after ykt6 KD in differentiated SH-SY5Y a-syn cells (n=4). Values are the mean+/−SEM, *p<0.05.

Figure 1A:
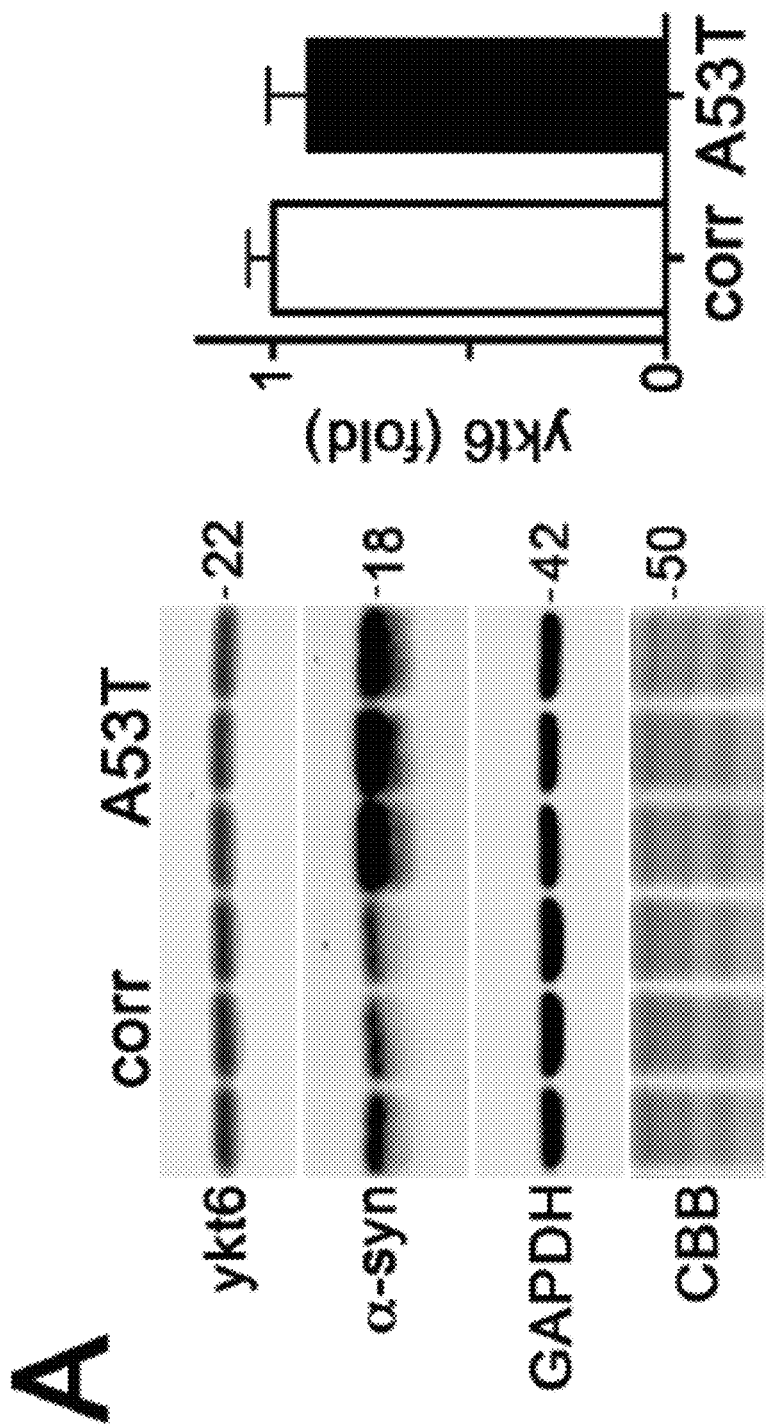
FIGS. 1A, 1B, 1C, 1D, 1E, 1F, and 1G. a-Synuclein interacts with ykt6 and disrupts SNARE complex assembly. 1A) Western blot of ykt6 in A53T or isogenic corrected (corr) iPSn at day 75 (n=6). GAPDH or Coomassie brilliant blue (CBB) are loading controls. 1B) Co-immunoprecipitation (co-IP) of a-syn and ykt6 in d75 iPSn. Right, quantification (n=3). 1C) Analysis of cytosolic (cyt) or membrane bound (mem) ykt6 in wt a-syn SH-SY5Y cells, or d90 iPSn from A53T and SNCA triplication (trp) patients compared to multiple controls. Calnexin (CNX) and GAPDH are loading controls (n=3-4). 1D) SEC/western blot of ykt6 SNARE complexes in SH-SY5Y cells. Neuron specific enolase (NSE) is a loading control (n=3). 1E) SEC analysis of PD brain lysates (n=3). 1F) Co-IP/western blot from transfected HEK cells (empty vector (v) or A53T a-syn, with GFP-ykt6) (n=3). 1G) Schematic showing the effects of a-syn on ykt6 (n=3). Farnesyl and Palmitoyl are illustrated. Molecular weights (MW) are in kilodaltons (kDa), molecular radius is in angstroms (A). Values are the mean+/−SEM, *p<0.05.

3 biological replicates are shown. 9C) Samples were analyzed as in A, after 90 days post-differentiation. 9D) Samples were analyzed as in A, after 110 days post-differentiation. A-syn was detected with both C-20 (total) and syn303 (preferentially detects oxidized a-syn) anti-a-syn antibodies. 9E) Quantification of soluble and insoluble a-syn blots at different times post-differentiation. For all quantifications, values are the mean+/−SEM, *p<0.05, **p<0.01, Student's T-test.

FIGS. 10A, 10B, 10C, 10D, 10E, 10F, 10G, 10H, 10I, 10J, 10K, 10L, and 10M. Temporal analysis of lysosomal dysfunction and neuron degeneration in PD patient midbrain neurons. 10A) Lysosomal b-glucocerebrosidase (GCase) activity was assessed within lysosomes of living midbrain DA neurons derived from an A53T PD patient iPSn using a compartment specific assay as described (Mazzulli et al., 2016a) at different days post-differentiation, indicating an age-dependent decline in activity compared to isogenic control lines (corr) (n=4). Lysosomal activity was defined as activity that is responsive to the lysosomal inhibitor, Bafilomycin A1 (BafA1). 10B) Lysosomal activity of hexosaminidase, sulfatase, and beta-galactosidase was done as in 10A. 10C) Lysosomal GCase activity was assessed within lysosomes of living midbrain DA neurons of a SNCA trp patient and compared to a healthy control line, as in 20A. 10D) Quantification of GCase substrates, hexosylceramide species, separated by acyl fatty acid chain lengths, in A53T and corr iPSn, normalized to inorganic phosphate (Pi). 10E) Analysis of hexosylsphingosine levels at 85 days post-differentiation. (n=3). 10F) Analysis of lysosomal protein levels and maturation by western blot of day 60 and 90 lysates (M, mature; I, Immature). biii-Tubulin, GAPDH or Coomassie brilliant blue (CBB) were used as loading controls. Total levels were normalized to biii-Tubulin, while maturation was assessed by calculating M/I ratios. Values are expressed as fold changed compared to corr at day 60 (n=3). 10G) Non-lysosomal activity (ie, not BafA1 responsive) was measured in living corr or A53T neurons, as well as in vitro using whole-cell lysates at day 75. 10H) Nicastrin maturation was analyzed by western blot and quantified to the right (n=3). 10I) Confocal immunofluorescence analysis of TFEB and a-syn (in A53T and corr cultures at d70, demonstrating nuclear translocation of TFEB within cells that accumulate cell body a-syn inclusions (white arrows). Two focal planes are shown, 0 and +2 μm, to demonstrate that nuclei (DAPI) colocalize with TFEB in A53T neurons. 10J) Measurement of a TFEB target, GBA1 mRNA, in d70 cultures, normalized to beta-actin mRNA (n=3). 10K) Neuron degeneration was assessed over time in A53T vs. corrected iPSn by quantification of neurofilaments and normalized to total cell volume (n=4). A representative immunostaining result is shown above the graph. 10L) Toxicity analysis was done at day 130 by counting TH/Tuj1/FOXA2 immunoreactive cells and normalized to nuclei (DAPI). 10M) Neuron degeneration was assessed as in K, in SNCA trp vs control iPSn. For all quantifications, values are the mean+/−SEM, *p<0.05, p<0.01, **p<0.0001, Student's T-test.

FIGS. 11A, 11B, 11C, 11D, 11E, 11F, 11G, 11H, 11I, 11J, and 11K. a-Synuclein forms a complex with ykt6 and disrupts its Golgi localization. 11A) Western blot analysis of sec22b in A53T or isogenic corrected (con) iPSn at day 60 (3 replicates shown). Quantification is on the right (n=6). Coomassie brilliant blue (CBB) was used as a loading control. 11B) Western blot analysis of STX5 in A53T or con iPSn at day 60 and 90. CBB and GAPDH were used as loading controls. Quantification is on the right. 11C) Co-IP of a-syn and ykt6 in inducible H4 cells expressing wt a-syn (tetoff) (n=2). 11D) a-syn/ykt6 interactions were confirmed by analyzing immunodepleted (I.D.) fractions of H4 lysates, showing that a-syn can be immunodepleted by ykt6 antibodies (n=3). 11E) Co-IP analysis in PD patient SNCA trp iPSn at day 80 (n=3). 11F) Co-IP analysis of PD patient iPSn derived from idiopathic PD (iPD), or PD patients harboring a GBA1 mutation (N370S/wt), SNCA trp or PARK9 mutations (from ref (Mazzulli et al., 2016b)). 11G) Inducible H4 cells were used for co-IP of a-syn followed by western blot of STX5. 11H) Extracts from H4 cells were separated into cytosolic or membrane fractions followed by co-IP for a-syn/western blot for ykt6, demonstrating that ykt6 interacts with a-syn in cytosolic fractions. Below, co-IP of cytosol or membrane fractions from PD iPSn expressing SNCA trp, as done in panel F. 11I) Immunofluorescence analysis of H4 cells of Golgi (GM130) or ykt6, showing that a-syn accumulation (−DOX) results in a more diffuse ykt6 staining (n=3 culture wells, data points represent individual cells). 11J) Gel filtration/western blot analysis of extracts from isogenic corrected (con) or A53T PD iPSn at day 75. Complexes eluted at ca. 120A were quantified on the right. NSE indicates equal column loading. 11K) Quantifications of SEC/western blot analysis of post-mortem brain lysates, corresponding to the blots shown in FIG. 1E (n=3). For all quantifications, values are the mean+/−SEM, *p<0.05, p<0.01, *p<0.001.

FIGS. 12A, 12B, 12C, 12D, 12E, and 12F. The effects of ykt6 knock-down on the lysosomal system and characterization of GD-SNCA KO iPSCs. 12A) Western blot analysis of SH-SY5Y cells indicates that ykt6 KD results in a-syn accumulation at 10 days post-differentiation, subsequent to lysosomal dysfunction. 12B) Protein secretion was measured by radioactive pulse-chase from the same culture wells that correspond to proteolysis data of FIG. 2H. 12C) Control iPSn were treated with 50 mM sucrose for 7 days followed by membrane shift analysis of ykt6. 12D) Control iPSn were infected with scrambled (S) or ykt6 shRNA (KD) and treated with or without sucrose as done in panel B. LAMP1 levels were analyzed by western blot. GAPDH is a loading control (n=4). 12E) Cultures were treated as described in panel C, and analyzed for GCase maturation by western blot analysis (n=4). For all quantifications, values are the mean+/−SEM, *p<0.05. 12F) Analysis of off-target edits by CRISPR/Cas9 in SNCA knock out (KO) Gaucher disease iPSCs. The targeting strategy has been previously published (Zunke et al., 2018). Genomic sequences showing the closest homology to SNCA were analyzed for mis-matched mutations by T7 digestion, and compared to the parental GD line. PCR amplicons were analyzed by agarose gel electrophoresis stained with ethidium bromide. For all quantifications, values are the mean+/−SEM, *p<0.05. Student's T-test was used in panel 12A, while ANOVA with Tukey's post-hoc test was used in panels 12D and 12E.

FIGS. 13A, 13B, 13C, 13D, 13E, 13F, 13G, 13H, and 13I. Enhancement of hydrolase trafficking and lysosomal activity by ykt6 wt or CS overexpression. 13A) H4 cells expressing a-syn were transfected to express ykt6 wild-type or ykt6 CS, followed by western blot analysis (n=3). 13B) Maturation of GCase was analyzed as in FIG. 4B (n=3). 13C) Overexpression of ykt6 wild-type or farnesyl-deficient mutant C195S (CS) in SH-SY5Y wt a-syn cells by lentiviral infection was assessed by western blot at 5 days post-infection (n=6). 13D) Maturation of GCase in SH-SY5Y wt asyn cells expressing ykt6 constructs was assessed by endoglycosidase H or PNGase F digest followed by western blot for GCase (8E4). Quantification is shown on the right (n=6). 13E)

Western blot analysis of lysosomal hydrolases hexosaminidase A and Iduronate-2-sulfatase reveals that ykt6 wt and CS enhance the levels of mature enzymes in SNCA trp iPSn. (n=3). 13F) ER-Golgi trafficking was directly assessed in H4 cells by live-cell microscopy using a RFP reporter fusion that can be induced to move out of the ER upon addition of a ligand (see methods). 13G) Upon induction, movement of the reporter into the Golgi was analyzed by co-localization analysis with a live-cell Golgi marker at different times after induction. Initial Golgi entry was analyzed by integrating the area under the curve between 0-200 seconds (n=4). 13H) Live-cell lysosomal GCase activity was measured as in FIG. 10A in transfected H4 cells at 3 days post transfection (left) or in PD patient iPSn at 6 weeks post-infection (right). 13I) Analysis of cell surface proteins in SH-SY5Y wt a-syn cells, infected with GFP control, wild-type ykt6 (wt) or CS mutant, was done by cell-surface biotinylation, followed by pull-down of biotinylated proteins with streptavidin beads. Total cell surface proteins were analyzed by SDS-PAGE and detected with streptavidin-conjugated secondaries. CBB staining shows the total protein. Quantification is shown below (n=6). For all quantifications, values are the mean+/− SEM, $*p<0.05$, $**p<0.01$. N.S, not significant.

FIGS. 14A, 14B, 14C, 14D, 14E, 14F, and 14G. The effects of FTI treatment on ykt6 and lysosomes. 14A) Farnesylation of ykt6 was measured in SH-SY5Y cells expressing GFP-ykt6. Cells treated with or without FTI (LNK-754) were cultured with farnesyl-azide to label farnesyl-modified proteins, immunoprecipitated with GFPaffinity beads, and then conjugated with phosphine-biotin. Biotin was detected with streptavidin-conjugated IRDye800, and normalized to total levels of GFP-ykt6. See methods for details. The merged blot image shows total ykt6 and farnesylated forms (n=3). 14B) Membrane shift analysis of SH-SY5Y cells stably expressing GFP-ykt6-CS, treated with 5 nM FTI. Calnexin (CNX) and Coomassie blue (CBB) were used as a loading controls. 14C) Gel filtration/western blot analysis of FTI treated A53T iPSn. Ykt6 complex levels eluting at ca. 120A were quantified on the right (n=2). 14D) Analysis of GCase localization in H4 cells treated with 5 nM FTI demonstrates an increase in the levels of lysosomal marker LAMP2A and GCase (n=3). 14E) Raw quantification data of LAMP2A immunofluorescence intensity of individual cells from H4 cells treated with FTI, +/−ykt6 KD. Each data point represents LAMP2A intensity from individual cells, from 3 different culture wells. 14F) Analysis of ER-Golgi trafficking of GCase by endo H resistance after treatment with FTI in SH-SY5Y cells overexpressing wt a-syn (n=3). 14G) Western blot analysis of Triton X-100 soluble a-syn in SH-SY5Y wt a-syn cells after treatment with various concentrations of FTI for 5 days. For all quantifications, values are the mean+/−SEM, $*p<0.05$.

FIGS. 15A, 15B, 15C, 15D, 15E, and 15F. FTI treatment of wild-type mice enhances ykt6 SNARE complexes, lysosomal activity, and reduces a-syn. 15A) Wild-type mice (C57Bl/6) were i.p. injected daily with FTI for 14 days at 0.9 mg/kg and compared to vehicle injected mice. Extracts from the cortex were analyzed for cytosolic (cyt) and membrane (mem) distribution of ykt6 (veh, n=5; FTI, n=6). 15B) Representative gel filtration/western blot analysis of cortical extracts of veh or FTI injected wild-type mice. Inputs are shown on the left. NSE indicates equal column loading. 15C) Quantification of ykt6 and STX5 complexes (ca. 120A) from gel filtration analysis in C (n=4 mice). Fraction 1 corresponds to complexes at 120A, while fractions 7-9 correspond to ykt6 monomers at 22-14 A. 15D) The levels of post ER (endo H resistant) GCase were analyzed by western blot and post ER/ER ratios were quantified from the cortex of FTI treated mice (veh, n=5; FTI, n=6). 15E) GCase activity was assessed in cortical lysates and normalized to total protein (veh, n=4; FTI, n=6). 15F) a-Syn levels were quantified from cytosolic or membrane isolated fractions from the cortex of wild-type FTI treated mice (veh, n=4; FTI, n=6). For all quantifications, values are the mean+/− SEM, $*p<0.05$.

Figure 16:
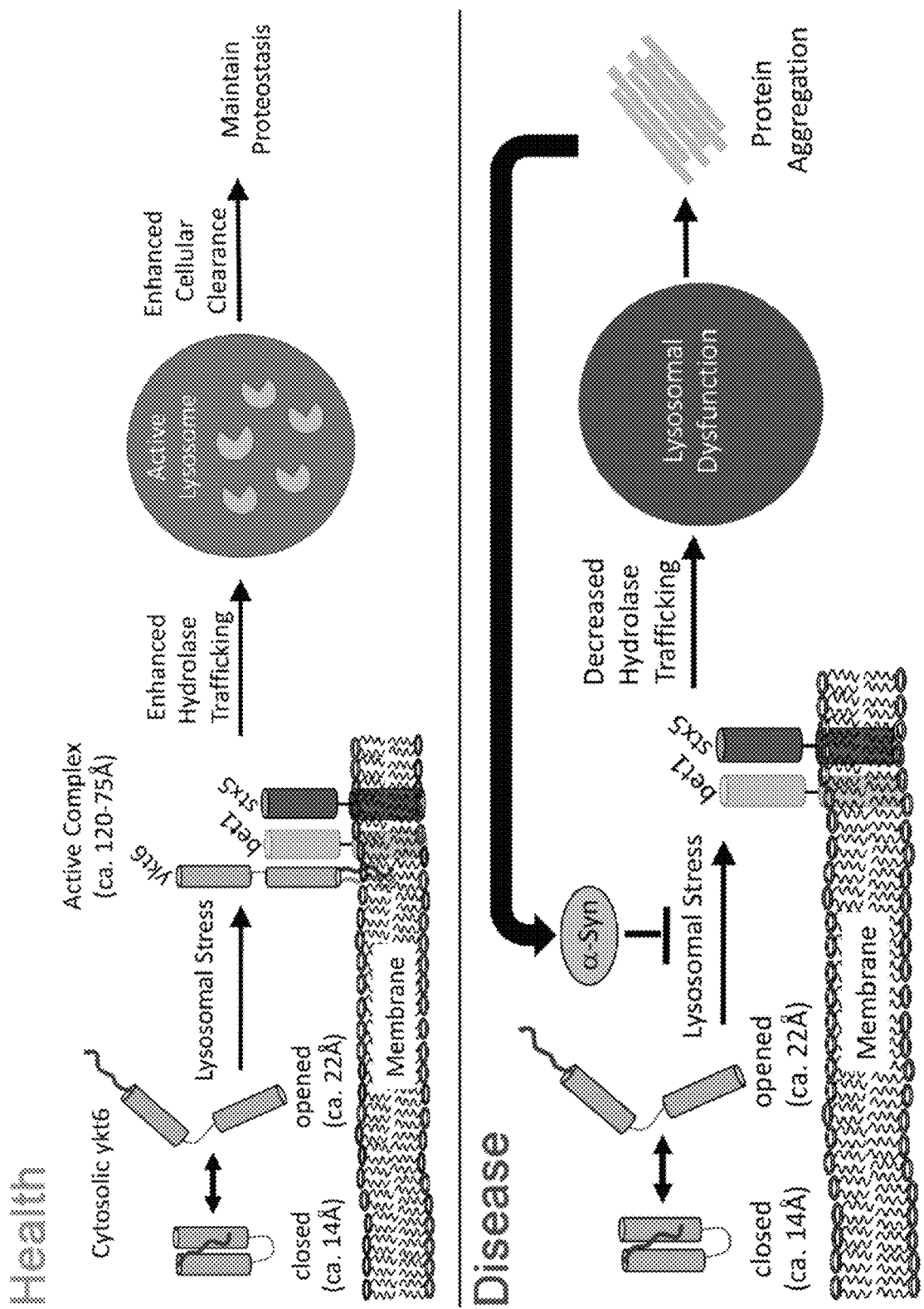

FIG. 16. Self-propagating protein aggregation of a-syn occurs by disabling the physiological response to lysosomal stress. Top, Under physiological conditions, human midbrain neurons can respond to lysosomal stress by activating ykt6 SNARE assembly. This homeostatic response can rebalance proteostasis by promoting hydrolase trafficking into lysosomal compartments, increasing activity, and enhancing cellular clearance. Bottom, Under conditions of pathological protein accumulation, a-syn disables the lysosomal stress response by interfering with ykt6 SNARE assembly and inducing lysosomal dysfunction. This in turn, creates a permissive environment for aggregate persistence by rendering the lysosomal system incapable of meeting the degradation requirements of the cell, eventually resulting self-propagating protein aggregation and cell death.

Figure 17:
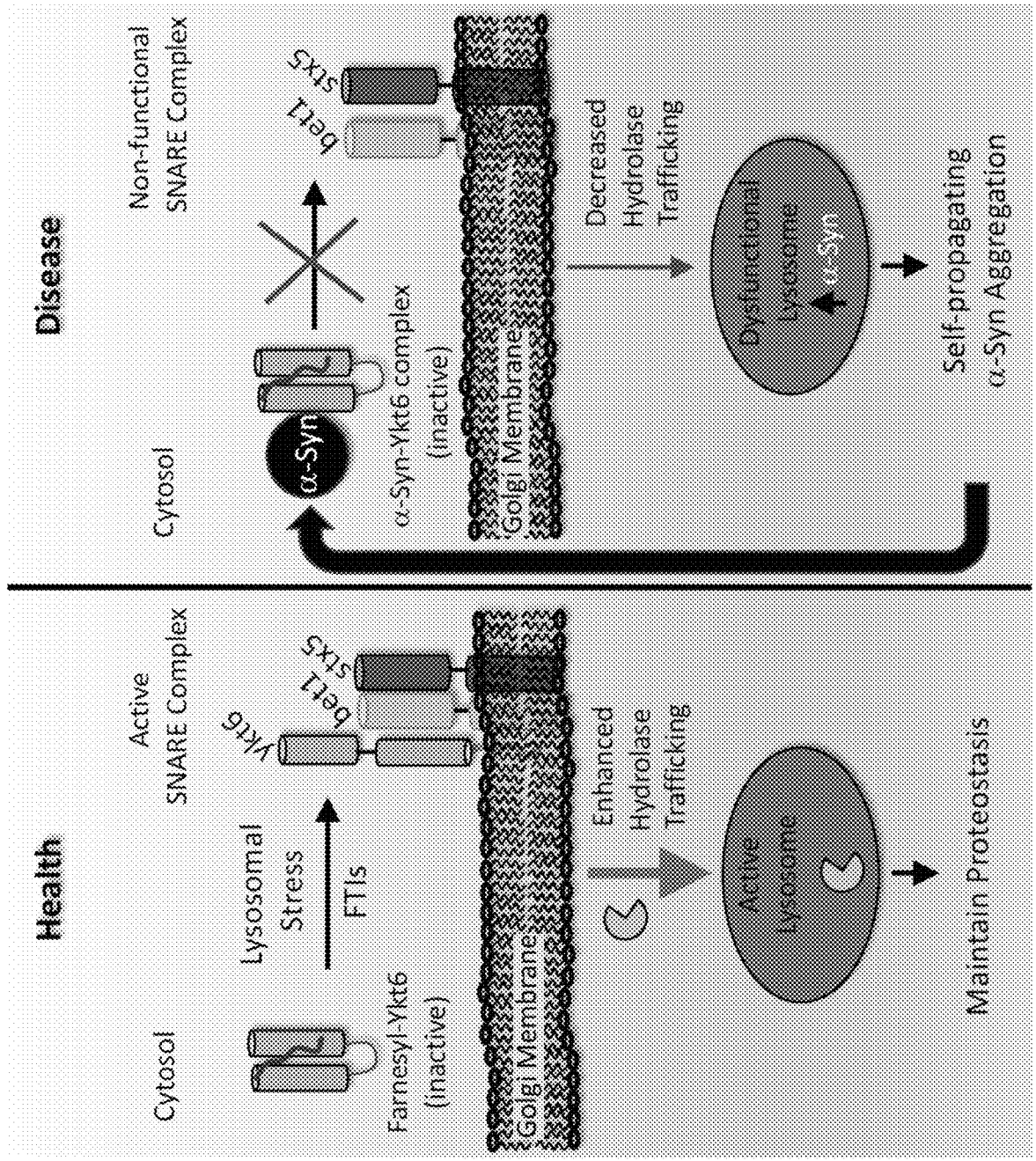

FIG. 17. Graphical abstract of health versus disease states in view of Ykt6 activity.

Figure 18:
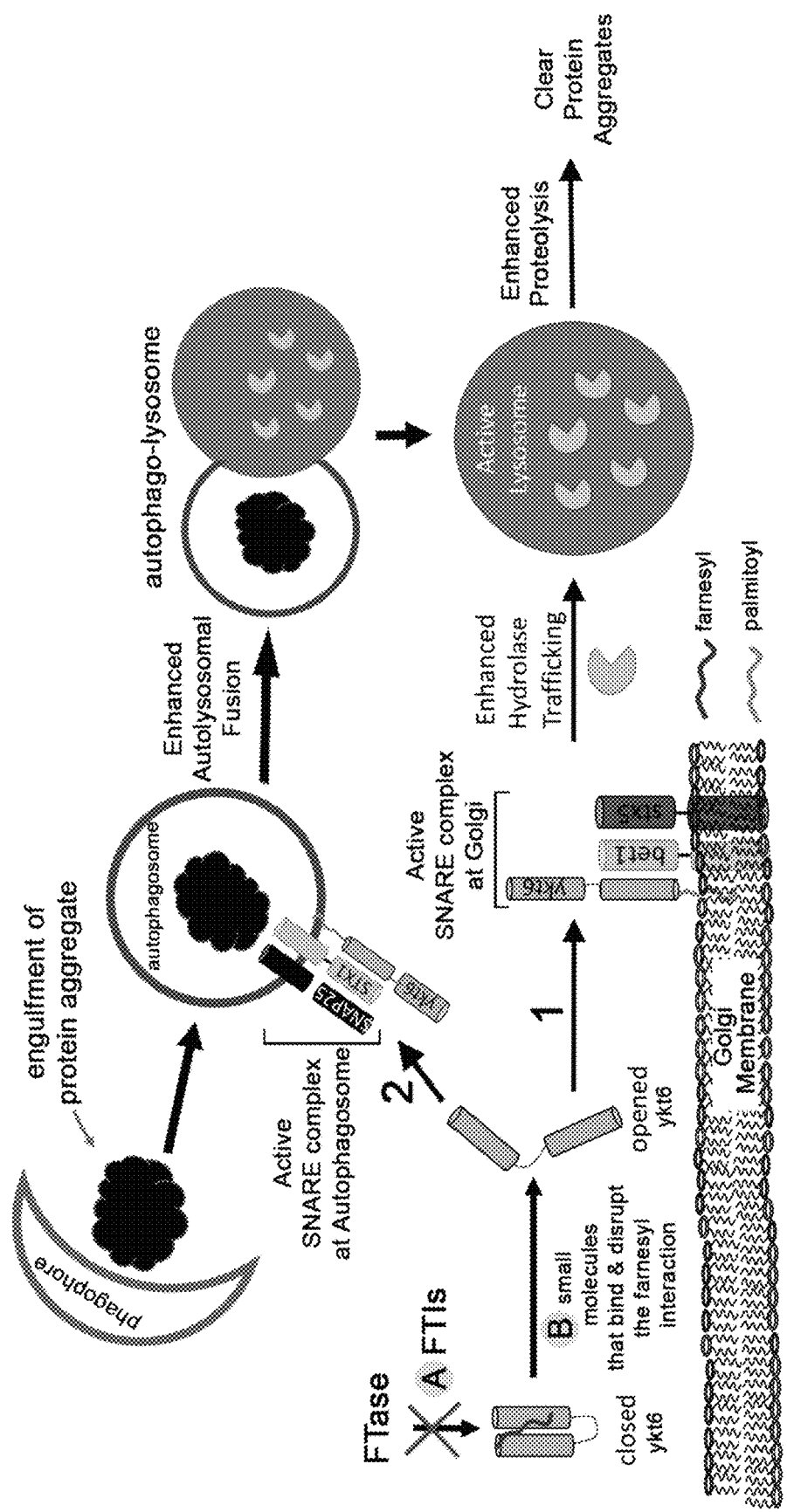

FIG. 18. Two methods (A and B) to enhance ykt6, autophagic delivery of aggregates, and lysosomal clearance. We discovered that reducing the farnesylation of ykt6 can enhance SNARE assembly, improve lysosomal function, and reduce pathological protein aggregates in PD patient neurons. The invention includes methods to enhance the activity of this pathway including A) reducing the farnesylation of ykt6 through the use of farnesyltransferase inhibitors (FTIs), and B) employing small molecules that bind and disrupt the farnesyl-ykt6 intramolecular interaction, thereby promoting an open, active conformation, and employing small molecules that bind to any region of ykt6 that acts to promote an open, active conformation. Ykt6 promotes membrane fusion at the ER-Golgi step to enhance hydrolase trafficking (arrow 1), and simultaneously enhances autophagosome biogenesis and cargo delivery to lysosomes (arrow 2). In addition, novel biomarkers are disclosed that can be used to track the progression of synucleinopathies by detection of closed and open forms of ykt6, as well as prenylated, farnesylated, and palmitoylated forms of ykt6 in the blood.

Figure 19:
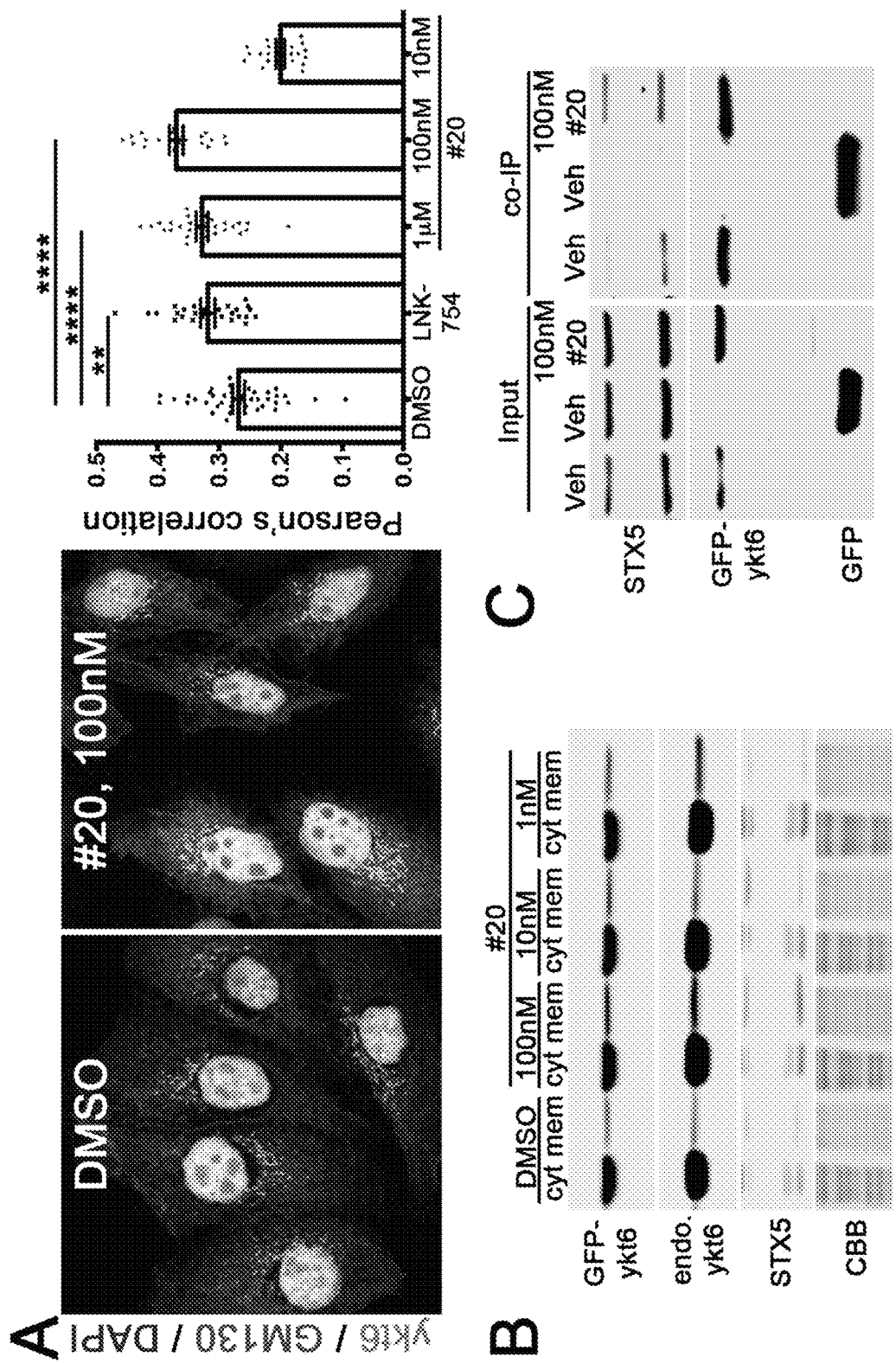

FIG. 19. Compound #20 ((3R)-1-[(1-{[1-(4,5-dimethylthiophene-2-carbonyl)piperidin-4-yl]methyl}-1H-1,2,3-triazol-4-yl)methyl]pyrrolidin-3-amine), designed to impede the farnesyl-ykt6 intramolecular interaction, increases ykt6 activity in Hela cells. A) Hela cells stably expressing GFP-ykt6 (green) were treated with #20 for 2 days at various concentrations, fixed, stained with Golgi marker GM130 (red), and colocalization was quantified by Pearson's correlation. Each plot represents an individual cell, from 3 culture wells. LNK-754 was used at 10 nM. B) Stable transfected Hela cells were incubated as in A followed by biochemical fractionation/western blot to detect cytosolic (cyt) or membrane (mem) ykt6. The assay was repeated 3 times, representative blot shown. C) co-IP using GFP affinity beads and western blot analysis for ykt6 binding partner STX5 shows that #20 increases SNARE binding.

Figure 20:
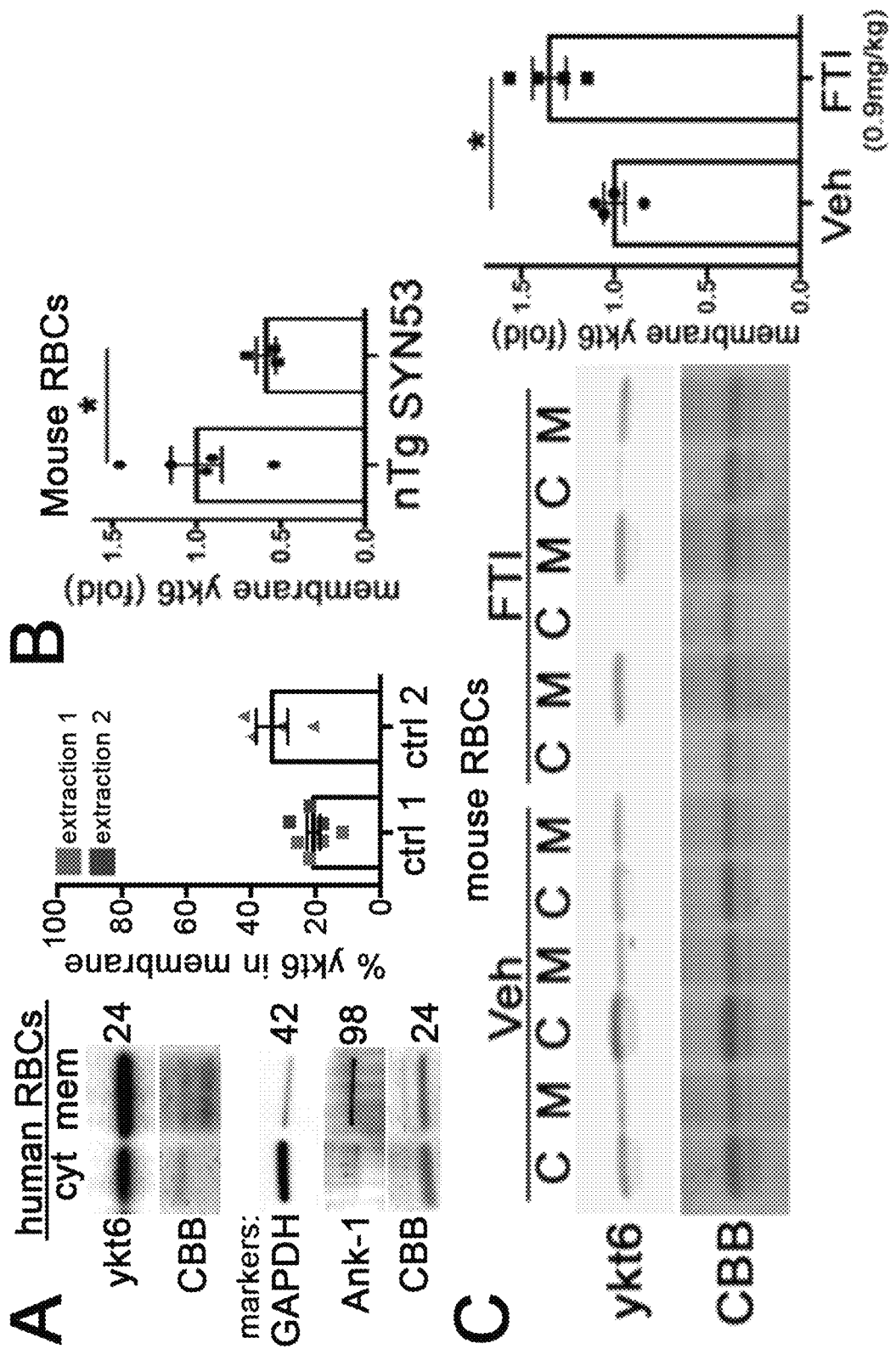

FIG. 20. Ykt6 in red blood cells of human and mice. A) Fractionation of RBCs/western blot of ykt6. Markers indicate efficient separation of cytosol (GAPDH) and membrane (Ank, Ankyrin-1). Right, quantification from two separate extractions, from two healthy volunteers shows low variability. B) Ykt6 from RBCs of nTg of symptomatic 12 mo old A53T mice (ref 12) (n=3-5). C) FTI LNK-754 increases membrane Ykt6 in WT mice (n=4).

DETAILED DESCRIPTION

Disclosed are methods and compositions for enhancing cellular clearance of pathological molecules. In particular, the invention relates to methods and compositions for enhancing cellular clearance of pathological molecules via activating the cellular protein ykt6. The disclosed methods may be utilized in order to treat a subject having or at risk for developing a proteinopathy or other cellular storage disorders. The methods and compositions are described herein using several definitions, as set forth below and throughout the application.

As used in this specification and the claims, the singular forms "a," "an," and "the" include plural forms unless the context clearly dictates otherwise. For example, "a therapeutic agent" should be interpreted to mean "one or more therapeutic agents" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods and compositions relate to therapeutic treatment of subjects in need thereof. As used herein, the term "subject," which may be used interchangeably with the terms "patient" or "individual," refers to one who receives medical care, attention or treatment and may encompass a human or non-human patient.

As used herein, the term "subject" is meant to encompass a person who has a proteinopathy or cellular storage disorder or is at risk for developing a proteinopathy or cellular storage disorder. The term "subject" is meant to encompass a person having or at risk for developing a neurogenerative disorder, such as an age-related neurodegenerative disorder. A "subject" is meant to encompass a patient having or at risk for developing Parkinson's disease (PD), Lewy body Dementia (LBD), Alzheimer's disease (AD), amyotrophic lateral sclerosis (ALS), multiple system atrophy, Huntington's disease, Prion disease, frontotemporal dementia, Picks disease, progressive supranuclear palsy, and progeria.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

The disclosed methods and compositions relate to treating and/or preventing diseases and disorders such as a proteinopathy or cellular storage disorder in a subject in need thereof by enhancing cellular clearance of pathological molecules in the subject. In some embodiments, the disclosed methods and compositions relate to treating and/or preventing diseases and disorders such as a proteinopathy or cellular storage disorder in a subject in need thereof by administering a therapeutic agent that activates the cellular protein ykt6 in the subject.

The methods disclosed herein may include a step of administering a therapeutic agent that activates the biological activity of ykt6. As used herein, the term "activate" means increasing or augmenting activity. The therapeutic agents utilized in the disclosed methods may activate the biological activity of ykt6 directly and/or indirectly by interacting with ykt6 directly and/or indirectly. In some embodiments, the therapeutic agents activate ykt6 by inhibiting the biological activity of farnesyltransferase. In other embodiments, the therapeutic agents inhibit and/or disrupt the molecule interaction between farnesyl-ykt6 and the therapeutic agents may promote the open, active conformation of ykt6 versus the closed, inactive conformation of ykt6.

The therapeutic agents utilized in the treatment methods disclosed herein may exhibit one or more biological activities. The disclosed compounds may function to activated the biological activity of ykt6. In some embodiments, the disclosed compounds activate the biological activity of ykt6 by at least 50%, 60%, 70%, 80%, 90%, 95%, 96%, 97%, 98%, or 99% relative to a control at a concentration of less than about 100 µM, 50 µM, 10 µM, 1 µM, 0.1 µM, 0.05 µM, 0.01 µM, 0.005 µM, 0.001 µM, or less.

The disclosed therapeutic agents may be formulated as therapeutics for treating proteinopathies and cellular storage disorders. In some embodiments, the disclosed therapeutic agents are small molecule compounds. As such, compounds are disclosed herein for use in the disclosed methods and compositions. The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

The therapeutic agents utilized in the methods disclosed herein may be formulated as pharmaceutical compositions that include: (a) a therapeutically effective amount of one or more therapeutic agents as disclosed herein; and (b) one or more pharmaceutically acceptable carriers, excipients, or diluents. The pharmaceutical composition may include the therapeutic agents in a range of about 0.1 to 2000 mg (preferably about 0.5 to 500 mg, and more preferably about 1 to 100 mg). The pharmaceutical composition may be administered to provide the therapeutic agent at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the therapeutic agent at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µM).

In some embodiments of the disclosed treatment methods, the subject may be administered a dose of a therapeutic agent as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a therapeutic agent as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the therapeutic agent may include doses falling within dose ranges having as end-points any of these disclosed doses (e.g., 2.5 mg-200 mg).

In some embodiments, a minimal dose level of a therapeutic agent for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a therapeutic agent for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the therapeutic agent for achieving therapy in the disclosed methods of treatment may include dose levels falling within ranges having as end-points any of these disclosed dose levels (e.g., 500-2000 ng/kg body weight of the subject).

The therapeutic agent utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The disclosed therapeutic agent or pharmaceutical compositions comprising the disclosed therapeutic agent may be administered in methods of treatment. For example, the disclosed therapeutic agent or pharmaceutical compositions comprising the disclosed therapeutic agent may be administered in methods of treating and/or preventing proteinopathies and cellular storage disorders.

Optionally, the disclosed therapeutic agent that activate the biological activity of ykt6 or pharmaceutical compositions comprising the disclosed therapeutic agent that activates the biological activity of ykt6 may be administered with additional therapeutic agents, optionally in combination, in order to treat and/or prevent proteinopathies and cellular storage disorders. In some embodiments of the disclosed methods, one or more additional therapeutic agents are administered with the disclosed therapeutic agent that activates the biological activity of ykt6 or with pharmaceutical compositions comprising the disclosed therapeutic agent that activates the biological activity of ykt6, where the additional therapeutic agent is administered prior to, concurrently with, or after administering the disclosed therapeutic agent that activates the biological activity of ykt6 or the pharmaceutical compositions comprising the disclosed compounds. In some embodiments, the disclosed pharmaceutical composition are formulated to comprise the disclosed that therapeutic agent activates the biological activity of ykt6 and further to comprise one or more additional therapeutic agents, for example, one or more additional therapeutic agents for treating proteinopathies and cellular storage disorders.

Methods for Enhancing Cellular Clearance of Pathological Molecules Via Activation of the Cellular Protein YKT6

Disclosed are methods and compositions for treating and/or preventing a disease or disorder associated with proteinopathy or cellular storage in a subject in need thereof. The disclosed methods typically utilize and/or the disclosed compositions comprise an effective amount of a therapeutic agent that activates or augments the activity of ykt6. As such, pharmaceutical methods and pharmaceutical compositions are disclosed herein.

Diseases and disorders that may be treated and/or preventing by practicing the disclosed methods and/or administering the disclosed compositions may include, but are not limited to neurodegenerative diseases and disorders, which include age-related neurodegenerative diseases and disorders. Diseases and disorders that may be treated and/or preventing by practicing the disclosed methods and/or administering the disclosed compositions may include, but are not limited to Parkinson's disease (PD), Lewy body Dementia (LBD), Alzheimer's disease (AD), amyotrophic lateral sclerosis (ALS), multiple system atrophy, Huntington's disease, Prion disease, frontotemporal dementia, Picks disease, progressive supranuclear palsy, and progeria.

The disclosed methods utilize and the disclosed compositions comprise a therapeutic agent that activates or augments the activity of ykt6. In some embodiments, the disclosed therapeutic agent inhibits farnesylation of ykt6. In some embodiments, the therapeutic agent is an inhibitor of farnesyltransferase. In other embodiments, the therapeutic inhibits and/or disrupts an interaction between farnesyltransferase and ykt6. In other embodiments, the therapeutic can directly or indirectly inhibit the interaction between any prenylation moiety attached to ykt6, including farnesyl and/or geranylgeranylation. In other embodiments the therapeutic can promote the open, activation conformation of ykt6 independently of prenylation status. In further embodiments, the therapeutic agent promotes the open, active conformation of ykt6 versus the closed, inactive conformation of ykt6.

The therapeutic agent may include, but is not limited to a so-called small molecule compound. In some embodiments, the therapeutic agent comprises a compound selected from the following compounds or a salt thereof:

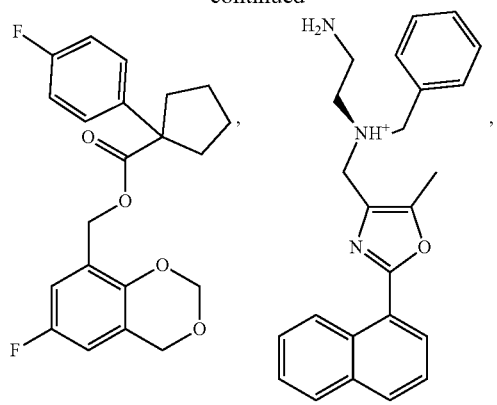

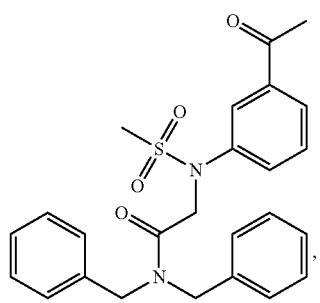

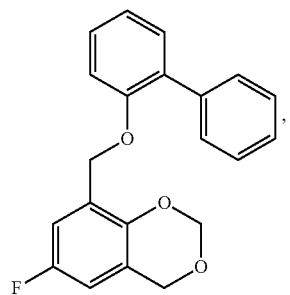

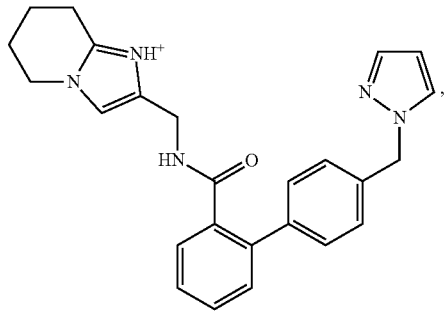

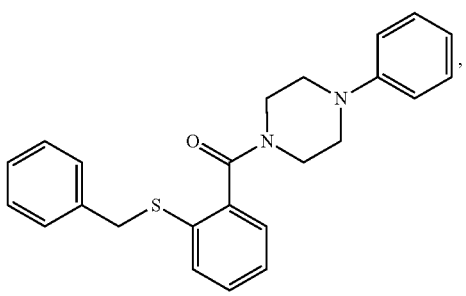

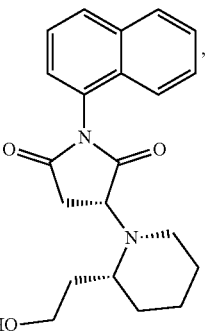

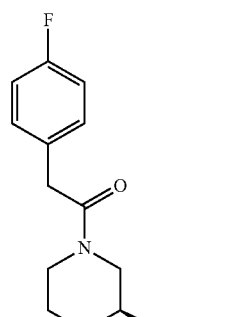

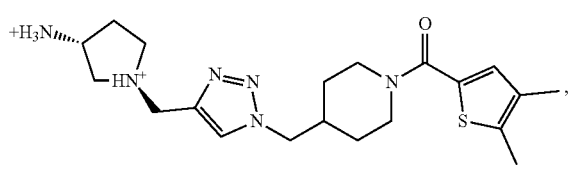

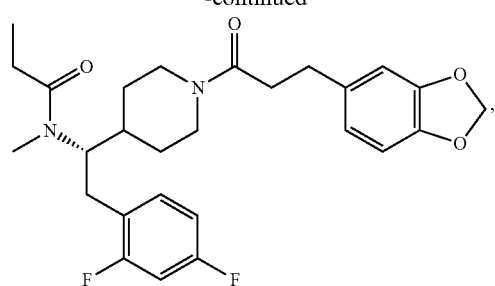
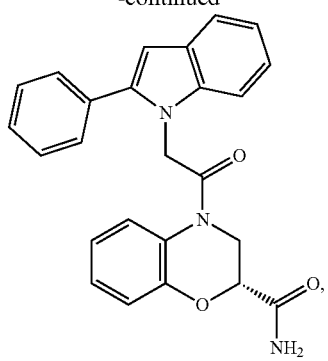
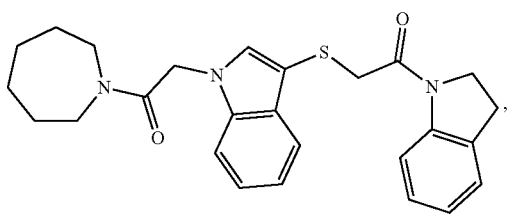
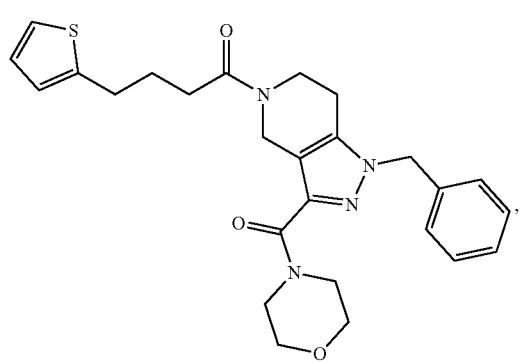
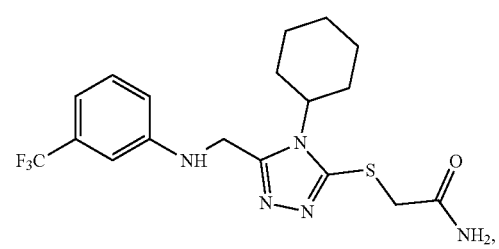
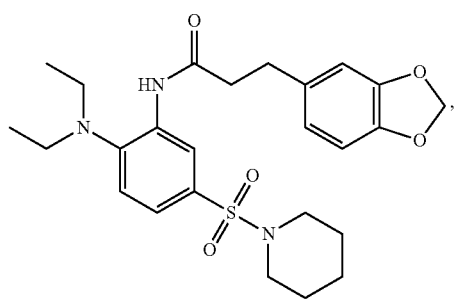
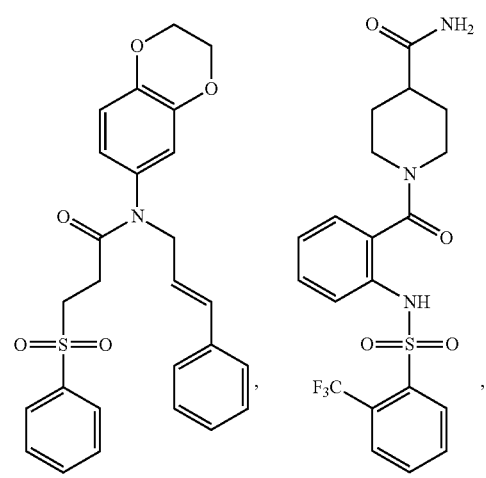
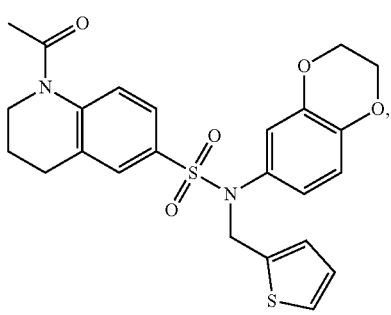
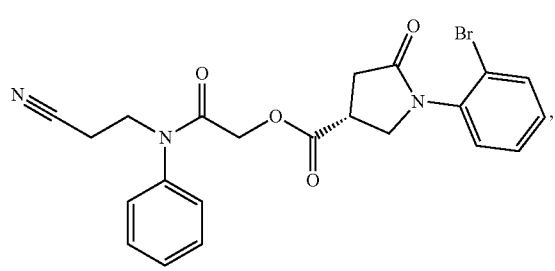
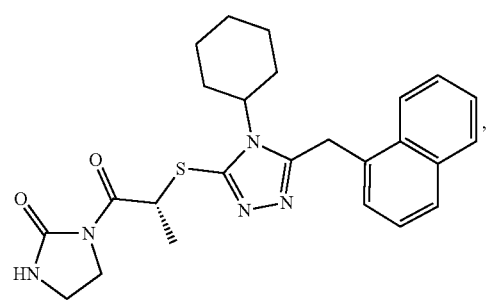

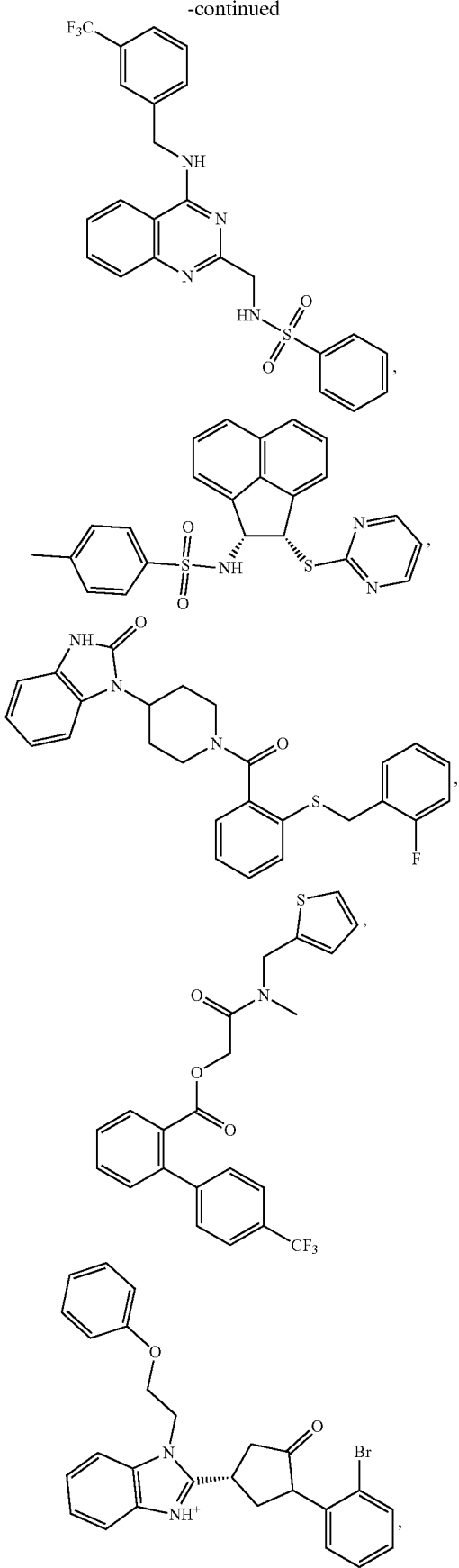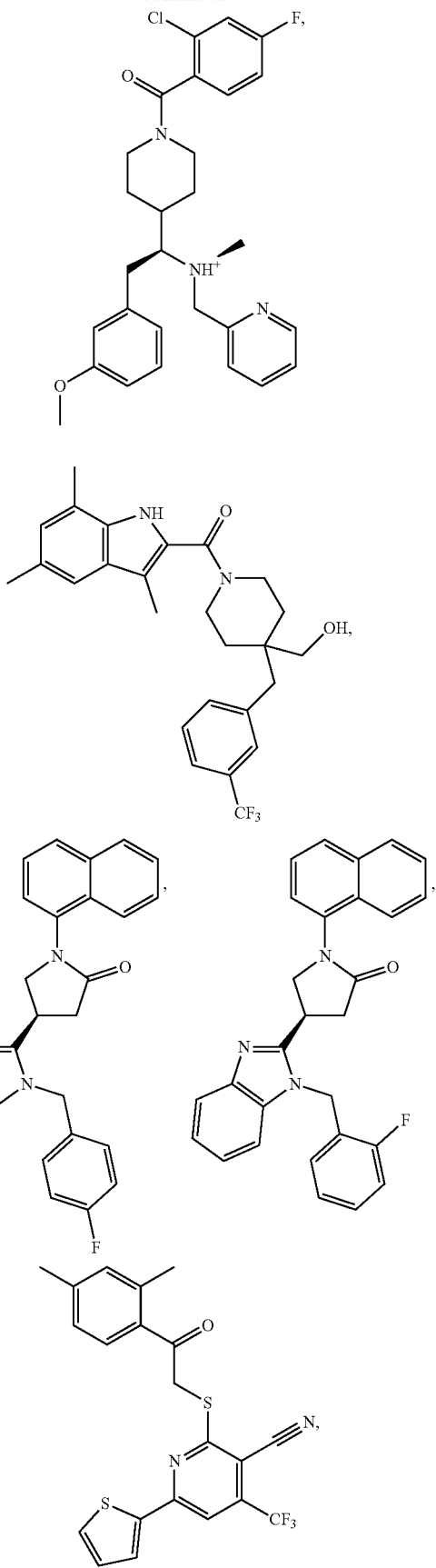

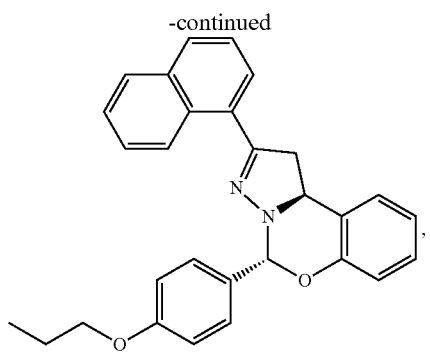
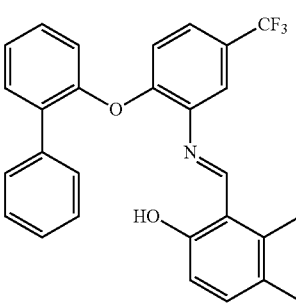
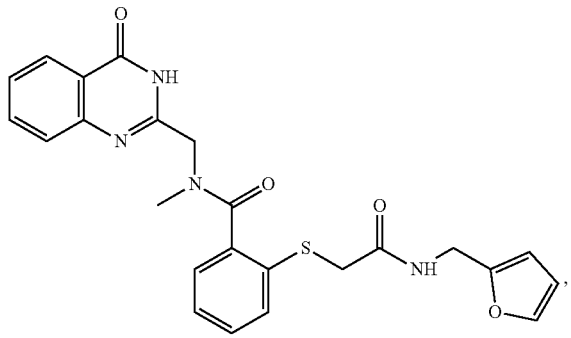
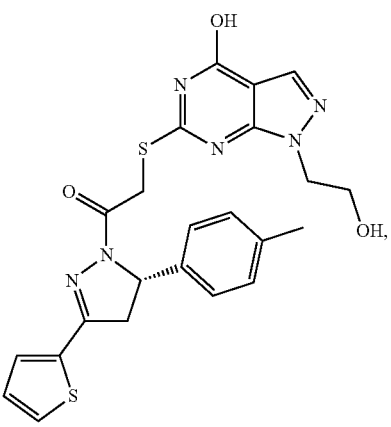
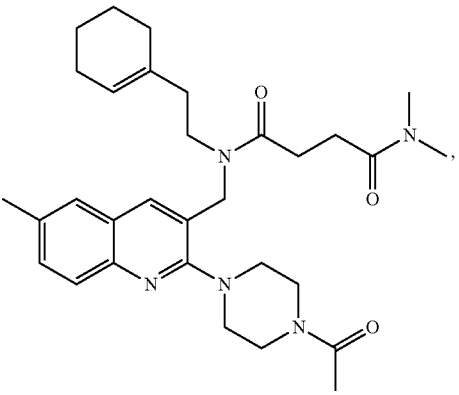
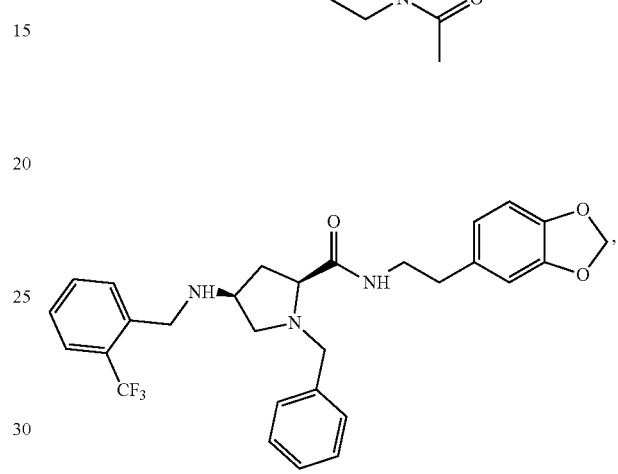
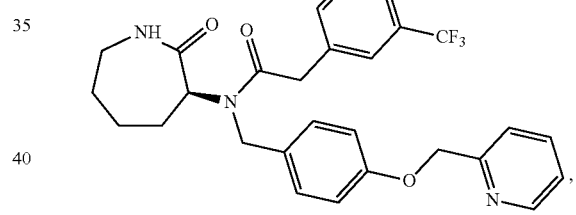
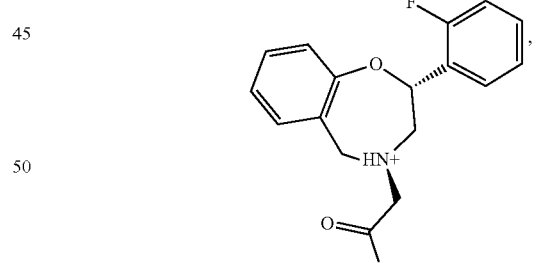
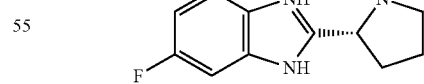
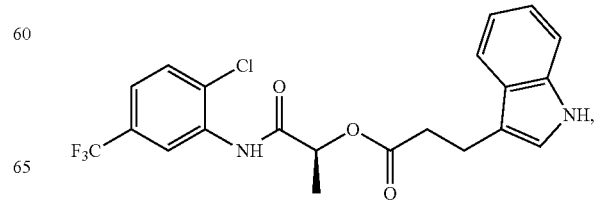

21
-continued
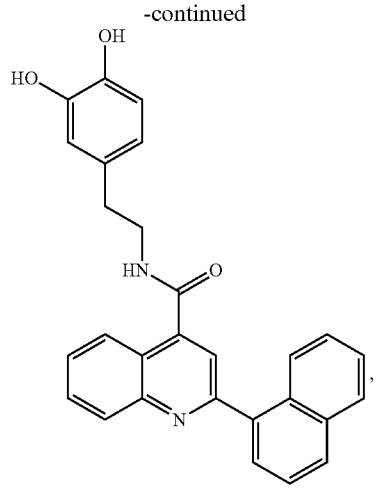
22
-continued
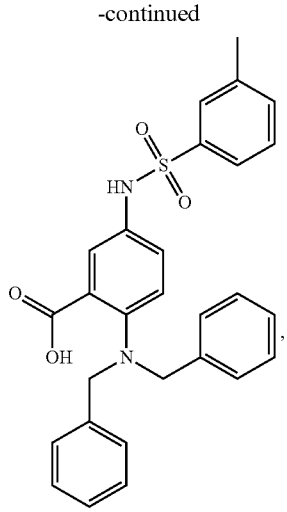
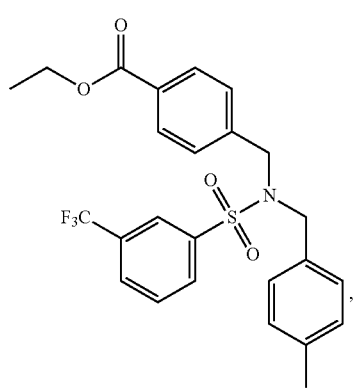

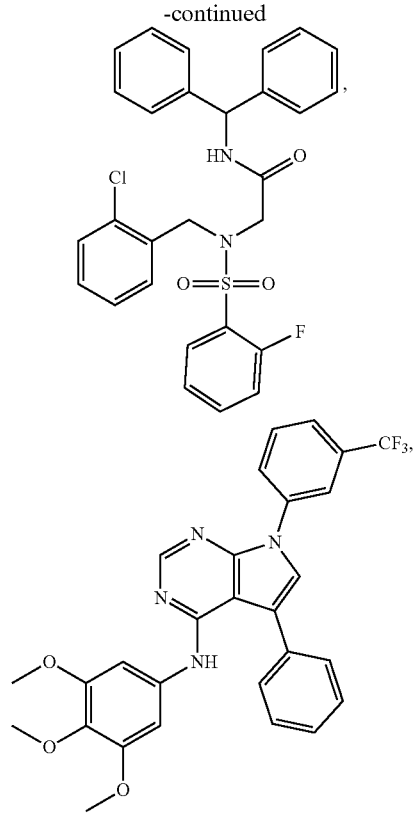
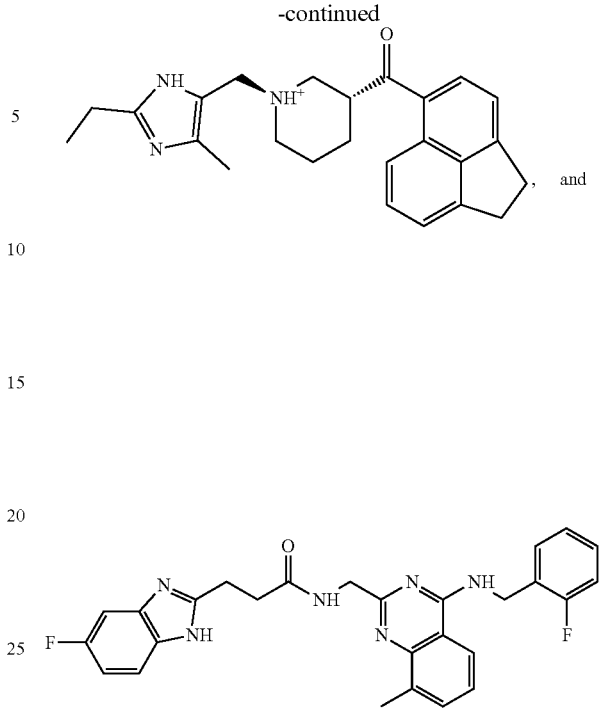
In some embodiments, the therapeutic agent comprises a compound selected from the following compounds or a salt thereof:
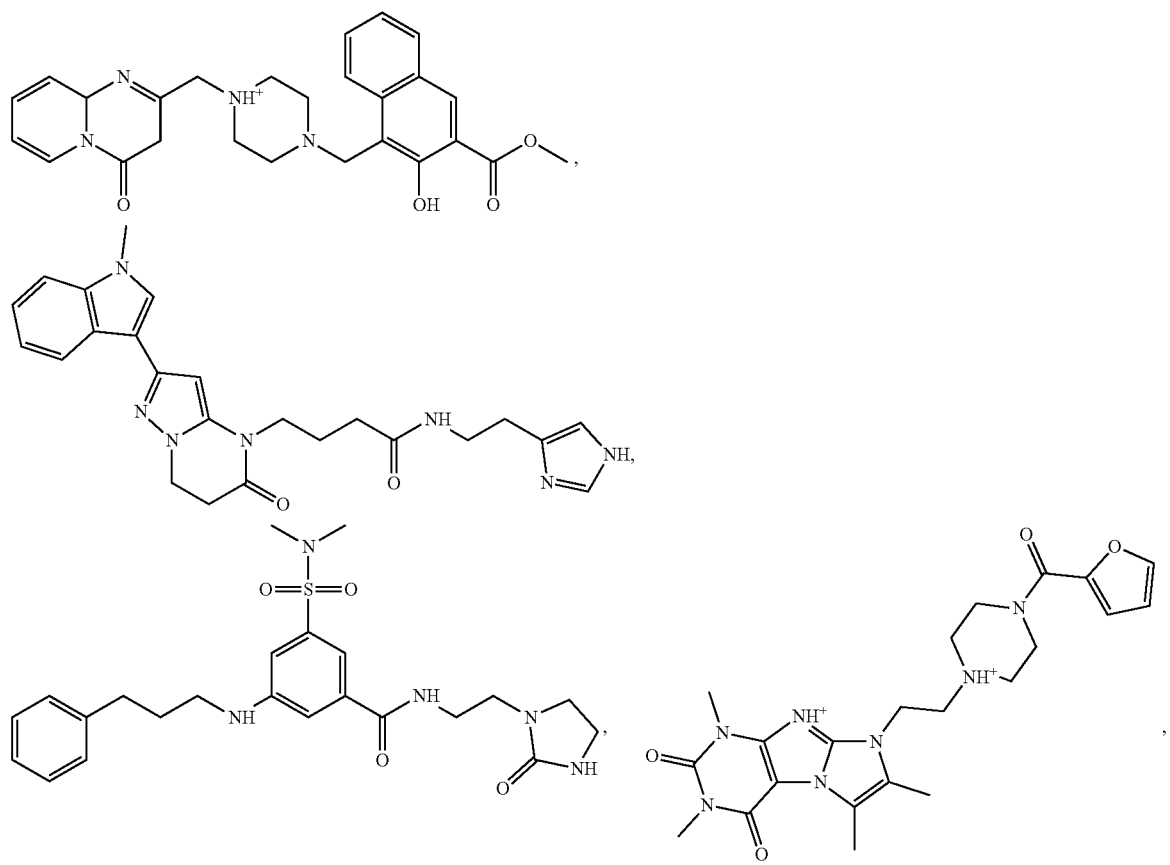

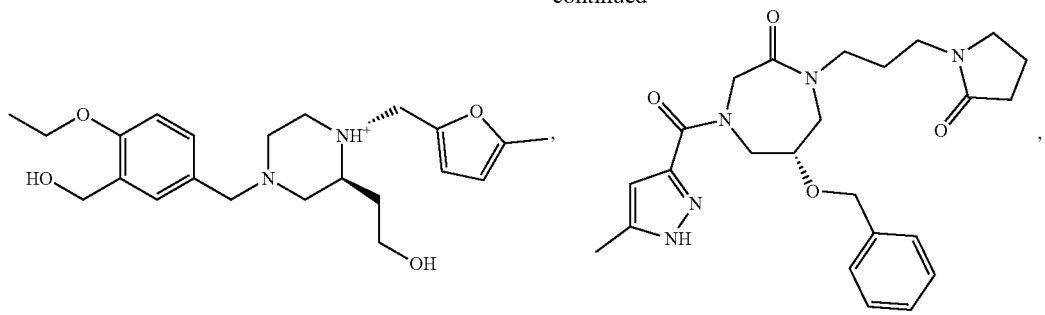
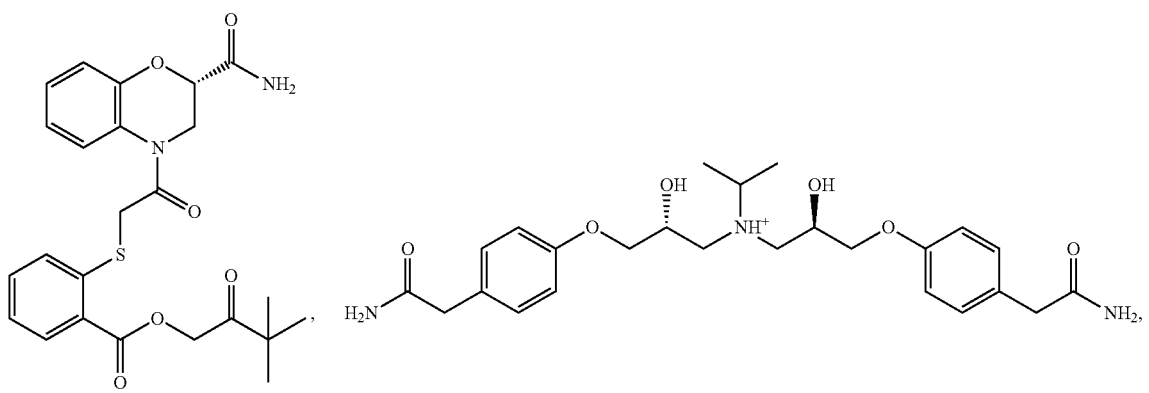
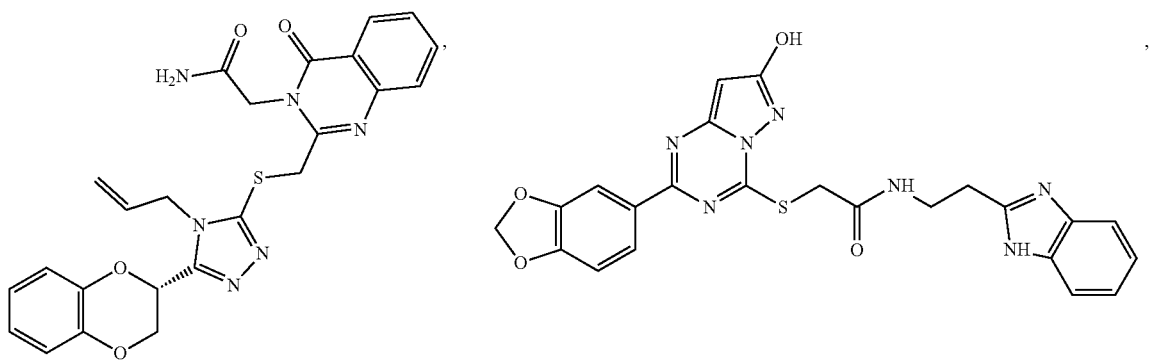
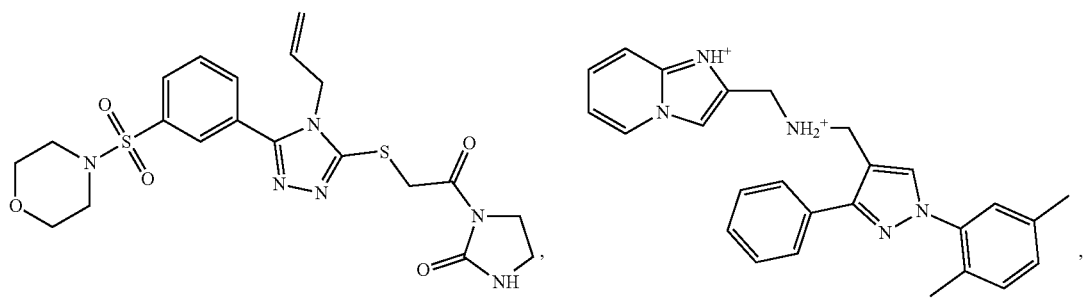

-continued
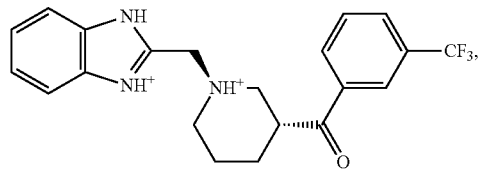
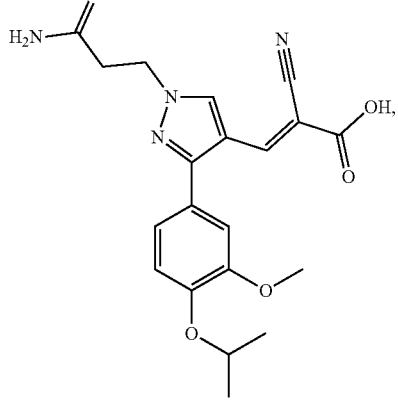
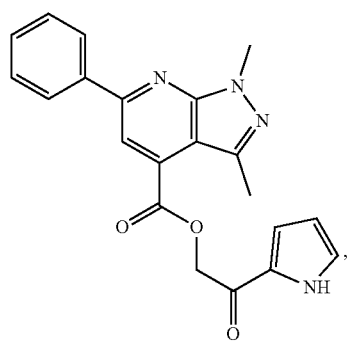
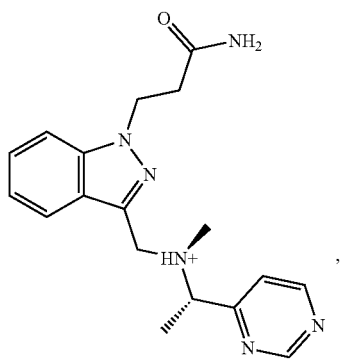
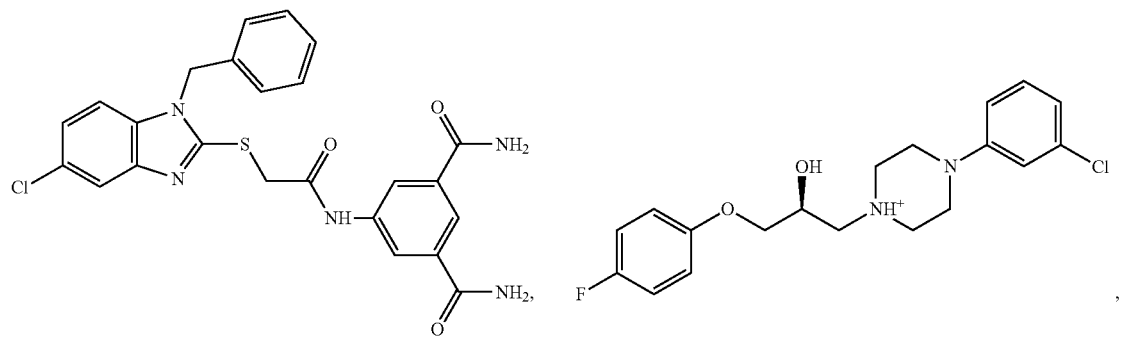
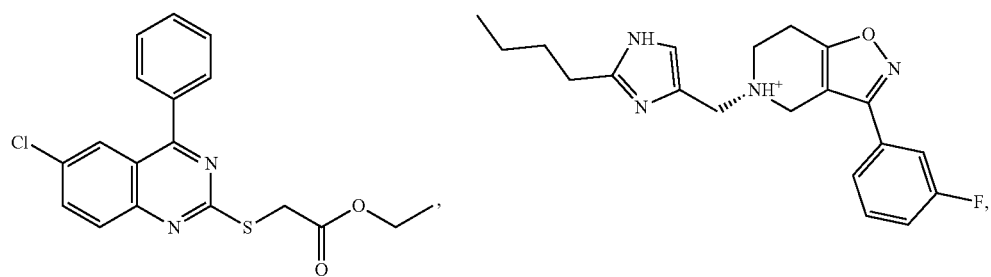
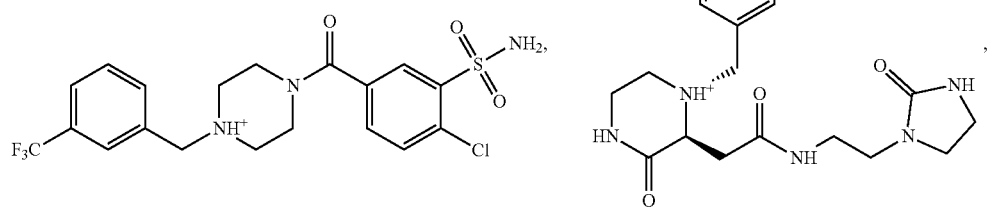

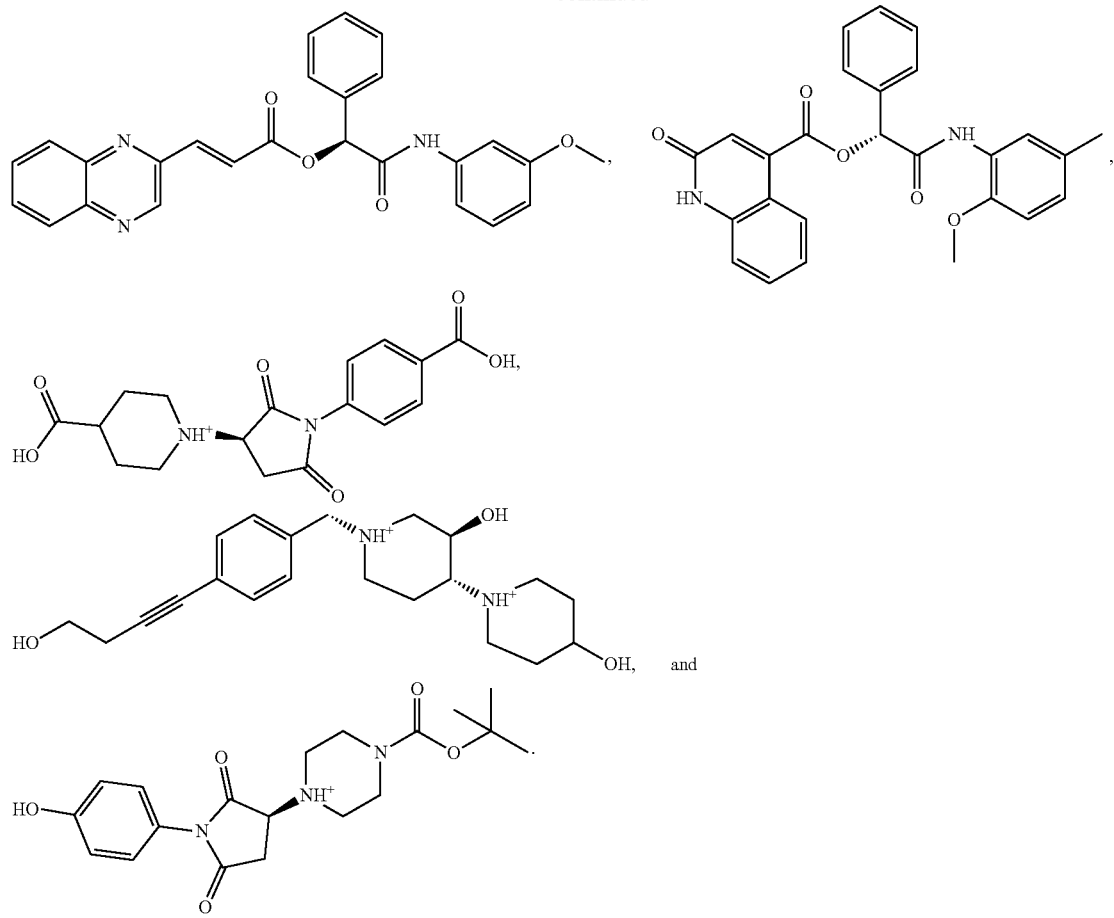

Pharmaceutical compositions and methods of using pharmaceutical compositions in methods of treatment are disclosed herein. In some embodiments, the disclosed pharmaceutical compositions comprise any compound disclosed herein and a suitable pharmaceutical carrier, diluent, or excipient. The pharmaceutical compositions may be formulated for use in treating diseases or disorders associated with proteinopathies and/or cellular storage.

Also disclosed are diagnostic methods and/or prognostic methods. In some embodiments, the disclosed methods include detecting in a biological sample from a subject ykt6. Optionally, the methods may include detecting ykt6 in a biological sample, wherein the detected ykt6 in the biological sample is in an open conformation, a closed conformation, or both of an open conformation and a closed conformation. The disclosed methods may include determining the relative amount of ykt6 in the open conformation in the biological sample versus total ykt6 in the biological sample (or versus the amount of ykt6 in the closed conformation).

Suitable biological samples may include, but are not limited to cerebral spinal fluid, peripheral nerve and/or muscle biopsy, skin fibroblast biopsy, saliva, urine, blood or a blood product. Blood products may include plasma and serum.

In the disclosed diagnostic methods and/or prognostic methods, the subject may have or may be suspected of having a disease or disorder associated with proteinopathy or cellular storage. In some embodiments, the subject has or is suspected of having a neurodegenerative disease or disorder and optionally an age-related neurodegenerative disease or disorder. In specific embodiments, the subject has or is suspected of having a disease or disorder is selected from the group consisting of Parkinson's disease (PD), Lewy body Dementia (LBD), Alzheimer's disease (AD), amyotrophic lateral sclerosis (ALS), multiple system atrophy, Huntington's disease, Prion disease, frontotemporal dementia, Picks disease, progressive supranuclear palsy, and progeria.

The disclosed diagnostic methods and/or prognostic methods, optionally may include a step wherein the subject is administered a treatment for a disease or disorder that is associated with proteinopathy or cellular storage. In some embodiments, the treatment comprises administered to the subject an effective amount of a therapeutic agent that activates or augments the activity of ykt6, optionally wherein the therapeutic agent promotes the open, active conformation of ykt6 versus the closed, inactive conformation of ykt6. In some embodiment, in the disclosed diagnostic methods and/or prognostic methods the treatment may be administered before ykt6 is detected in the biological sample. In other embodiments, in the disclosed diagnostic methods and/or prognostic methods the treatment may be administered after ykt6 is detected in the biological sample.

ILLUSTRATIVE EMBODIMENTS

The following embodiments are illustrative and should not be interpreted to limit the claimed subject matter.

Embodiment 1. A method for treating and/or preventing a disease or disorder associated with proteinopathy or cellular storage in a subject in need thereof, the method comprising administering to the subject an effective amount of a therapeutic agent that activates or augments the activity of ykt6.

Embodiment 2. The method of embodiment 1, wherein the disease or disorder is a neurodegenerative disease or disorder and optionally an age-related neurodegenerative disease or disorder.

Embodiment 3. The method of embodiment 1, wherein the disease or disorder is selected from the group consisting of Parkinson's disease (PD), Lewy body Dementia (LBD), Alzheimer's disease (AD), amyotrophic lateral sclerosis (ALS), multiple system atrophy, Huntington's disease, Prion disease, frontotemporal dementia, Picks disease, progressive supranuclear palsy, and progeria.

Embodiment 4. The method of any of the foregoing embodiments, wherein the therapeutic agent inhibits farnesylation or other type of prenylation of ykt6, including geranylgeranylation.

Embodiment 5. The method of any of the foregoing embodiments, wherein the therapeutic agent is an inhibitor of farnesyltransferase or gemanyltransferase.

Embodiment 6. The method of any of embodiments 1-3, wherein the therapeutic inhibits and/or disrupts an interaction between farnesyltransferase and ykt6.

Embodiment 7. The method of any of the foregoing embodiments, wherein the therapeutic agent promotes the open, active conformation of ykt6 versus the closed, inactive conformation of ykt6; and/or the therapeutic agent promotes organelle membrane association of ykt6 through enhancing protein palmitoylation or direct ykt6-membrane binding; influences other regulatory proteins that result in the activation of ykt6.

Embodiment 8. The method of any of the foregoing embodiments, wherein the therapeutic agent comprises a compound selected from the following compounds or a salt thereof:

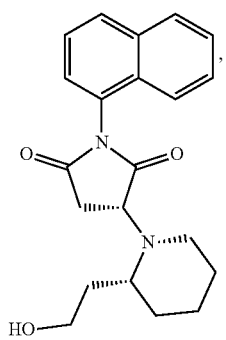

-continued

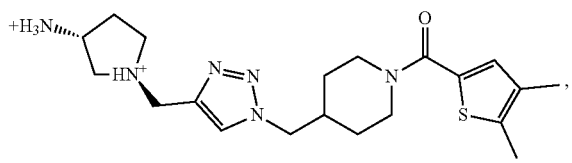

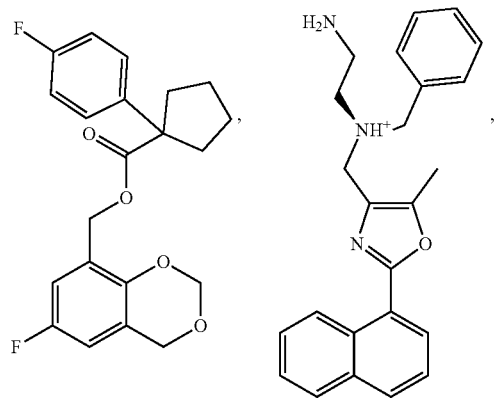

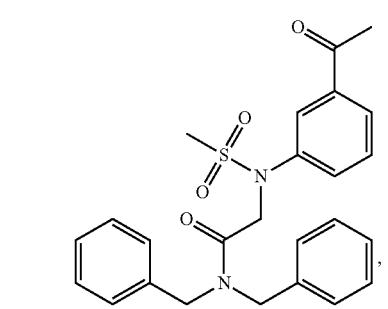

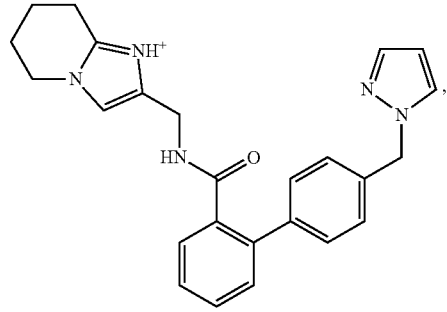

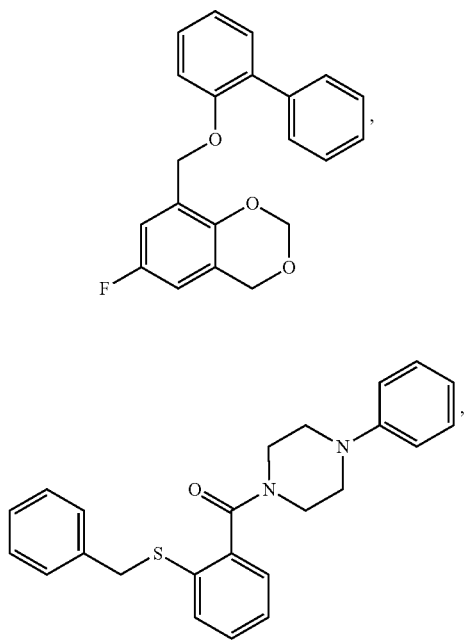

33
-continued
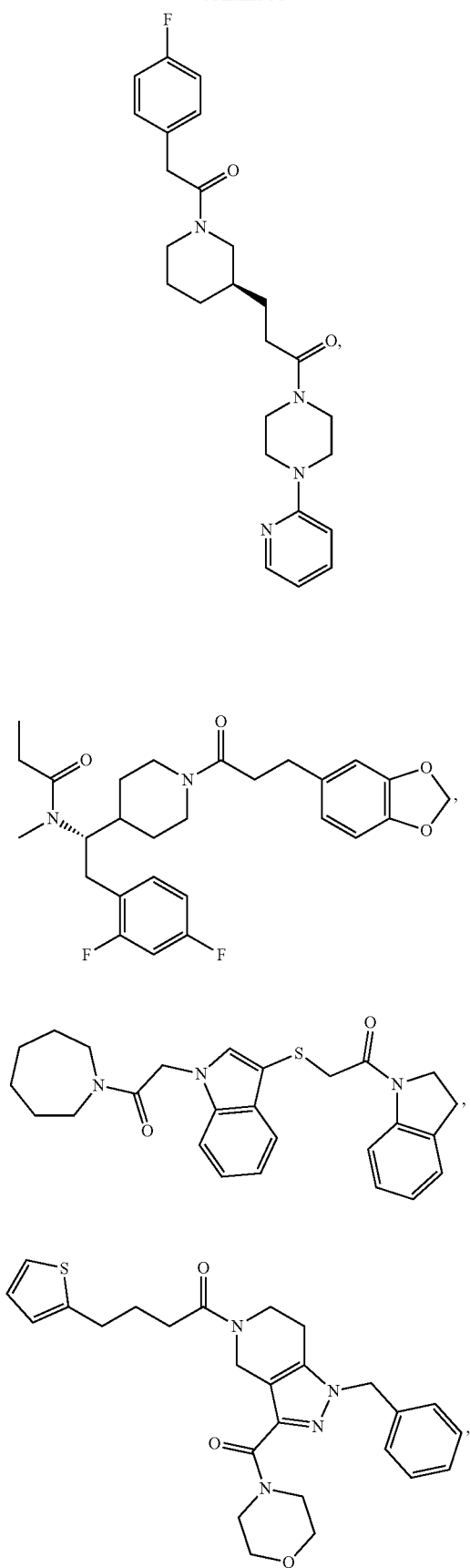
34
-continued
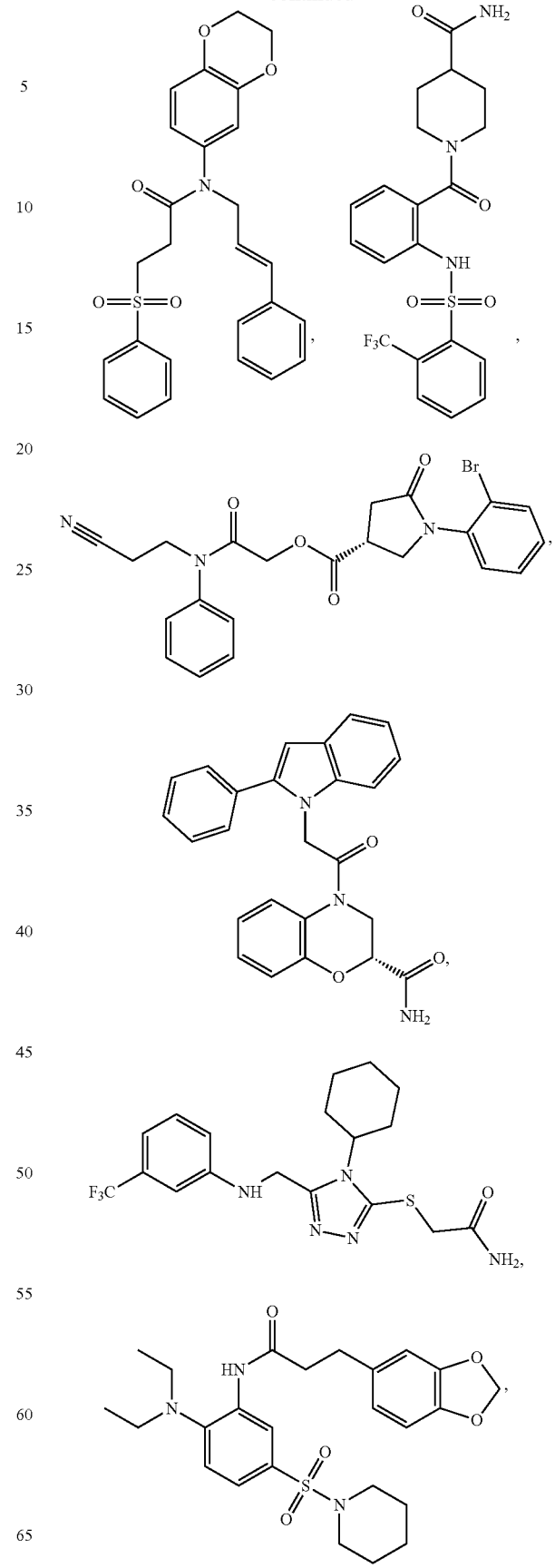

35
-continued
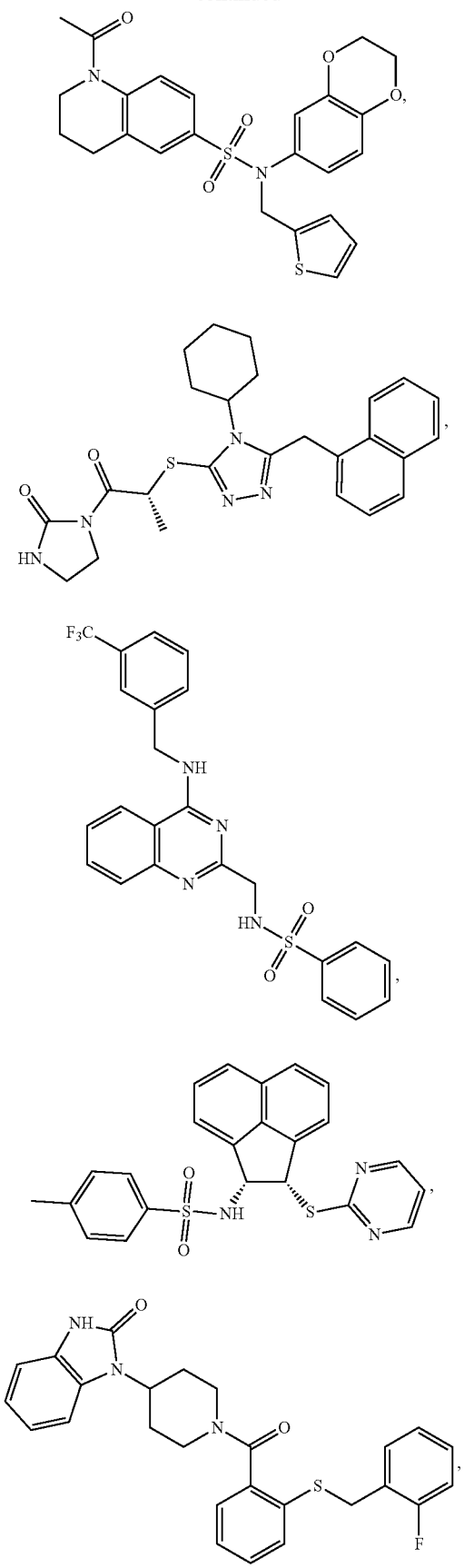
36
-continued
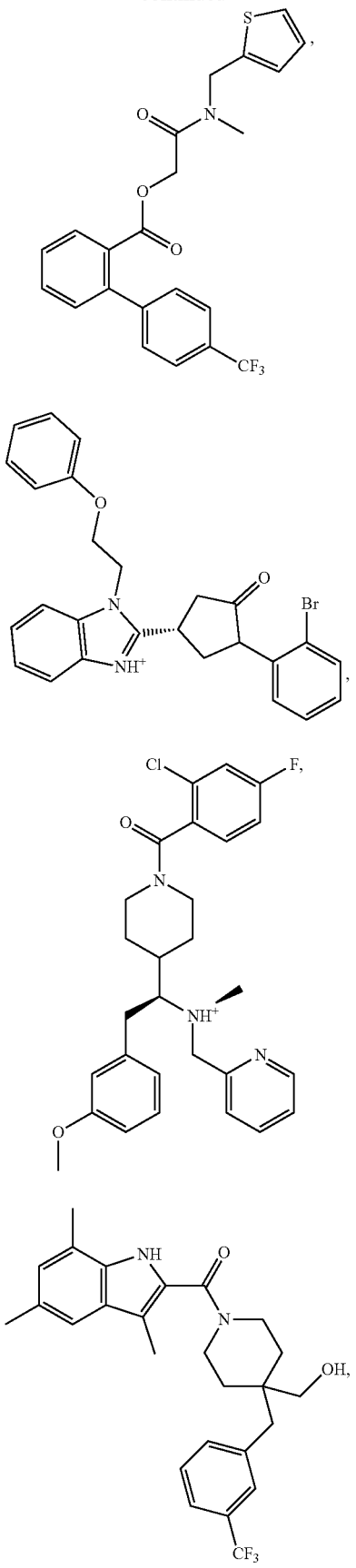

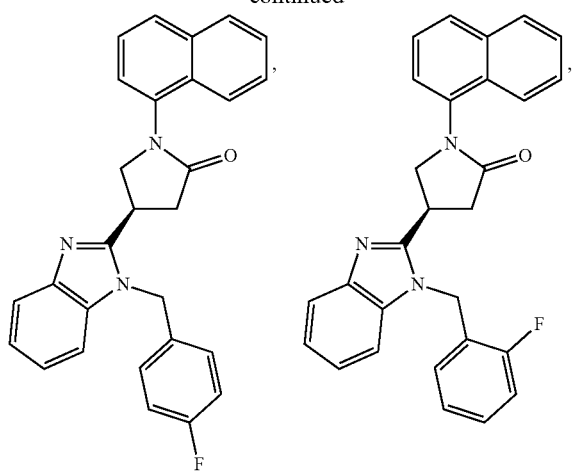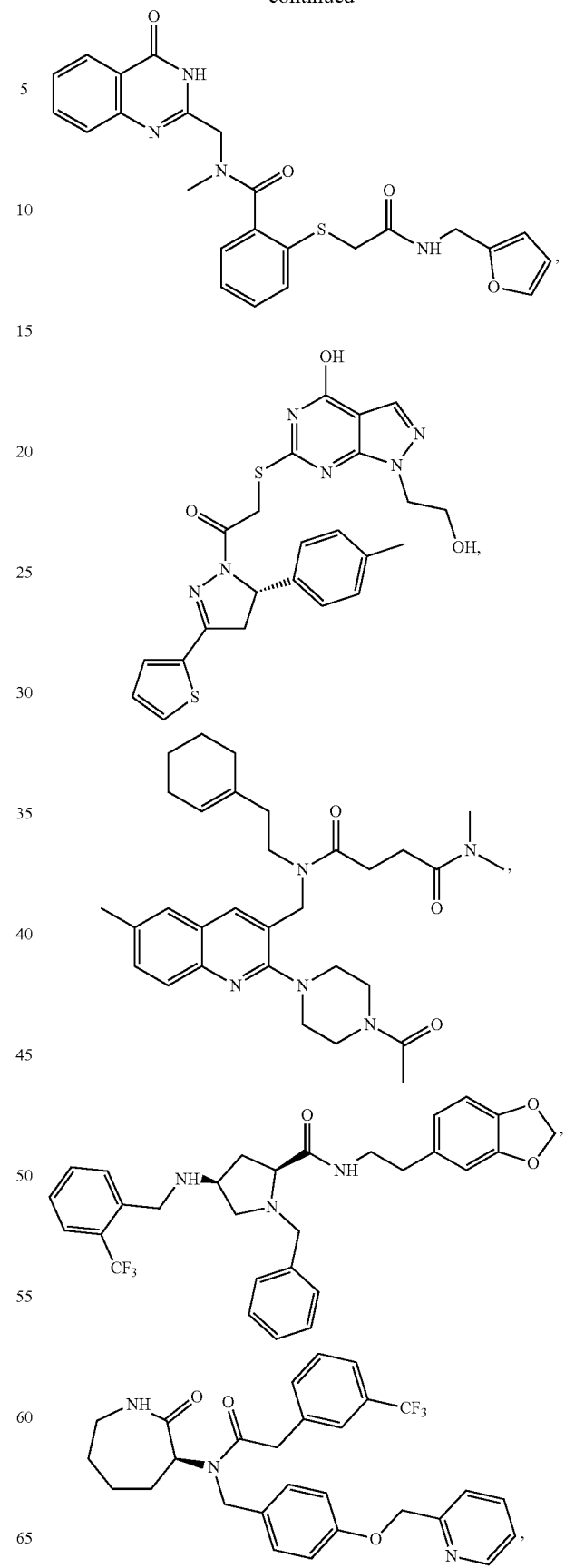

39
-continued
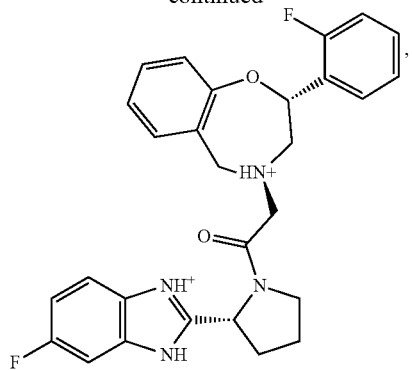
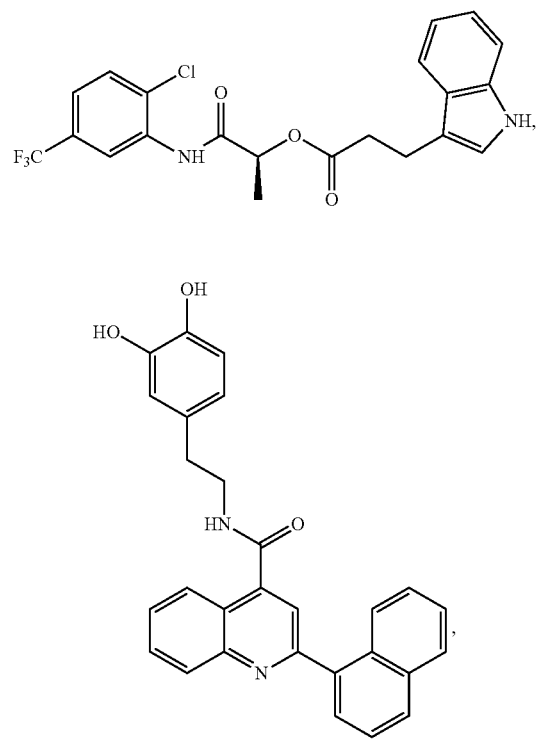
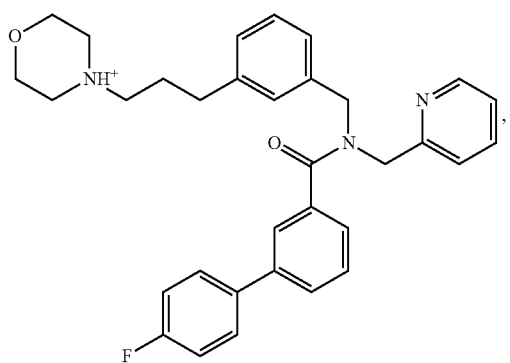
40
-continued
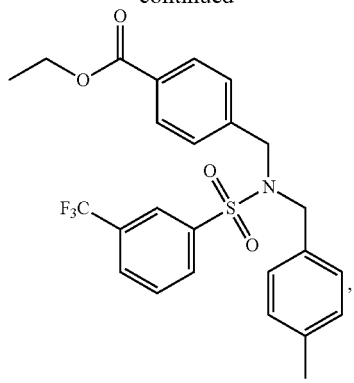
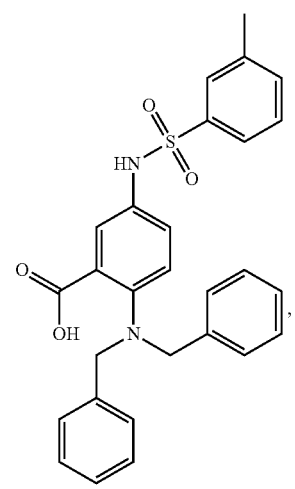
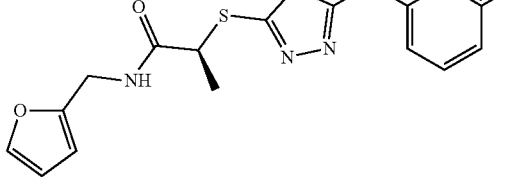

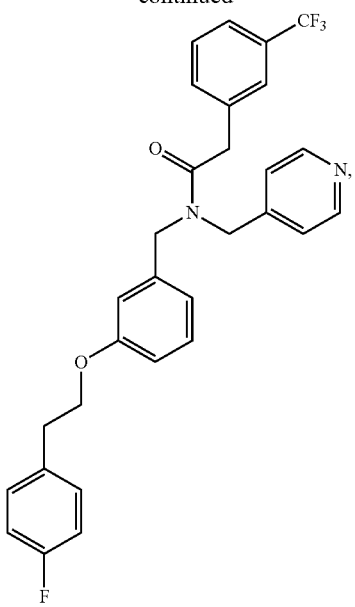
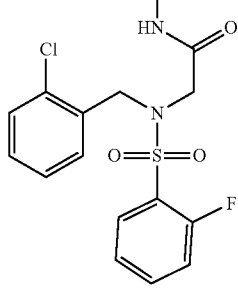
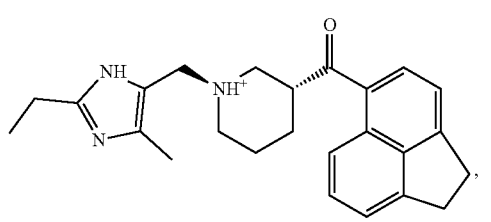
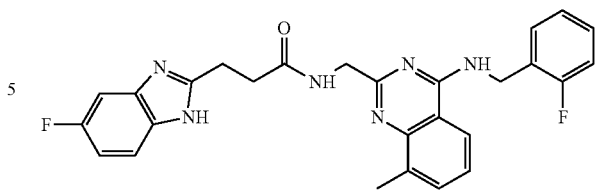
Embodiment 9. The method of any of the foregoing embodiments, wherein the therapeutic agent comprises a compound selected from the following compounds or a salt thereof:
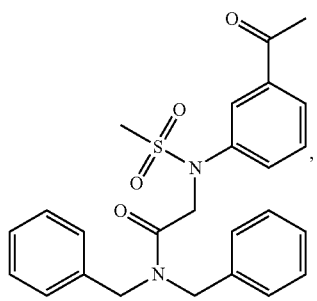
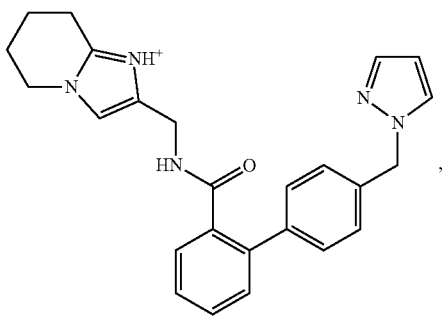
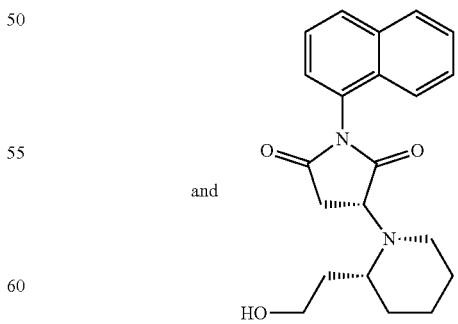
and
Embodiment 10. The method of any of the foregoing embodiments, wherein the therapeutic agent comprises a compound selected from the following compounds or a salt thereof:

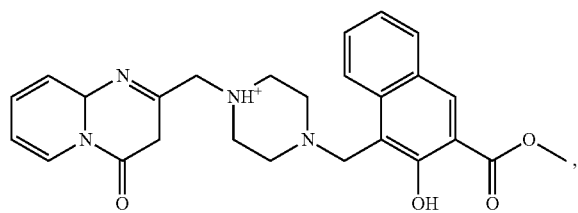
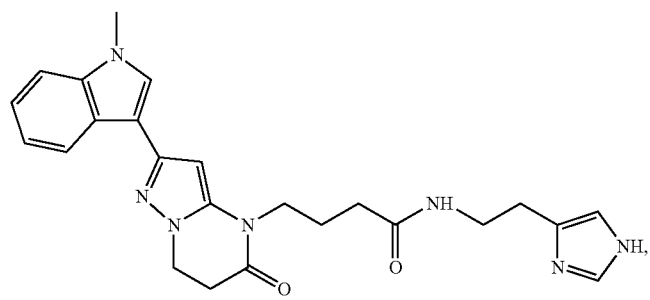
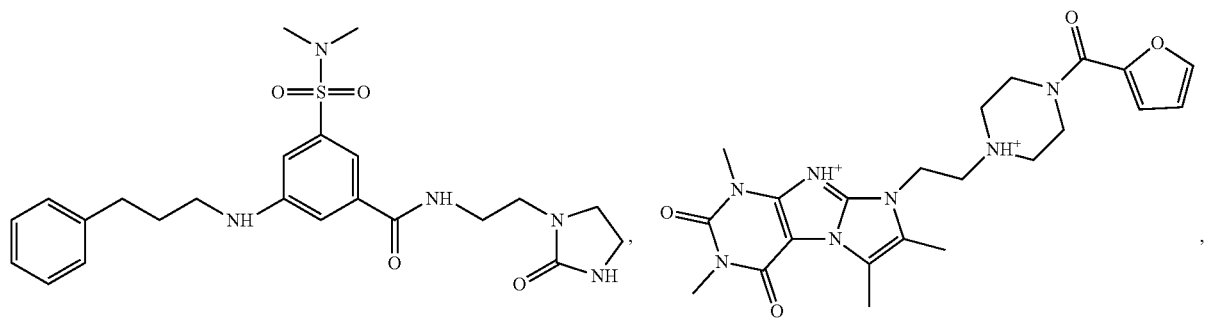
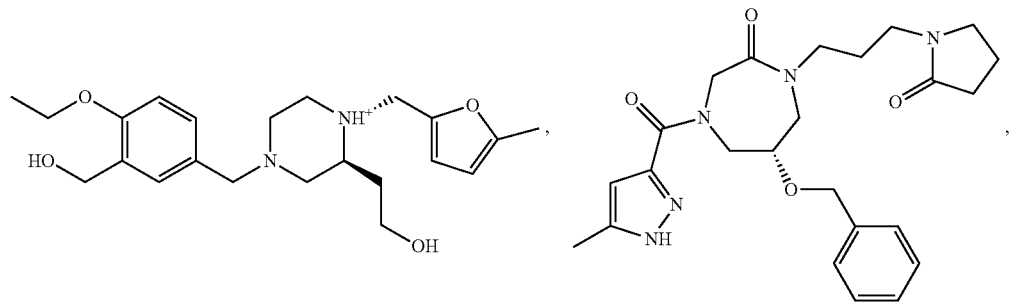
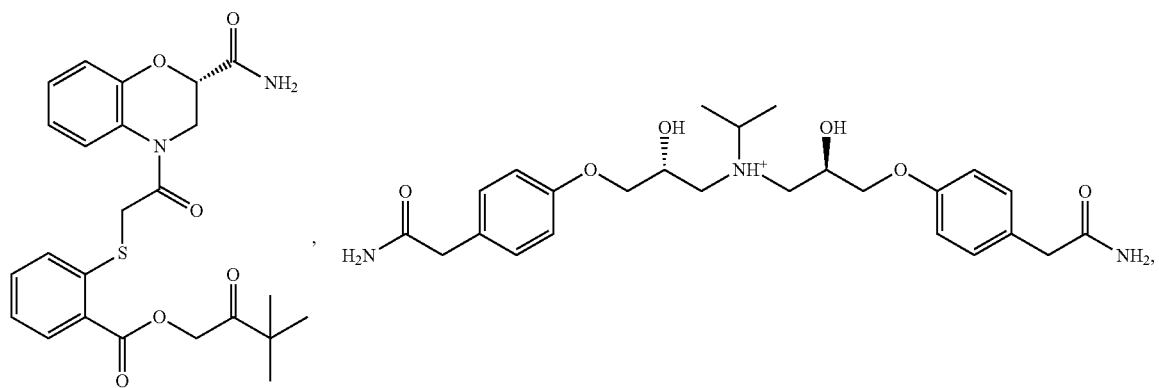

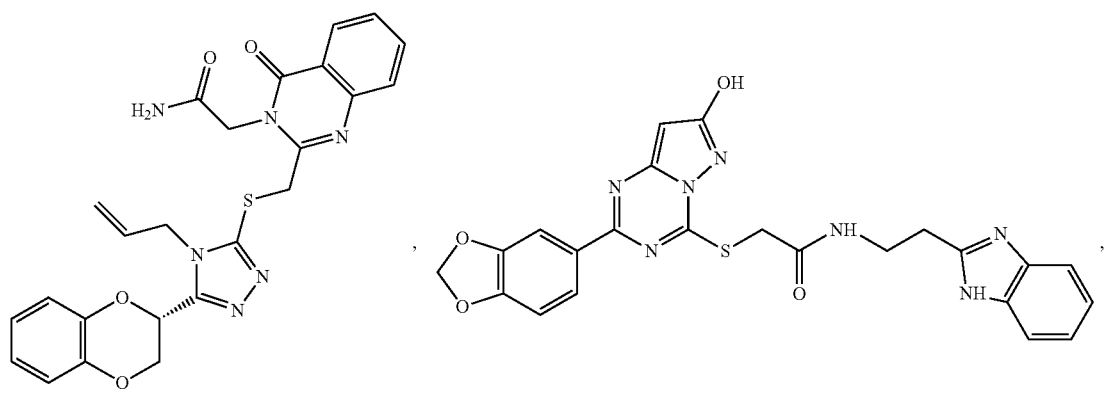
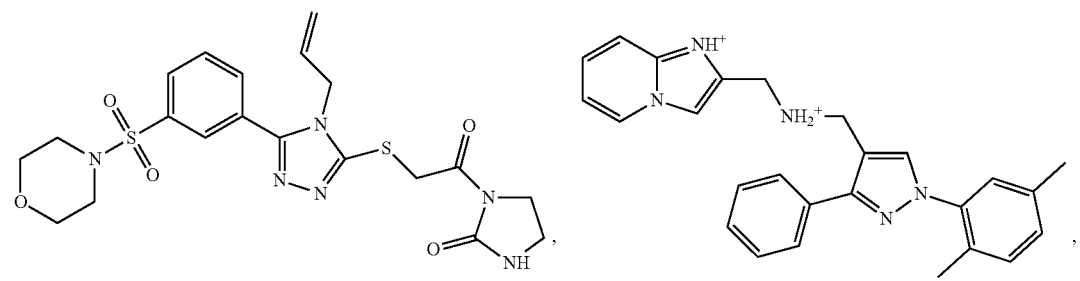
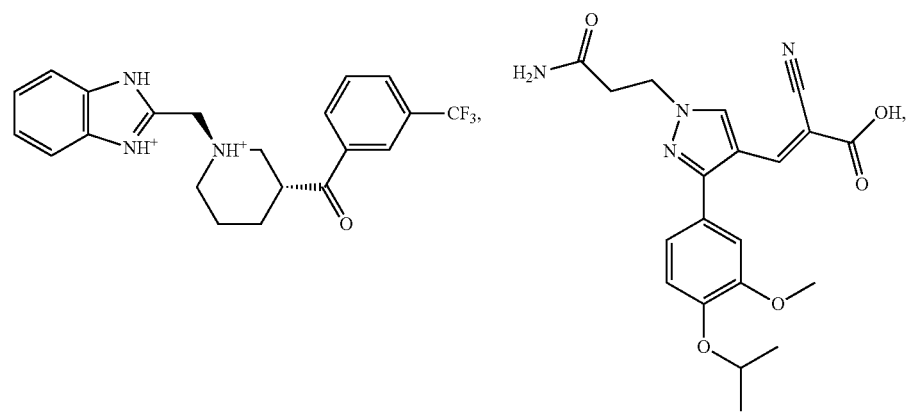
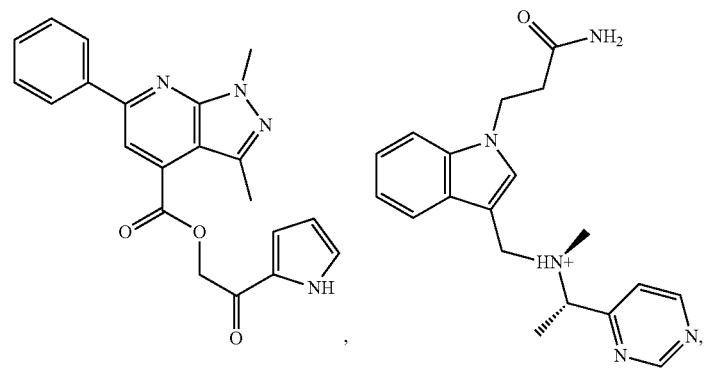

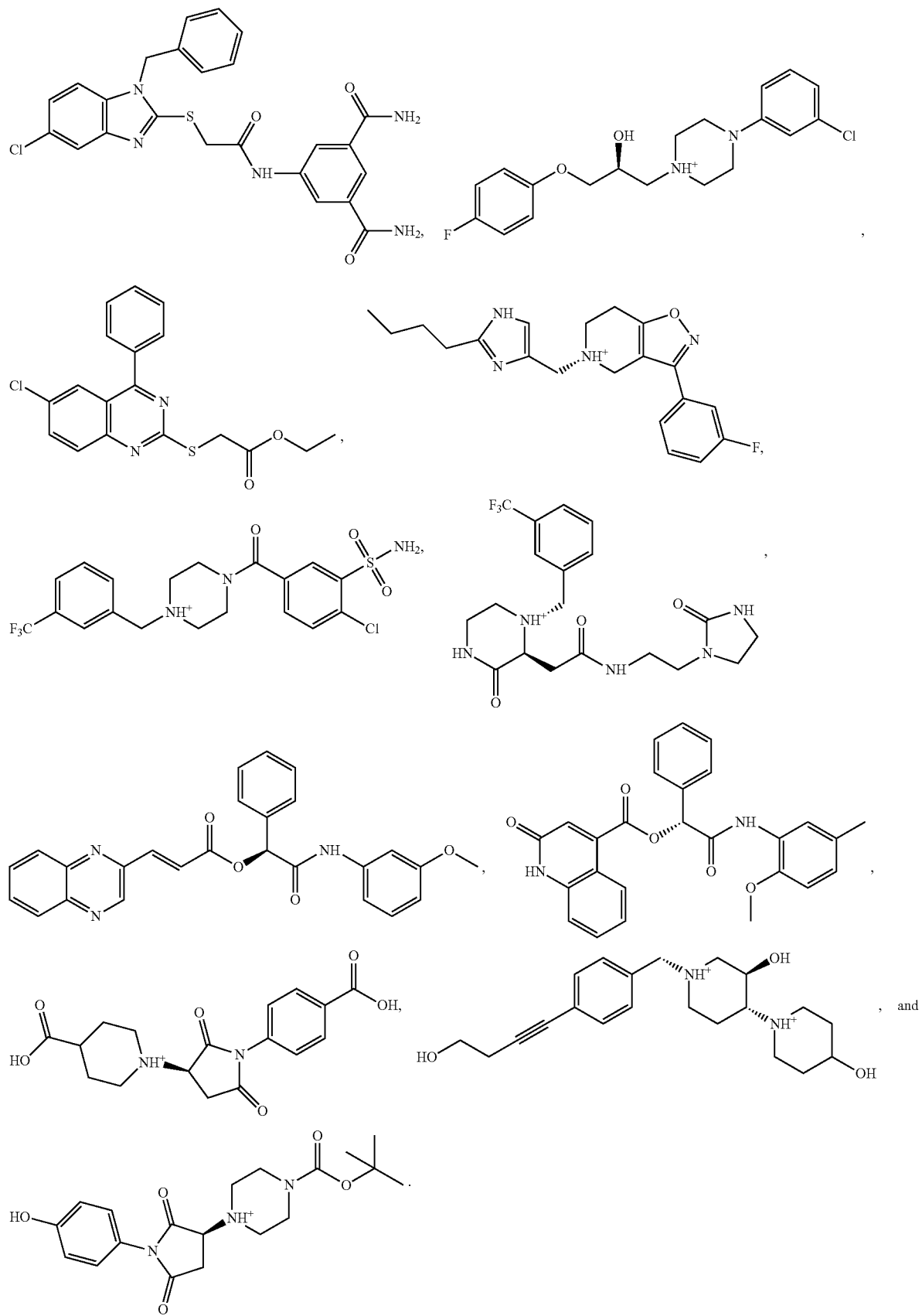

Embodiment 11. A pharmaceutical composition comprising any compound disclosed herein and a suitable pharmaceutical carrier, diluent, or excipient.

Embodiment 12. A method comprising detecting in a biological sample from a subject ykt6, optionally wherein the detected ykt6 in the biological sample is in an open conformation, a closed conformation, or both of an open conformation and a closed conformation.

Embodiment 13. The method of embodiment 12, wherein the biological sample is a blood or a blood product (e.g., plasma or serum).

Embodiment 14. The method of embodiment 12 or embodiment 13, wherein the subject has or is suspected of having a disease or disorder associated with proteinopathy or cellular storage.

Embodiment 15. The method of embodiment 14, wherein the disease or disorder is a neurodegenerative disease or disorder and optionally an age-related neurodegenerative disease or disorder.

Embodiment 16. The method of embodiment 15, wherein the disease or disorder is selected from the group consisting of Parkinson's disease (PD), Lewy body Dementia (LBD), Alzheimer's disease (AD), amyotrophic lateral sclerosis (ALS), multiple system atrophy, Huntington's disease, Prion disease, frontotemporal dementia, Picks disease, progressive supranuclear palsy, and progeria.

Embodiment 17. The method of any of embodiments 12-16 further comprising administering to the subject treatment for a disease or disorder that is associated with proteinopathy or cellular storage.

Embodiment 18. The method of embodiment 17, wherein the treatment comprises administered to the subject an effective amount of a therapeutic agent that activates or augments the activity of ykt6.

Embodiment 19. The method of embodiment 18, wherein the therapeutic agent promotes the open, active conformation of ykt6 versus the closed, inactive conformation of ykt6.

Embodiment 20. The method of any of embodiments 17-19, wherein the therapeutic agent is administered before ykt6 is detected in the biological sample.

Embodiment 21. The method of any of embodiments 17-19, wherein the therapeutic agent is administered after ykt6 is detected in the biological sample.

EXAMPLES

The following Example is illustrative and should not be interpreted to limit the claimed subject matter.

Example 1

Title: Methods to Enhance the Cellular Clearance of Pathological Macromolecules

Abstract

Proteinopathies and other storage disorders result from the inability to degrade and clear waste material from the cell, leading to pathological accumulation and toxicity. Cellular storage material also builds up in a chronic manner during the normal aging process, reflecting compromised clearance and cellular self-renewal. The toxicity of protein accumulation is best exemplified by age-related neurodegenerative disorders, including Parkinson's disease (PD), Lewy body Dementia (LBD), and Alzheimer's disease (AD), which are all characterized by the accumulation of insoluble protein and lipid aggregates within the nervous system. By examining the mechanisms of cellular dysfunction in PD and LBD, we discovered a novel therapeutic target that can be drugged by small molecules and is capable of enhancing cellular clearance by amplifying the cell's degradation system called the lysosome. We provide evidence that the target can be activated by clinically safe small molecules that penetrate the brain, and reduce protein inclusions in PD patient-derived neuronal culture models and transgenic mice. In the current invention, we disclose novel methods to amplify cellular clearance by small molecules, as well as novel blood biomarkers for the diagnosis and progression of neurological symptoms. The identification of this therapeutic pathway will open novel opportunities for the treatment of neurodegenerative disorders that are characterized by protein inclusions including PD, LBD, Alzheimer's disease, and ALS, as well as other peripheral storage disorders where toxic materials accumulate.

Applications

Applications of the disclosed technology may include, but are not limited to: (i) Treatment of proteinopathies that encompass age-related neurodegenerative disorders, including but not limited to PD, LBD, Alzheimer's disease, amyotrophic lateral sclerosis (ALS), multiple system atrophy, Huntington's disease, Prion disease, frontotemporal dementia, Picks disease, progressive supranuclear palsy, and progeria; (ii) Potential Biomarker for PD, LBD, and other synucleinopathy; (iii) Blood or other biological fluids (including but not limited to cerebral spinal fluid, saliva, and urine) peripheral nerve/muscle derived biomarkers of target engagement for the development of farnesyltransferase inhibitors as treatments for neurodegenerative disorders; (iv) Treatment of REM sleep disorder linked to GBA1 mutations or idiopathic REM sleep disorder with no genetic component; (v) Treatment of pediatric lysosomal storage disorders, including glycogen storage, neuronal ceroid lipofuscinosis, sphingolipid storage, cholesterol, and fatty acid storage disorders; and (v) Treatment of protein misfolding diseases and amyloidosis, including cataracts caused by a-crystallin aggregation, systemic amyloidoses, type 2 diabetes characterized by amylin aggregation, alpha-1-antitrypsin deficiency liver disease.

Advantages

Advantages of the disclosed technology may include, but are not limited to: (i) There are currently no disease modifying drugs capable of stimulating cellular clearance for any storage disorder. The current technology provides a method to stimulate cellular clearance in multiple cell types; (ii) There are no disease modifying drugs capable of treating neurodegenerative disorders. The current technology provides a target that can be activated in the central nervous system by clinically safe small molecules; and (iii) the disclosed technology provides a blood or other biological fluid/sample biomarker for synucleinopathies and methods to track target engagement of FTIs in the clinic.

Brief Summary of the Technology

Age-related neurodegenerative disorders are characterized by slow, persistent accumulation of aggregated proteins. Although cells can elicit physiological responses to enhance cellular clearance and counteract accumulation, it is unclear how pathogenic proteins evade this process in disease. We found that Parkinson's disease a-synuclein perturbs the physiological response to lysosomal stress by impeding the SNARE protein ykt6. Cytosolic ykt6 is normally autoinhibited by a unique farnesyl-mediated regulatory mechanism however during lysosomal stress, it activates and redistributes into membranes to preferentially promote hydrolase trafficking and enhance cellular clearance. a-Synuclein aberrantly binds and deactivates ykt6 in patient-derived neurons, thereby disabling the lysosomal stress response and facilitating protein accumulation. We describe novel methods of activating ykt6 by either small-molecule farnesyltransferase inhibitors, or small molecules that directly bind and promote the open, active conformation of ykt6. This in turn can enhance trafficking, restore lysosomal activity and reduce a-synuclein in patient-derived neurons and mice. Our findings indicate that a-synuclein creates a permissive environment for aggregate persistence by inhibiting regulated cellular clearance, and provide a therapeutic strategy to restore protein homeostasis by harnessing SNARE activity. (See also Example 2 below).

Technical Description

Published data indicates that ykt6 is a SNARE protein that mediates vesicle fusion between the ER and Golgi (McNew et al, *J. Biol. Chem* 1997). During periods of proteomic stress, we discovered that ykt6 selectively enhances the transport of hydrolases into lysosomal compartments in human iPSC neurons (Cuddy et al, *Neuron* 2019 (in press)). Once this occurs, lysosomal activity and proteolysis is enhanced, which acts to rebalance protein homeostasis. In PD and other synucleinopathies, we found that this homeostatic pathway is not functional, resulting in dysfunctional lysosomes and protein accumulation (Cuddy et al, *Neuron* 2019 (in press)). In the current invention, we plan to exploit the unusual regulatory properties of Ykt6, which make it an attractive and novel druggable target to enhance lysosomal activity and reduce protein aggregates. While most SNAREs are constitutively active and bound to membranes, the fusogenic activity of ykt6 is tightly regulated by farnesylation. Farnesyl moiety keeps ykt6 in a locked, inactive conformation where it is kept in a reserve pool within the cytosol (see FIG. 18). The non-farnesylated form opens up into an active conformation and pairs with cognate binding partners bet1 and STX5 (Wen et al, *Mol. Cell*, (37) 383, 2010; and Cuddy et al, *Neuron* 2019 in press). We discovered that activated ykt6 can selectively enhance hydrolase trafficking into lysosomes in human iPSC-neurons. This in turn, increases proteolytic activity and reduces protein aggregates. Interestingly, other work has indicated that ykt6 is involved in autophagosome biogenesis and delivery of protein cargo into lysosomes (FIG. 18, Arrow 2) (Nair et al, *Cell*, 2011), in addition to its known function between the ER and Golgi. Therefore, ykt6 acts as a 'master regulator' of protein trafficking that can both enhance lysosomal activity (FIG. 18, Arrow 1) as well as improve delivery of toxic substrates into lysosomes for degradation (FIG. 18, Arrow 2). The current invention discloses novel methods to enhance cellular clearance in any cell type that expresses ykt6, by promoting an open, active conformation. This can be achieved by either reducing farnesyl-ykt6 (FIG. 18, Pathway A) or small molecules that directly bind and disrupt the farnesyl-ykt6 interaction (FIG. 18, Pathway B).

In addition, we have discovered that ykt6 may serve as a potential biomarker for Parkinson's disease, Lewy body dementia, and other synucleinopathies. In our mouse models of Parkinson's disease, we find a higher percentage of the closed, inactive form of ykt6 within the blood of these mice. Furthermore, when mice are treated with farnesyltransferase inhibitors (FTIs), we can detect the change of ykt6 into open, active conformation within blood. Therefore, measuring the conformation (open vs. closed) of ykt6 may provide a novel biomarker for the synucleinopathies, as well as provide a measure of target engagement for FTIs during clinical trials from accessible patient fluid.

Conclusion

Disclosed are methods to enhance lysosomal activity and reduce pathological accumulations of proteins and other macromolecules that occur in age-related neurodegenerative diseases and multiple genetic storage disorders. There are no therapies that are capable or harnessing SNARE activity to simultaneously enhance protein trafficking and lysosomal activity, which are two main dysfunctional pathways in synucleinopathies and other neurodegenerative diseases such as ALS.

Example 2

Title: Stress-Induced Cellular Clearance is Mediated by the SNARE Protein Ykt6 and Disrupted by α-Synuclein Reference is made to Cuddy et al., "Stress-Induced Cellular Clearance Is Mediated by the SNARE Protein ykt6 and Disrupted by α-Synuclein," Neuron. 2019 Dec. 4; 104(5): 869-884, the content of which his incorporated herein by reference in its entirety.

SUMMARY

Age-related neurodegenerative disorders are characterized by slow, persistent accumulation of aggregated proteins. Although cells can elicit physiological responses to enhance cellular clearance and counteract accumulation, it is unclear how pathogenic proteins evade this process in disease. We find that Parkinson's disease a-synuclein perturbs the physiological response to lysosomal stress by impeding SNARE protein ykt6. Cytosolic ykt6 is normally autoinhibited by a unique farnesyl-mediated regulatory mechanism however during lysosomal stress, it activates and redistributes into membranes to preferentially promote hydrolase trafficking and enhance cellular clearance. a-Synuclein aberrantly binds and deactivates ykt6 in patient-derived neurons, thereby disabling the lysosomal stress response and facilitating protein accumulation. Activating ykt6 by small-molecule farnesyltransferase inhibitors restores lysosomal activity and reduces a-synuclein in patient-derived neurons and mice. Our findings indicate that a-synuclein creates a permissive environment for aggregate persistence by inhibiting regulated cellular clearance, and provide a therapeutic strategy to restore protein homeostasis by harnessing SNARE activity.

Introduction

Age-related neurodegenerative disorders are characterized by the progressive accumulation of misfolded and aggregated proteins. In Parkinson's disease (PD) and Dementia with Lewy bodies (DLB), the pre-synaptic protein alpha-synuclein (a-syn) forms insoluble inclusions and accumulates within Lewy bodies that histopathologically define the disease (Spillantini et al., 1997). Pathological a-syn aggregates persist for decades in PD patients and emerge in a predictable manner within circumscribed regions of the nervous system, including midbrain dopamine neurons of the substantia nigra that mediate movement (Braak et al., 2003). Genetic studies have provided clues into the etiology of PD and further implicate a-syn accumulation in disease pathogenesis. For example rare, early-onset familial PD-dementia is caused by increasing a-syn synthesis through SNCA triplication (Singleton et al., 2003), or point mutations such as A53T that enhance stability and aggregation (Conway et al., 1998; Li et al., 2004; Polymeropoulos et al., 1997; Stojkovska et al., 2017). GWAS has identified SNCA variants as risk factors in common sporadic forms of PD, some of which have been shown to elevate a-syn expression (Nalls et al., 2014; Soldner et al., 2016). While there is strong evidence that imbalanced protein homeostasis and a-syn aggregation are involved in familial and sporadic PD pathogenesis, the downstream toxic mechanisms induced by a-syn are not completely understood.

Protein homeostasis (proteostasis) relies on a careful balance of synthesis and degradation machinery. Cells that experience aggregation-induced proteomic stress can normally elicit a homeostatic response that activates adaptive cellular clearance pathways involving the lysosomal system, in an attempt to degrade accumulated material and restore proteostasis (Settembre et al., 2013). These pathways are controlled by transcription factor EB (TFEB), which responds to lysosomal stress through activating the transcription of autophagic and lysosomal proteins (Sardiello et al., 2009; Settembre et al., 2011). While the mechanisms that control the synthesis of lysosomal components under stressful conditions are known, the regulated trafficking pathways that respond to and synergize with this pathway are not completely understood. Such pathways must be capable of rapidly responding to changing cellular environments, in order to enhance the delivery of lysosomal machinery through the early secretory pathway between the endoplasmic reticulum (ER) and Golgi, and then finally into lysosomal compartments. Vesicular transport of newly synthesized lysosomal proteins require the pairing of cognate soluble N-ethylmaleimide-sensitive factor attachment protein receptors (SNARE) proteins, which promote membrane fusion and delivery of cargo from the ER into the Golgi (Hay et al., 1997; Sollner et al., 1993). The mechanisms involved in constitutive transport at the early secretory pathway are well described, however regulated SNARE-mediated transport that occurs in response to proteomic stress is not completely understood. Furthermore, it is unclear how disease-linked proteins such as a-syn can persist and evade regulated clearance pathways in synucleinopathies.

Here, we sought to determine the mechanisms of aggregate persistence using patient-derived midbrain cultures that harbor endogenous SNCA mutations, and can accumulate a-syn for hundreds of days (Mazzulli et al., 2016a). We identify synaptobrevin-2 homolog ykt6 as a critical SNARE involved in the lysosomal stress response. Ykt6 is an unusual SNARE, since it lacks a transmembrane domain that is required for membrane association. Instead, post-translational modifications, including farnesylation and palmitoylation, control its membrane association and fusogenic activity (Daste et al., 2015). Ykt6 occurs within a cytosolic reserve pool in an autoinhibited, closed conformation that is mediated by intramolecular farnesyl moiety (Fukasawa et al., 2004; Hasegawa et al., 2003; McNew et al., 1997; Wen et al., 2010). Upon activation by a heretofore unknown stimuli, ykt6 opens into an extended conformation to promote membrane association, SNARE binding, and vesicular transport (Daste et al., 2015; Tochio et al., 2001). The majority of studies show that ykt6 plays a key role in ER-Golgi trafficking (Fukasawa et al., 2004; Liu and Barlowe, 2002; McNew et al., 1997; Zhang and Hong, 2001), and can also rescue a-syn-induced toxicity in yeast and cell lines (Cooper et al., 2006; Thayanidhi et al., 2010). However, ykt6 can also facilitate other transport steps depending on the cell type examined, including intra-Golgi (Xu et al., 2002), endosome-Golgi (Tai et al., 2004), and autophagosome formation (Matsui et al., 2018; Nair et al., 2011; Takats et al., 2018). Here, we examined the role of ykt6 in PD patient cultures and evaluated its potential as a therapeutic target to enhance lysosomal activity and reduce protein accumulation.

Results

Figure 9A:
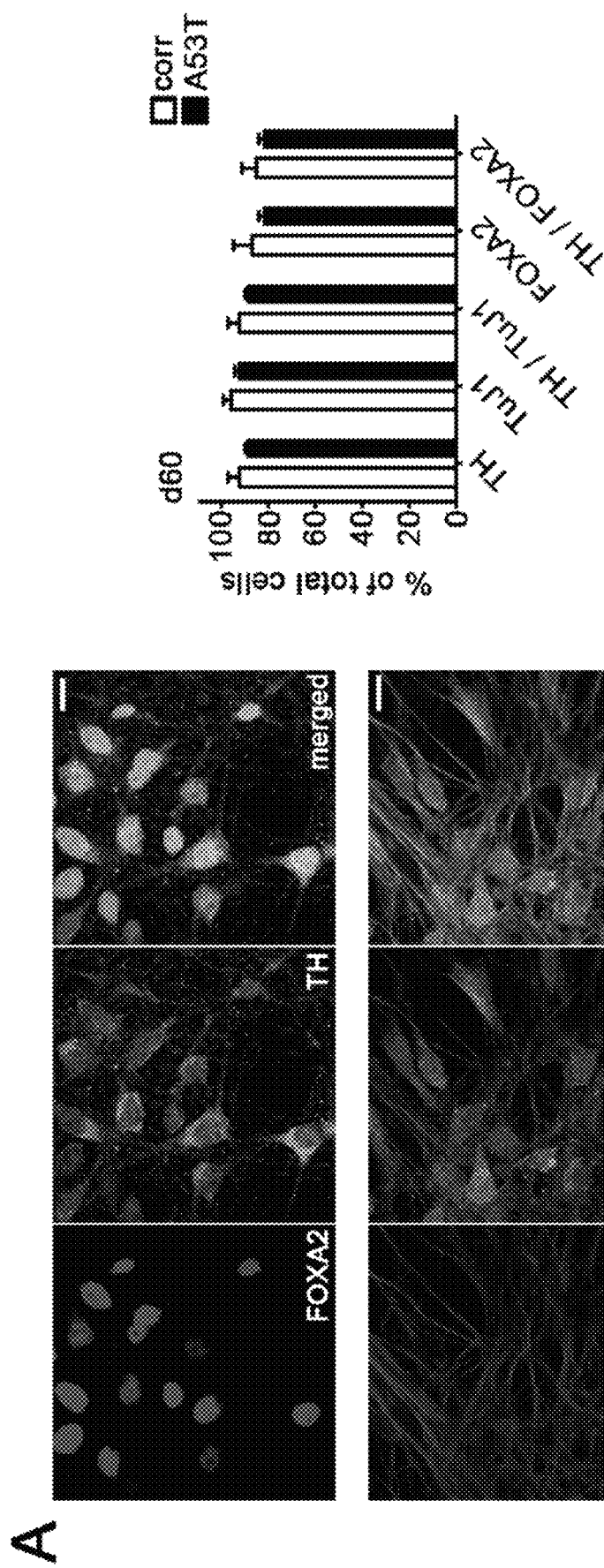
FIGS. 9A, 9B, 9C, 9D, and 9E. Analysis of a-syn solubility over time in cultured midbrain DA neurons from A53T PD patients. 9A) Characterization of iPSn cultures by immunocytochemistry indicates efficient differentiation of midbrain dopamine neurons, as indicated by the midbrain marker FOXA2 and tyrosine hydroxylase (TH). Tuj1 is an antibody against neuron-specific b-iii-tubulin. Nuclei are indicated. Scale bar, 10 µm. Shown is a representative image from A53T iPSn at day 60. Culture populations were quantified to the right at day 60. 9B) Sequential extraction/western blot of day 60 neurons extracted from A53T a-syn neurons, compared to isogenic corrected lines (corr). Neurons were extracted in 1% Triton X-100 (T-sol), followed by 2% SDS (T-insol). GAPDH was used as a loading control. The dotted line indicates cropped out lanes of samples from the same blot. The white space indicates two separate blots.
Figure 9B:
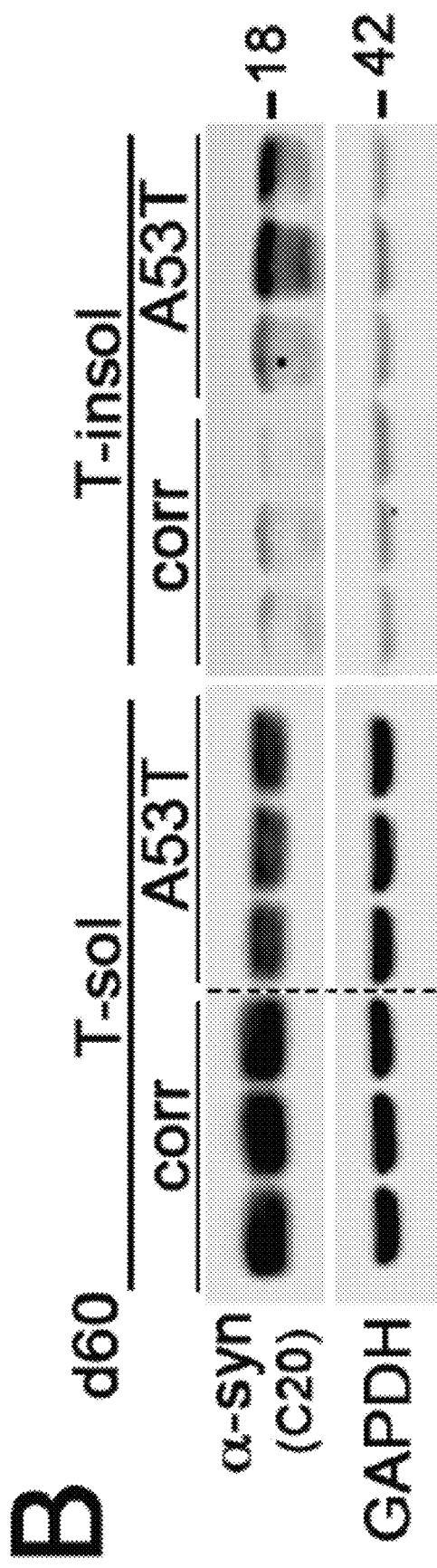
Figure 9C:
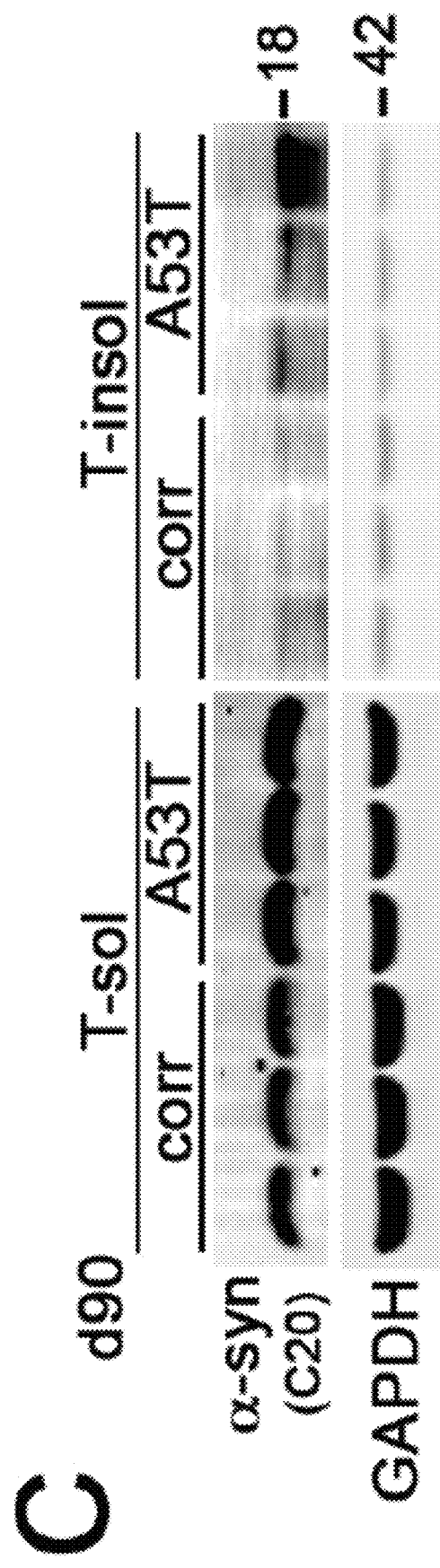
Figure 9D:
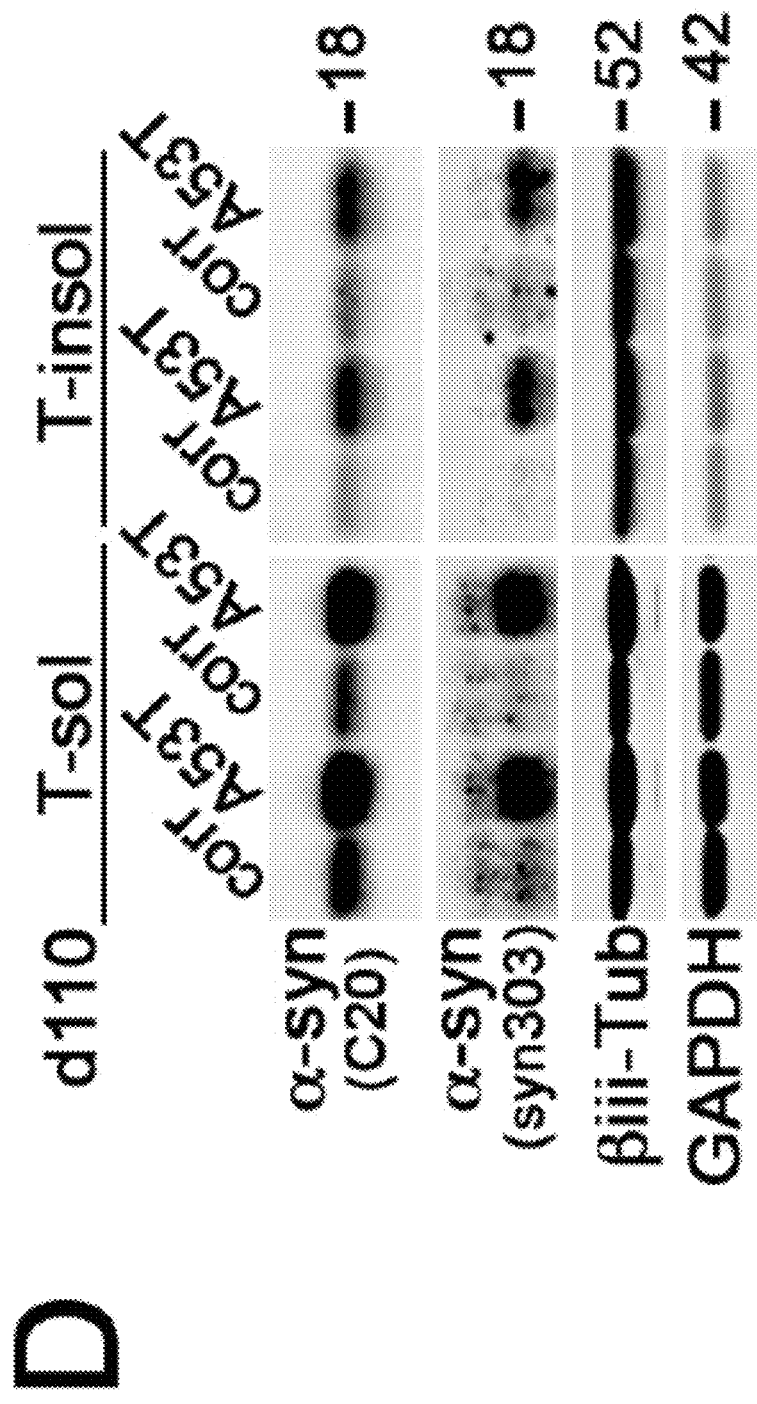
Figure 9E:
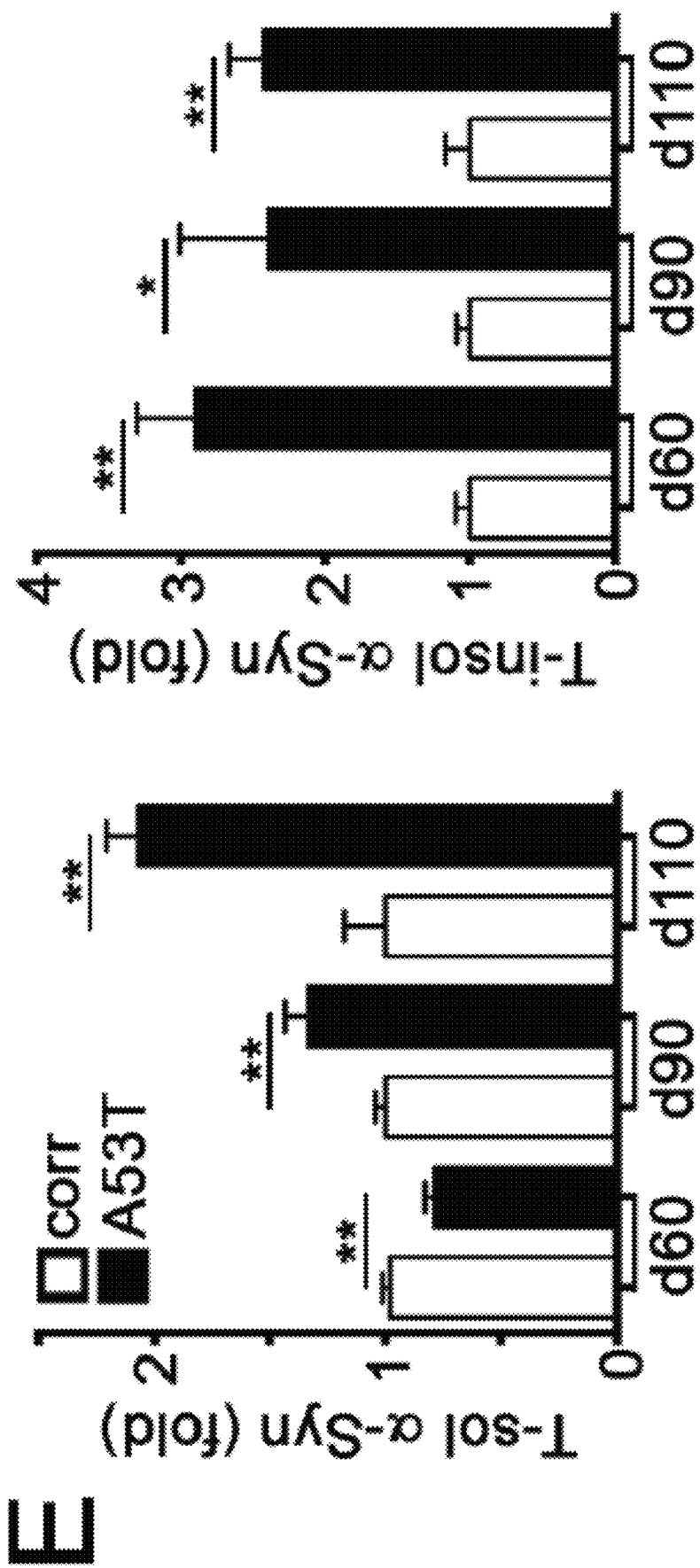
Figure 10A:
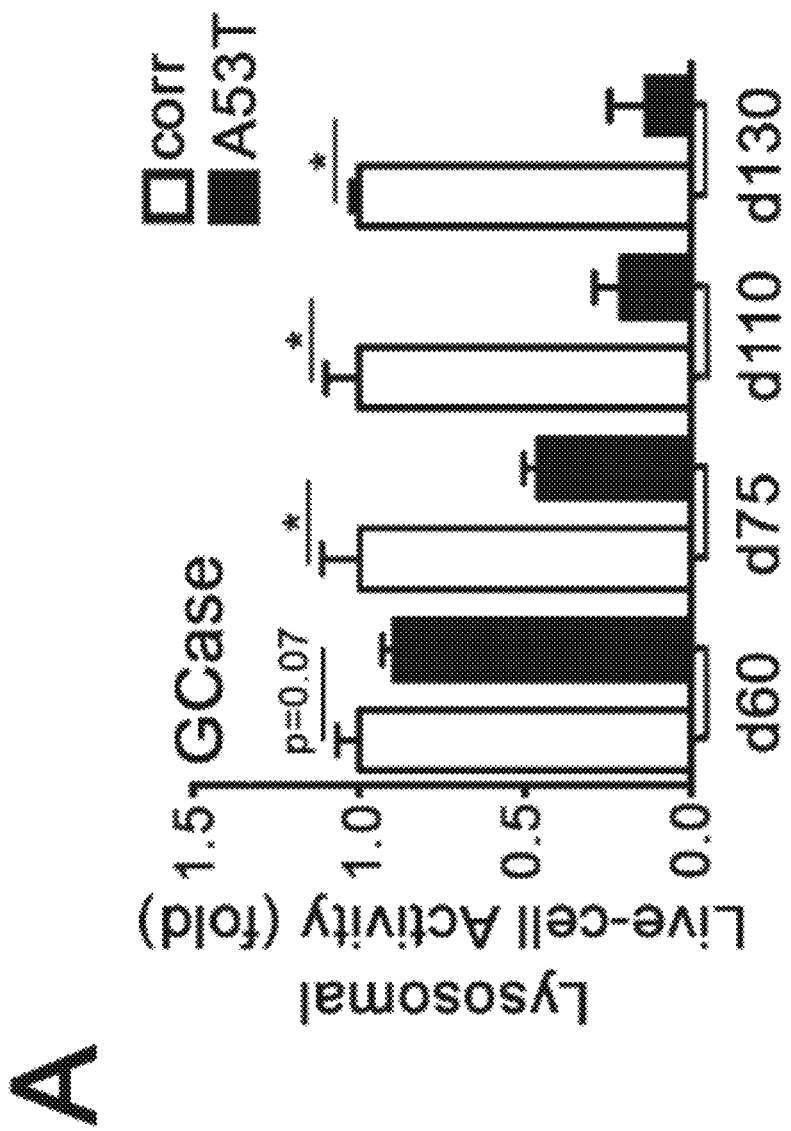
Figure 10B:
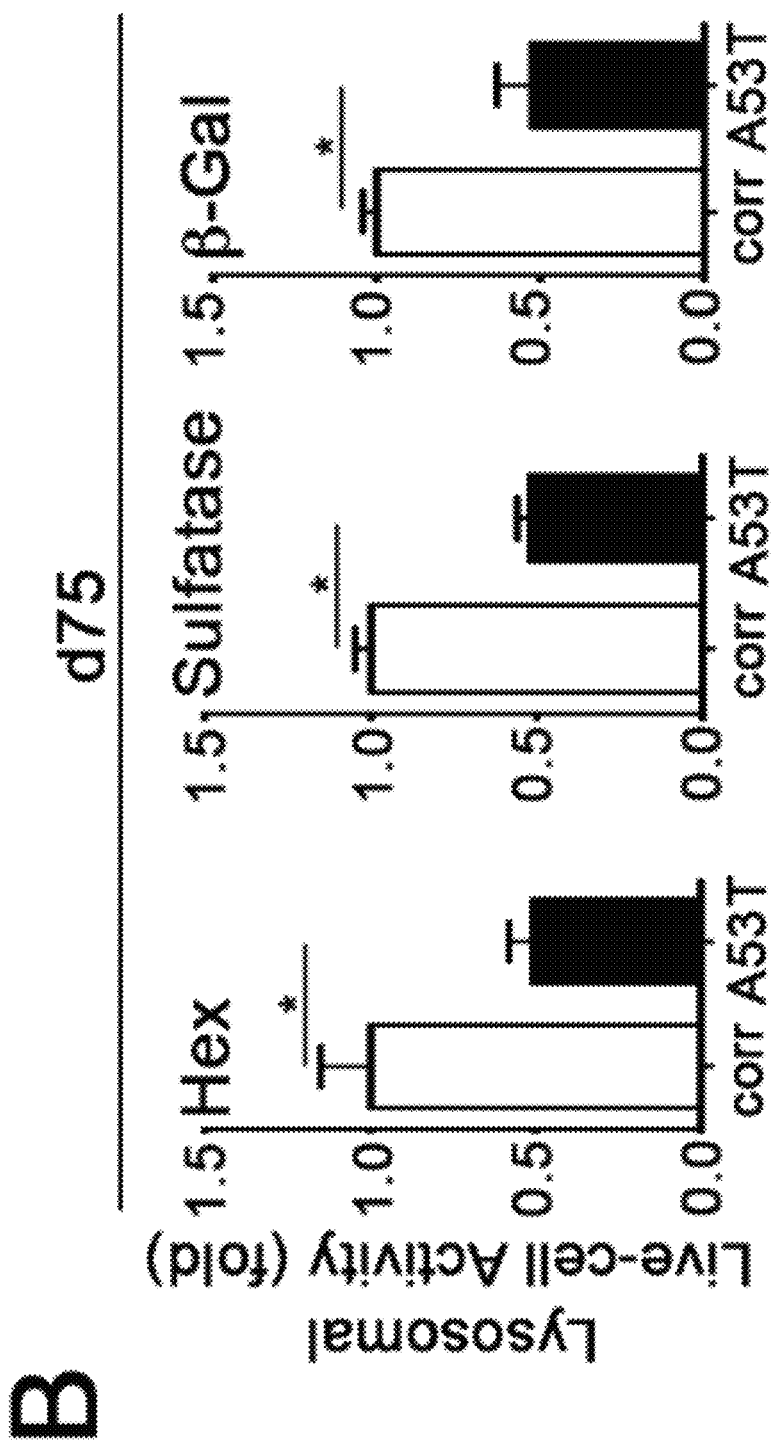
Figure 10C:
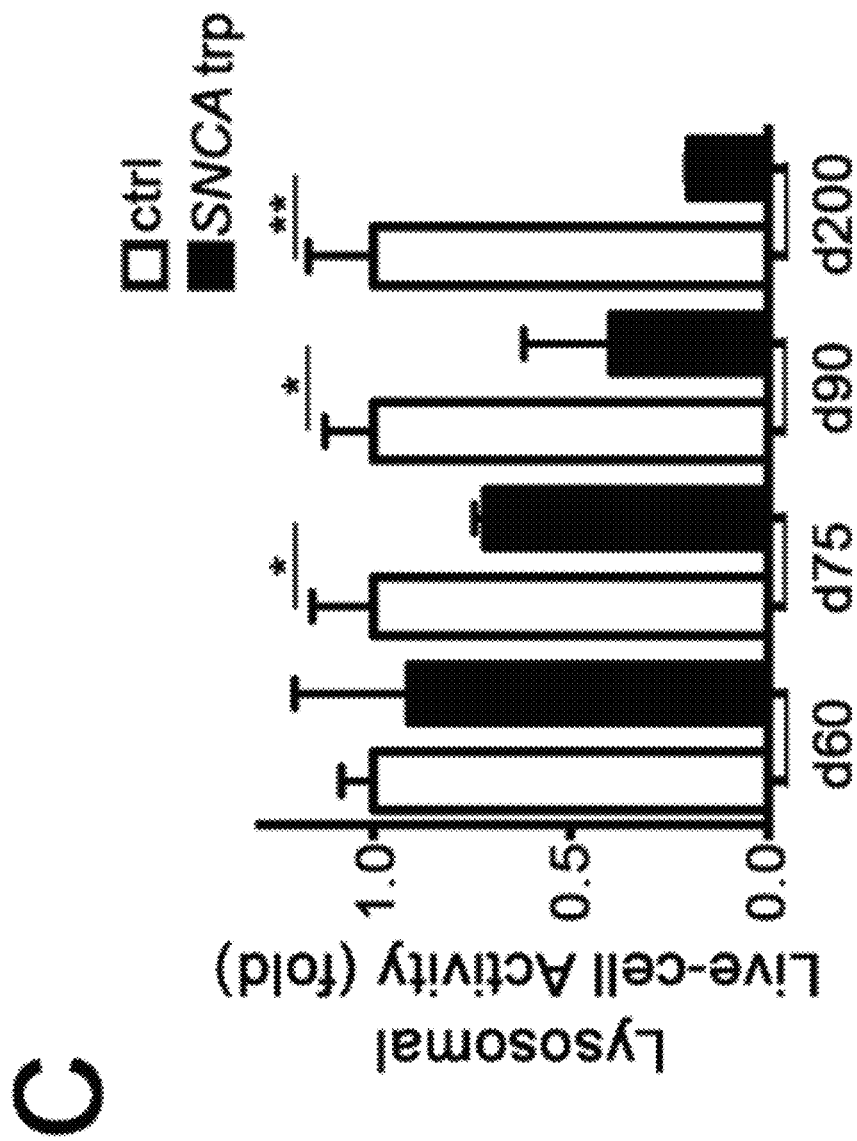
Figure 10D:
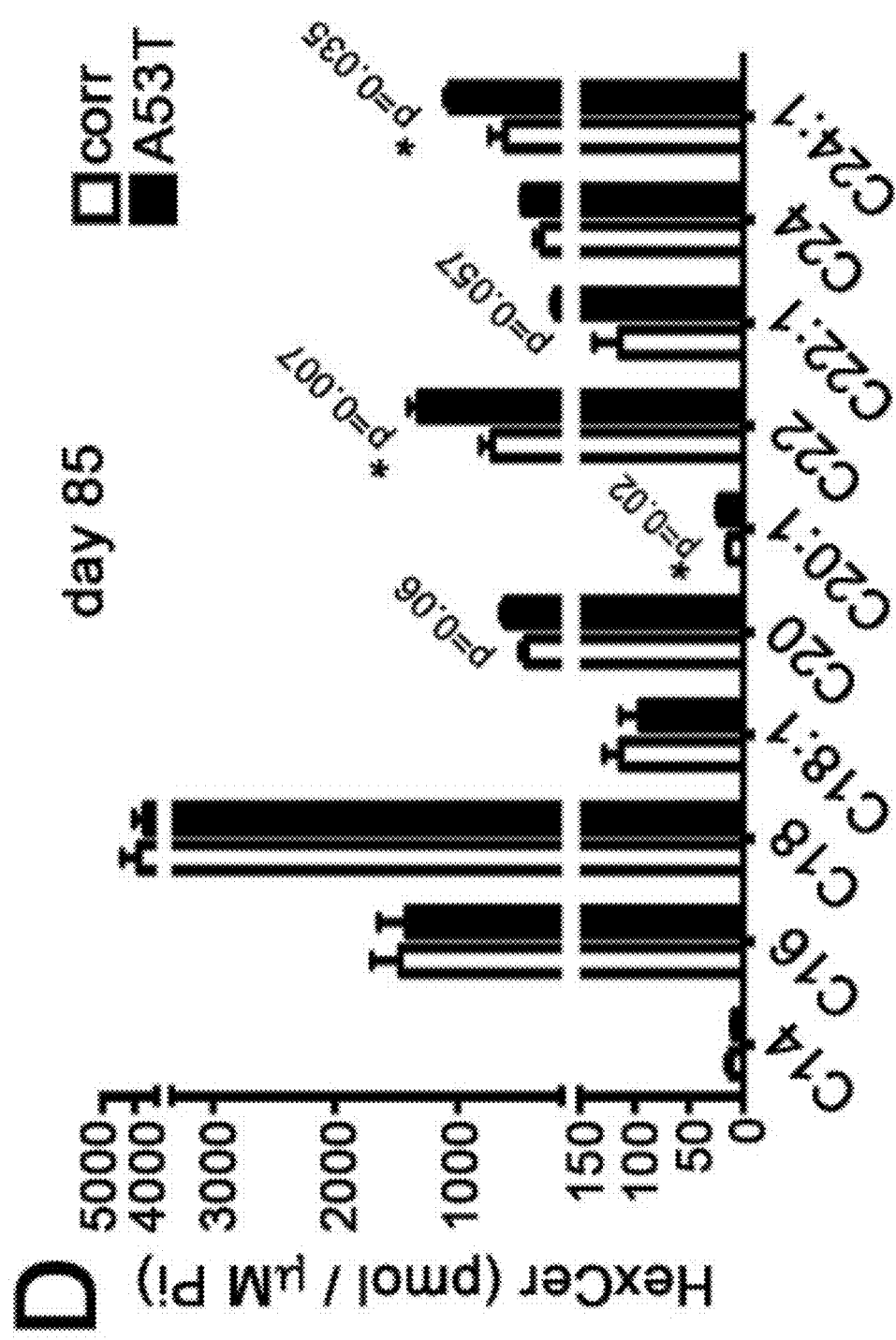
Figure 10E:
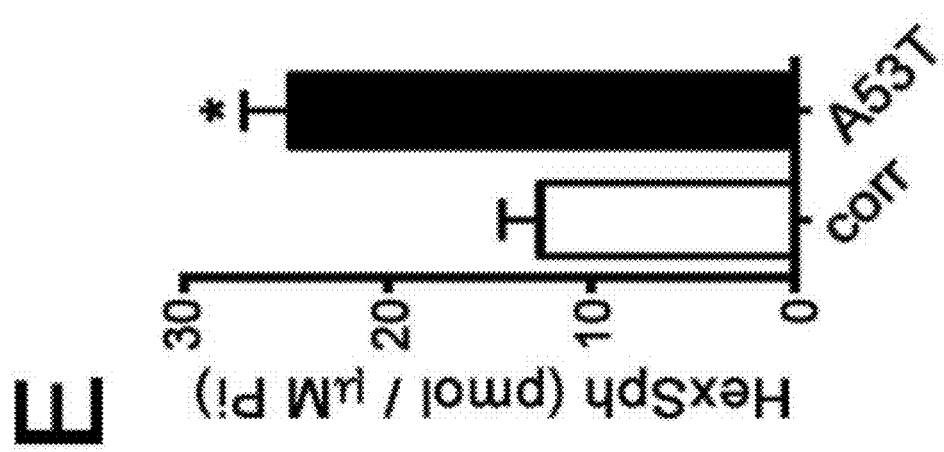
Figure 10F:
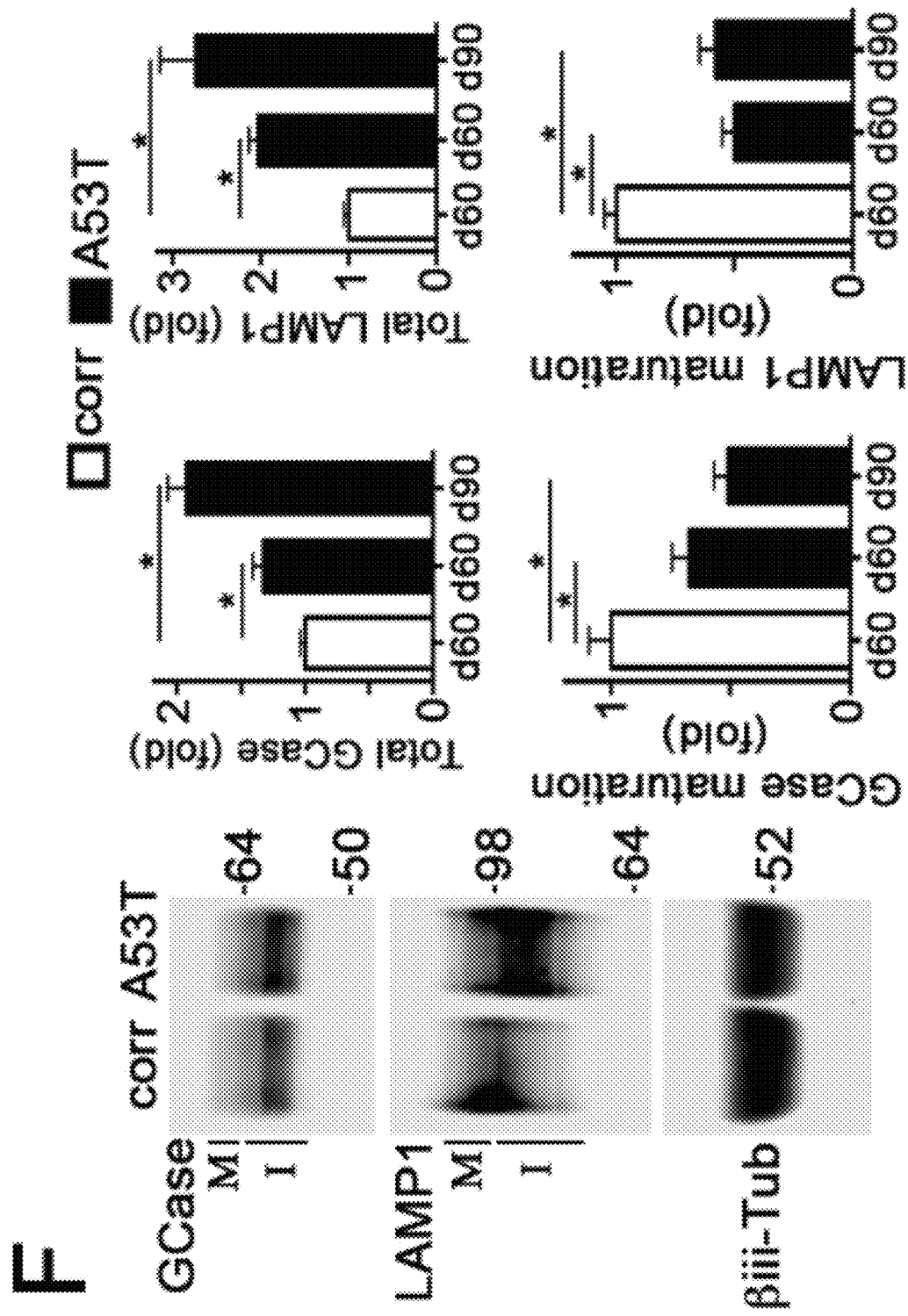
Figure 10G:
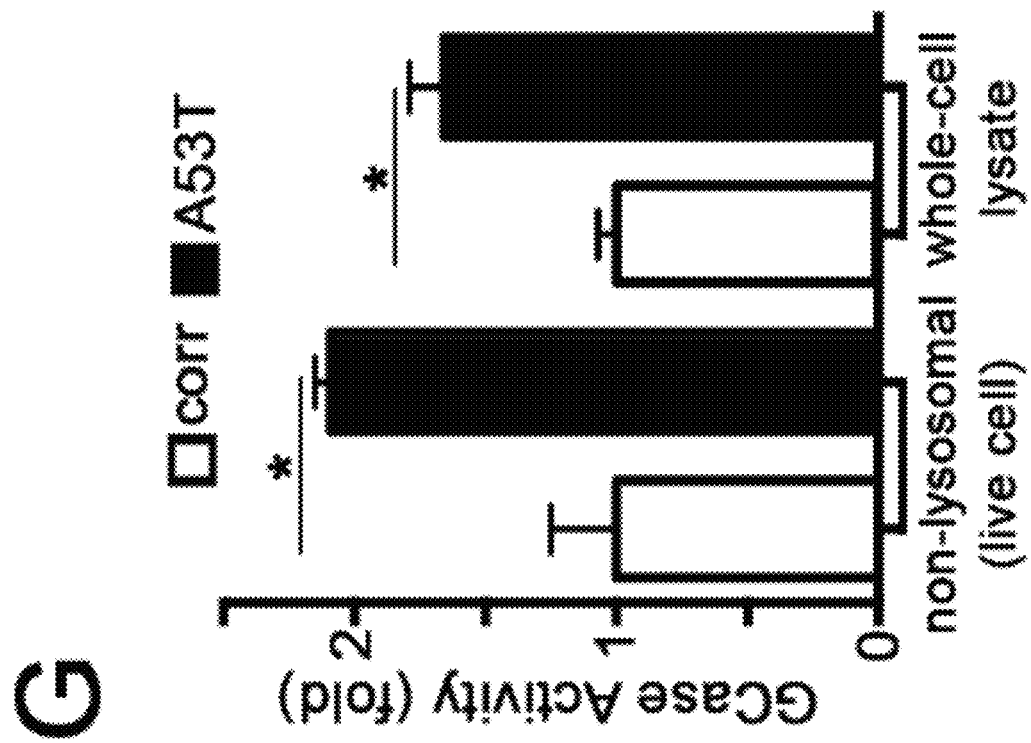

Lysosomal dysfunction occurs subsequent to a-syn aggregation in PD patient midbrain cultures. To gain mechanistic insights into the effects of pathological aggregates on protein homeostasis, we examined lysosomal function in PD patient-derived iPSC-midbrain neurons (iPSn). Differentiated iPSCs from patients expressing A53T a-syn and isogenic controls showed expression of midbrain markers FOXA2, tyrosine hydroxylase (TH), and beta-iii-tubulin (FIG. 9A), and accumulated pathological a-syn in an age-dependent between day 60 and 110 (FIG. 9B-E). Lysosomal function was measured in living cultures using an in situ beta-glucocerebrosidase (GCase) activity assay that is compartment-specific (Mazzulli et al., 2016a). This revealed an age-dependent decline in lysosomal activity between day 75 and 130 (FIG. 10A). The lysosomal activity of other hydrolases, including hexosaminidase, sulfatase, and beta-galactosidase, was also decreased (FIG. 10B). A similar age-dependent decline in GCase activity was observed in a distinct SNCA triplication (trp) line compared to a healthy control line (FIG. 10C). The reduction in GCase activity was sufficient to induce glycosphingolipid substrate accumulation (FIG. 10D, E), confirming lysosomal dysfunction. To probe the mechanism of this effect, we measured the levels of lysosomal proteins by western blot. This indicated that total levels of GCase and the lysosomal marker LAMP1 were not depleted as expected, but were elevated in A53T iPSn compared to isogenic controls (FIG. 10F). The molecular weight of GCase and LAMP1 increases as it matures through the ER and Golgi by protein glycosylation (Bergmann and Grabowski, 1989; D'Souza and August, 1986), and maturation can be estimated by molecular weight analysis. Western blot analysis showed the accumulation of low molecular weight, immature ER forms (corresponding to <62 kDa for GCase, and <98 kDa for LAMP1) suggesting perturbations in protein maturation (FIG. 10F). Consistent with disrupted GCase trafficking, measurement of in situ GCase activity from non-lysosomal compartments of living iPSn indicated a two-fold elevation in A53T lines (FIG. 10G, left). In vitro activity assays of whole cell lysates, containing a mix of lysosomal and non-lysosomal forms, revealed a similar elevation of activity (FIG. 10G, right). We attributed the elevated activity of whole-cell lysates to the accumulation of ER-GCase that is liberated during cell lysis and artificially activated in the acidic buffer that is optimized for the assay (FIG. 10G, right). Together, these data indicate that A53T a-syn aberrantly redistributes GCase activity outside of lysosomal compartments resulting in lysosomal dysfunction.

Figure 10H:
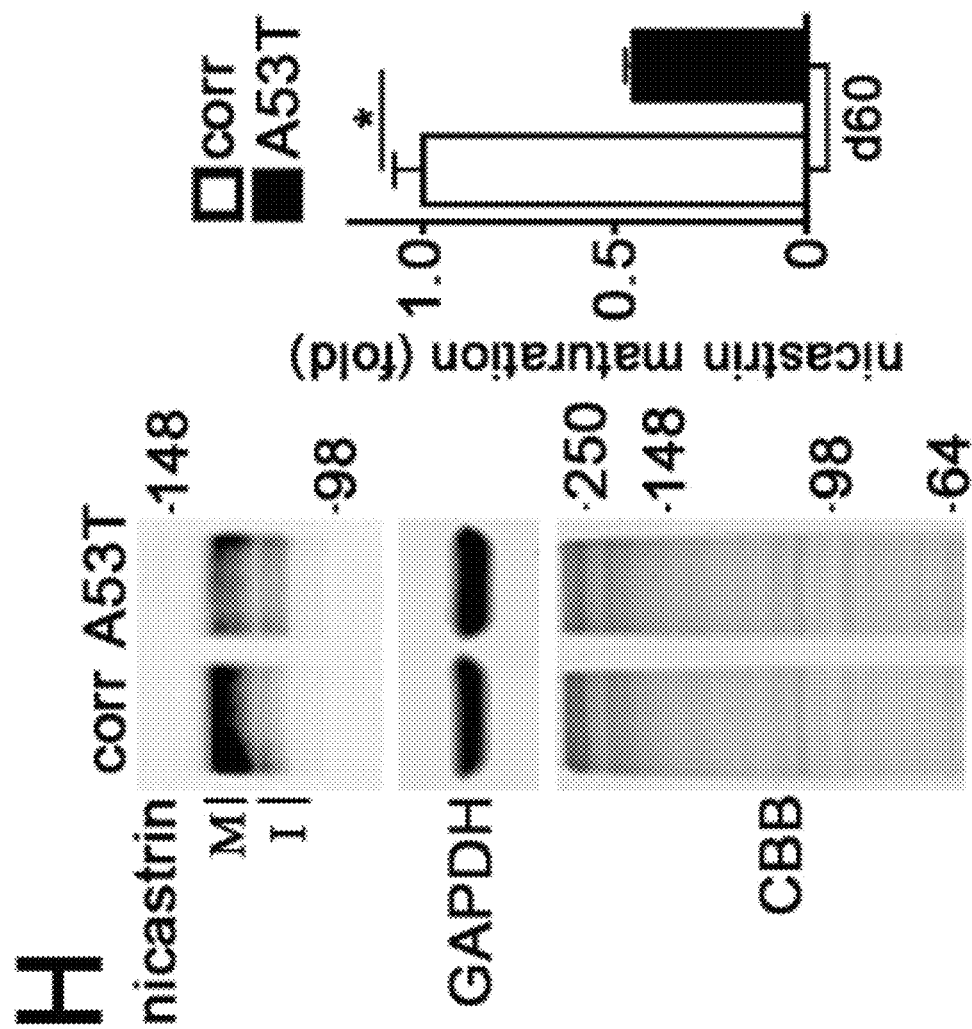
Figure 10I:
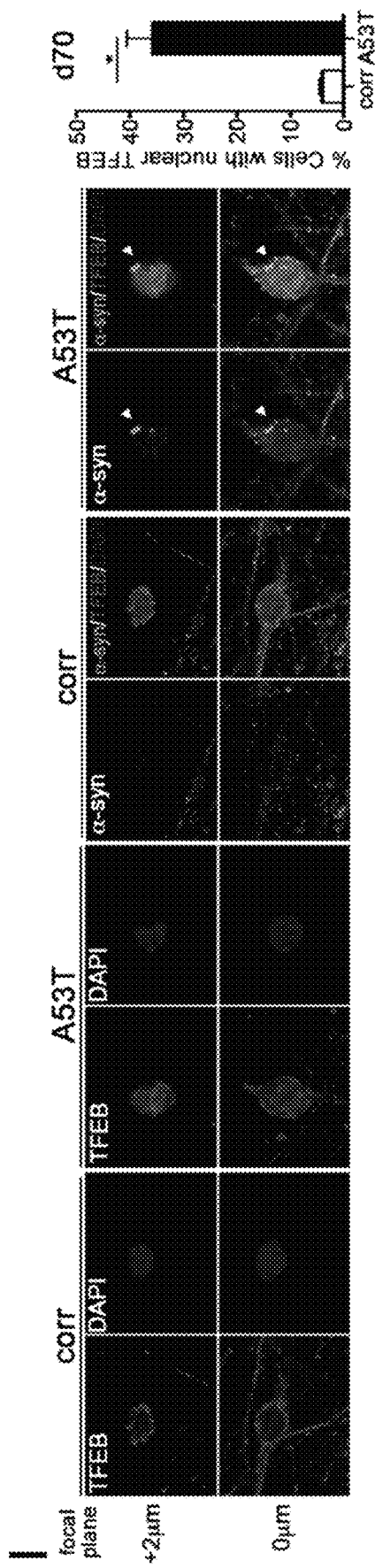
Figure 10J:
Figure 10K:
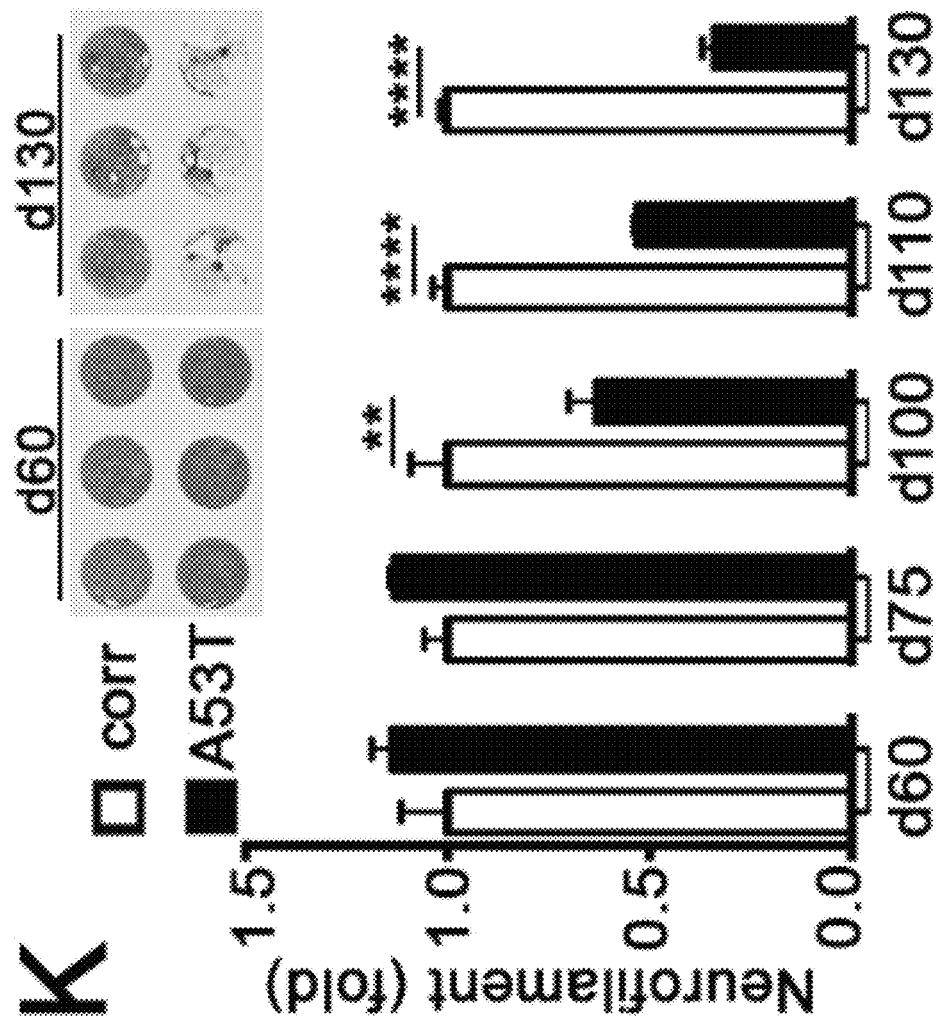
Figure 10L:
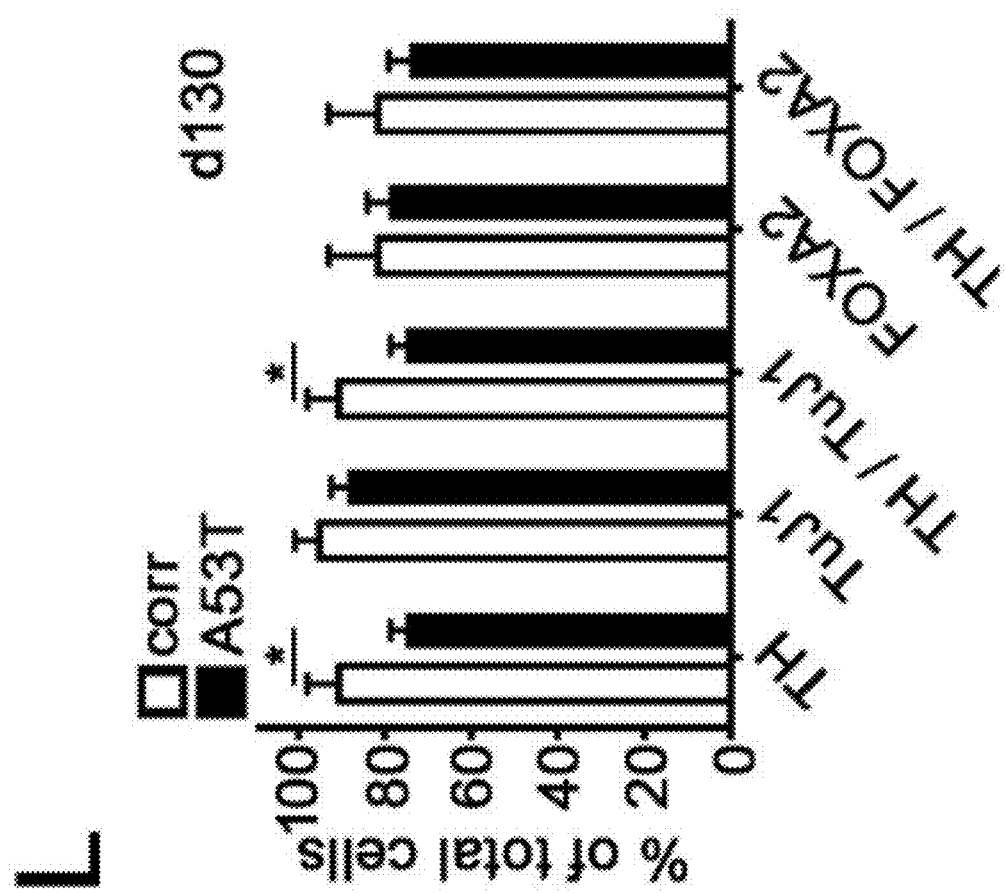
Figure 10M:
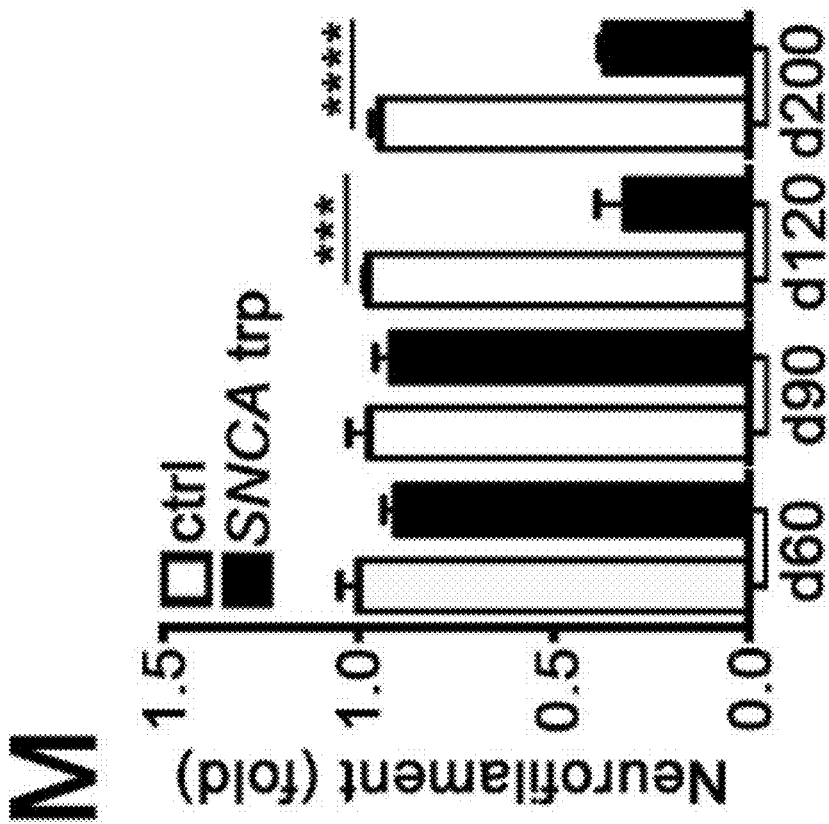

We confirmed disrupted protein trafficking in PD iPSn by analysis of nicastrin, a protein that matures similarly to GCase and LAMP1 (Bagshaw et al., 2003; Yang et al., 2002), which also showed accumulation of immature ER forms at day 60 (FIG. 10H). Together, this suggests that lysosomal dysfunction in A53T iPSn does not result from a depletion in lysosomal machinery, but is associated with disrupted protein maturation consistent with previous studies (Cooper et al., 2006). We also found that A53T iPSn could stimulate the synthesis of lysosomal components at the transcriptional level, since TFEB translocated into the nucleus of inclusion-bearing cells, and GBA1 mRNA was elevated compared to isogenic controls (FIG. 10I, J). To correlate lysosomal phenotypes with cell viability, we assessed neurite content by neurofilament staining, and cell body toxicity by counting TH/FOXA2/b-iii-Tubulin+neurons. Neurotoxicity of PD iPSn was not evident until day 100 and beyond (FIG. 10K-M), suggesting that lysosomal dysfunction does not occur as a result of non-specific toxicity. Collectively, this indicates that lysosomal dysfunction occurs subsequent to a-syn aggregation and is associated with perturbations in protein trafficking.

Figure 11A:
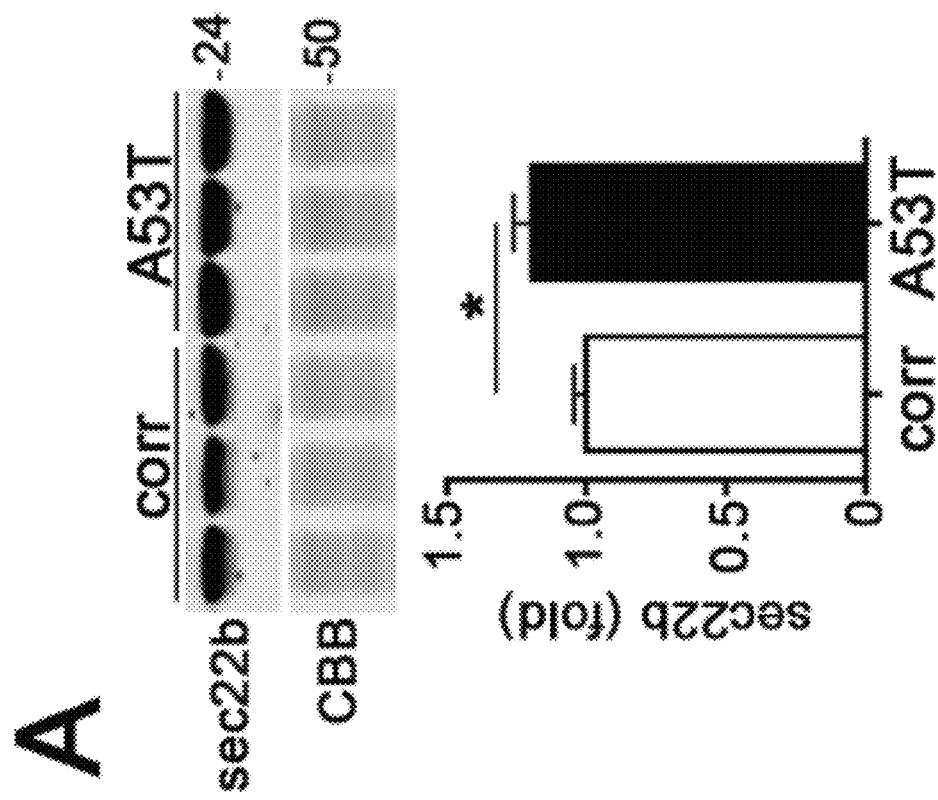
Figure 11B:
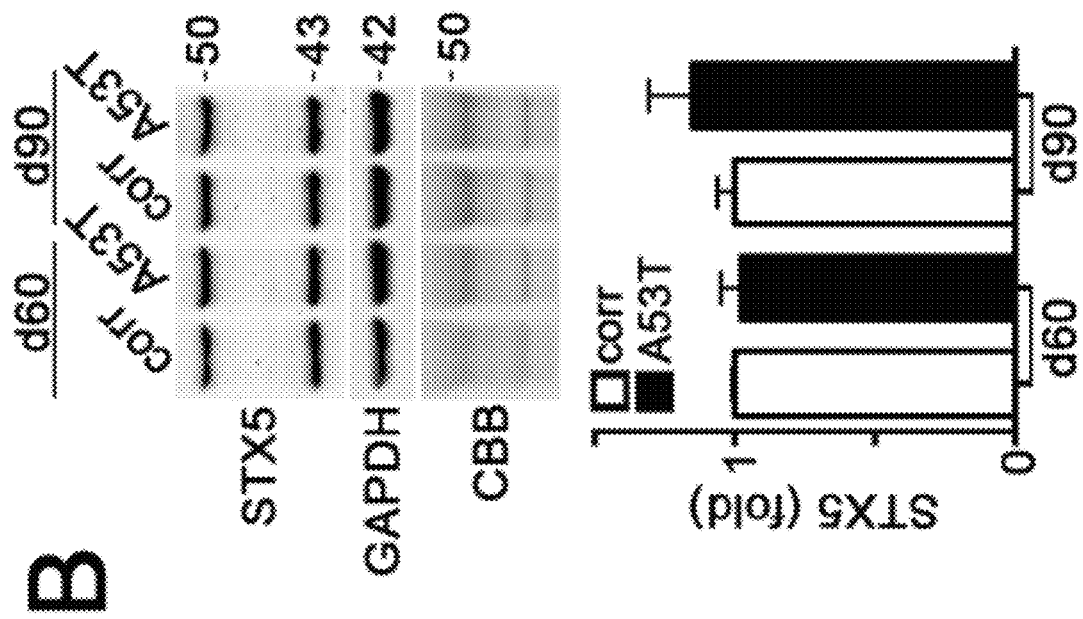
Figure 11C:
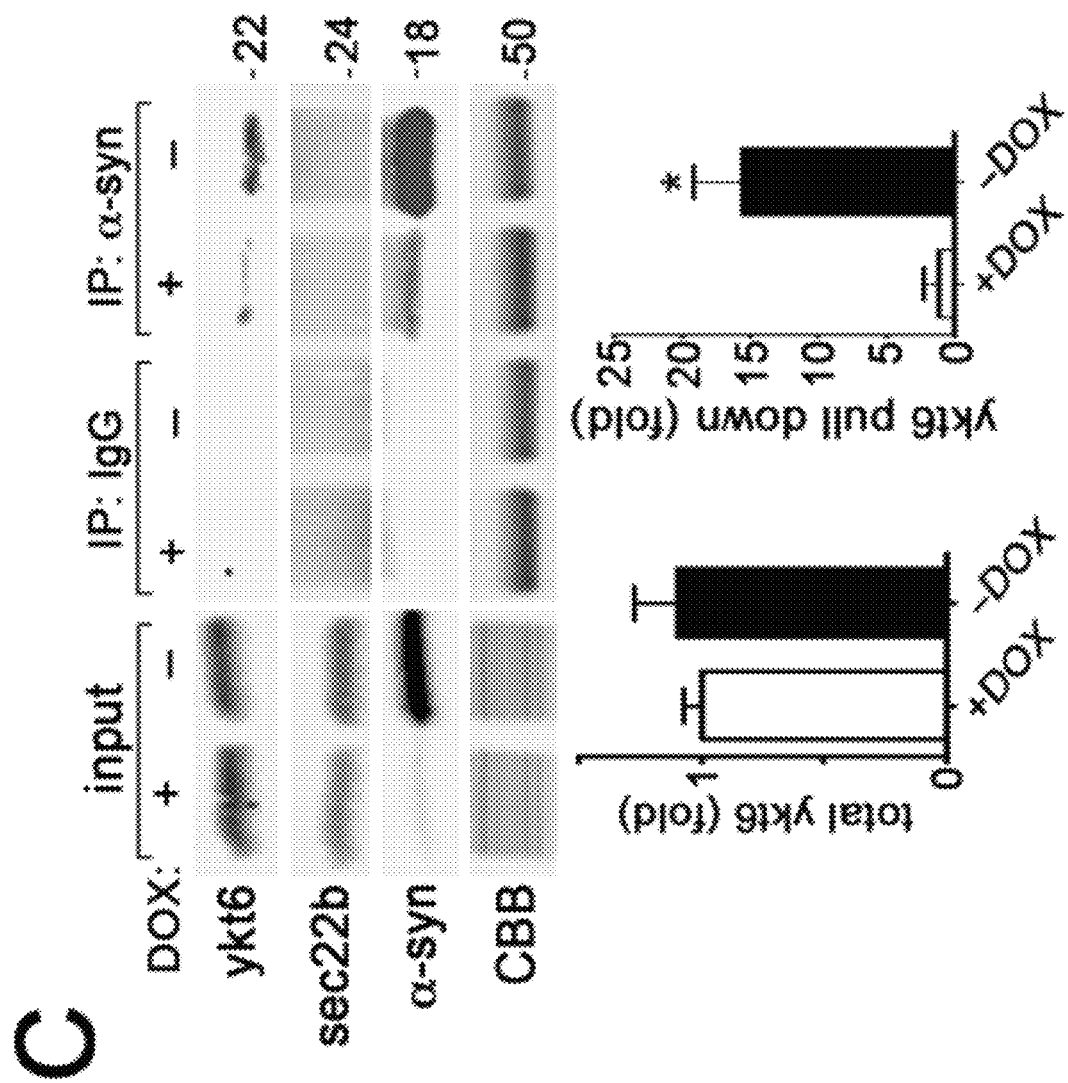
Figure 11D:
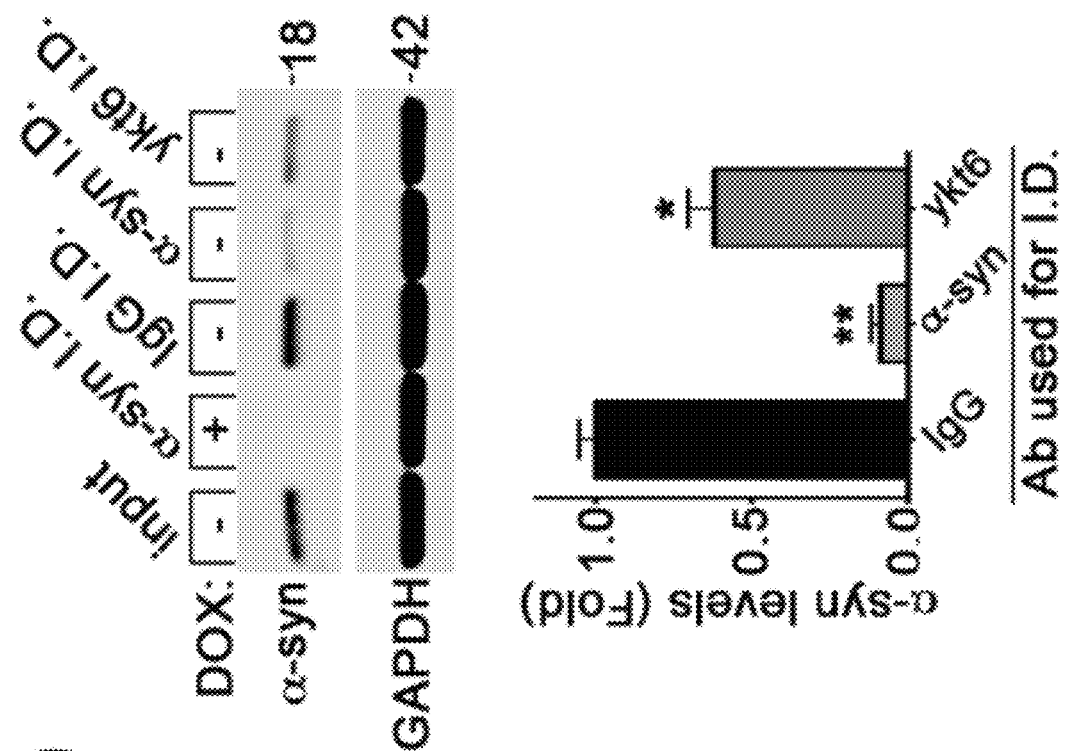
Figure 11E:
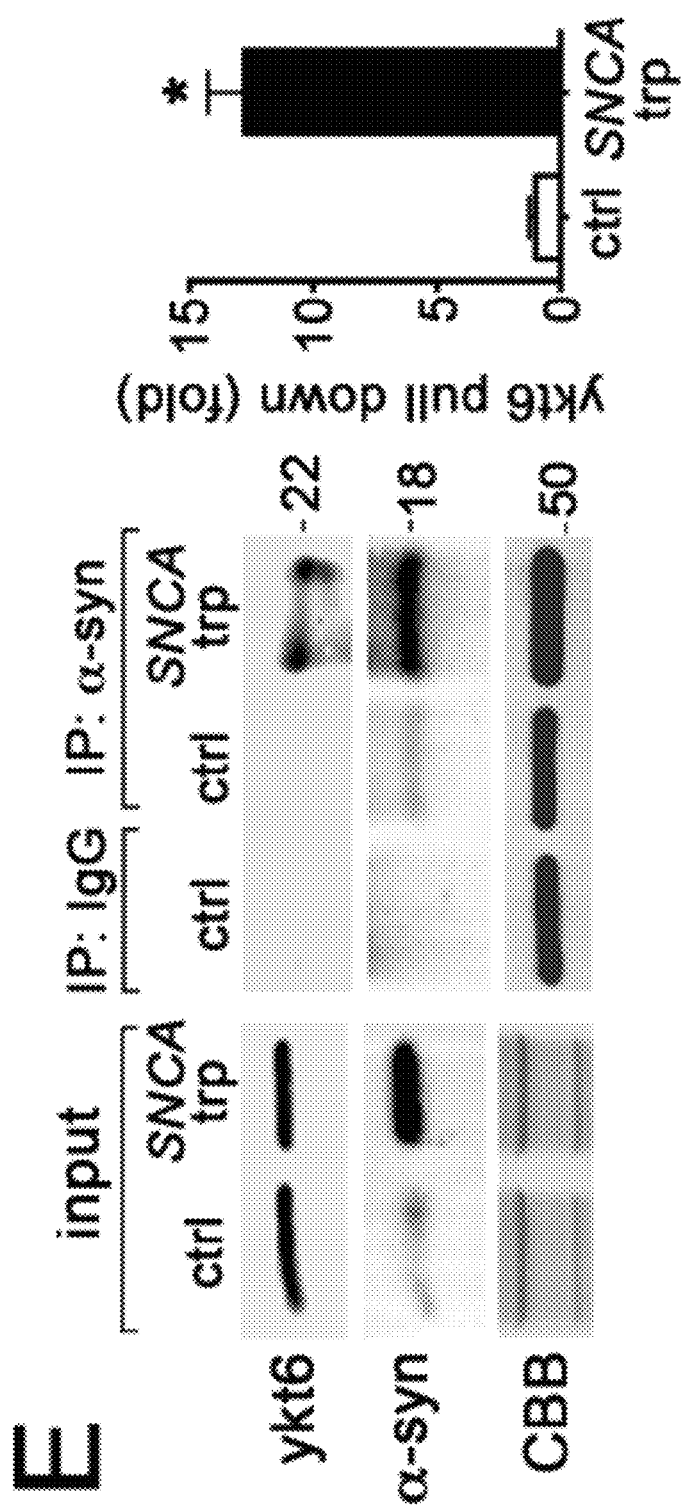
Figure 11F:
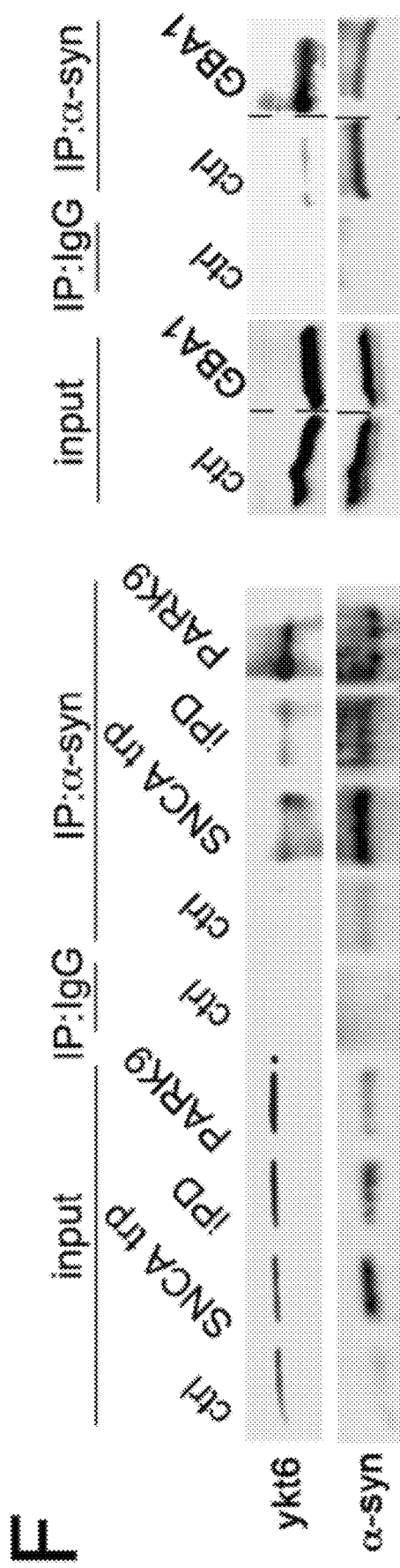
Figure 11G:
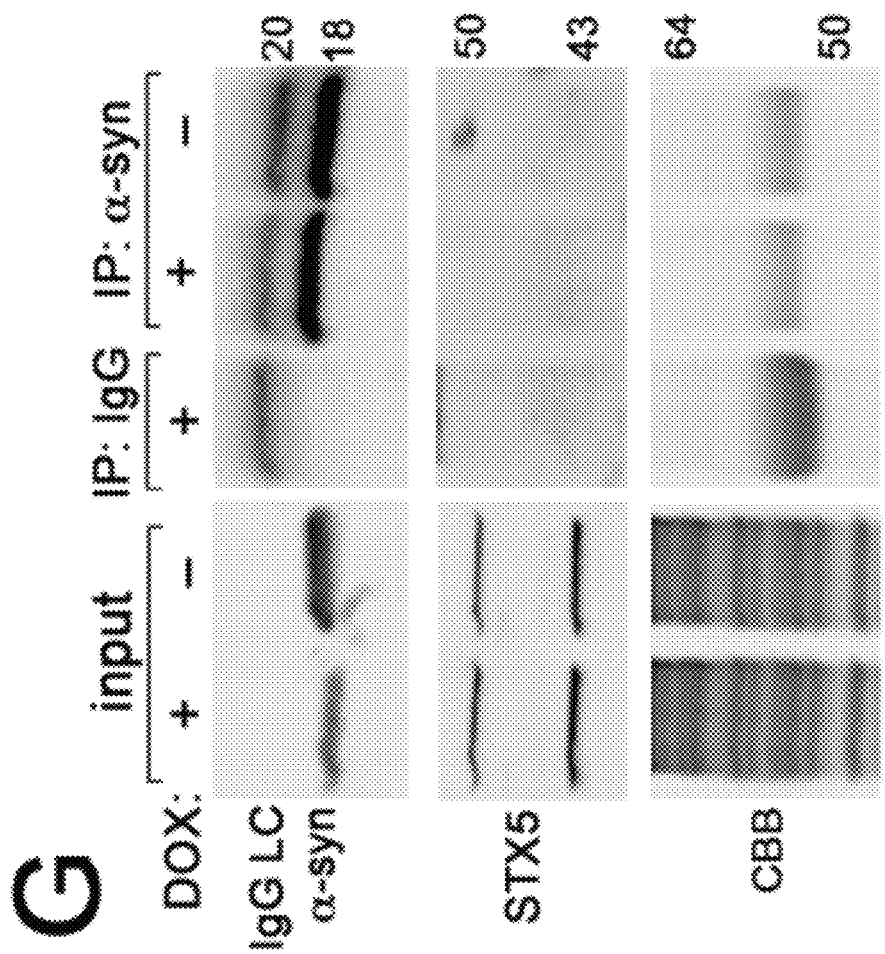

Ykt6 is disrupted by a-Synuclein and is deficient in PD brain. Since our data indicated disruptions in protein maturation, we examined the levels of SNAREs that facilitate trafficking between the ER and Golgi where sec22b, ykt6, and syntaxin 5 (STX5) are critical (Hay et al., 1997; Nichols and Pelham, 1998). Although ykt6 and sec22b are in distinct SNARE complexes, they can both bind STX5 and bet1 to form a functional complex (Xu et al., 2000; Zhang and Hong, 2001). Western blot analysis of A53T iPSn indicated a subtle elevation in sec22b but no change in other SNAREs, suggesting that perturbations in maturation are not associated with reduced SNARE levels (FIG. 1A, FIG. 11A, B). a-Syn can interact with synaptobrevin-2 (Burre et al., 2010; Sun et al., 2019), which shares sequence homology with ykt6 and sec22b. Therefore we assessed whether a-syn could form a complex with ykt6 or sec22b by co-immunoprecipitation (co-IP) in an established inducible H4 cell model of a-syn overexpression (Mazzulli et al., 2011). This showed that a-syn could co-IP with ykt6 but not sec22b (FIG. 11C, D).

Figure 1B:
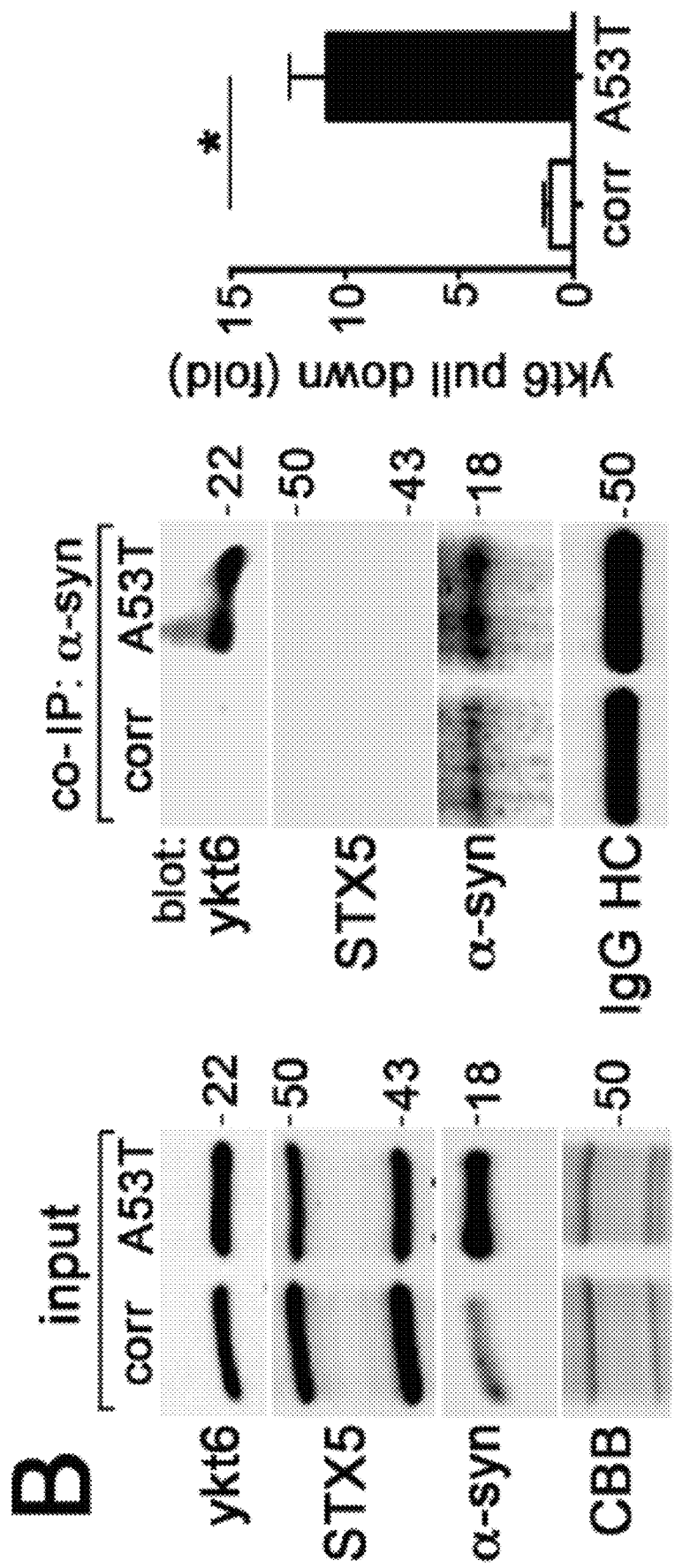
Figure 11H:
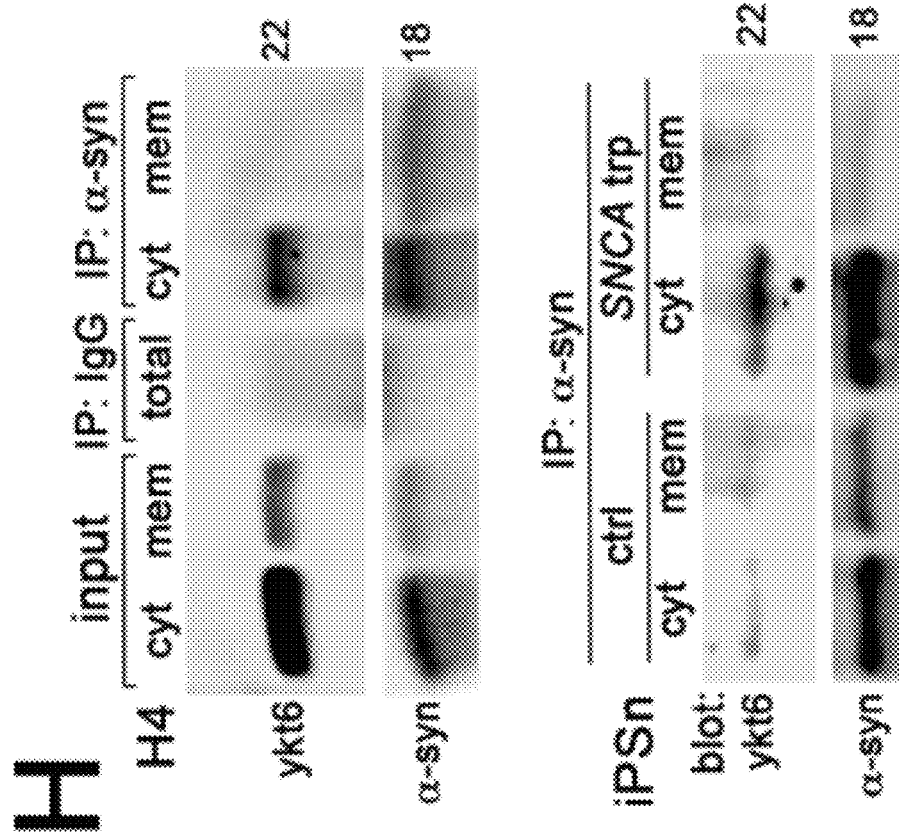

To determine if endogenously expressed a-syn and ykt6 form a complex, we analyzed PD patient iPSn lysates from A53T, SNCA trp, PARK9, or GBA1 mutation carriers, as well as idiopathic PD neurons that accumulate pathological a-syn at the cell body (Mazzulli et al., 2016a; Mazzulli et al., 2016b). This showed that a-syn pulled down ykt6 in all PD iPSn lines, but not in controls (FIG. 1B, 11E-F). a-Syn did not pull down the ykt6 cognate SNARE binding partner STX5 (FIG. 1B, 11G), suggesting that a-syn may form a complex with ykt6 in the cytosol prior to SNARE assembly. Consistent with this, co-IP from isolated cytosol and membrane fractions revealed that a-syn-ykt6 complexes occurred only in the cytosol (FIG. 11H).

Figure 1C:
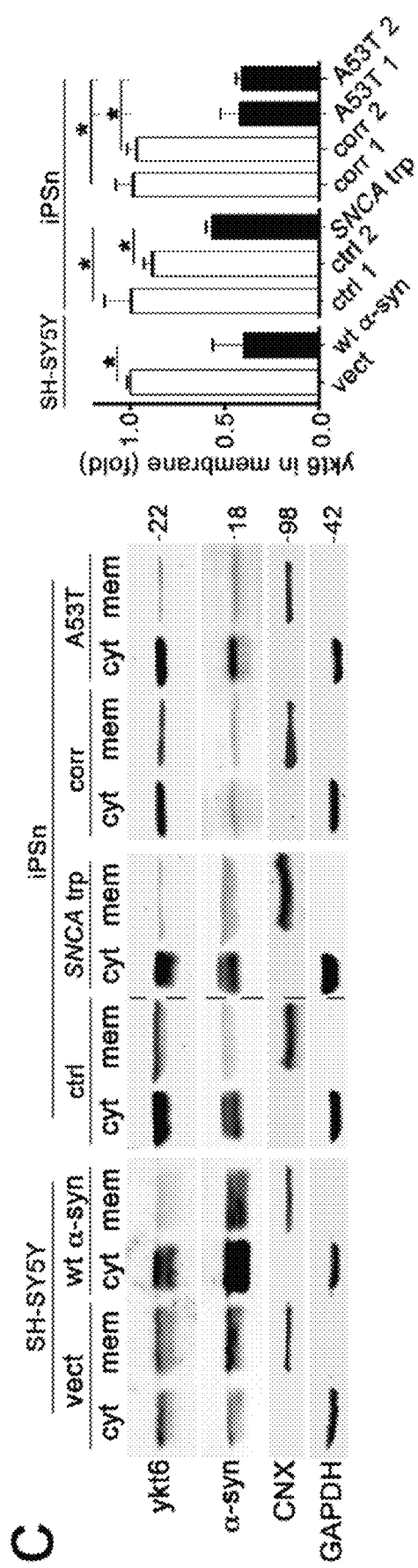
Figure 1D:
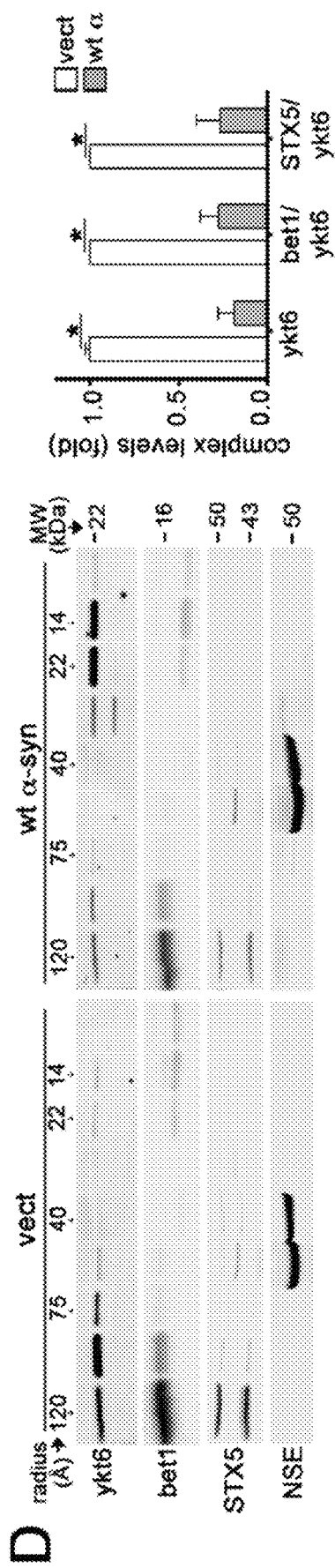
Figure 11I:
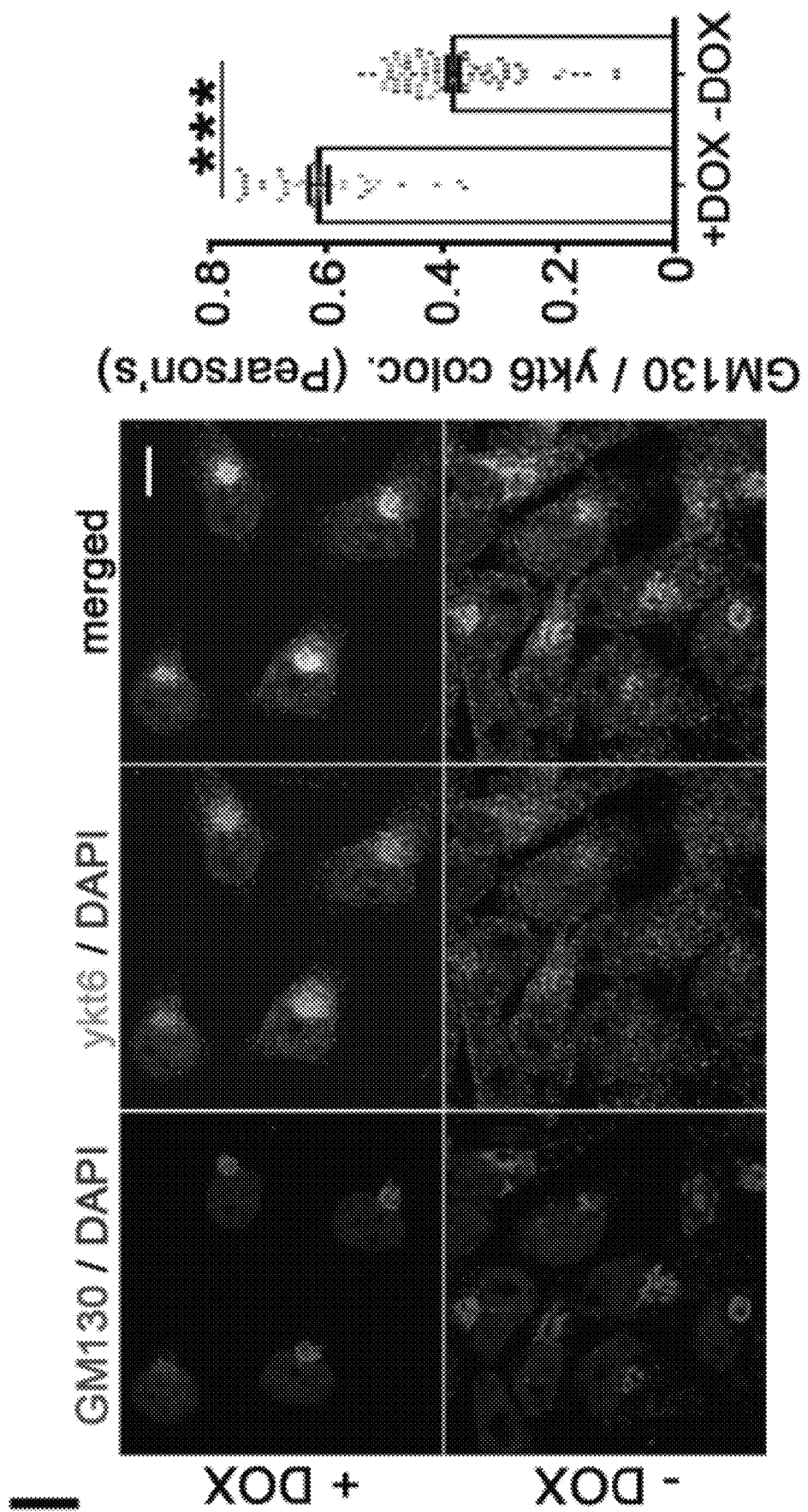
Figure 11J:
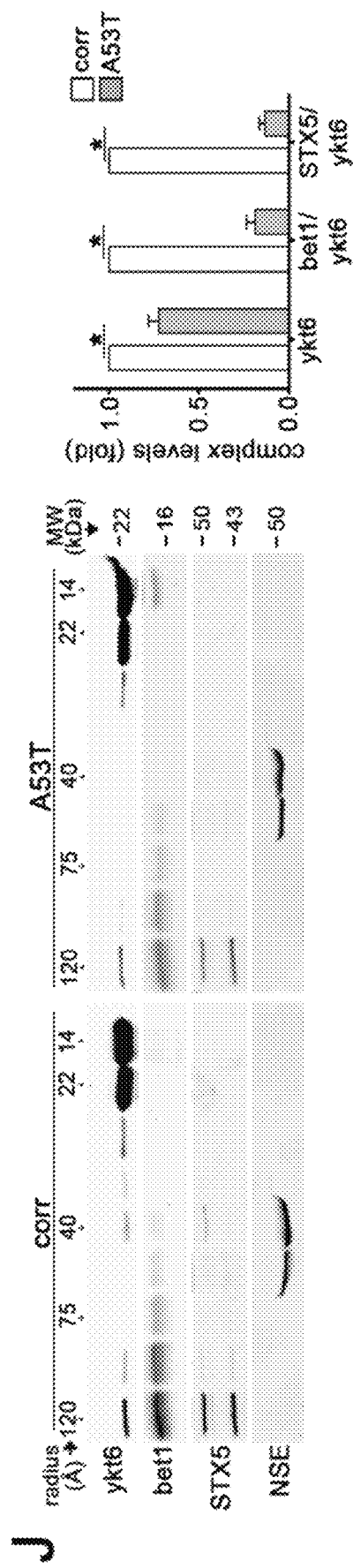

We then determined if a-syn could influence the function of ykt6 by altering its cytosol-membrane distribution. Membrane-associated ykt6 was reduced in differentiated human neuroblastoma cells (SH-SY5Y) that overexpress wt a-syn compared to empty vector control lines, a finding that was validated in SNCA trp and A53T iPSn (FIG. 1C). Immunostaining showed that a-syn overexpression reduced ykt6 colocalization with the Golgi marker GM130 (FIG. 11I). To determine if a-syn disrupted ykt6 SNARE complexes, we used size exclusion chromatography (SEC) to separate monomers from high molecular weight assemblies. Western blot of the collected fractions indicated that ykt6 complexes (120-75 Angstrom (A) radius species) were reduced, while monomeric ykt6 at 22 and 14 A were elevated in SH-SY5Y a-syn cells, suggesting break down of SNARE assemblies (FIG. 1D). The levels of STX5 and bet1, binding partners of ykt6 specifically at the ER-Golgi step, were also decreased (FIG. 1D). This result was confirmed in PD iPSn (FIG. 11J).

Figure 1E:
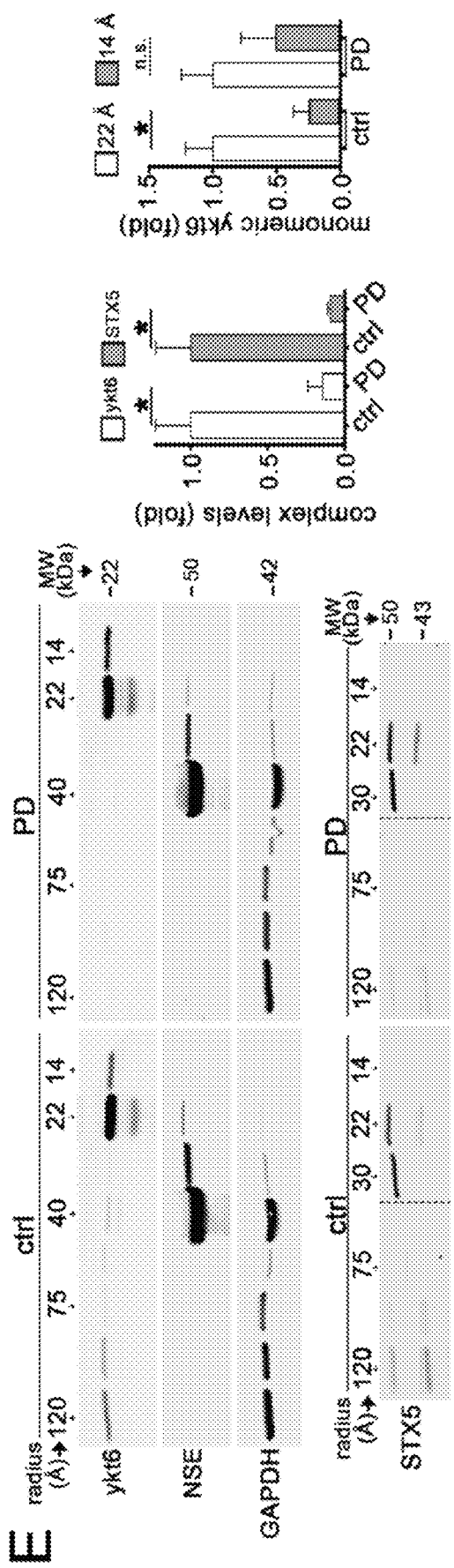
Figure 1F:
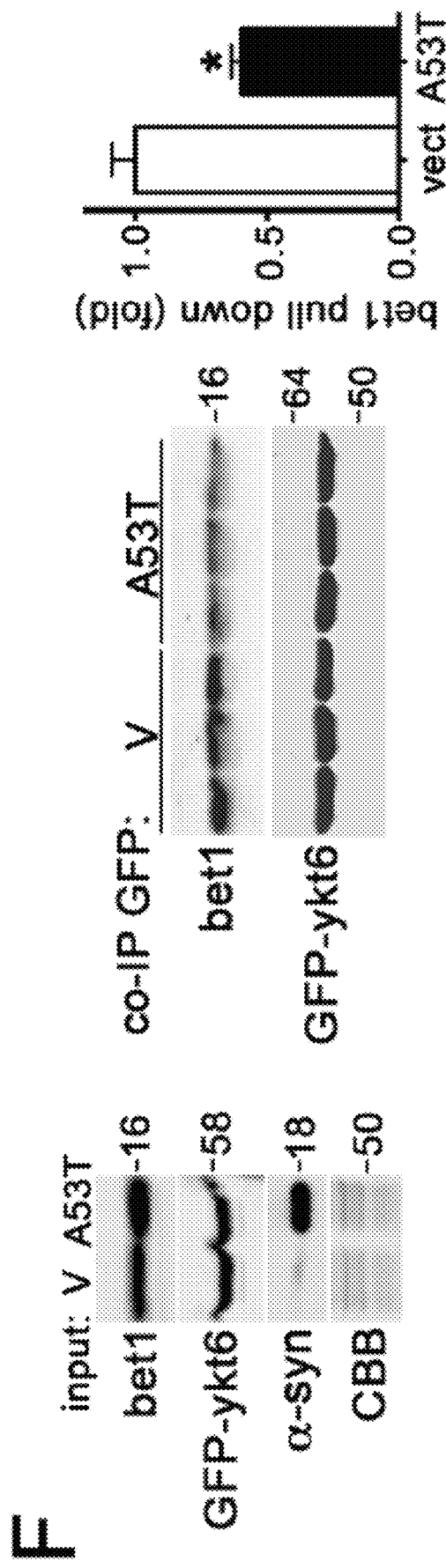
Figure 1G:
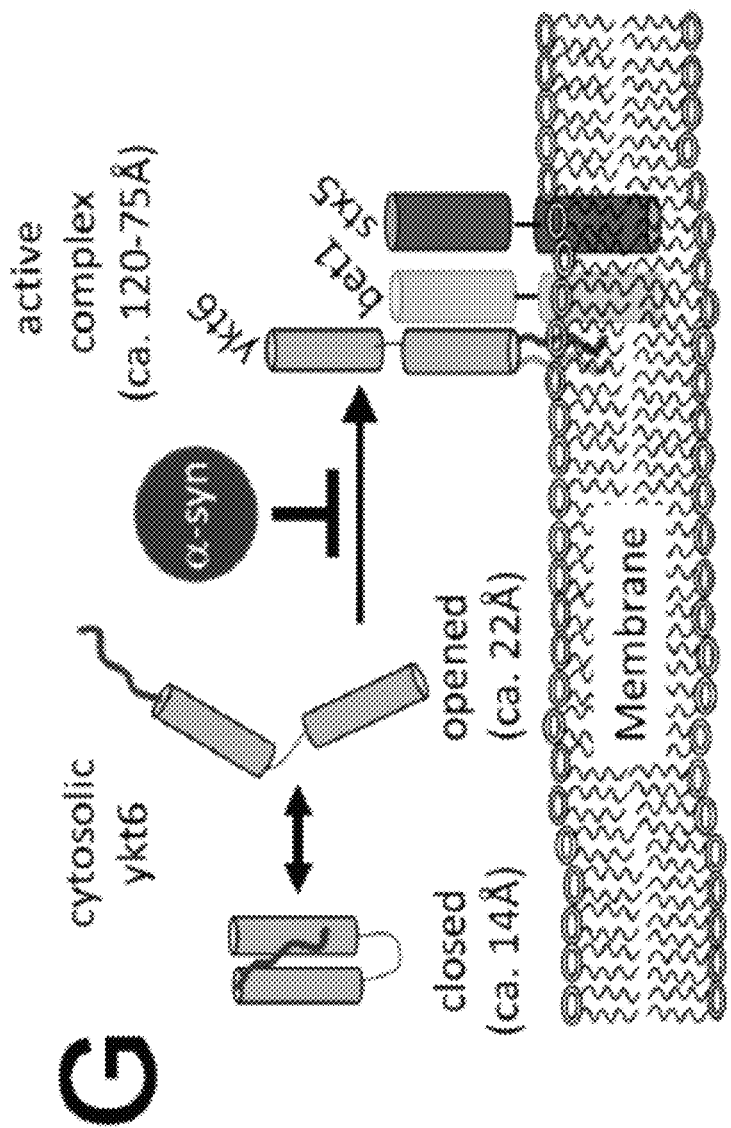
Figure 11K:
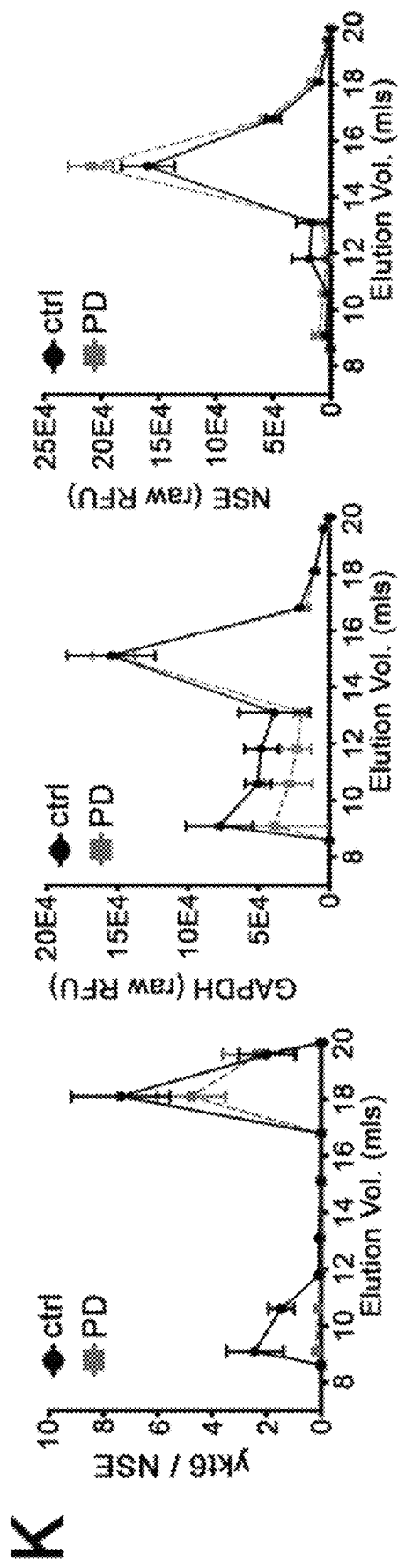

We next analyzed brain lysates from pathologically confirmed PD samples (Mazzulli et al., 2011) by SEC and found that ykt6 and STX5 complexes were depleted (FIG. 1E). SEC analysis of open (22A) and closed (14A) monomeric forms of ykt6 (Pylypenko et al., 2008) also indicated a minor change in the proportion of 22A and 14A species, where the 14A compact monomer was slightly elevated in PD brain (FIG. 1E). Changes in ykt6 were specific, since control proteins GAPDH and NSE showed the expected elution profiles (FIG. 1E, FIG. 11K). Finally, we confirmed that a-syn disrupted ykt6 SNARE complexes in a-syn overexpressing cells by co-IP, since ykt6 pulled down less bet1 compared to controls (FIG. 1F). Together, this shows that a-syn reduces membrane-associated ykt6 and SNARE complexes (FIG. 1G).

Figure 2A:
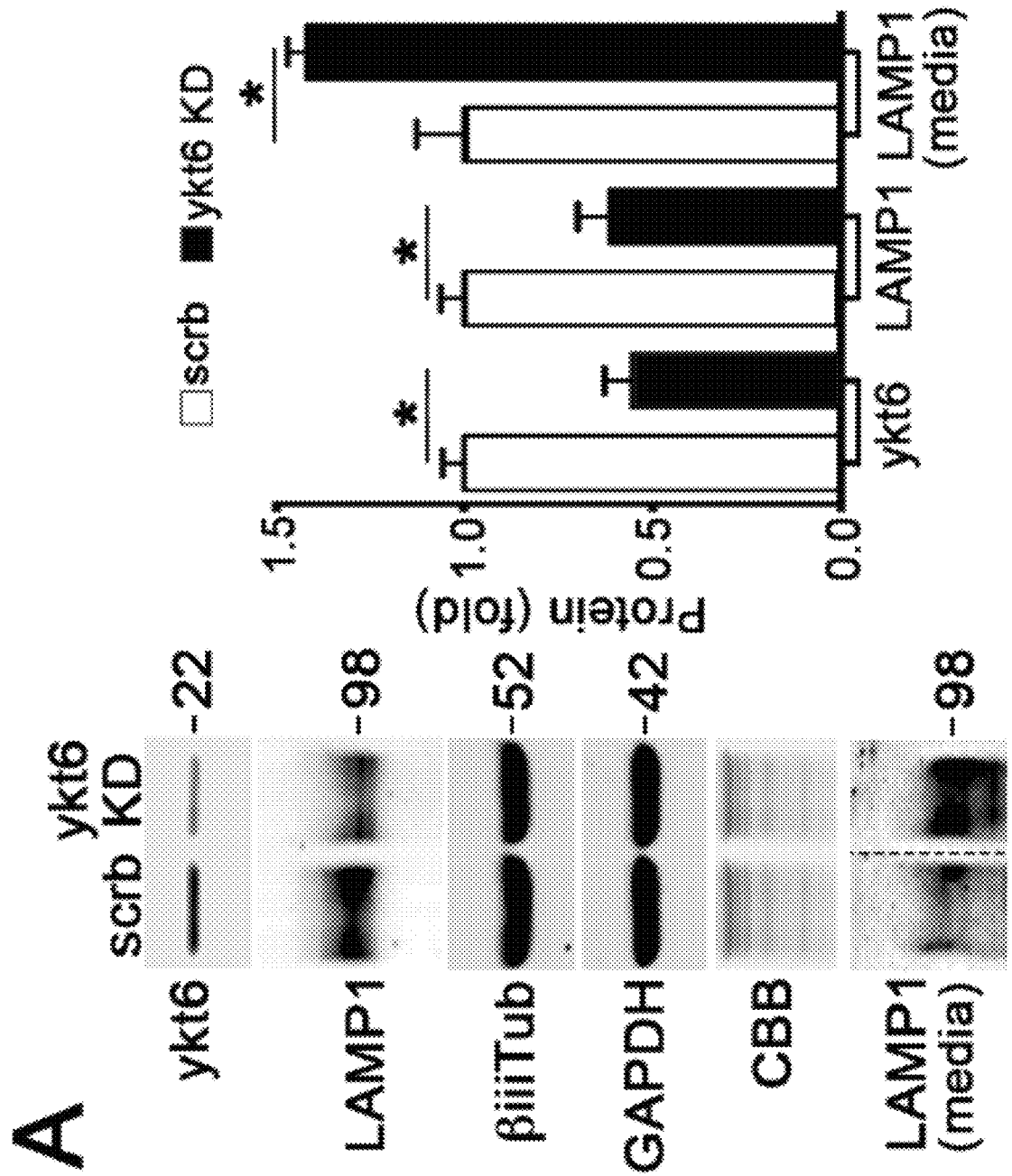
Figure 2B:
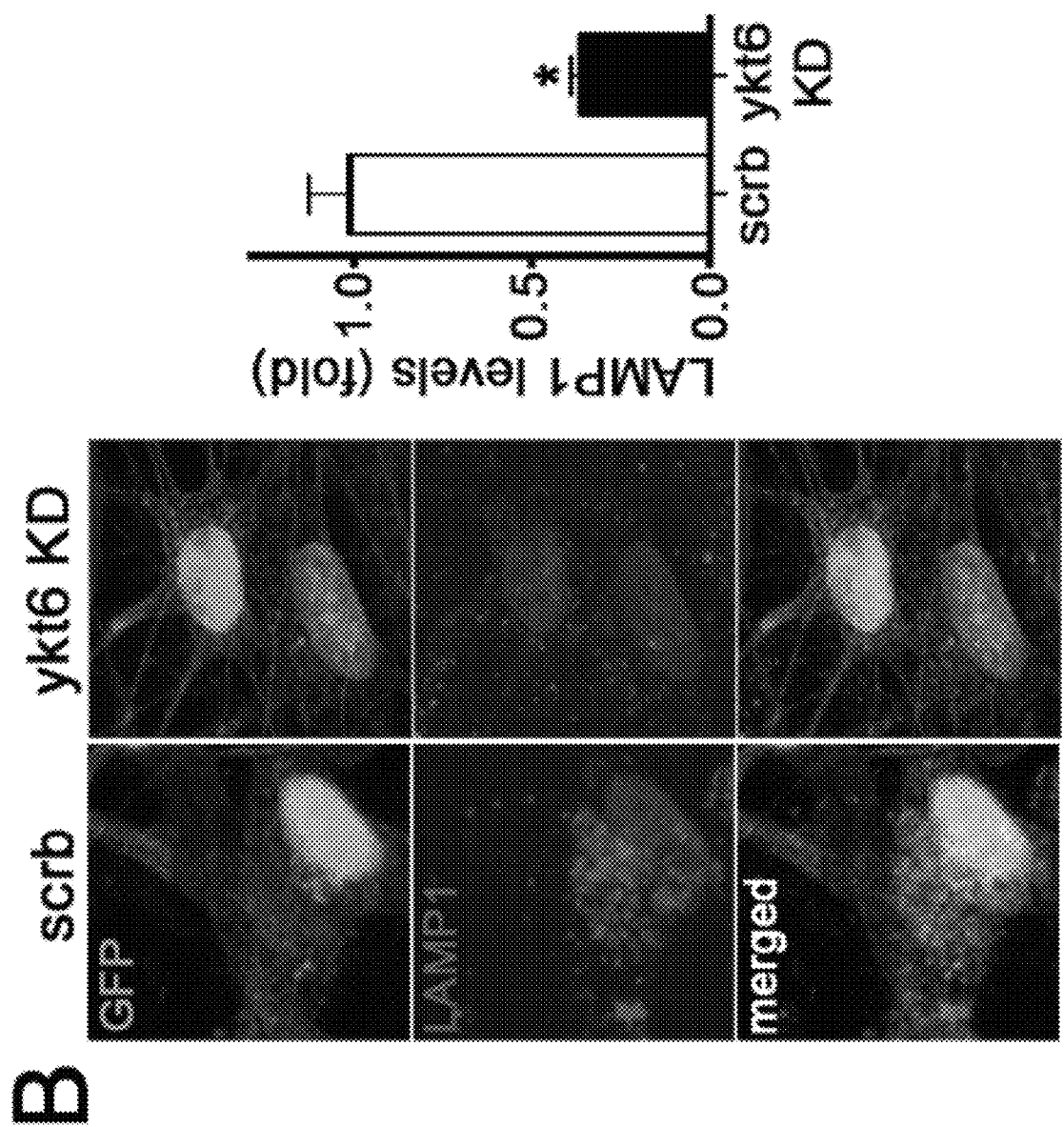
Figure 2C:
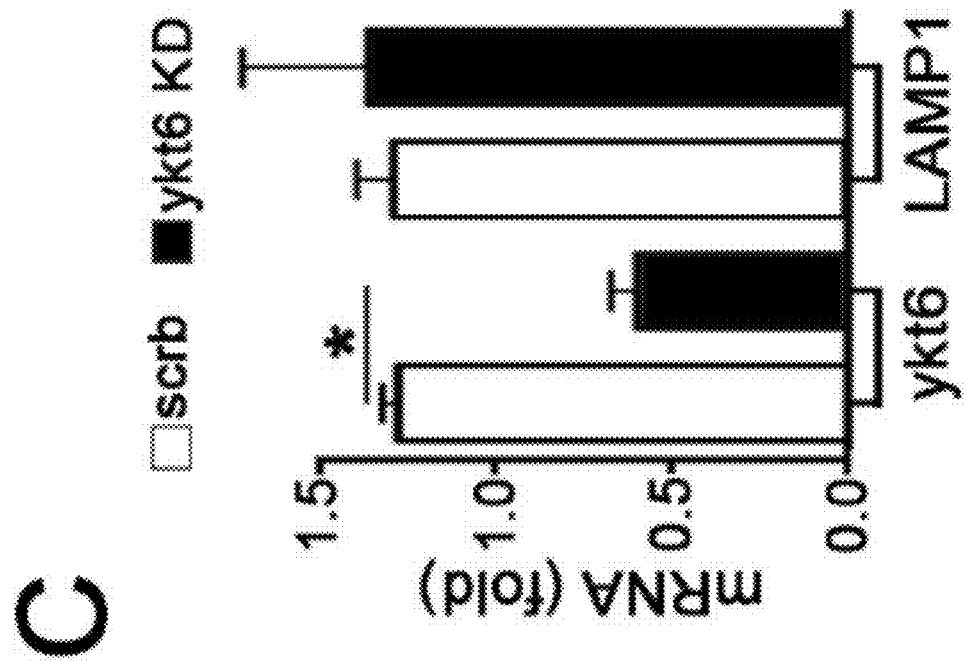
Figure 2D:
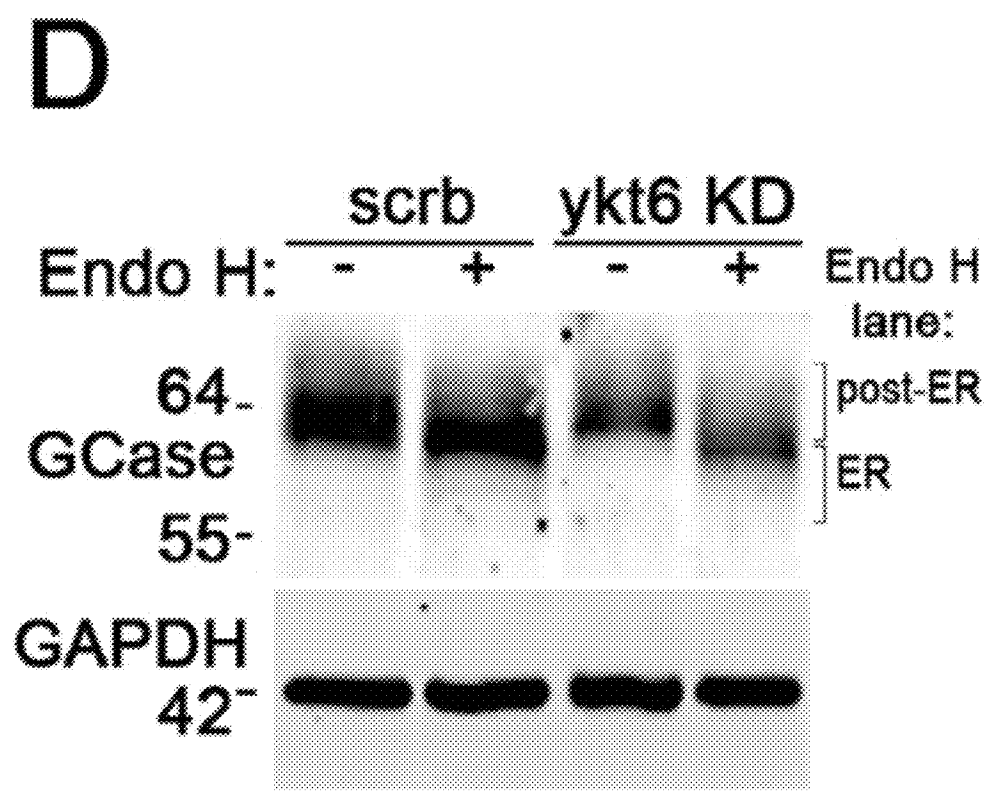
Figure 2E:
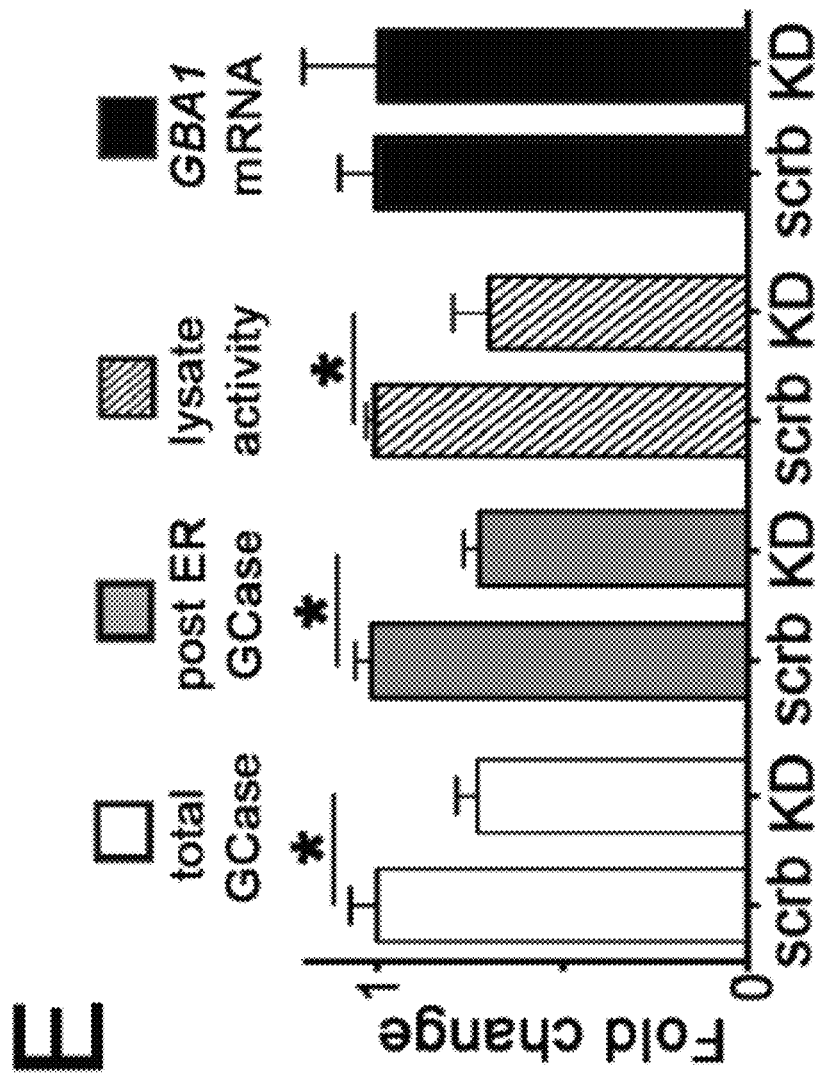
Figure 2F:
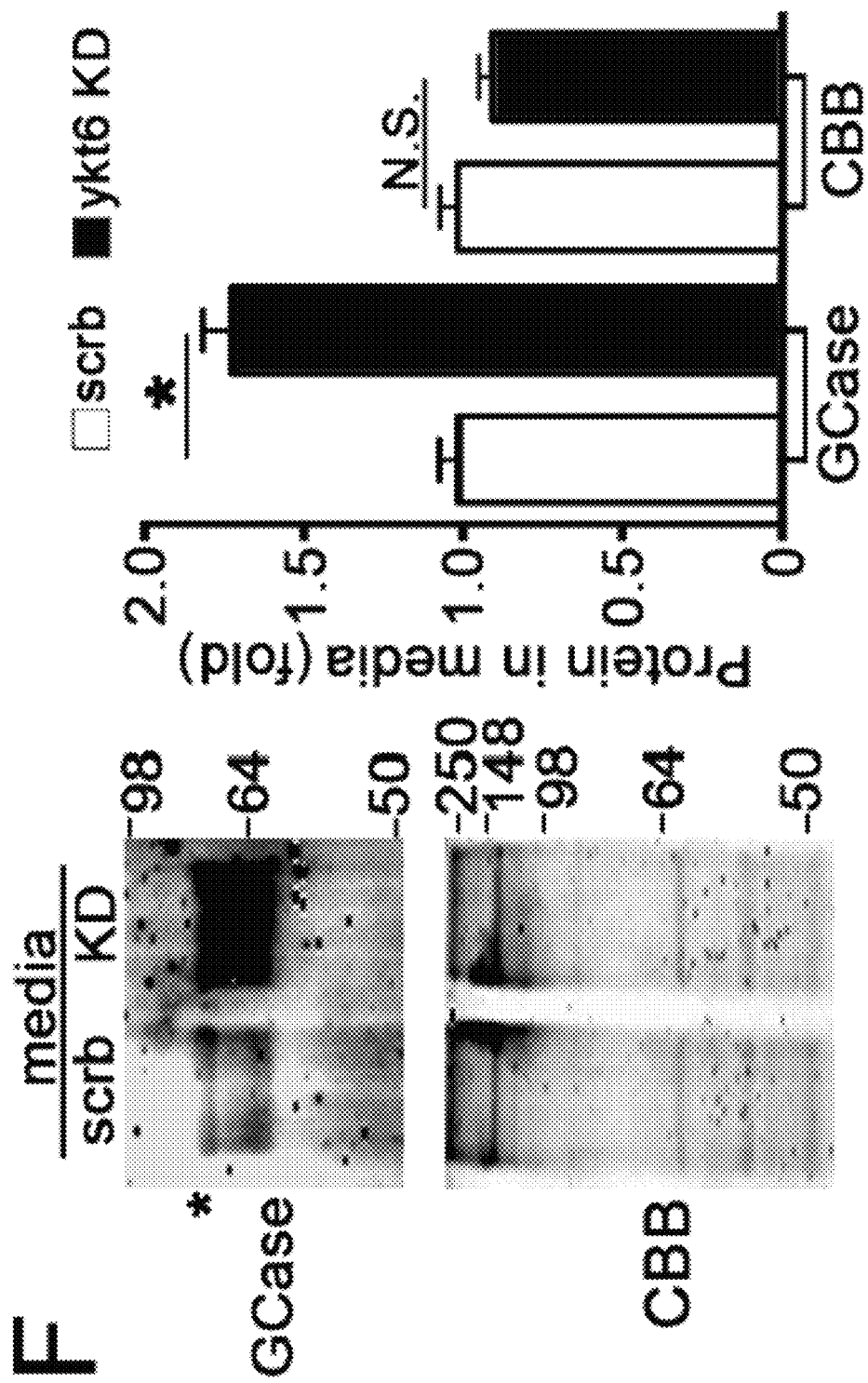
Figure 2G:
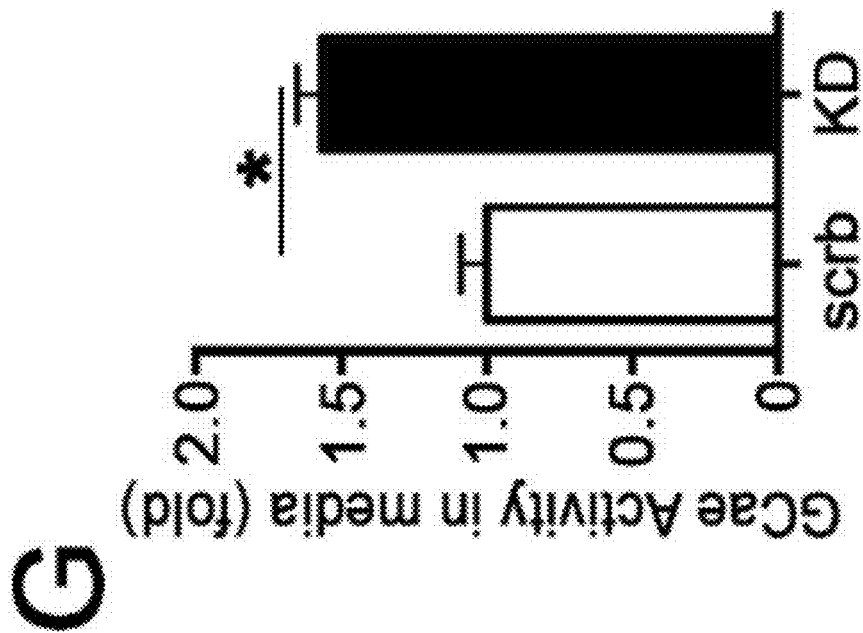
Figure 2H:
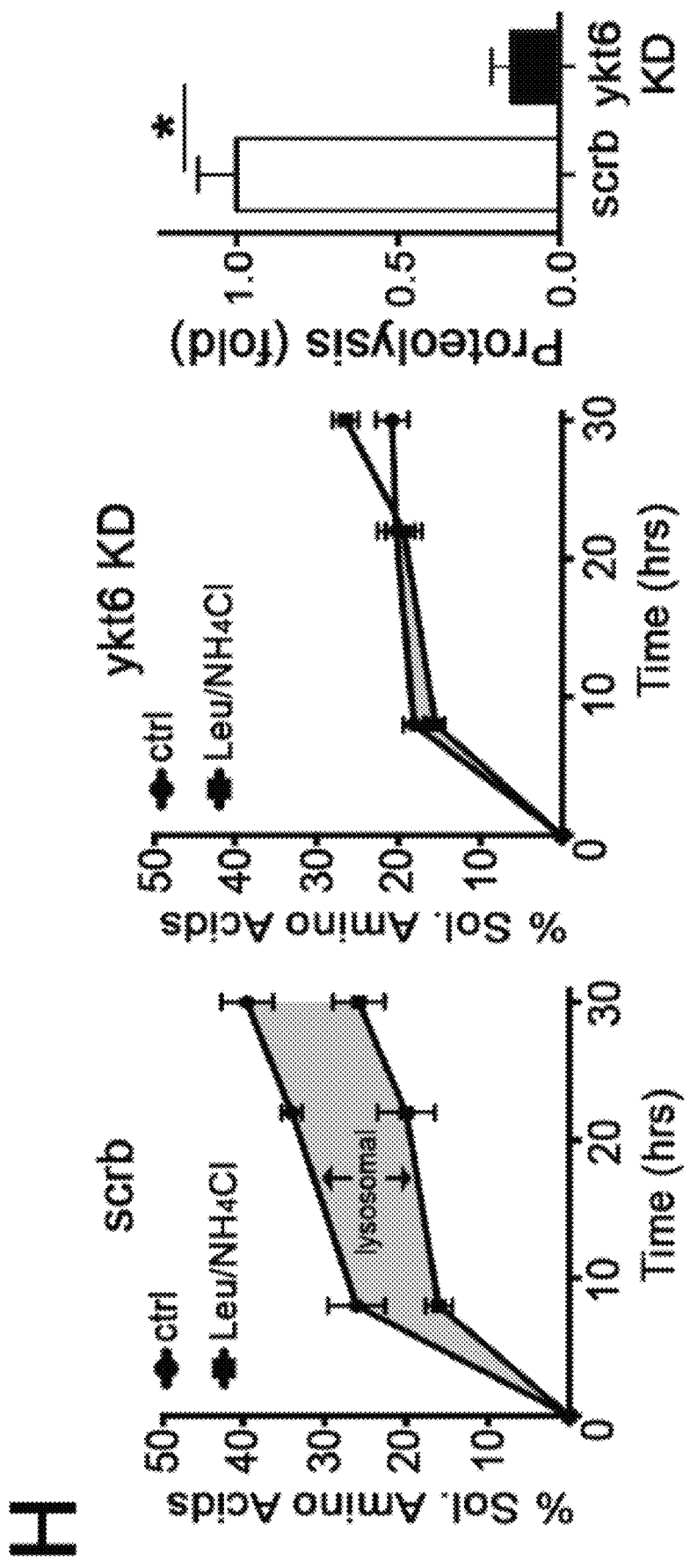
Figure 2I:
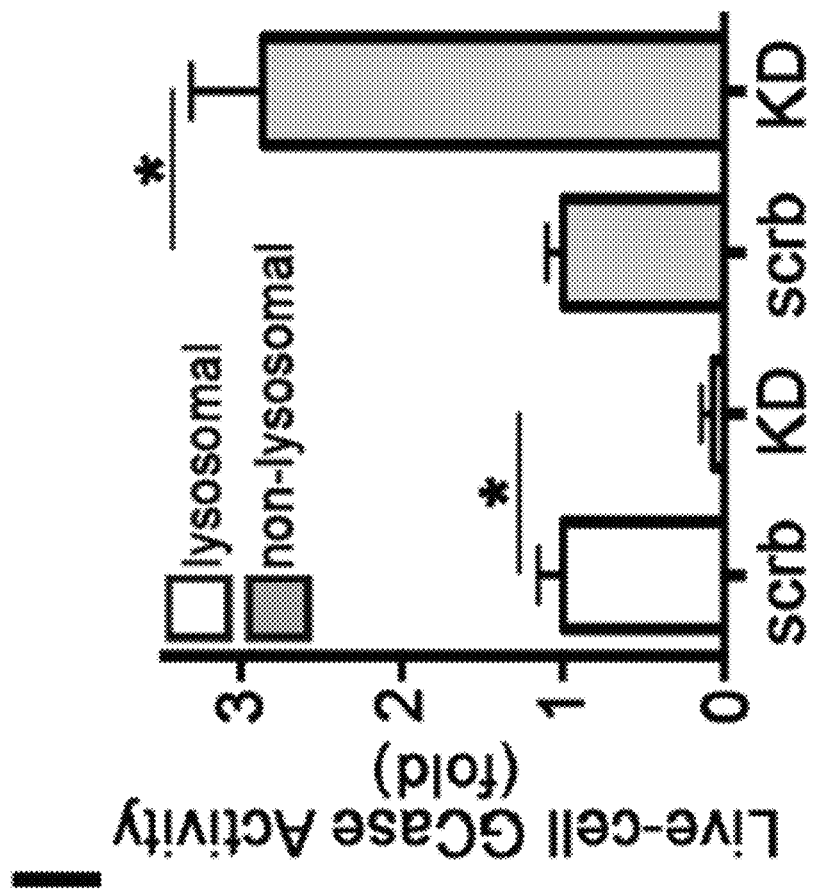
Figure 12A:
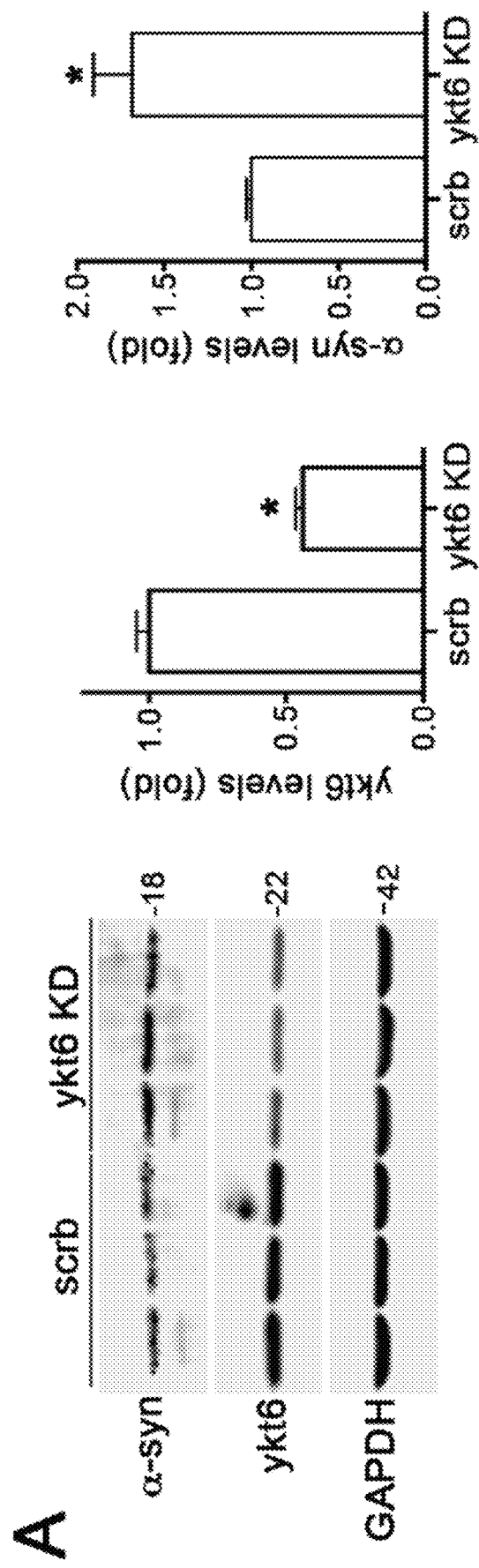
Figure 12B:
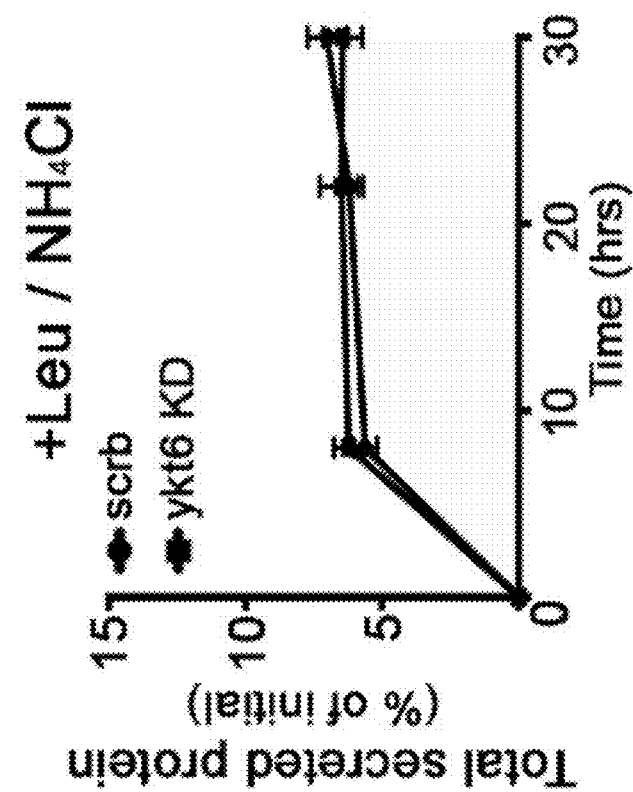
Figure 12B:
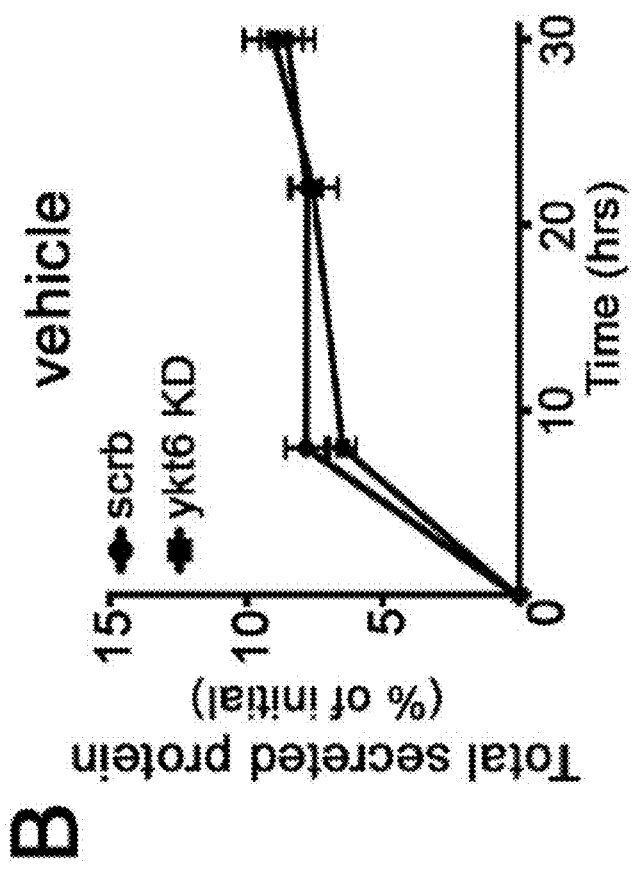
Figure 12C:
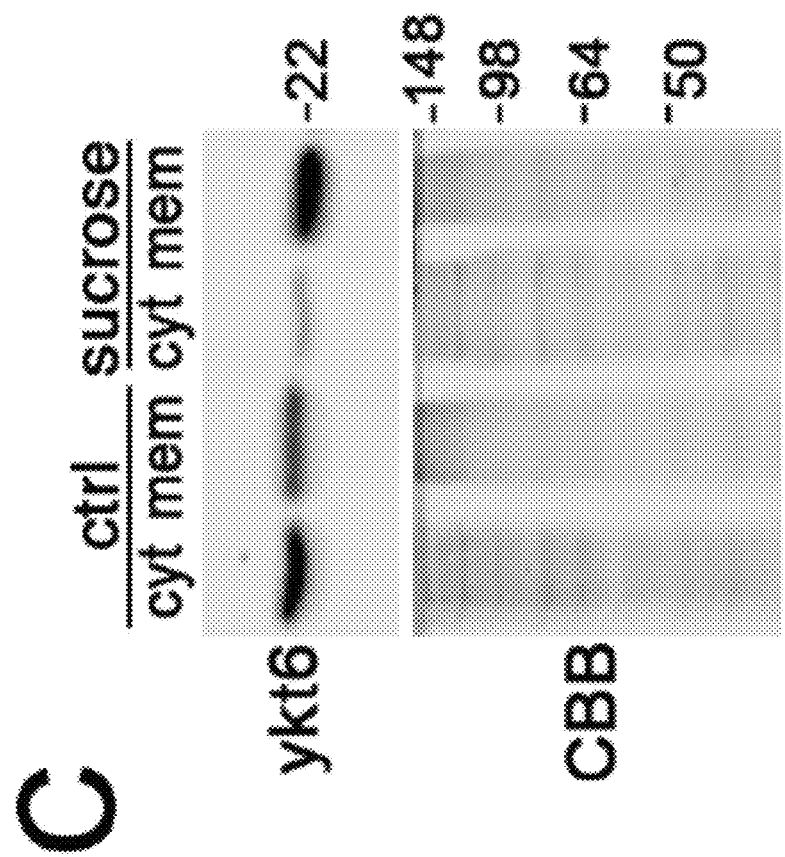

Ykt6 knock-down preferentially disrupts lysosomal protein trafficking and function. Since our data suggested an association between a-syn-induced lysosomal dysfunction and perturbations in ykt6, we next determined the effect of depleting ykt6 in healthy control iPSn on the lysosomal system. shRNA-mediated knock-down (KD) of ykt6 reduced intracellular LAMP1 protein by 50%, as shown by western blot and immunofluorescence analysis (FIG. 2A, B). This effect was post-transcriptional, since LAMP1 mRNA did not change (FIG. 2C). LAMP1 protein was elevated in the conditioned media of ykt6 KD iPSn, indicating that the decline of intracellular LAMP1 likely occurred by aberrant secretion into the media (FIG. 2A). Ykt6 KD also reduced the levels of total intracellular GCase protein and activity (FIG. 2D, E). The level of mature (post-ER) GCase was determined by resistance to endoglycosidase H (endo H), and enzyme that only cleaves high mannose residues of immature proteins, but not complex oligosaccharides of mature proteins (Tarentino et al., 1972). This showed that ykt6 KD reduced mature, endo H resistant GCase (FIG. 2D, E). GCase depletion also occurred post-transcriptionally, since GBA1 mRNA was unchanged (FIG. 2E), and elevated levels of GCase protein and activity were found in the conditioned media of ykt6 KD iPSn (FIG. 2F, G). Lysosomal function was directly assessed by measuring the degradation rates of long-lived proteins, and revealed a decline in proteolysis upon ykt6 KD (FIG. 2H). We also found reduced GCase activity within lysosomal compartments while non-lysosomal GCase activity was elevated (FIG. 2I), further suggesting hydrolase mistrafficking. Consistent with lysosomal dysfunction, we found that prolonged ykt6 KD resulted in a-syn accumulation (FIG. 12A). By sampling media from the same culture wells as used for proteolysis, we measured constitutive secretion of total proteins and found that ykt6 KD had no effect (FIG. 12B, left). Similarly, we found no changes in protein secretion when ykt6 was reduced in iPSn that were stressed with lysosomal inhibitors (FIG. 12B, right). Together, these data indicate that ykt6 is essential for lysosomal function. Partial ykt6 KD has dramatic effects on the lysosomal system, but no effect on constitutive protein secretion, indicating that ykt6 preferentially functions to traffic lysosomal machinery in iPSn.

Figure 3A:
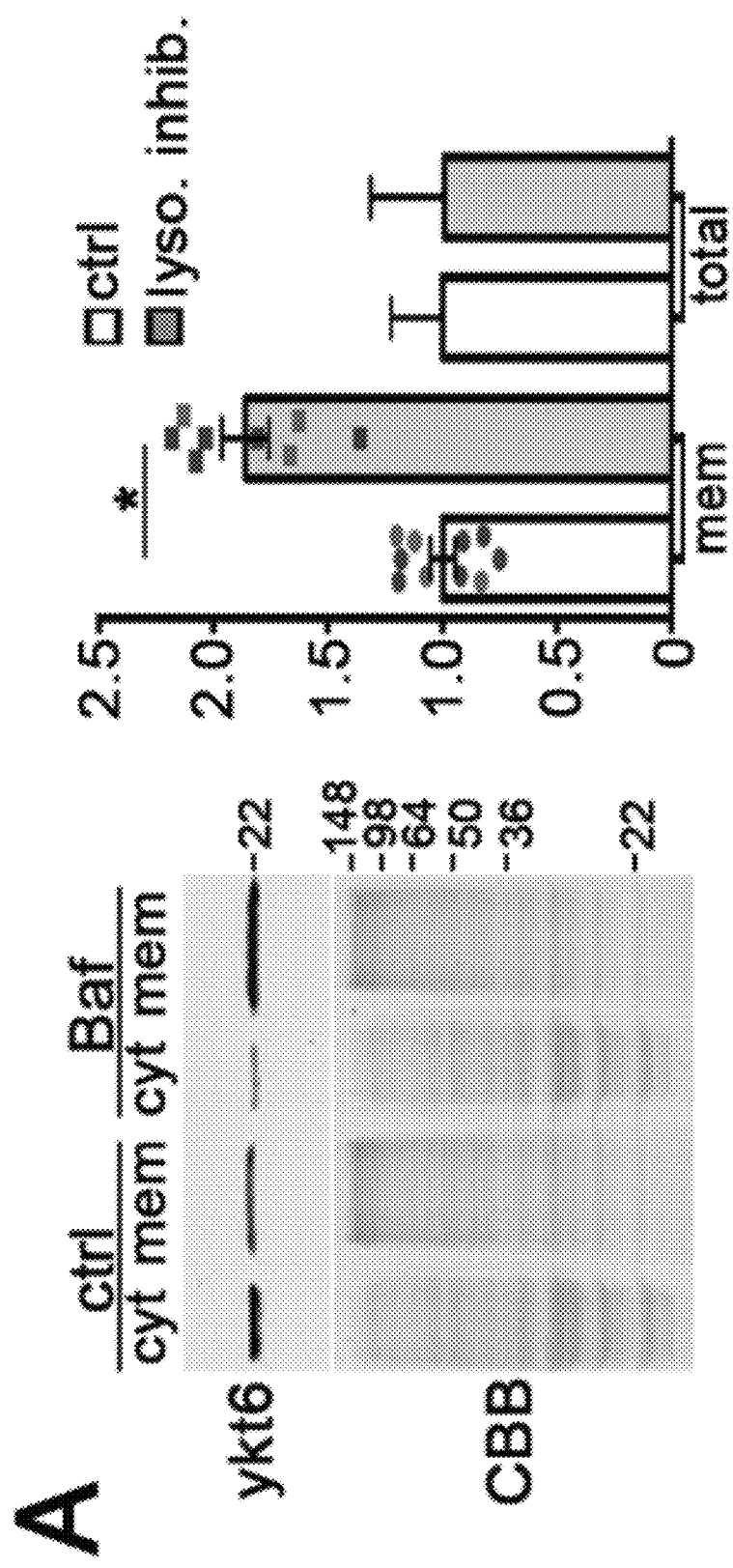
FIGS. 3A, 3B, 3C, 3D, 3E, 3F, 3G, 3H, 3I, 3J, and 3K. Ykt6 is activated in response to lysosomal stress. 3A) Ykt6 membrane shift analysis in bafA1 (200 nM, 2 hrs) or NH4Cl (1M, 12 hrs) treated iPSn (d60). CBB, coomassie brilliant blue, (BafA1 and NH4Cl are indicated, n=7-10). 3B) Co-IP of GFP-ykt6 and bet1 in control iPSn (d60) treated with bafA1 (n=3). 3C) Ykt6 and GM130 immunofluorescence analysis of bafA1-treated H4 cells (n=9). Scale bars=10 um. 3D) Ykt6 membrane shift analysis in CBE-treated SH-SY5Y cells (50 µM, 2d, n=3). 3E) Co-IP of GFP-ykt6, bet1 and STX5 in CBE-treated SHSY5Y cells (n=5). 3F) Ykt6 membrane shift analysis in control or Gaucher disease (GD) iPSn (d100). a-Syn was knocked-out (SNCA KO) in GD lines by CRISPR/Cas9. Two exposures are included to better visualize cyt and mem ykt6 (n=4). 3G) Ykt6 membrane shift analysis in lenti-infected SH-SY5Y cells (moi3, dpi 10) (n=3). C, cytosolic; N, nuclear. 3H) GCase maturation was assessed by endo H digest in lenti-infected SH-SY5Y cells. Empty vector (vect), scrambled (scrb). 3I) Control iPSn were infected as in 3H and analyzed for GCase maturation (n=3). 3J) Live cell GCase activity in lenti-infected iPSn (n=4). 3K) Lysosomal mass measurement in control iPSn (n=4). Values are the mean+/−SEM, *p<0.05.
Figure 3B:
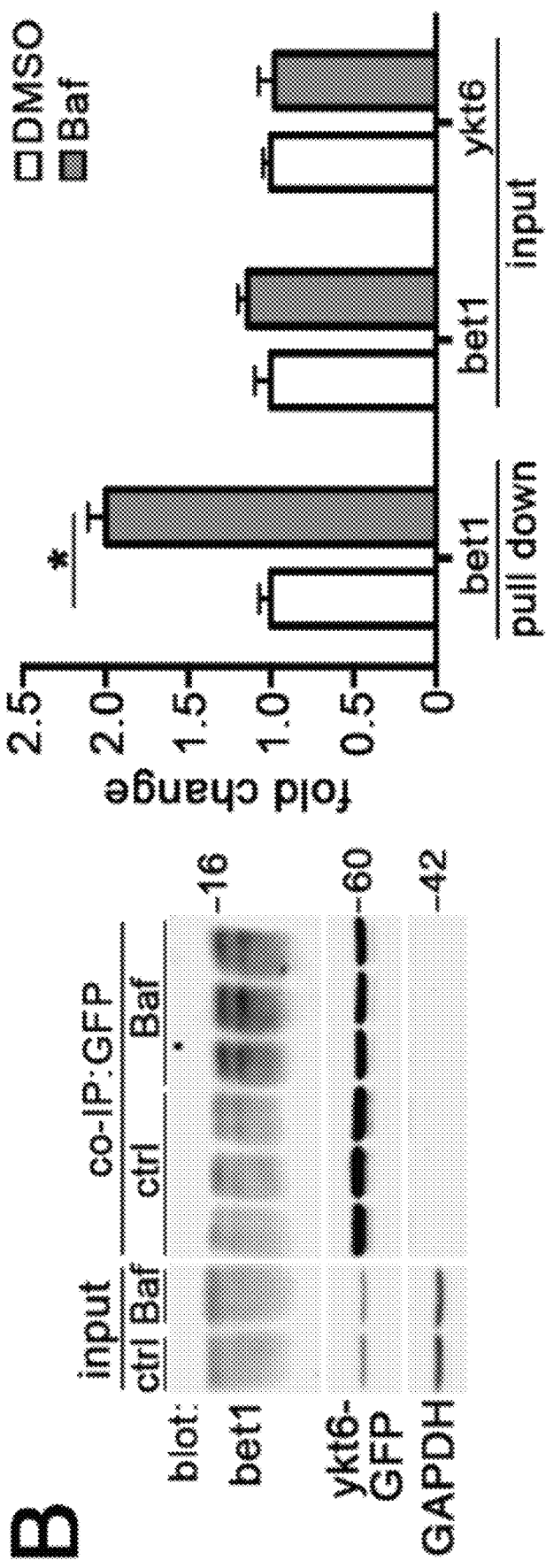
Figure 3C:
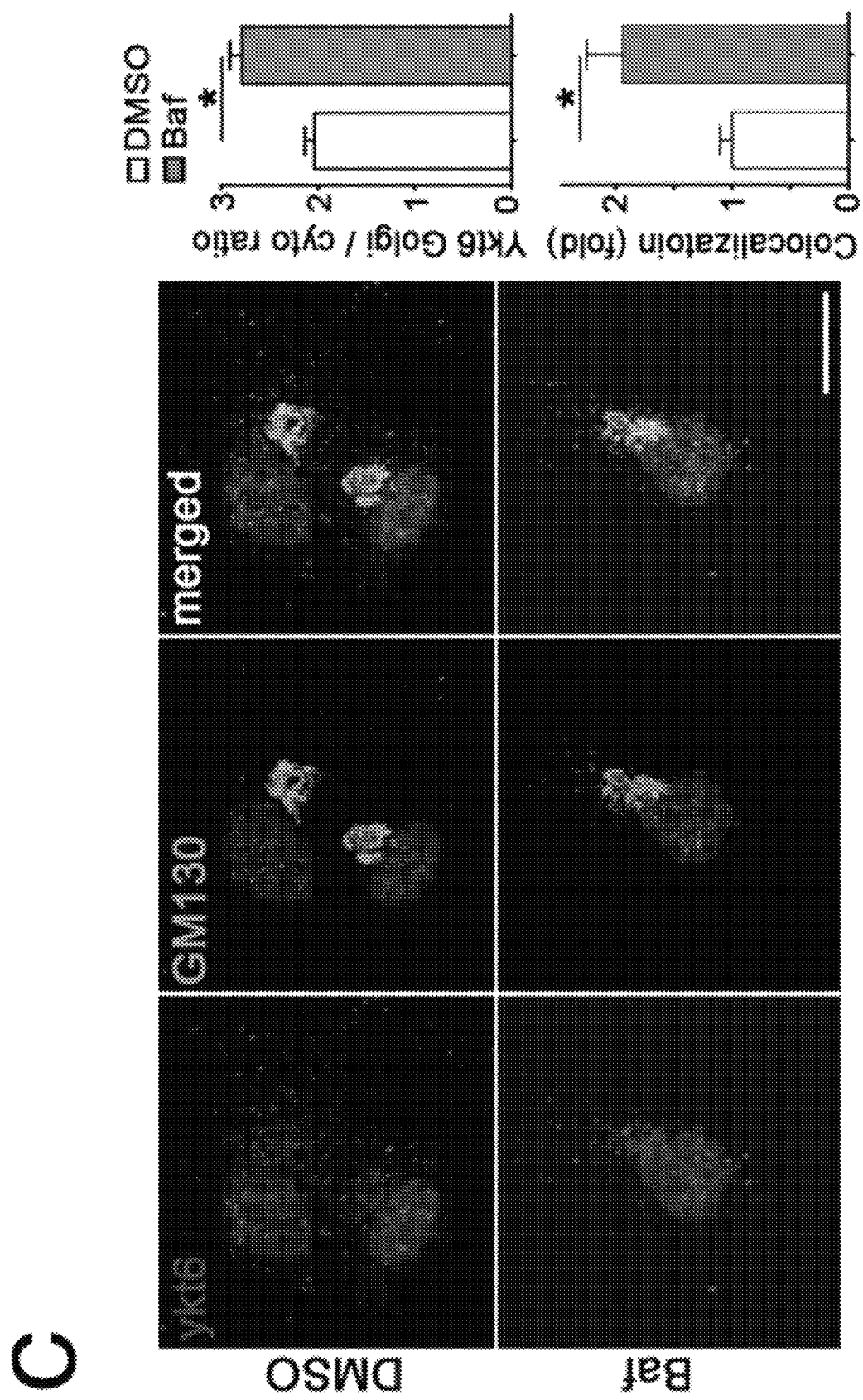
Figure 3D:
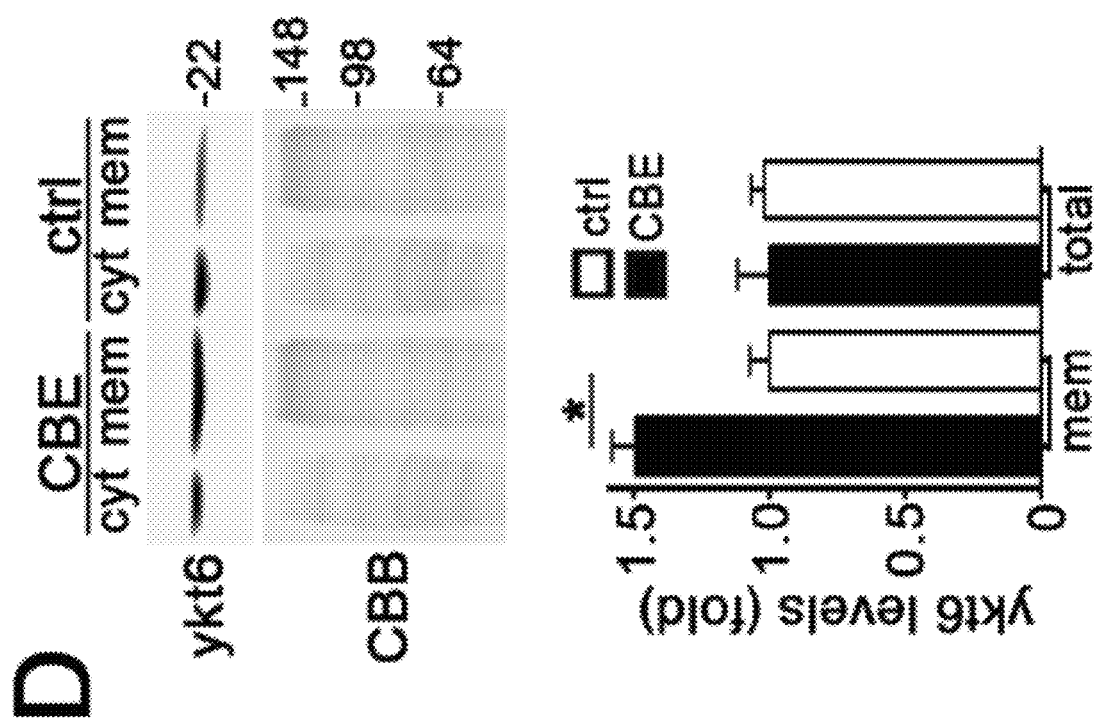
Figure 3E:
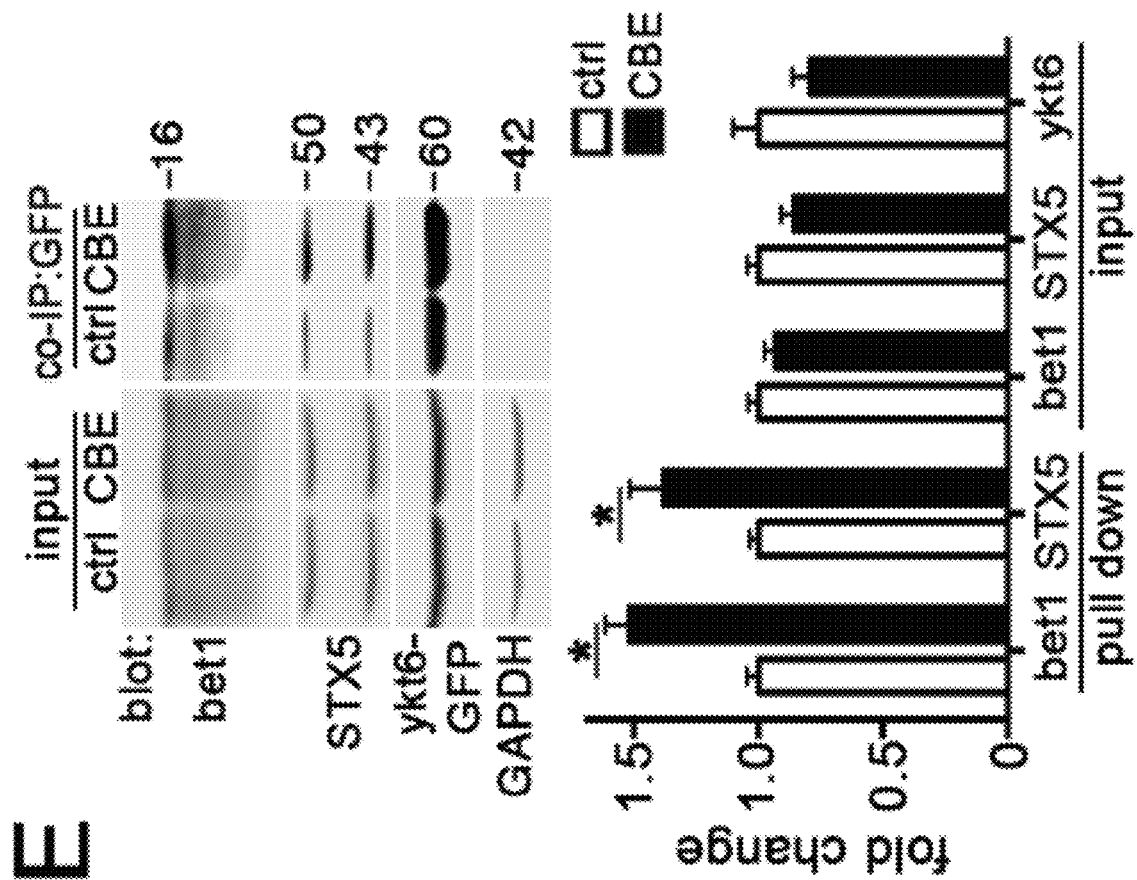
Figure 3F:
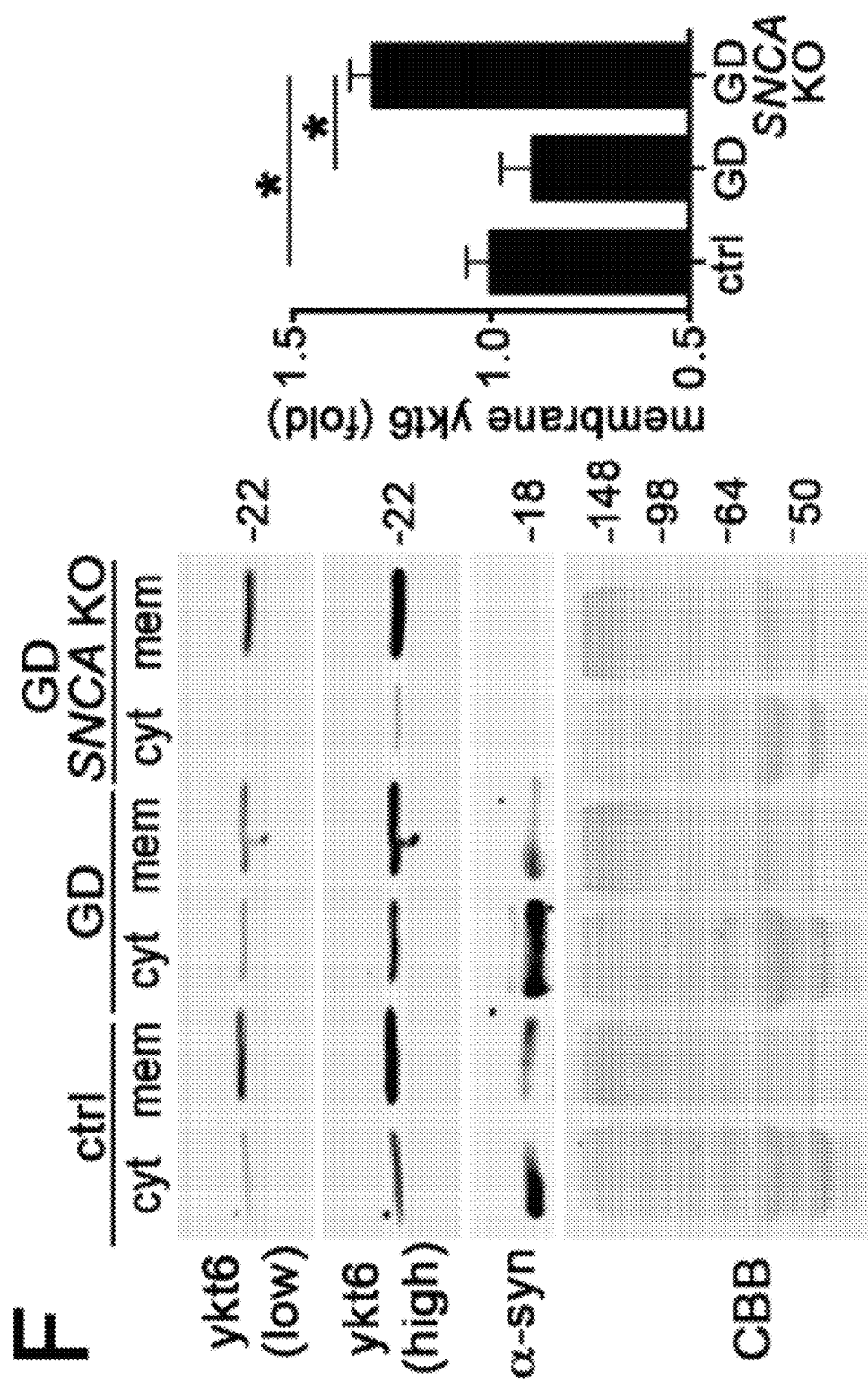
Figure 12D:
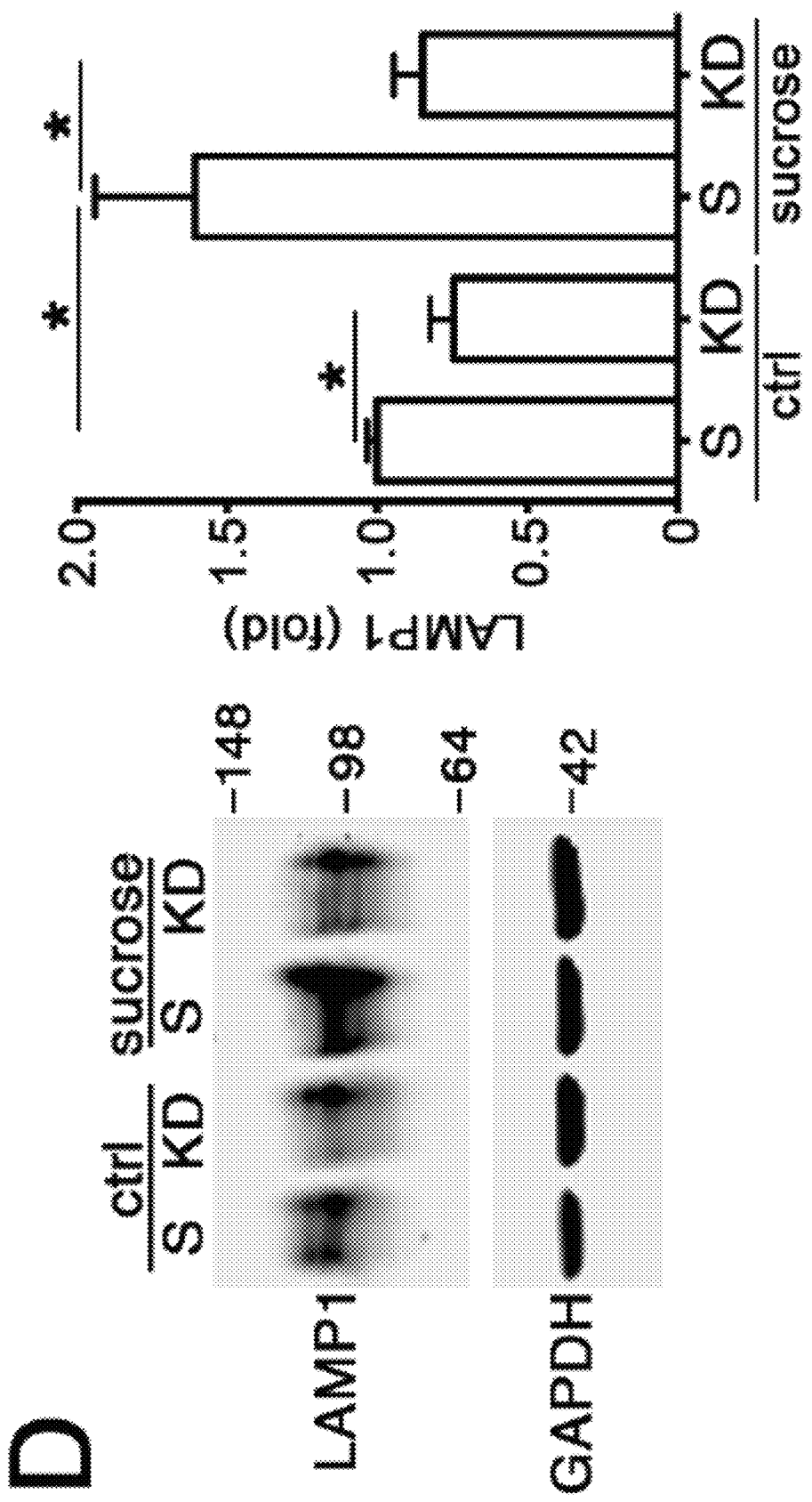
Figure 12E:
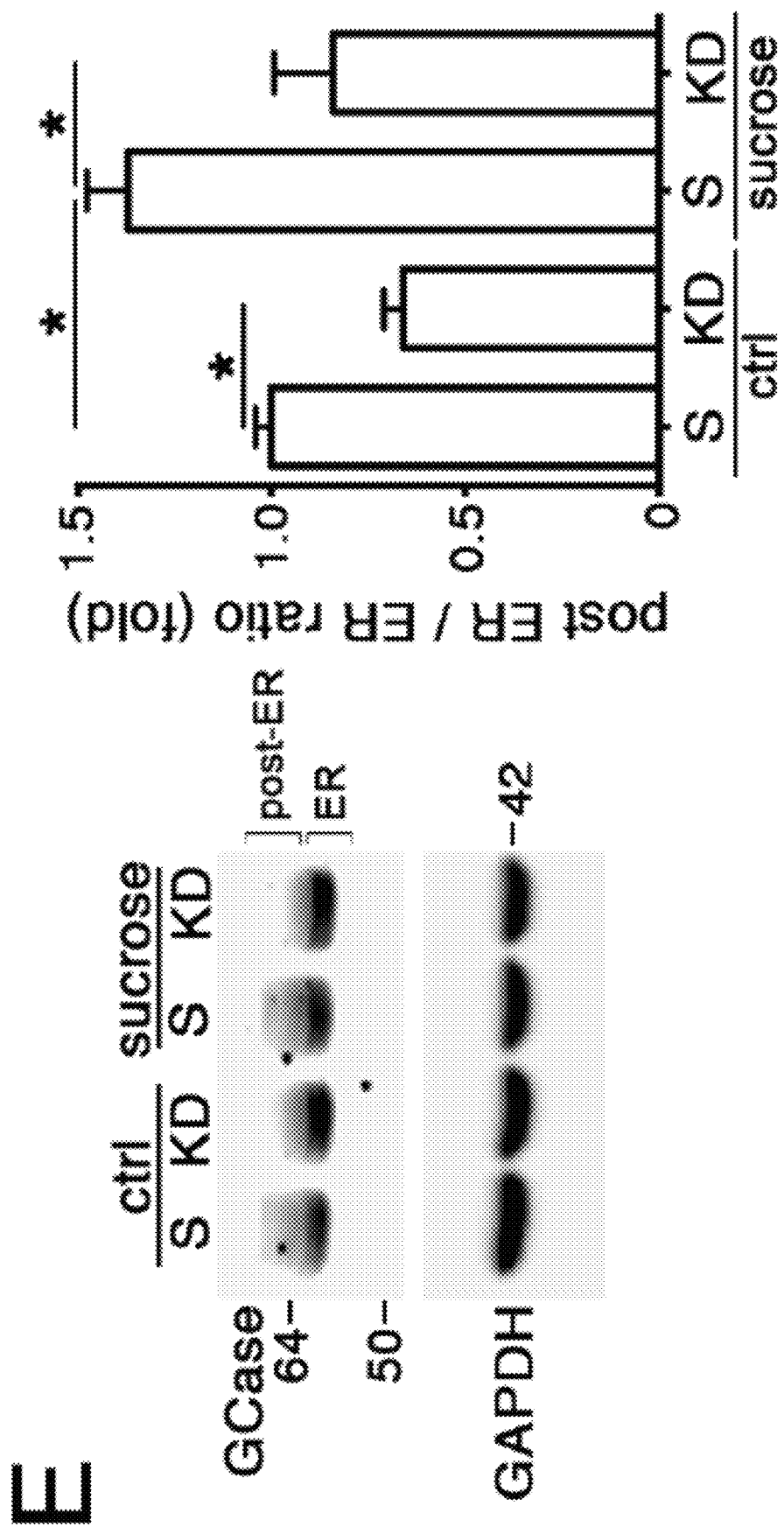
Figure 12F:
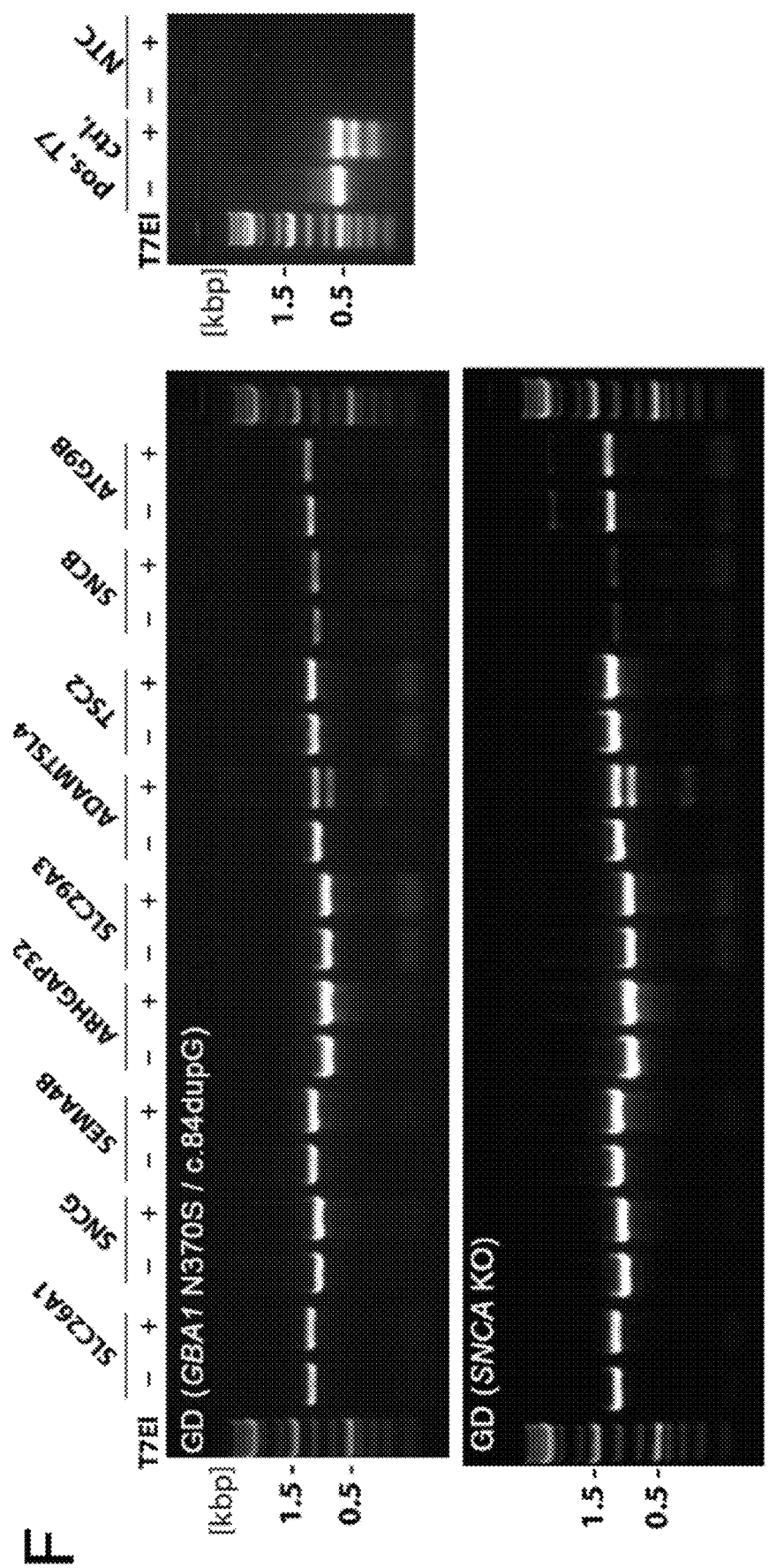

Ykt6 is required for the physiological response to lysosomal stress in human midbrain neurons. Our data indicates a preferential role of ykt6 in trafficking lysosomal proteins, and previous structural studies suggested tight regulatory features of ykt6 (Tochio et al., 2001) including an inactive reserve pool within the cytosol (Hasegawa et al., 2003; Thayanidhi et al., 2012; Tochio et al., 2001). While the cellular signals that activate ykt6 are unknown, we hypothesized that it may redistribute from the cytosol into membranes to promote trafficking of lysosomal machinery during periods of lysosomal stress. To test this, we treated healthy iPSn with lysosomal inhibitors bafilomycin A1 (baf) or NH4Cl, then measured ykt6 membrane distribution. Lysosomal inhibition caused a shift of ykt6 from the cytosol into membrane fractions, without changing total ykt6 (FIG. 3A). Baf treatment promoted the assembly of ykt6 ER-Golgi SNARE complexes and increased its localization to the Golgi (FIG. 3B, C). We confirmed that ykt6 responded to distinct initiators of lysosomal stress, including a chemically induced iPSn model of Gaucher disease (GD) using the GCase inhibitor CBE (Zunke et al., 2018), and sucrose-induced vacuolization (DeCourcy and Storrie, 1991). Both CBE and sucrose caused ykt6 to shift into membranes (FIG. 3D, 12C), and increased ykt6 SNARE complexes (FIG. 3E). Using the sucrose vacuolization iPSn model, we found that LAMP1 and GCase trafficking were elevated in a ykt6 dependent manner (FIG. 12D, E). To test a more natural, chronic model of lysosomal storage, we assessed ykt6 membrane association in a GD iPSn. Compared to healthy controls, GD iPSn showed only subtle changes in cytosolic and membrane ykt6 (FIG. 3F). This GD iPSn line accumulates pathogenic a-syn in a chronic manner (Mazzulli et al., 2016a), which may impede the response of ykt6. Therefore, we knocked-out (KO) SNCA in GD iPSn by CRISPR/Cas9 using a previously described editing strategy (Zunke et al., 2018). Analysis of off-target effects indicated a selective disruption of the SNCA gene (FIG. 12F), and western blot validated that no a-syn protein was made (FIG. 3F). GD-SNCA KO lines demonstrated a significant shift of ykt6 into membranes when compared to both its parental GD line and a healthy control (FIG. 3F). Together, this indicates that lysosomal stress activates ykt6, which results in enhanced trafficking of lysosomal components.

Figure 3G:
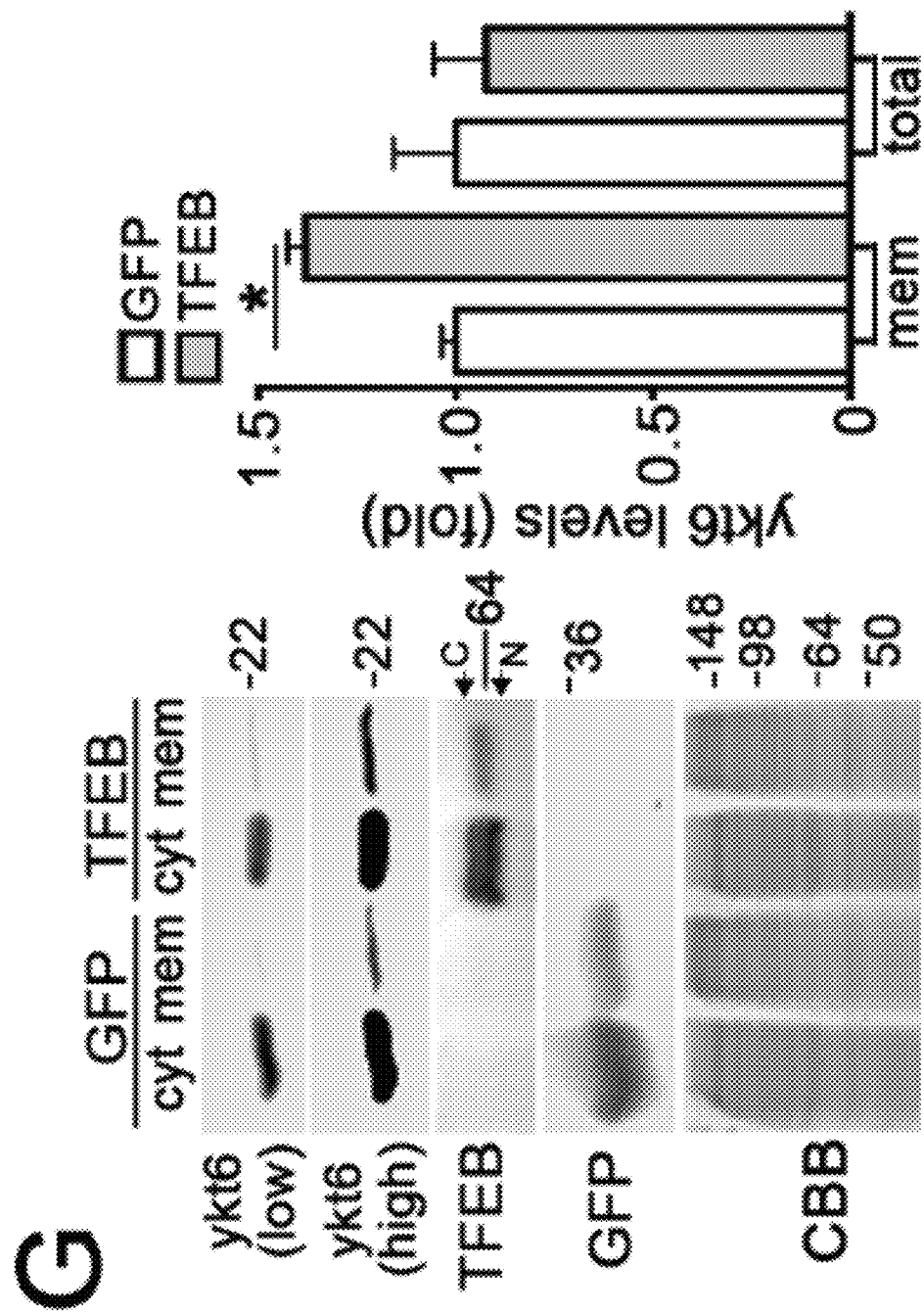
Figure 3H:
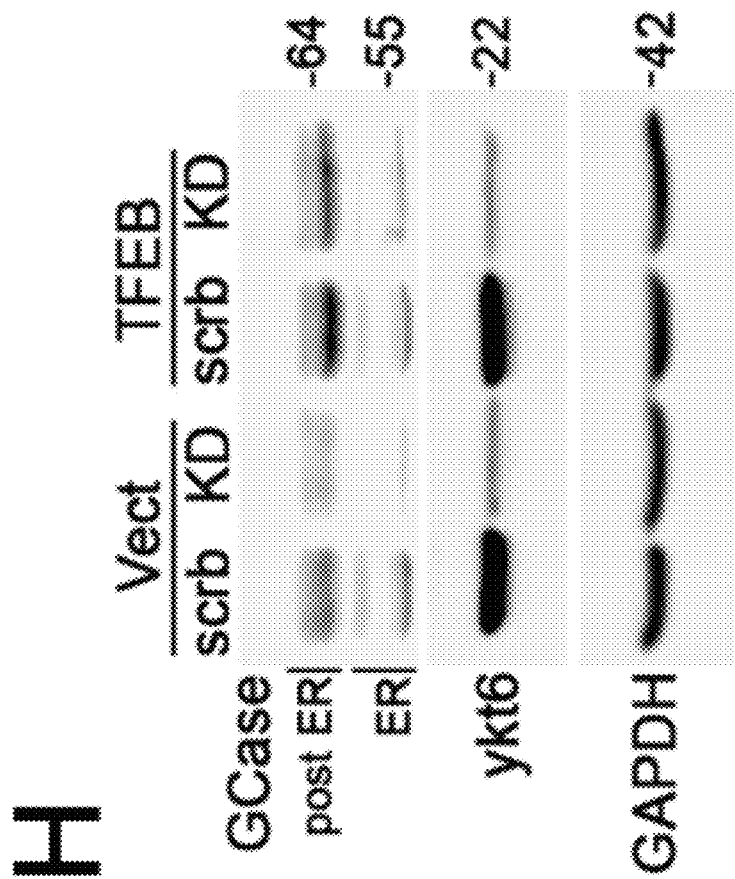
Figure 3I:
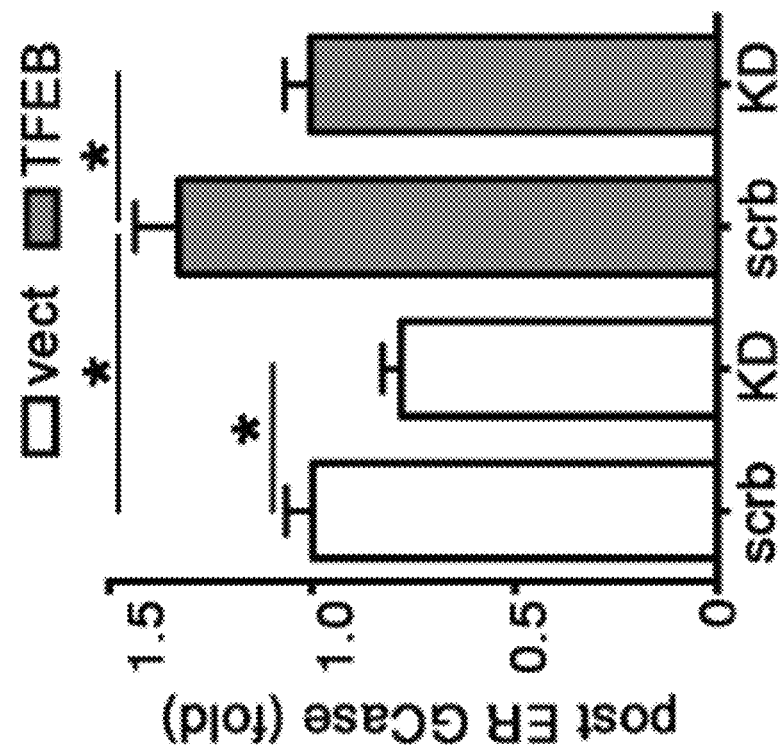
Figure 3J:
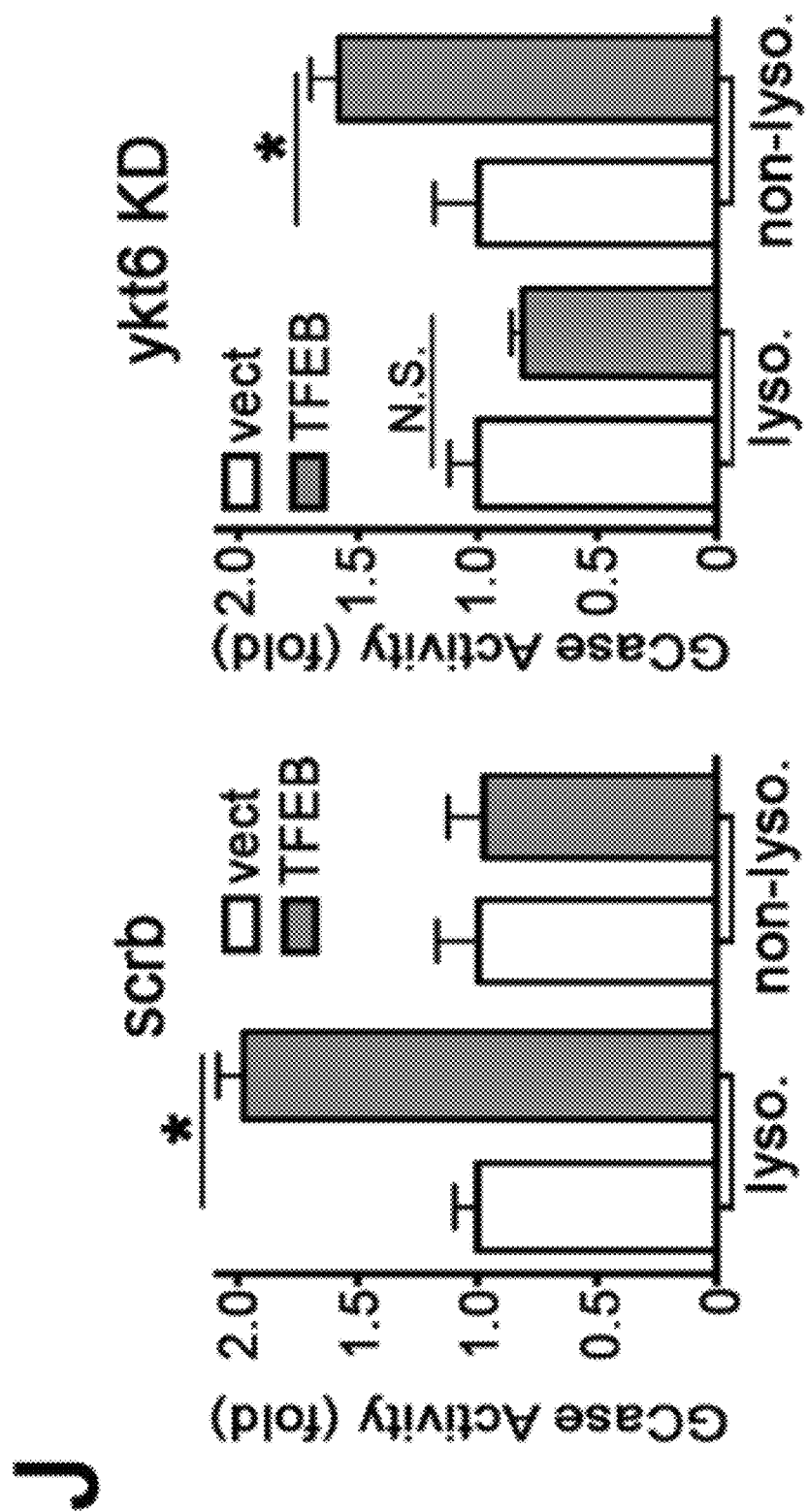
Figure 3K:
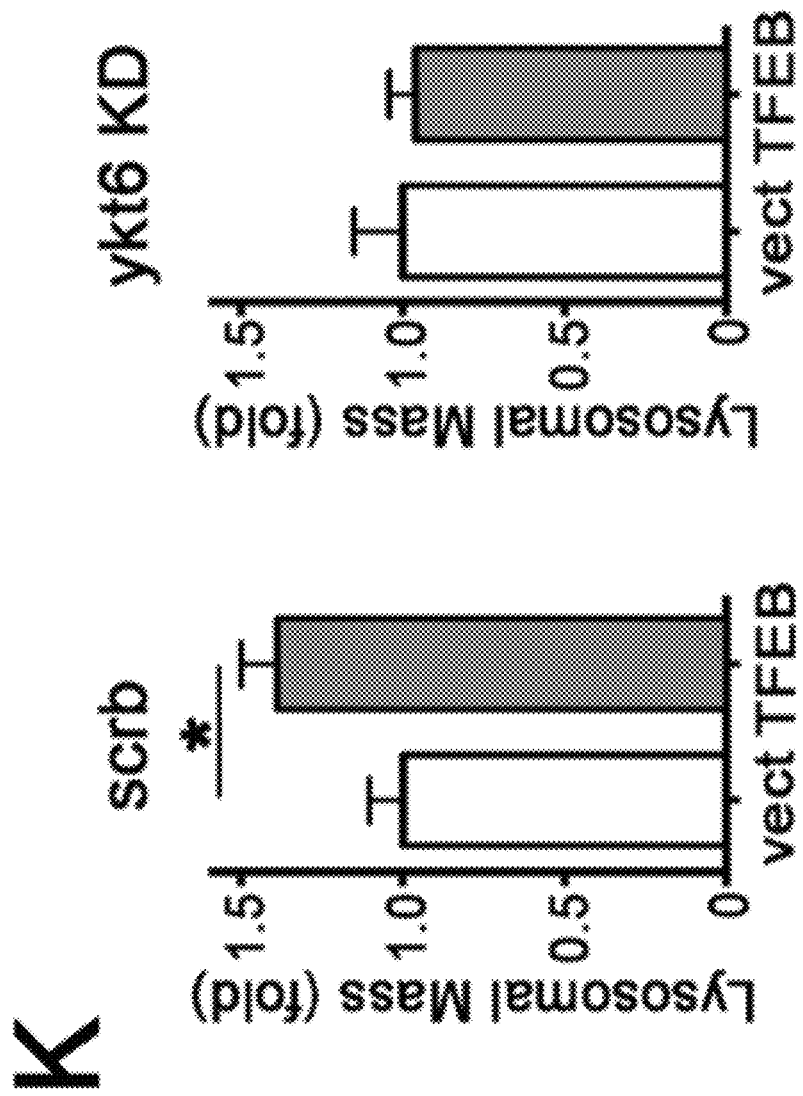

Since TFEB responds to lysosomal stress by inducing lysosomal biogenesis (Sardiello et al., 2009), we next determined if ykt6 was involved in hydrolase trafficking upon TFEB overexpression. We found increased levels of membrane-associated ykt6 upon TFEB overexpression (FIG. 3G), and enhanced GCase trafficking that was reduced by ykt6 KD (FIG. 3H, I). TFEB elevated GCase activity within lysosomes, however ykt6 KD abolished this effect, and instead elevated activity in non-lysosomal compartments (FIG. 3J). TFEB increased lysosomal mass as expected, and this effect was also diminished by ykt6 KD (FIG. 3K). Together, this indicates that ykt6 responds to distinct stress stimuli that converge on lysosomal pathways, by synergizing with TFEB to enhance cellular clearance during stressful metabolic conditions.

Figure 4A:
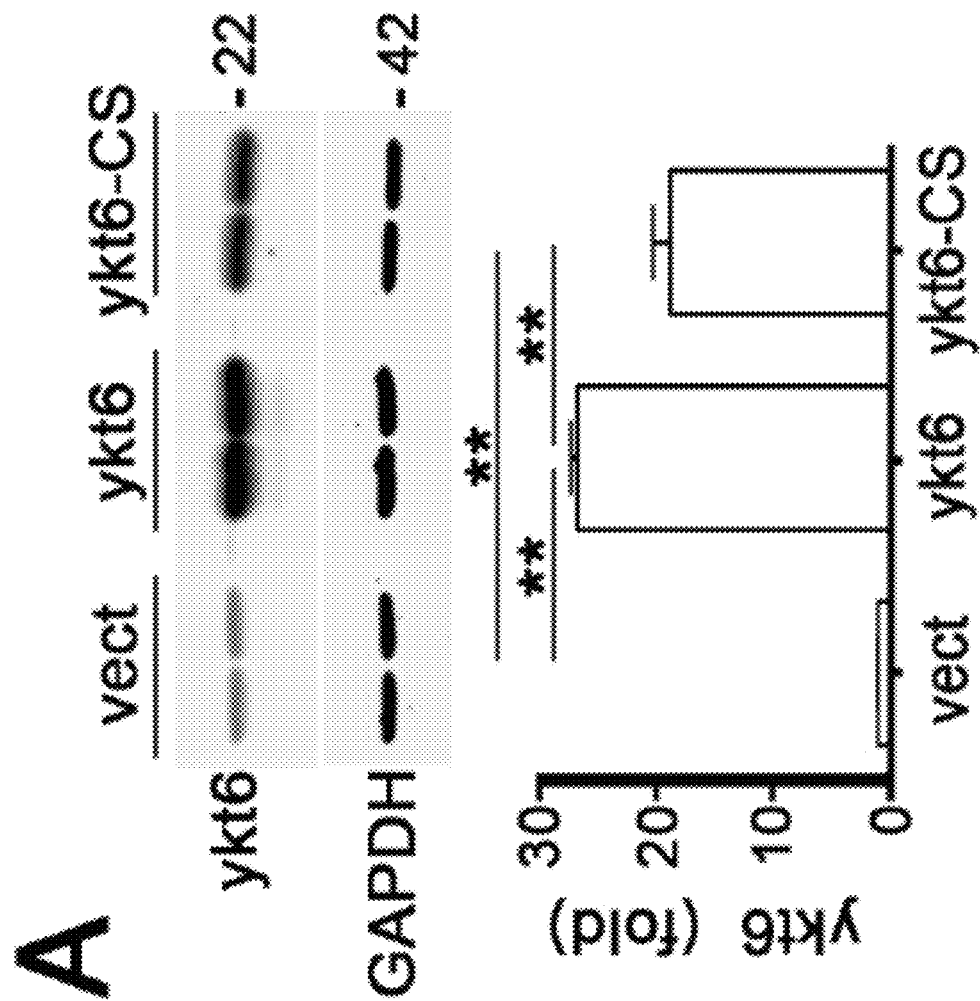
FIGS. 4A, 4B, 4C, 4D, 4E, 4F, 4G, 4H, and 4I. Ykt6 rescues lysosomal function and is activated by blocking its farnesylation. 4A) A53T iPSn and isogenic corrected lines (corr) were lenti-infected with empty vector (vect) or ykt6 constructs (wt or CS that cannot be farnesylated) and analyzed by western blot (moi 3, dpi 42). 4B) GCase maturation analysis in lenti-infected A53T iPSn by endo H digest/western blot (n=12). 4C) Analysis of ER-Golgi trafficking in living H4 cells-transfected with ykt6 wt or CS (n=4). 4D) Immunostaining analysis of GCase and LAMP2A in SH-SY5Y a-syn cells (n=3 wells, values from individual cells are plotted). Scale bars=10 um. 4E) Immunostaining analysis of GCase and LAMP2A in A53T iPSn at 42 dpi. Scale bars=5 um. 4F) GCase activity was assessed in living A53T iPSn (n=6). 4G) Sequential extraction/western blot analysis of a-syn using C20 (total a-syn) or syn303 (oxidized a-syn) (n=7). Recombinant a-syn was used as a positive control, and a-syn knock-out iPSn were used as a negative control. *, non-specific bands; M, MW marker. N=4, normalized to total protein (CBB). 4H) Cell-surface biotinylation assay in SH-SY5Y a-syn cells, expressing wt or CS ykt6, followed by ykt6 and NCAM western blot. Bound lanes represent biotinylated proteins on the cell surface (n=6). 4I) Quantification of neuroserpin levels in culture media by ELISA of lenti-infected SH-SY5Y cells (n=3). Values are the mean+/−SEM, *p<0.05, p0.01, **p<0.0001.
Figure 4B:
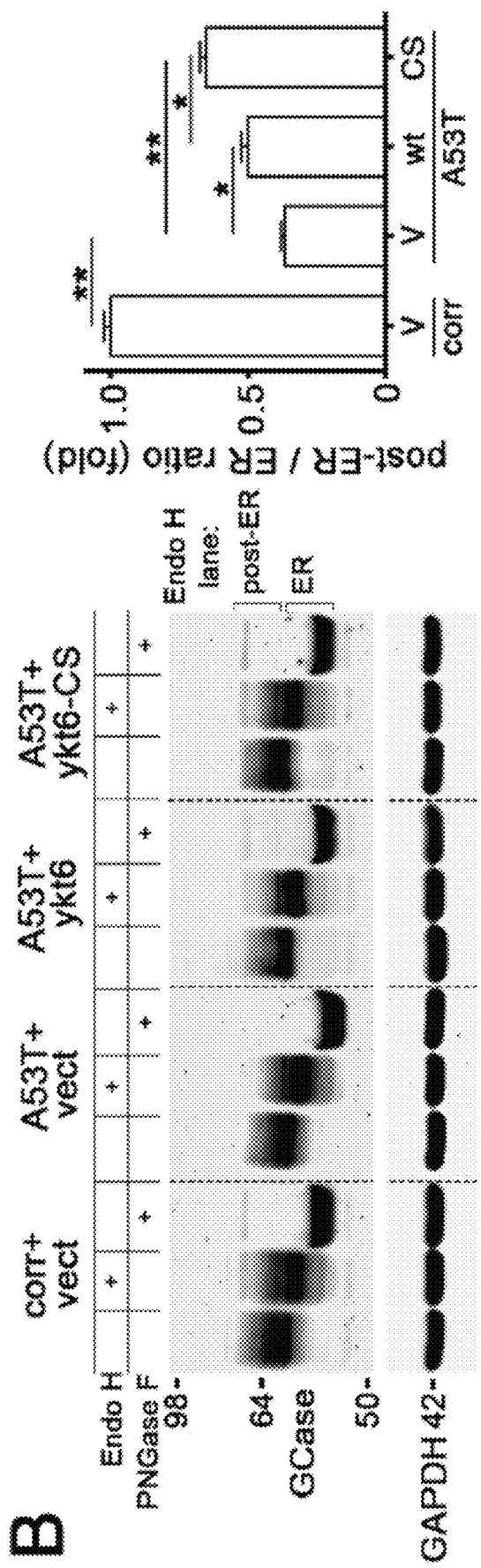
Figure 4C:
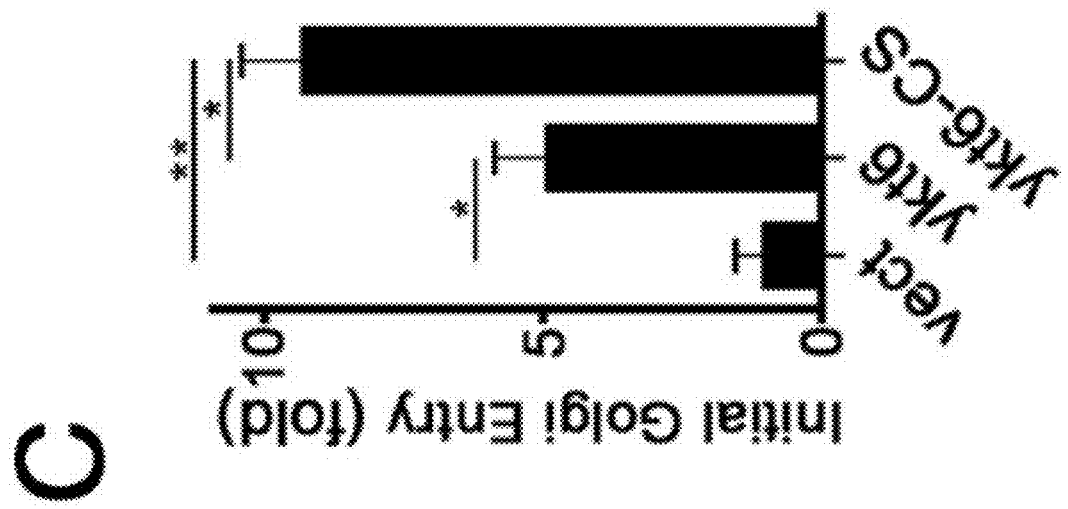
Figure 4D:
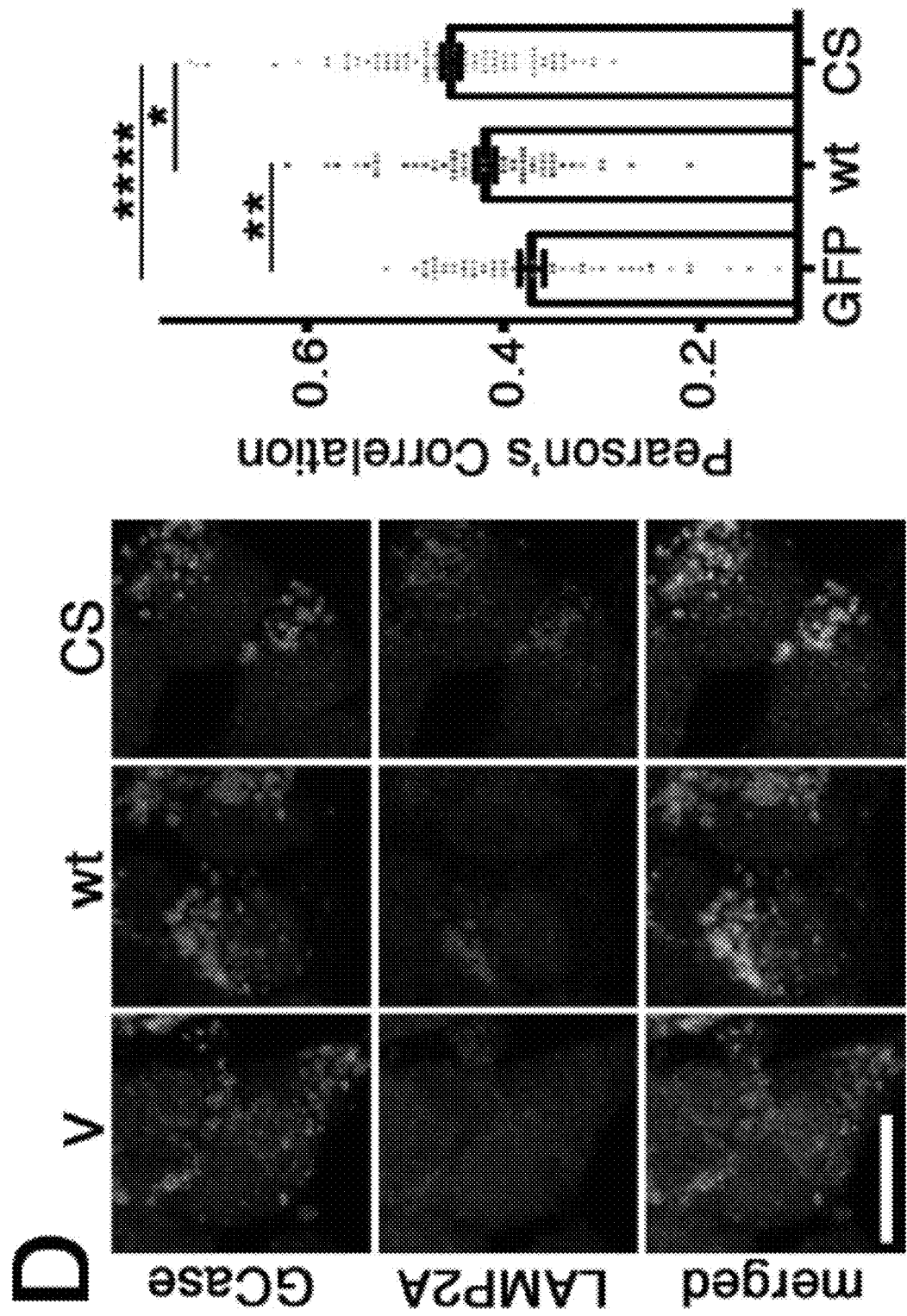
Figure 4E:
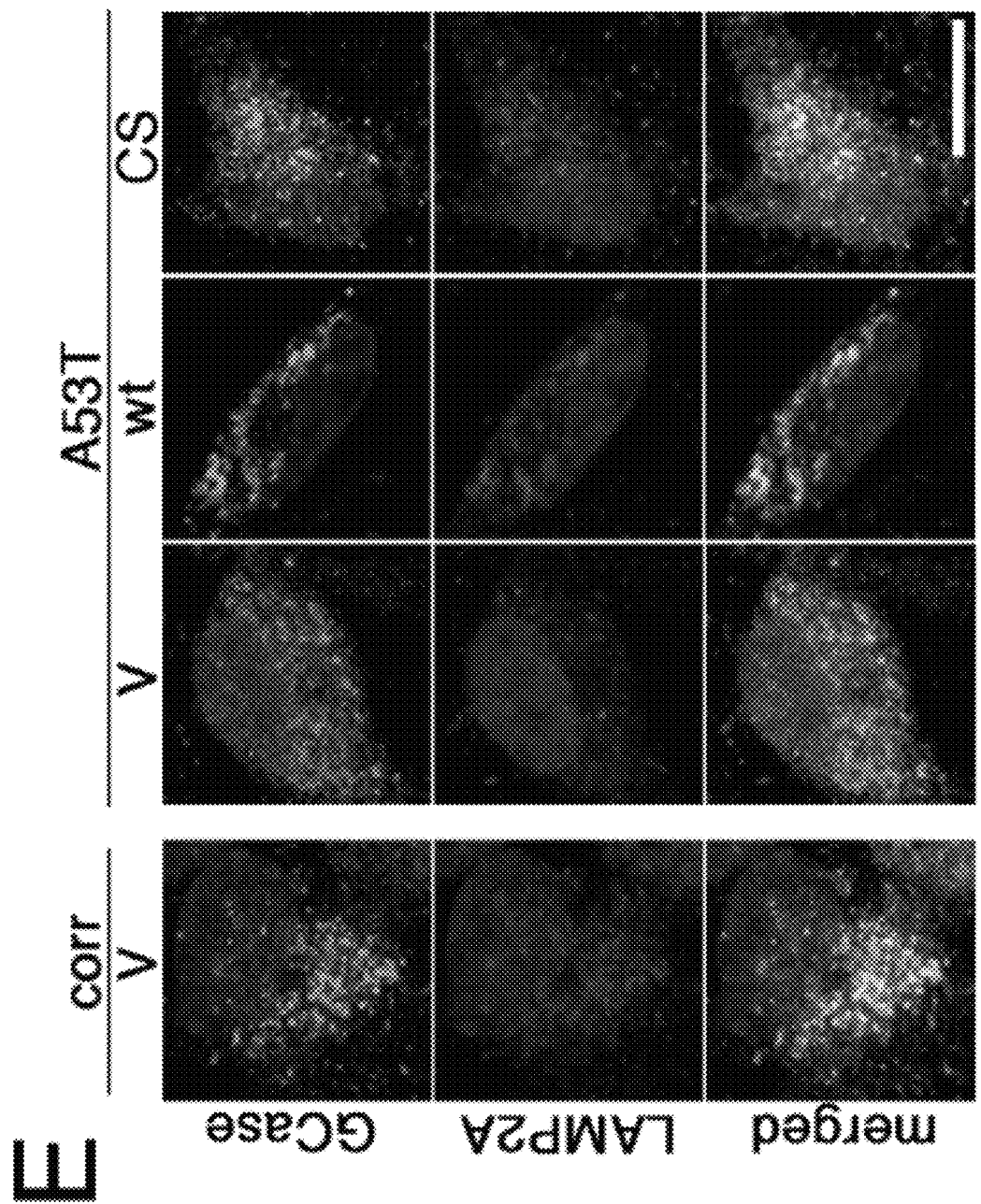
Figure 4F:
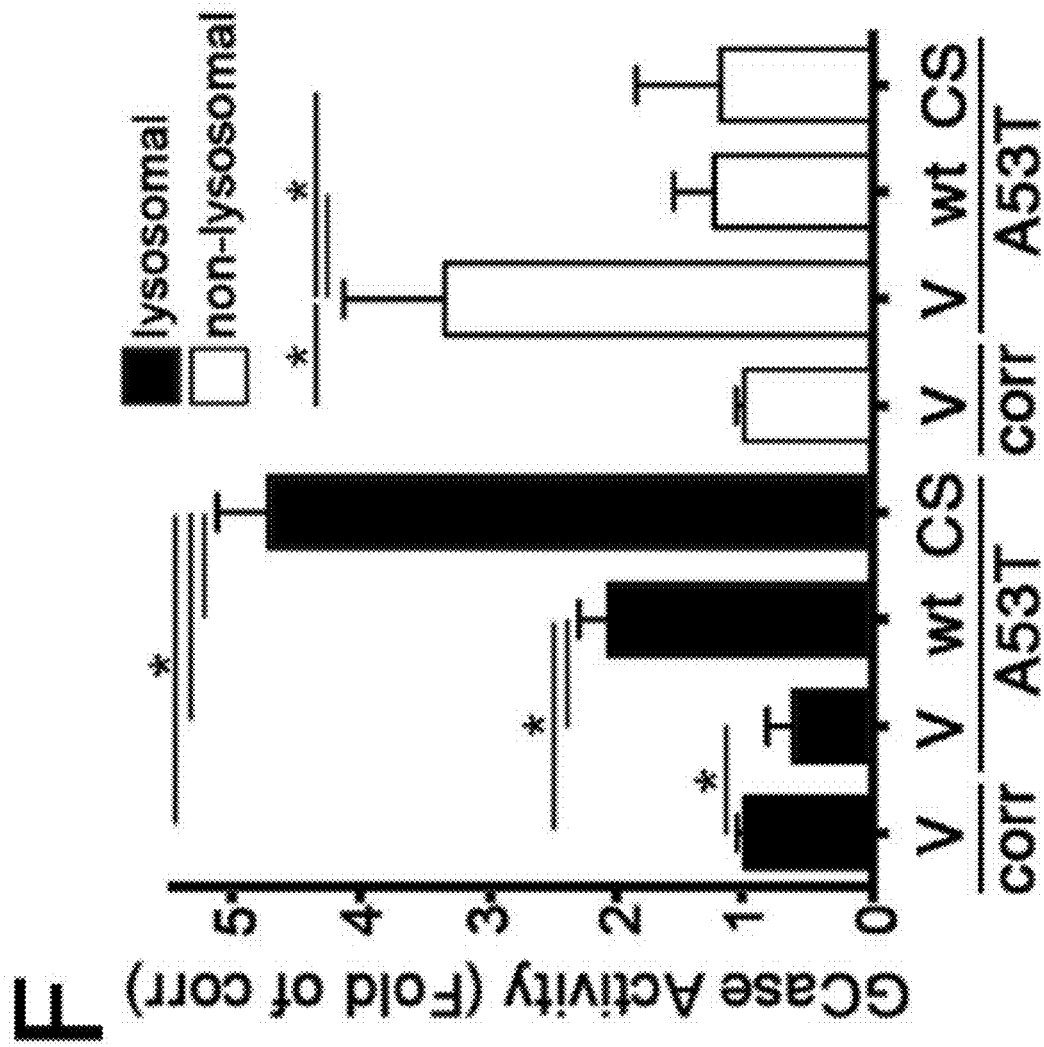
Figure 4G:
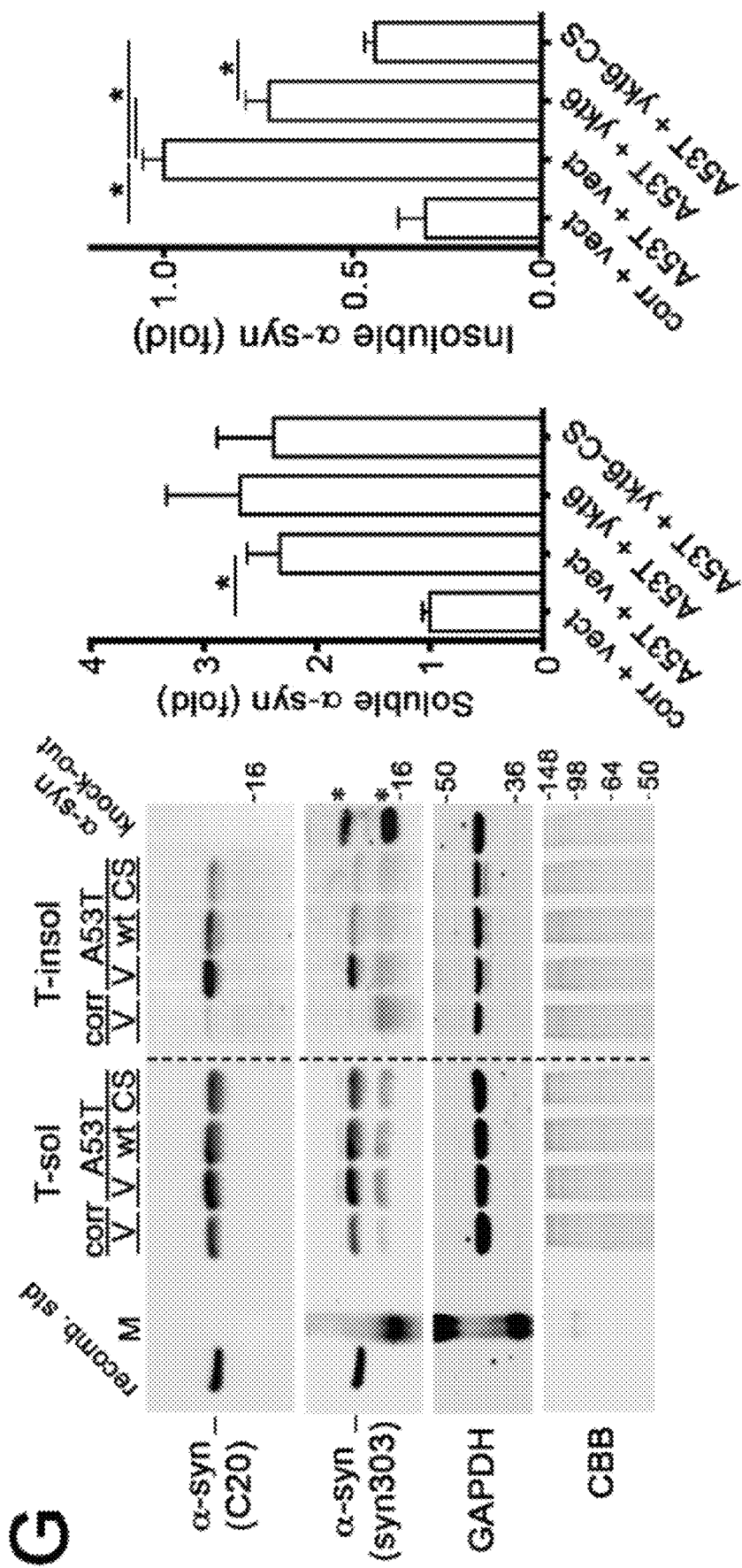
Figure 13A:
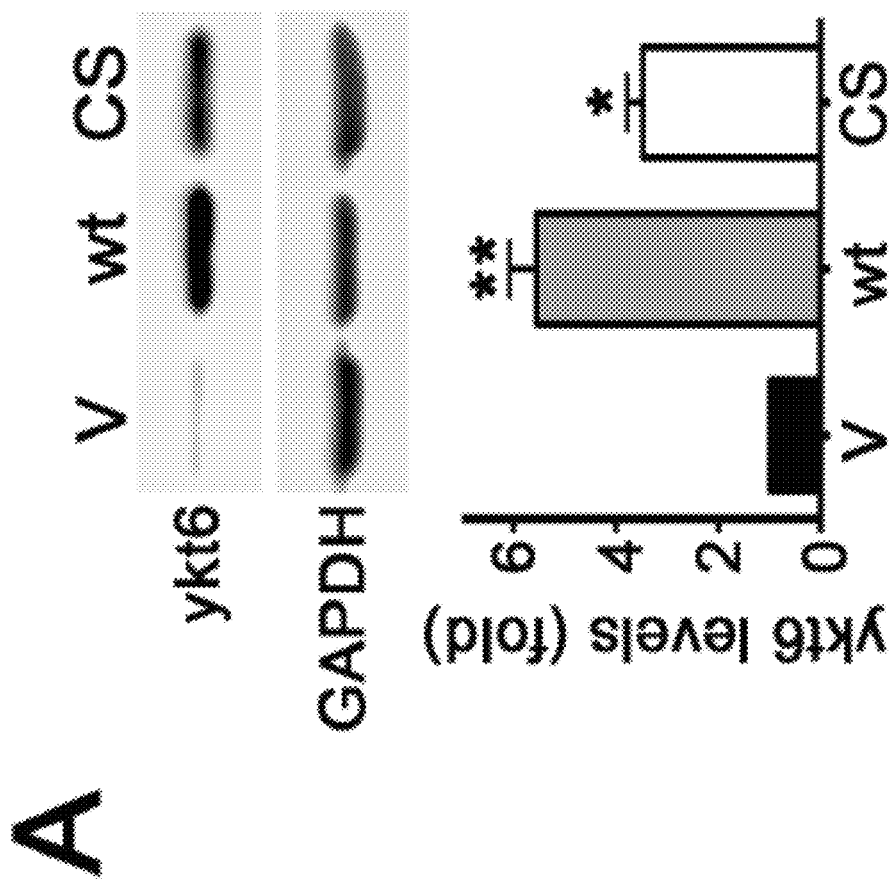
Figure 13B:
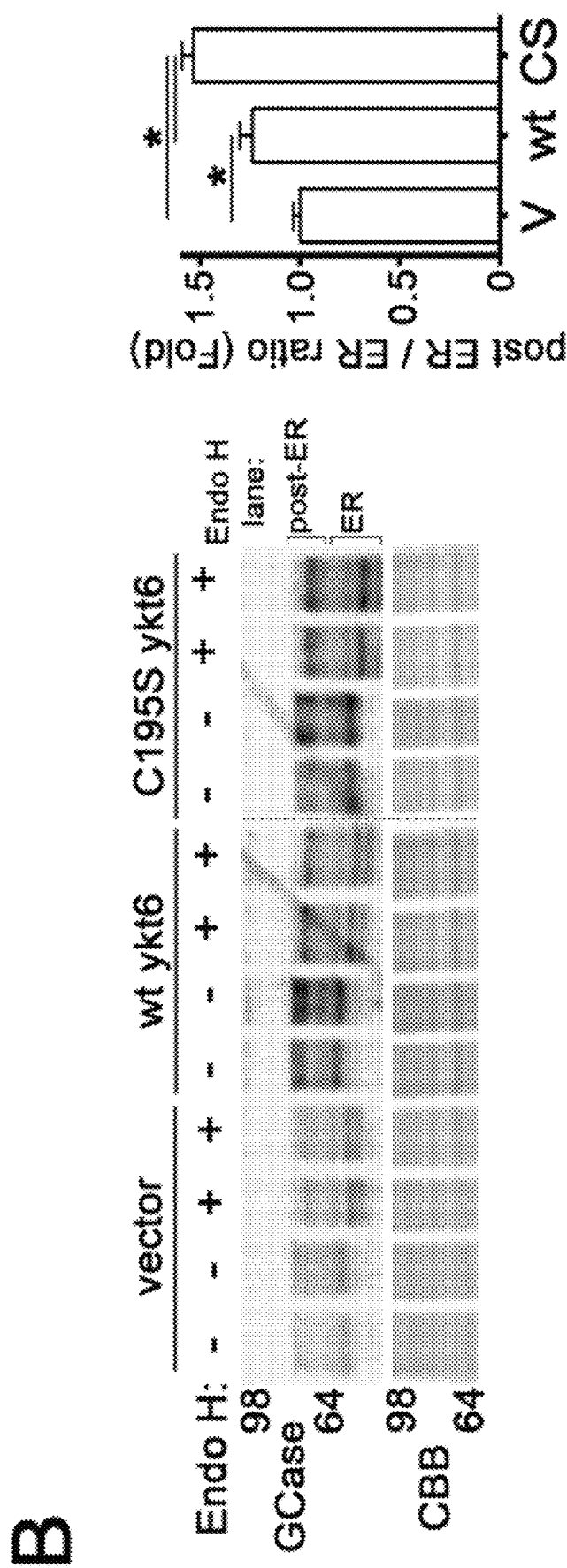
Figure 13C:
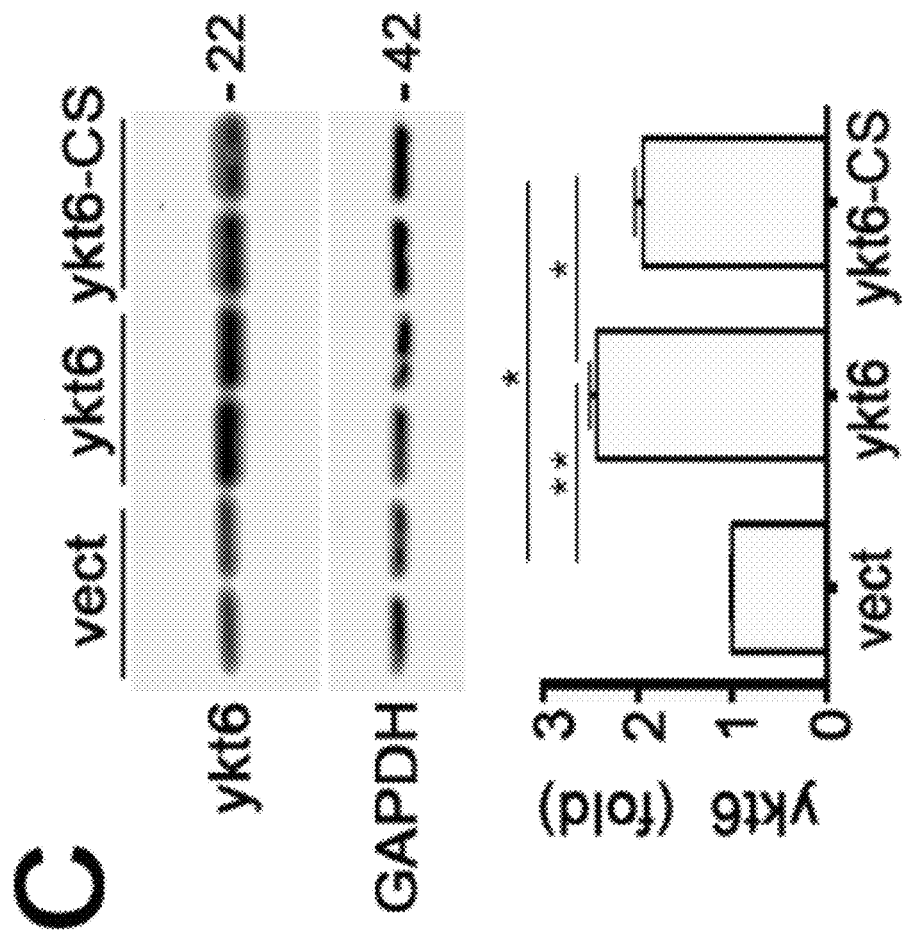
Figure 13D:
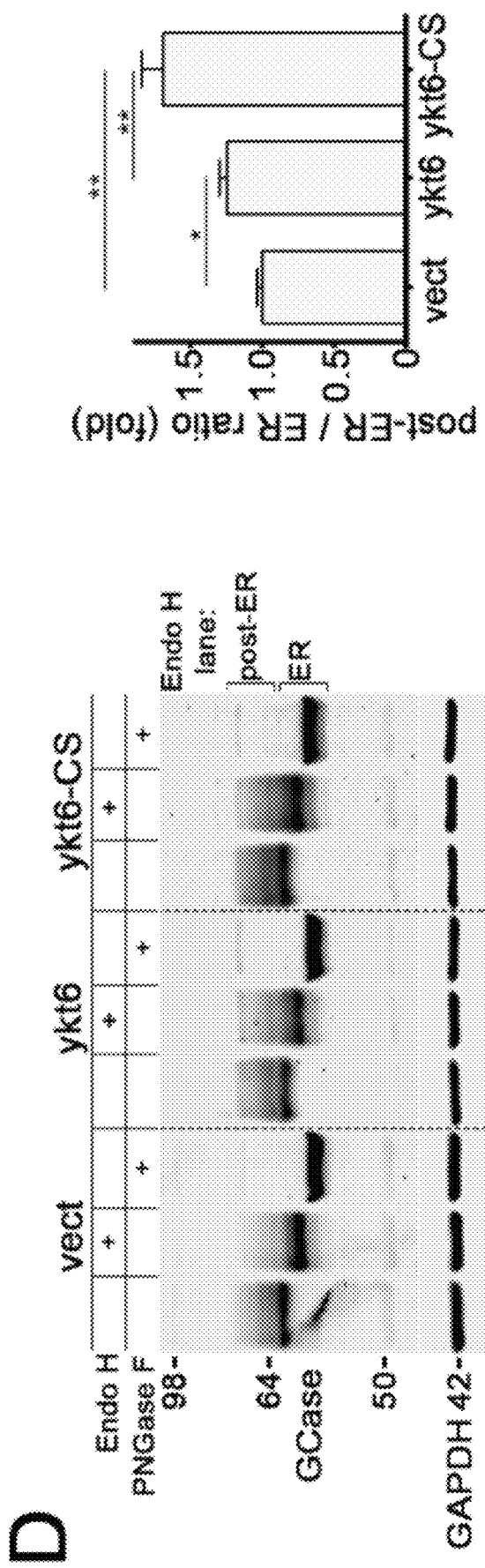
Figure 13E:
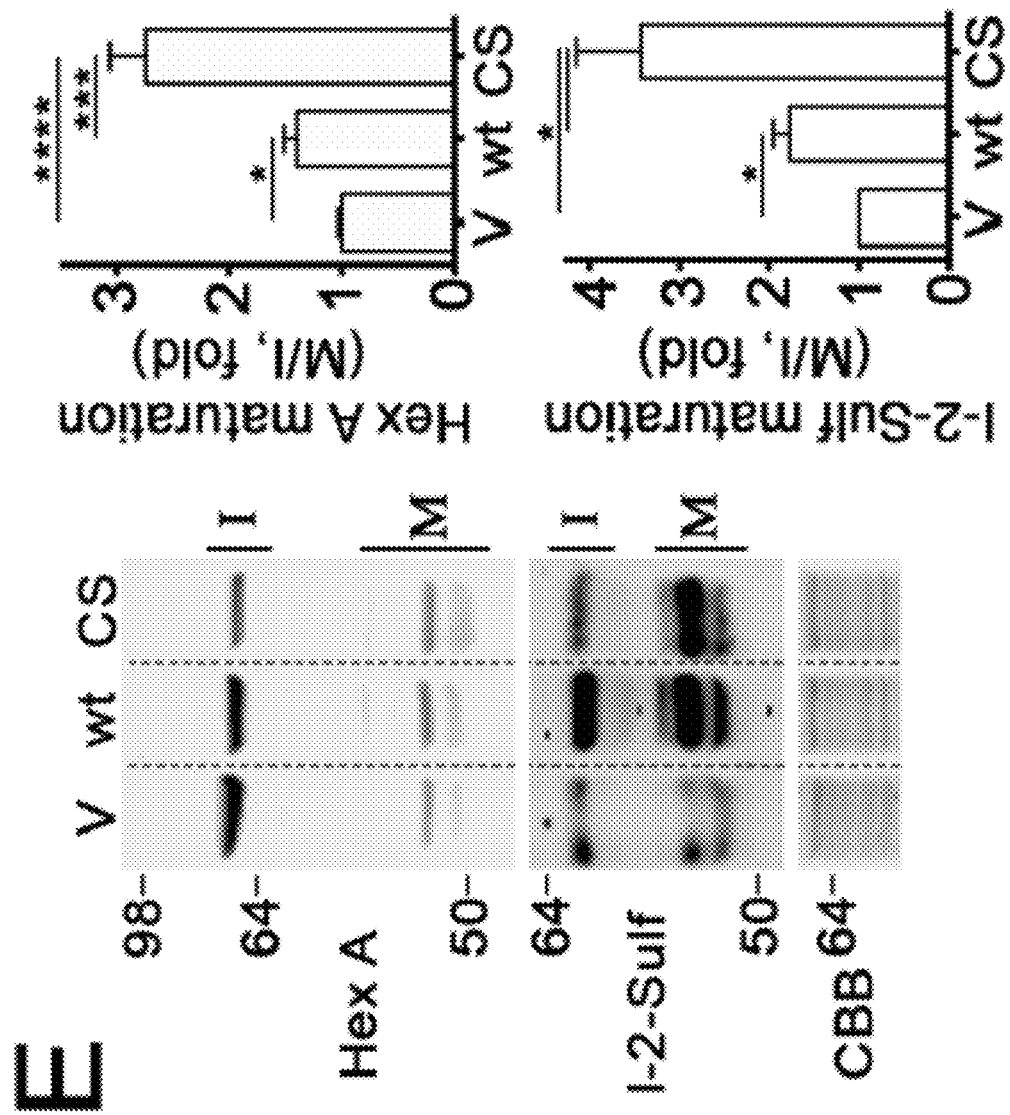
Figure 13F:
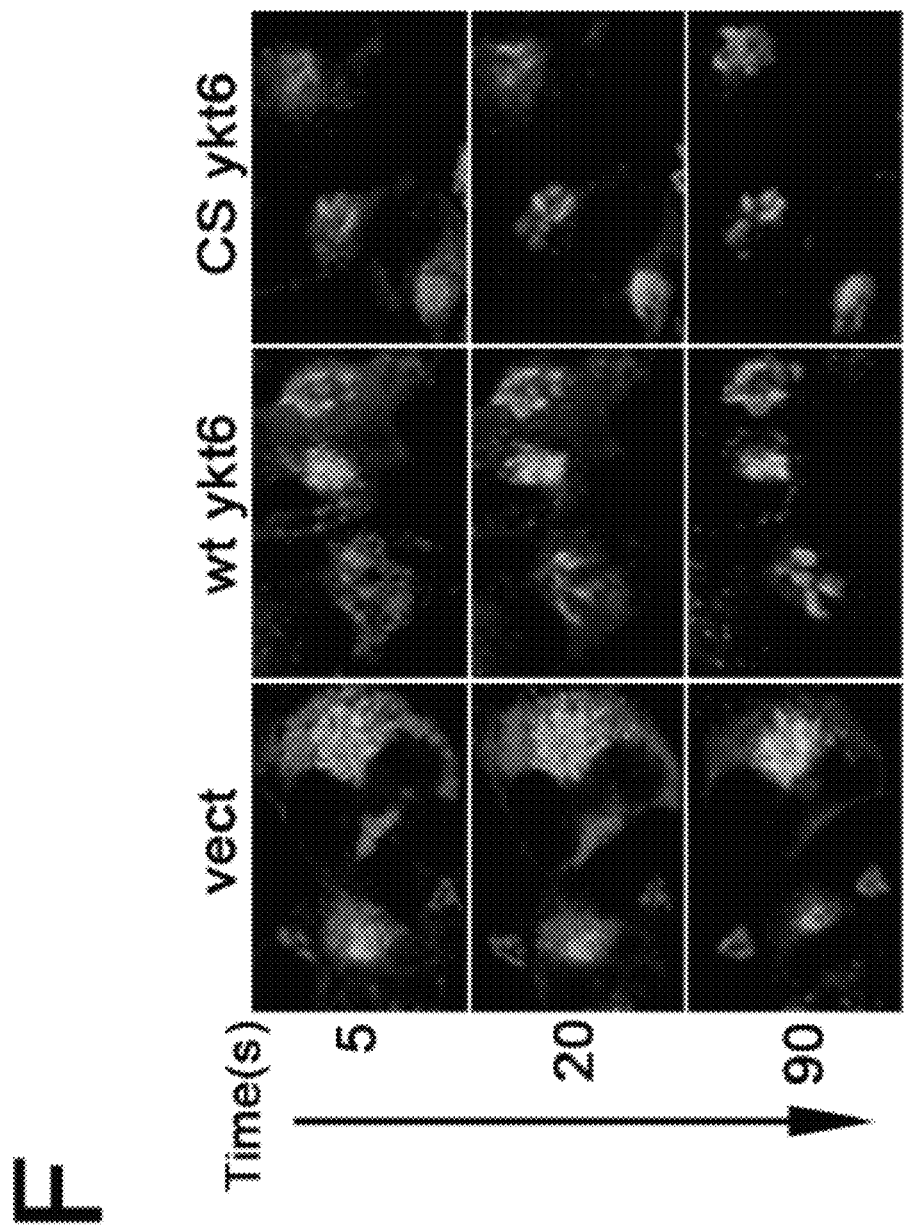
Figure 13G:
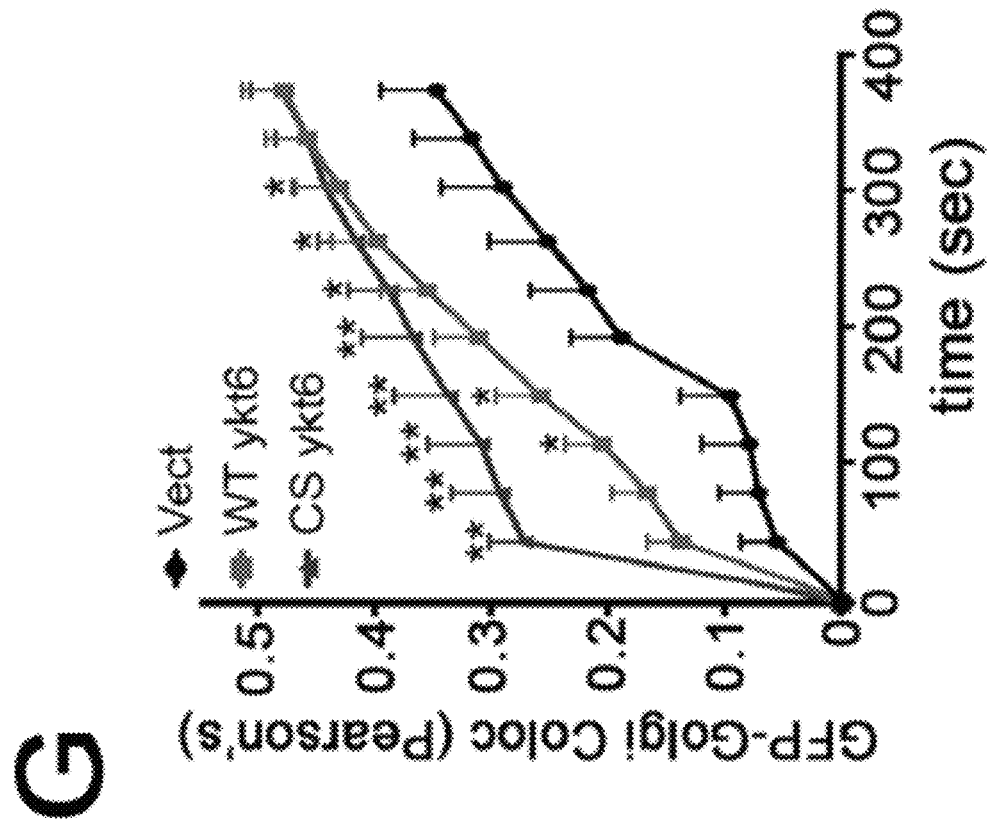
Figure 13H:
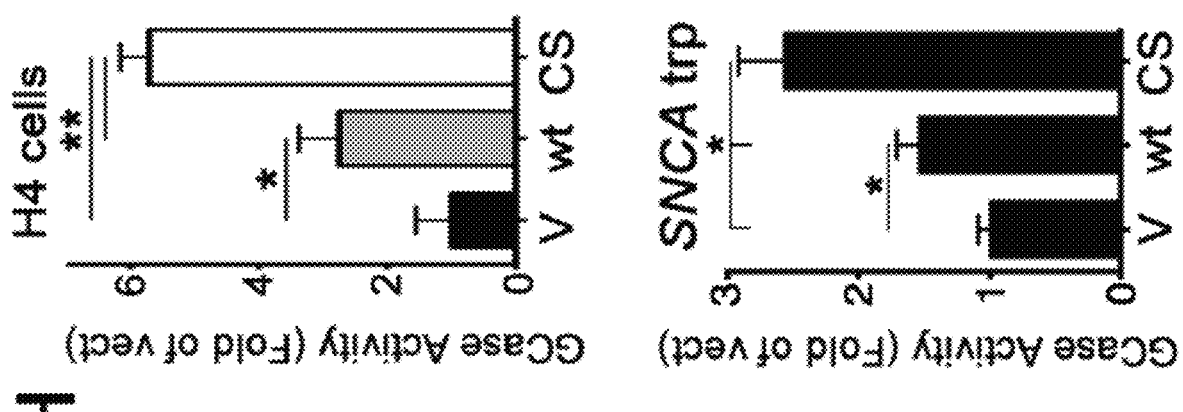

Ykt6 rescues lysosomal function in PD iPSn and is enhanced by blocking its farnesylation. To determine if overexpressing ykt6 could restore lysosomal function in PD iPSn, we overexpressed either wild-type (wt) ykt6 or a mutant form that cannot be farnesylated (C195S, or CS) by lentivirus. We reasoned that blocking farnesylation of ykt6 may enhance its function by promoting an open, active conformation (Wen et al., 2010). Expression of wt ykt6 rescued GCase trafficking in PD iPSn and blocking its farnesylation enhanced this effect, despite the lower expression levels of titer-matched ykt6-CS (FIG. 4A, B). This effect was reproducible in multiple synucleinopathy models (FIG. 13A-D). Ykt6 also improved the maturation of hexosaminidase A and iduronate-2-sulfatase, indicating a general effect for lysosomal hydrolases (FIG. 13E). ER-Golgi transport was directly assessed using a live-cell trafficking assay (Gordon et al., 2010). We found that wt ykt6 enhanced ER-Golgi transport, and this effect was nearly doubled by ykt6-CS (FIG. 3C; 13F, G). Colocalization of GCase with LAMP2A was increased upon expression of ykt6 wt or CS in both SH-SY5Y cells and A53T iPSn (FIG. 4D, E), consistent with increased targeting to lysosomes. Ykt6 enhanced GCase activity within lysosomes while decreasing non-lysosomal activity in PD iPSn and cell lines, which was augmented by expression of ykt6-CS (FIG. 4F; FIG. 13H). Finally, we tested if ykt6 could reduce pathological a-syn in PD iPSn, since previous studies showed that enhancing GCase activity could clear a-syn (Aflaki et al., 2016; Mazzulli et al., 2016b; Rocha et al., 2015; Sardi et al., 2013). We found that insoluble a-syn was decreased by ~25% with wt ykt6 and ~60% with ykt6-CS, while no consistent change was found in the soluble a-syn fraction (FIG. 4G).

Figure 4H:
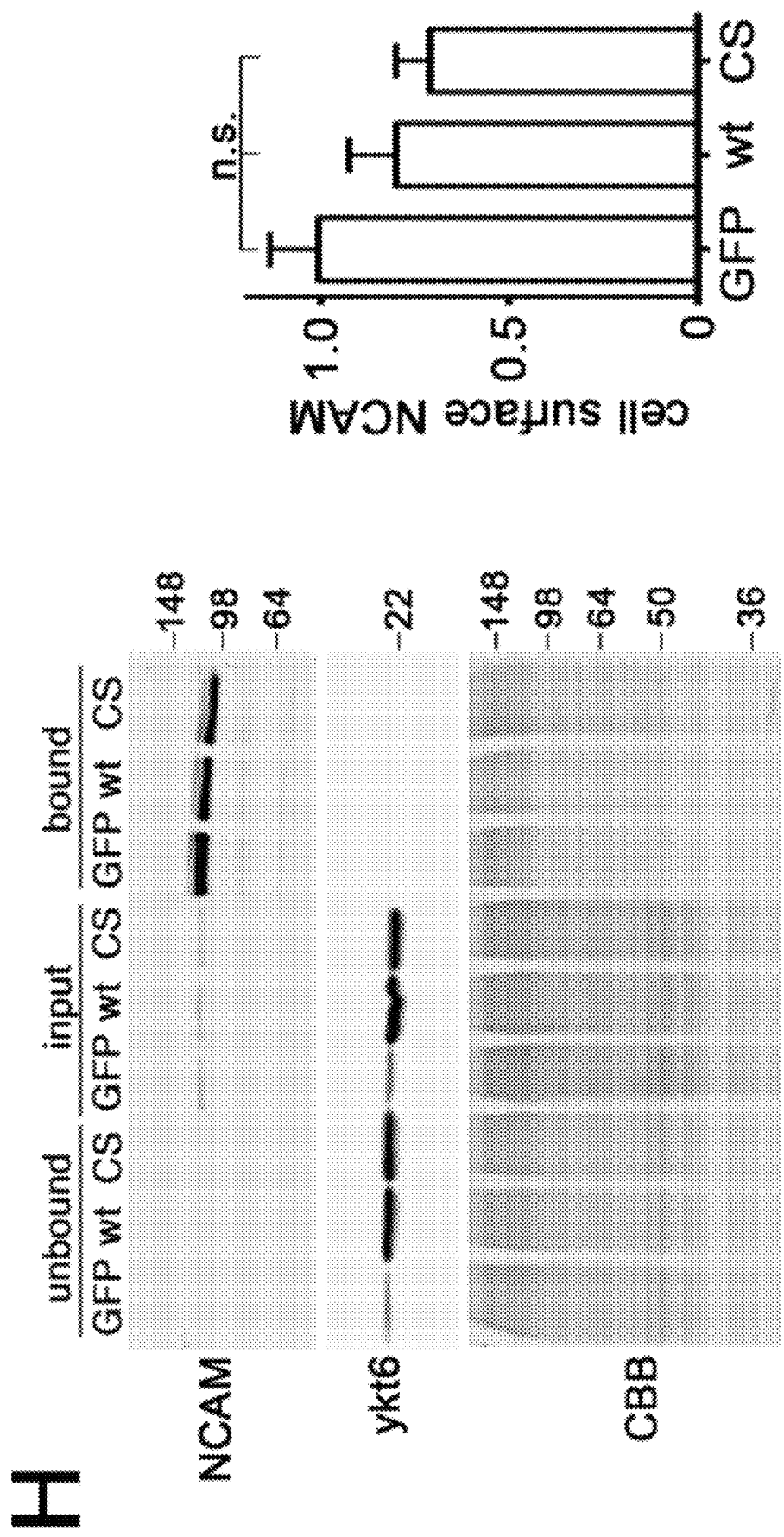
Figure 4I:
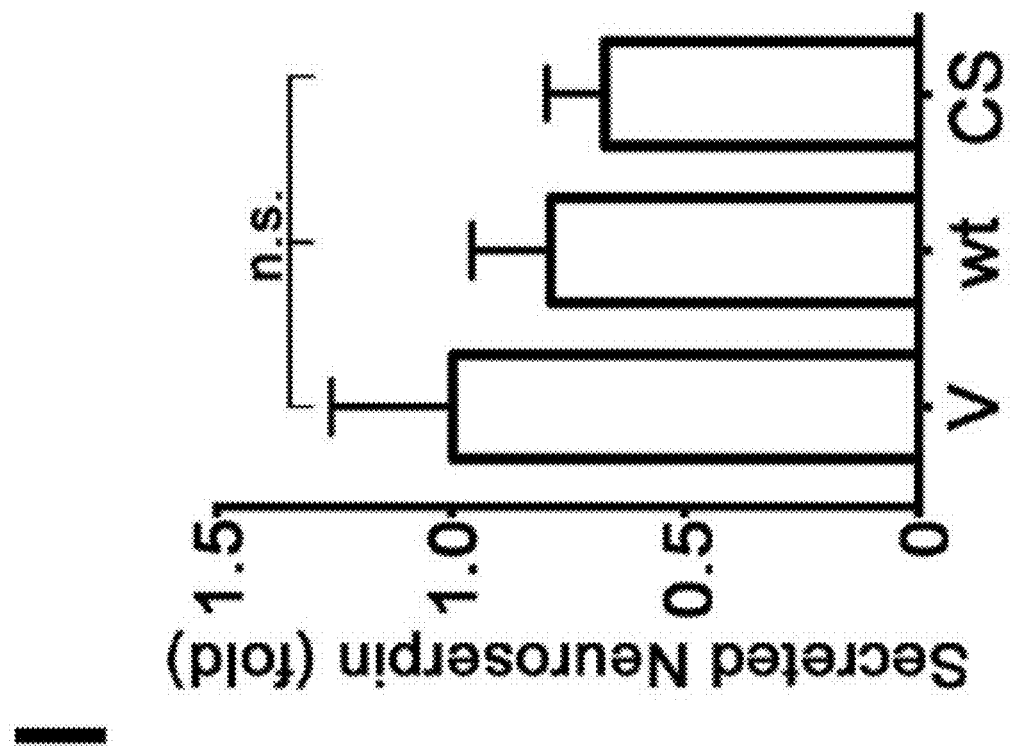
Figure 13I:
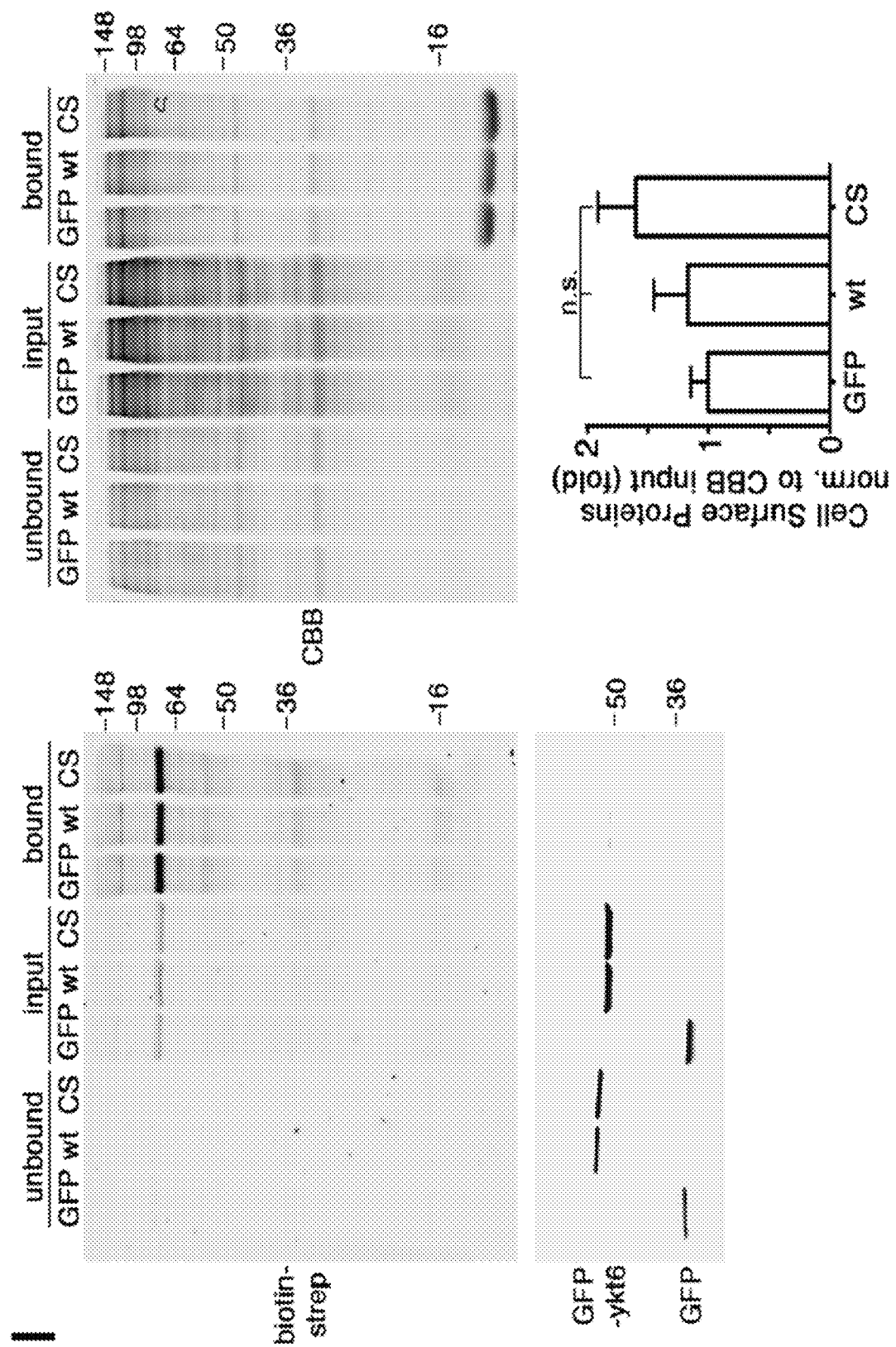

We next examined the specificity of ykt6 in enhancing lysosomal protein trafficking, by measuring the effect on cell surface or secreted proteins that also mature through the early secretory pathway. The cell surface levels of neural cell adhesion molecule (NCAM) was determined by surface biotinylation assays, and revealed a downward, non-significant trend when ykt6 wt or CS was expressed (FIG. 4H). Measurement of total cell surface proteins also showed no change (FIG. 13I). We then measured the levels of secreted neuroserpin in conditioned media, and found no change upon ykt6 wt or CS expression (FIG. 4I). This indicates that ykt6 preferentially enhances the trafficking of lysosomal proteins in PD culture models.

Figure 5A:
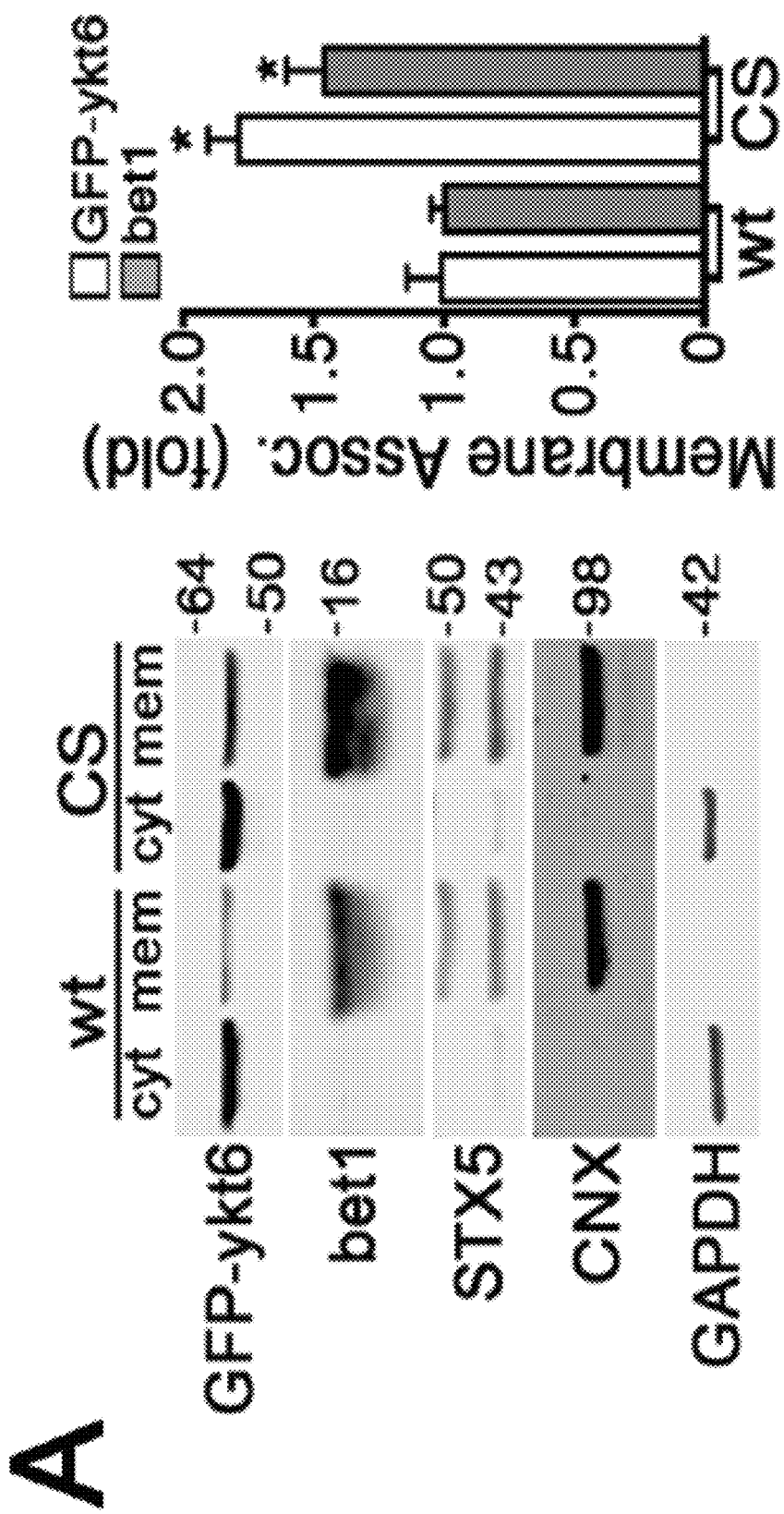
FIGS. 5A, 5B, 5C, 5D, 5E, 5F, and 5G. Reducing farnesyl-ykt6 enhances SNARE assembly and improves the lysosomal targeting of GCase. 5A) Ykt6 membrane shift analysis of SH-SY5Y cells expressing GFP-ykt6 wt or CS (n=3). 5B) Co-IP of GFP-ykt6 and bet1 in A53T iPSn (n=3). 5C) Ykt6 membrane shift analysis in FTI-treated SH-SY5Y wt a-syn cells or A53T iPSn (5 nM farnesyltransferase inhibitors (FTI) LNK-754 (FTI-1) or LNK-3248 (FTI-2) for 5 days) (n=4). Sec22b was measured to assess specificity. 5D) SEC/western blot of FTI-1 treated SH-SY5Y cells. Quantification is shown below. 5E) Co-IP of GFP-ykt6 wt or mutant ykt6-SS, (cannot be palmitoylated or farnesylated) in FTI-treated SHSY5Y cells (5 nM LNK-754, 5d) (n=2). 5F) Immunofluorescence of GCase and LAMP2A in FTI-treated H4 a-syn cells transfected with scrambled (scrb) or ykt6 shRNA (n=3). Scale bar=10 um. 5G) GCase maturation analysis in FTI-treated A53T iPSn by endo H (n=3). Values are the mean+/−SEM, *p<0.05.
Figure 5B:
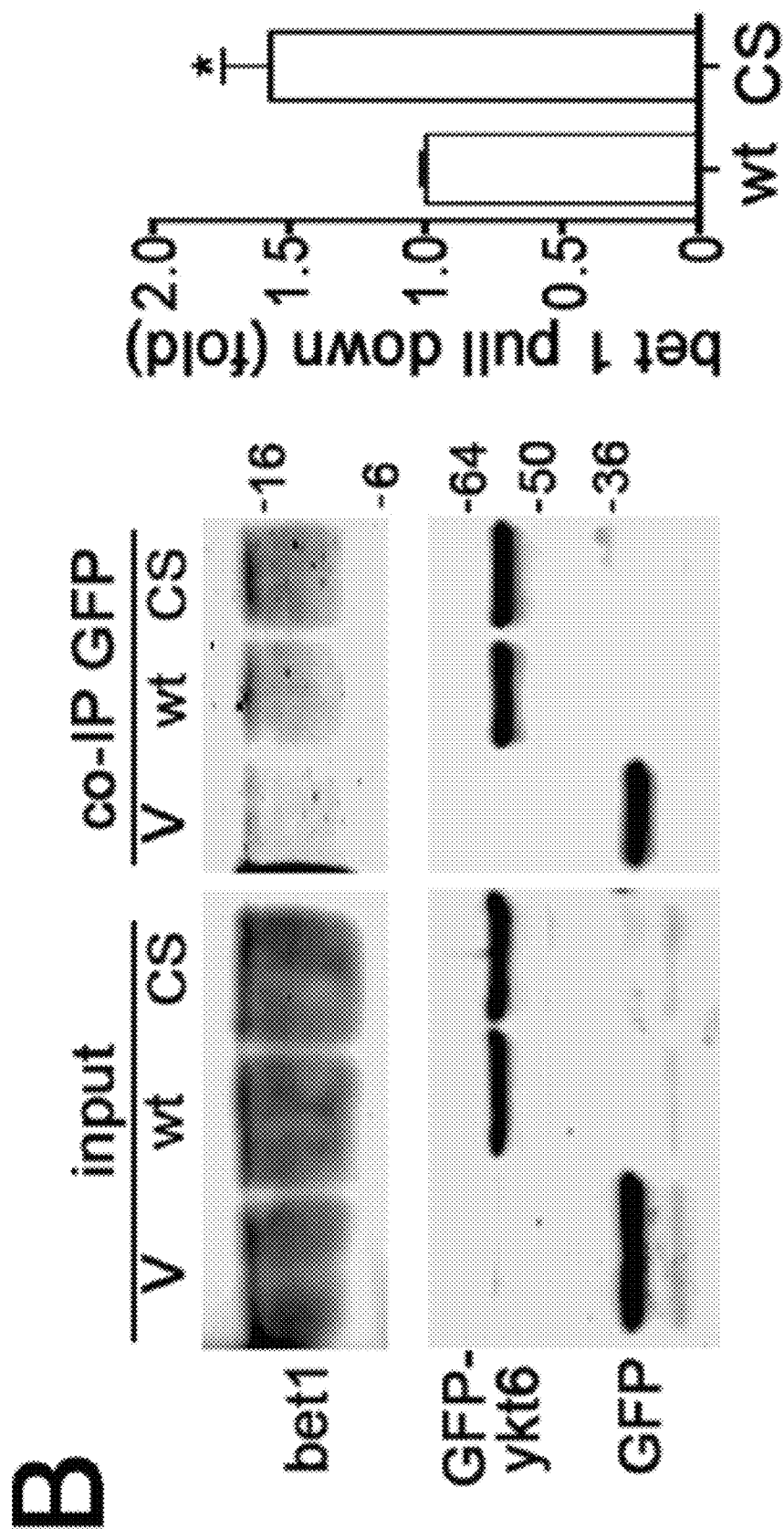

Since we found that expression of the non-farnesyl-ykt6 (CS) augmented lysosomal activity compared to wt ykt6, we next examined the effect of blocking ykt6 farnesylation on membrane binding and SNARE complex formation. Ykt6-CS was elevated in membrane fractions compared to wt, along with ER-Golgi binding partners bet1 and STX5 (FIG. 5A). Ykt6-CS also pulled down more bet1 compared to wt, consistent with increased membrane association (FIG. 5B). This indicates that blocking ykt6 farnesylation enhances membrane association and cognate SNARE binding, which then augments the trafficking of lysosomal hydrolases.

Figure 5C:
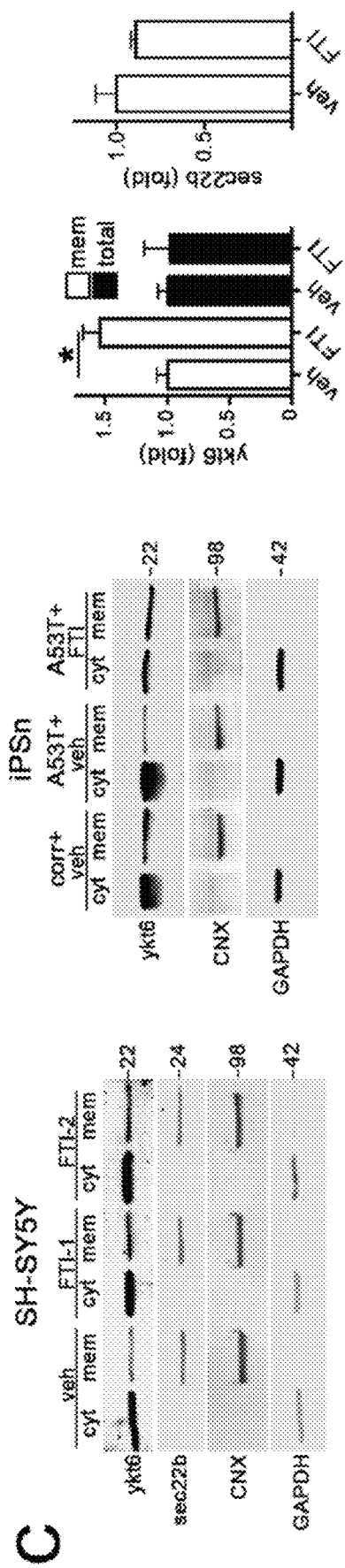
Figure 5D:
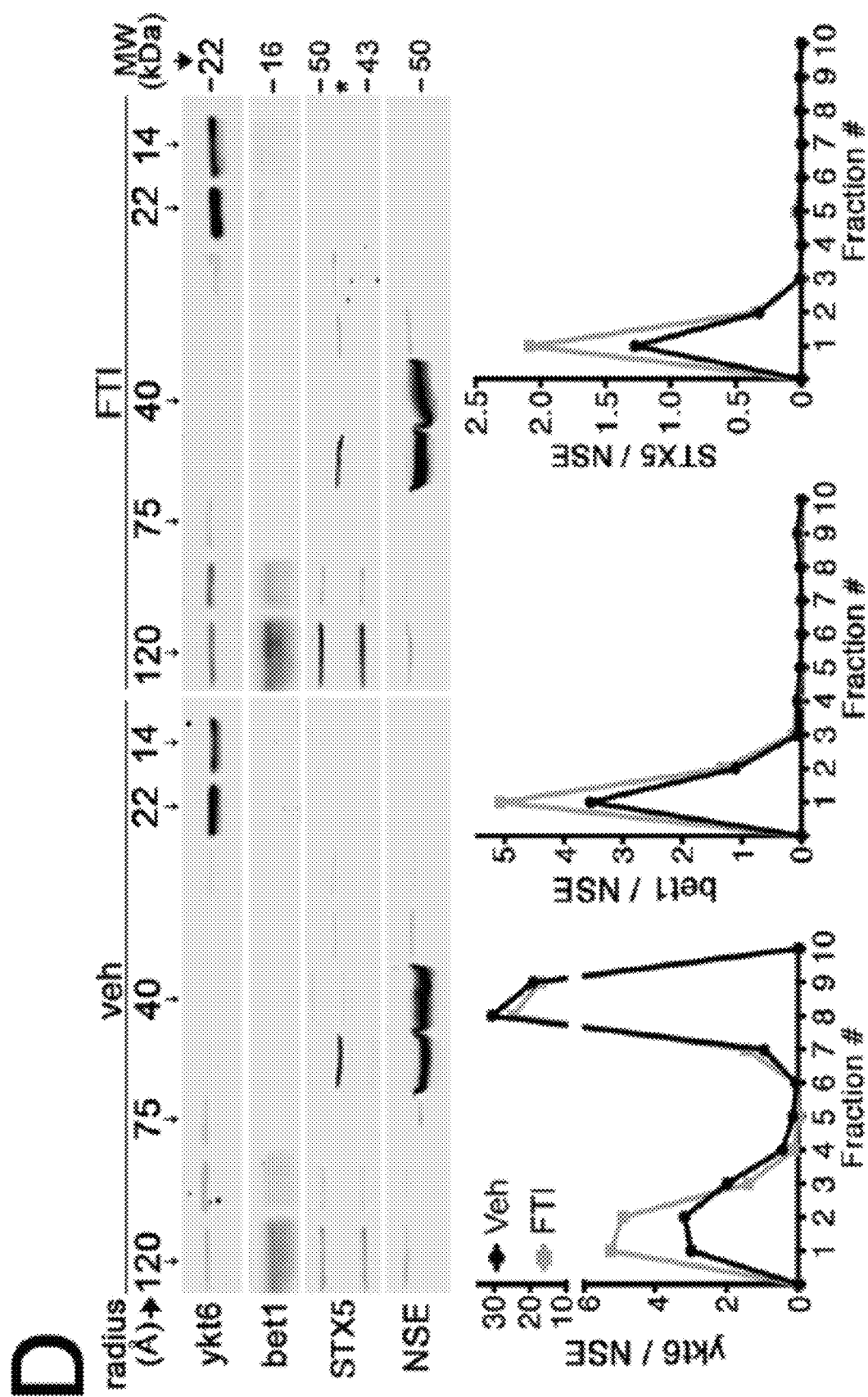
Figure 5E:
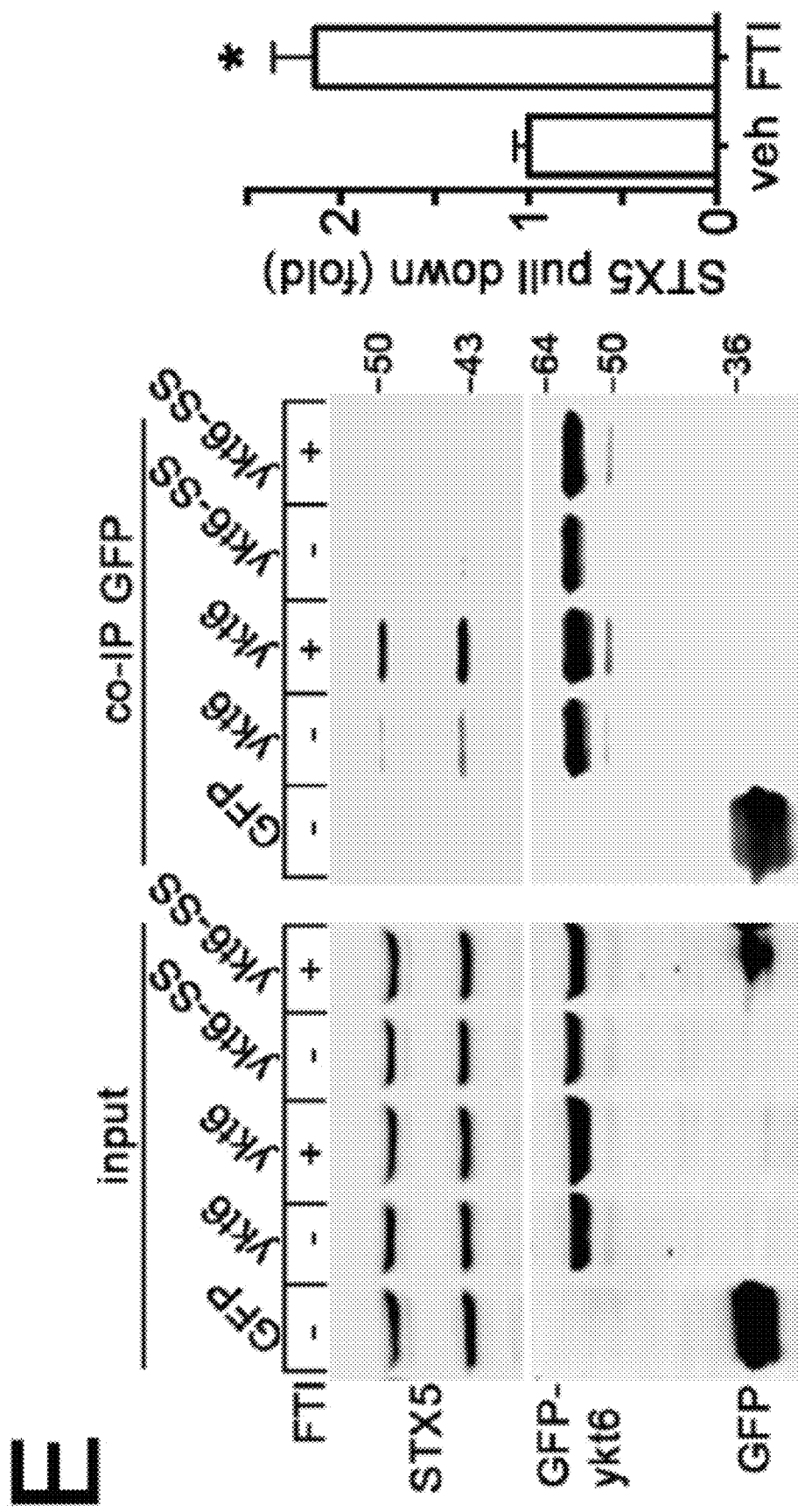
Figure 5F:
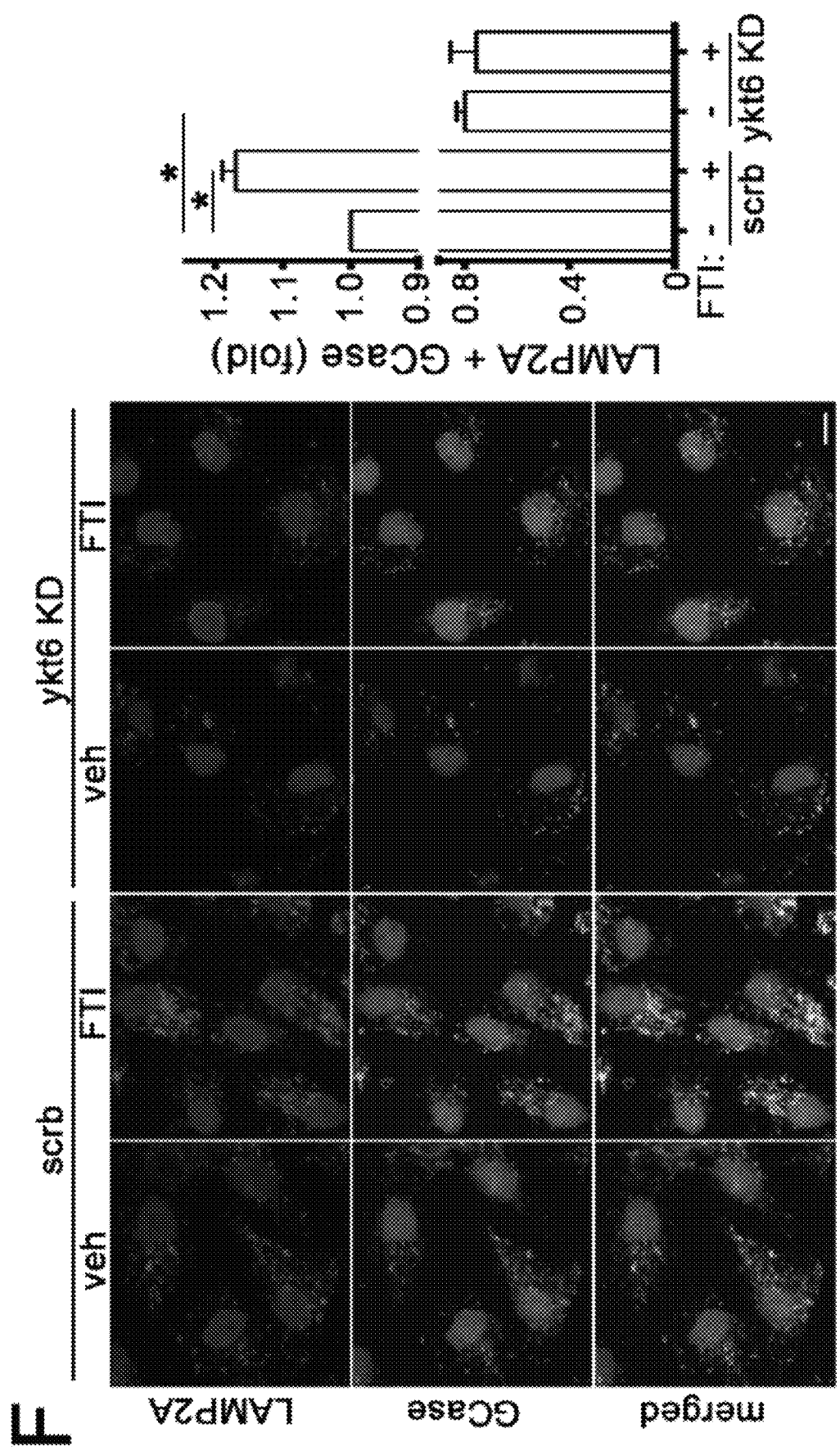
Figure 5G:
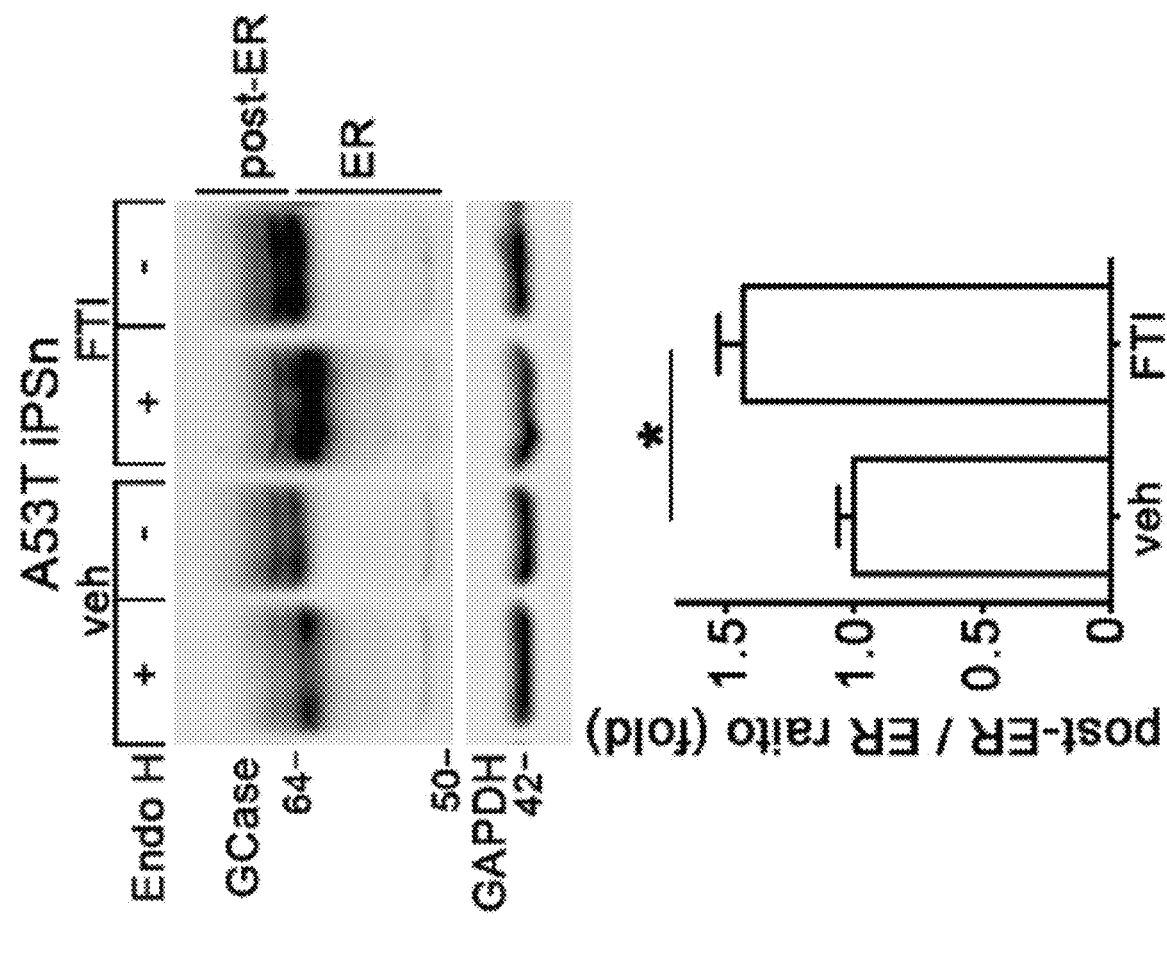
Figure 14A:
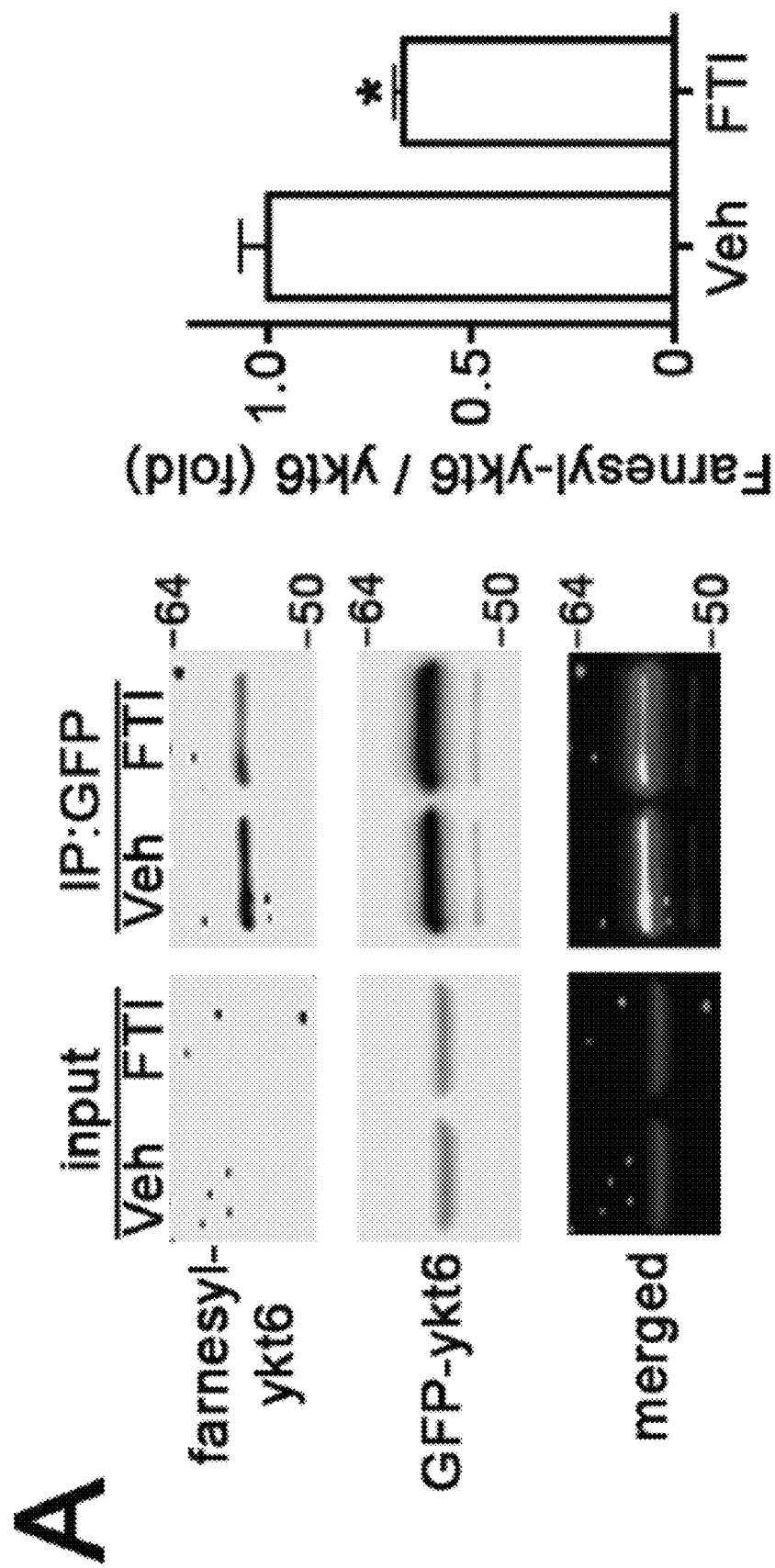
Figure 14B:
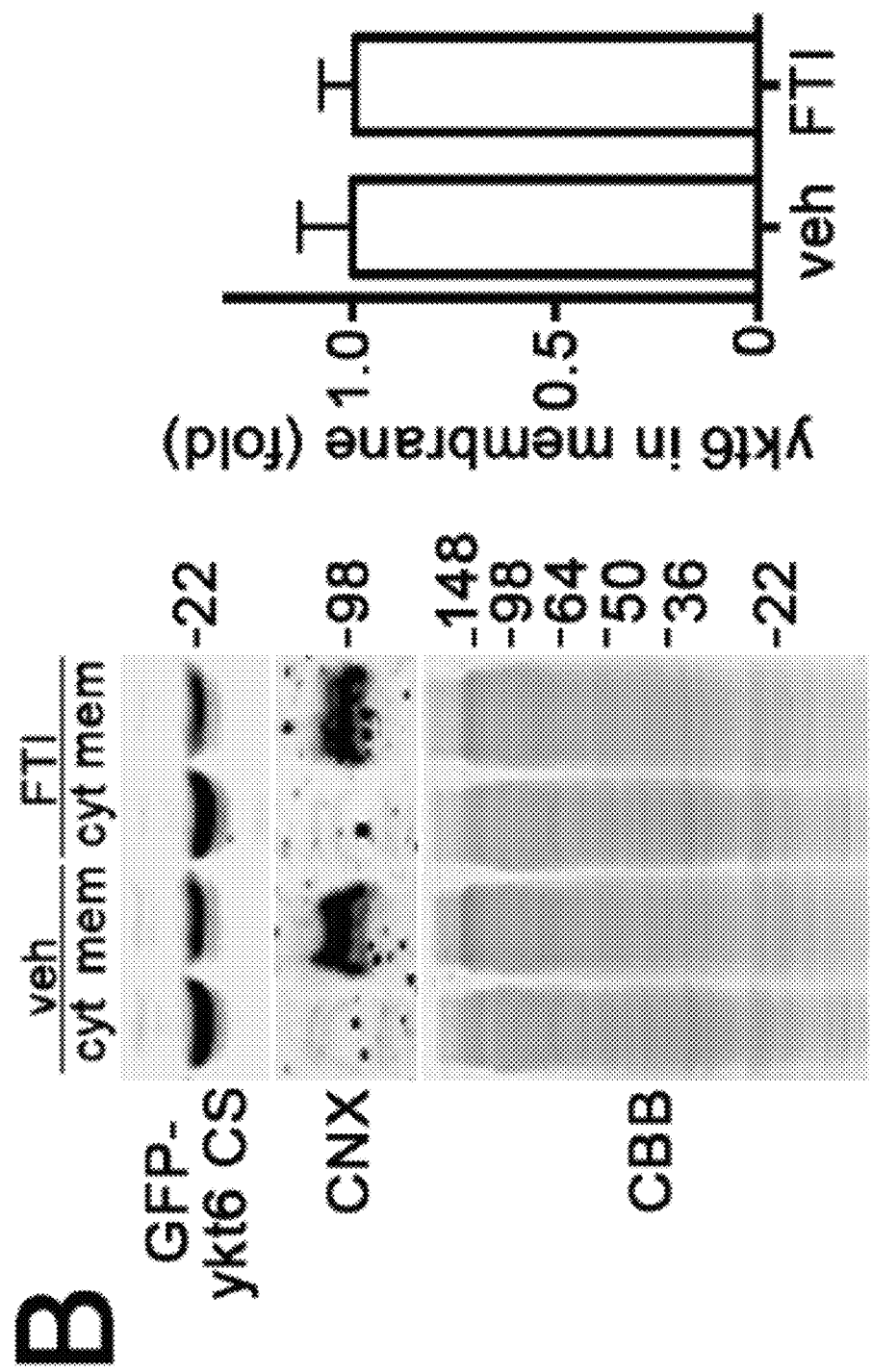
Figure 14C:
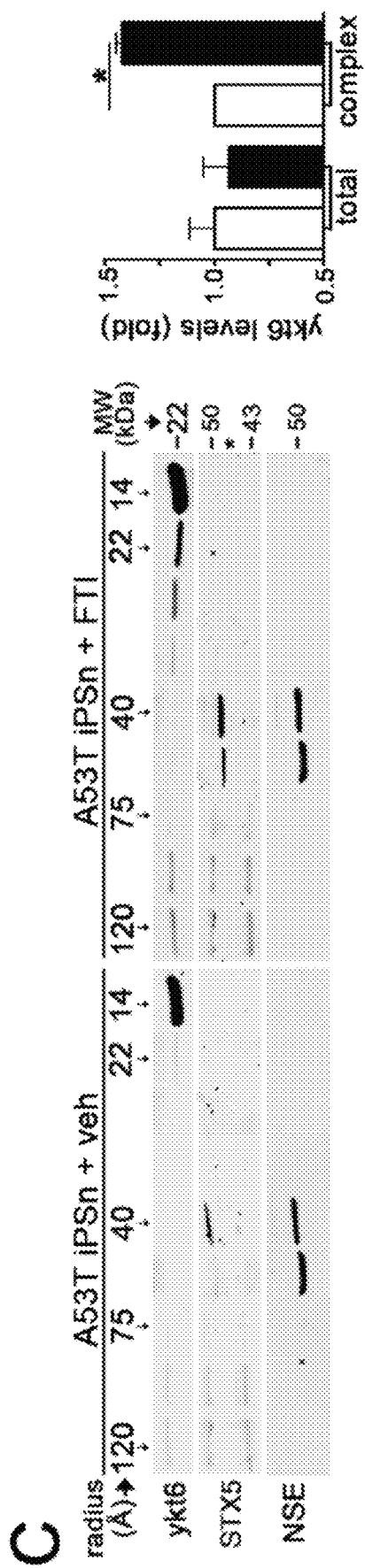
Figure 14D:
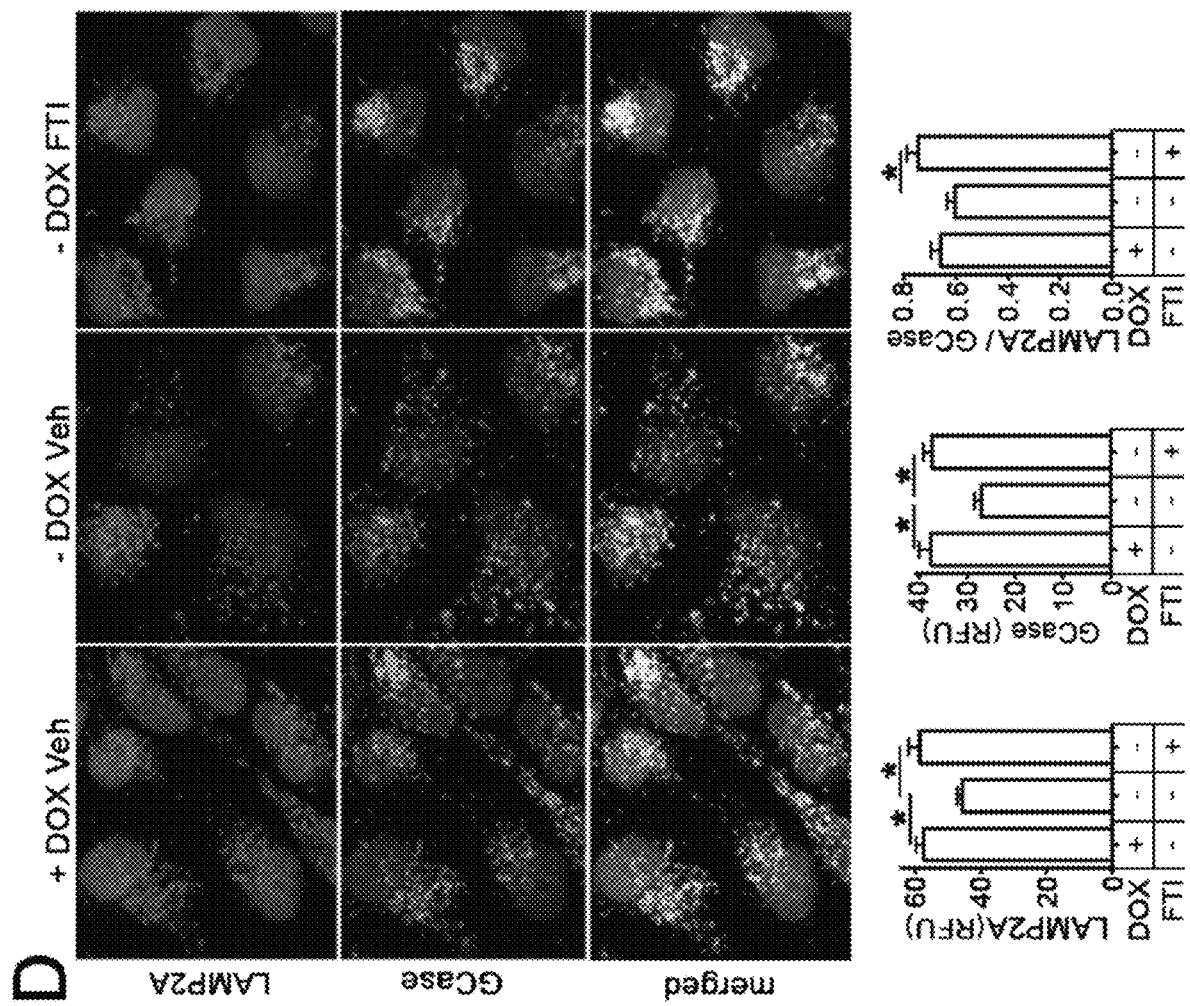
Figure 14E:
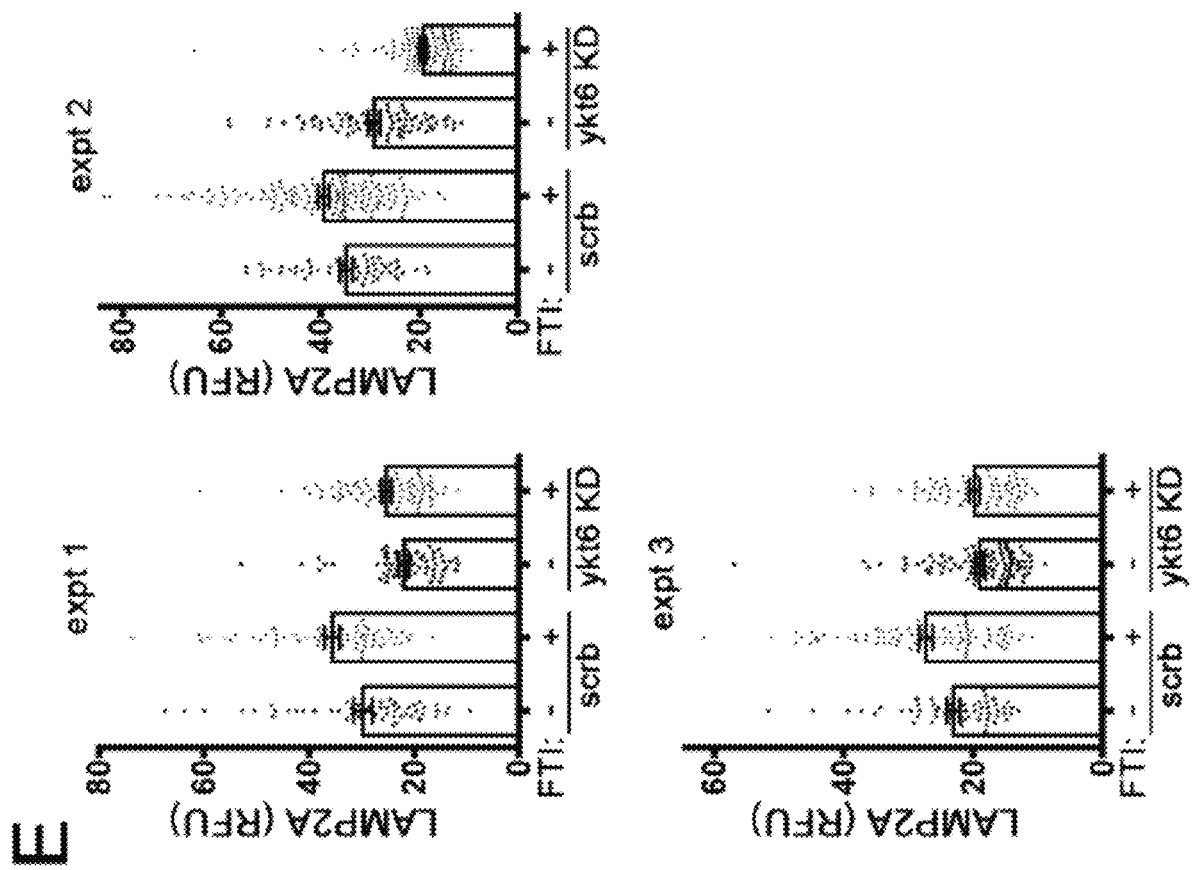
Figure 14F:
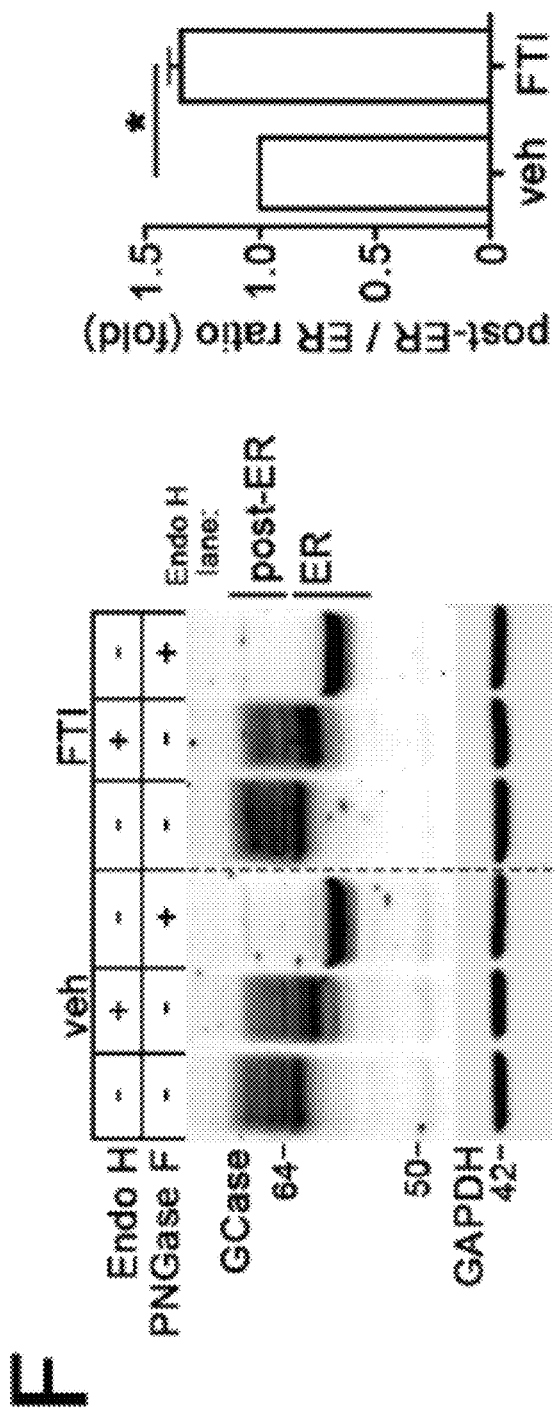

Ykt6 can be therapeutically targeted by farnesyltransferase inhibitors. We next determined if ykt6 could be targeted by small molecule farnesyltransferase inhibitors (FTIs). We utilized a previously characterized FTI, LNK-754, that was developed for clinical use as potential cancer therapy, and has shown selective in vivo target engagement of farnesyltransferase (Downward, 2003; Moulder et al., 2004). Upon culturing cells with the FTI, we found that it reduced the farnesyl-ykt6 signal by 40% (FIG. 14A). FTI treatment increased membrane association of ykt6 in cell lines and PD patient neurons, while sec22b levels did not change (FIG. 5C). The FTI-mediated increase of membrane ykt6 occurred through cysteine 195, since ykt6-CS was not affected by FTI treatment (FIG. 14B). SEC analysis showed that the FTI elevated the levels of ykt6 SNARE complexes in SH-SY5Y cells, a finding that was confirmed in A53T iPSn (FIG. 5D, 14C). Co-IP showed increased ykt6 SNARE complexes with FTI treatment, while no effect was seen with a ykt6 mutant lacking lipid modification sites (ykt6-SS) (FIG. 5E). Immunostaining for lysosomal markers indicated that FTIs elevated the levels of LAMP2A and GCase, which was abolished by ykt6 KD (FIG. 5F; FIG. 14D, E). Consistent with this, FTI treatment significantly elevated mature, endo H-resistant GCase in A53T iPSn and SHSY5Y cells (FIG. 5G, 14F). Together, this indicates that ykt6 activity can be modulated by FTIs, resulting in enhanced trafficking of lysosomal GCase.

Figure 6A:
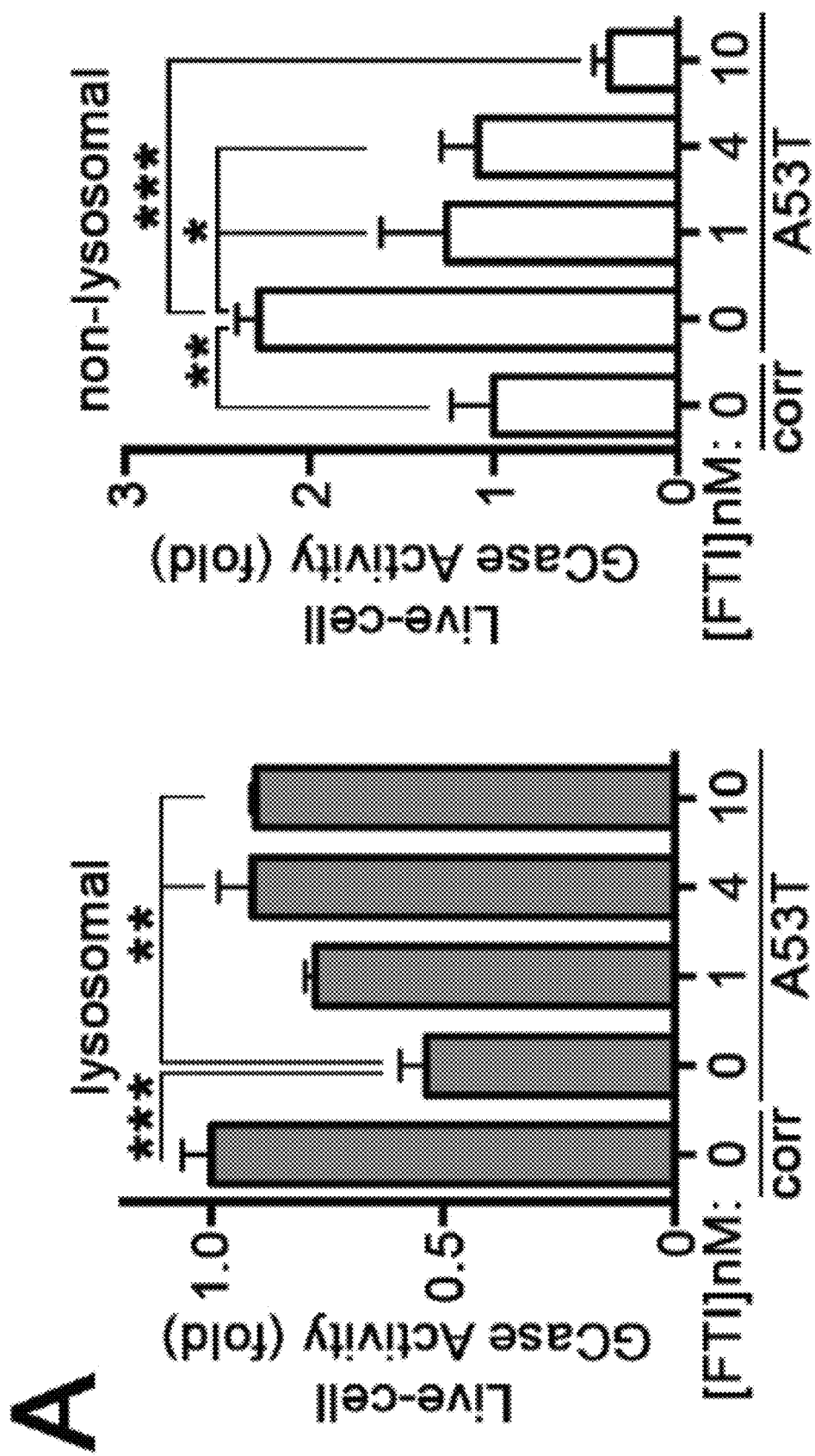
FIGS. 6A, 6B, 6C, 6D, 6E, 6F, and 6G. FTIs enhance lysosomal GCase activity and reduce pathological a-syn by blocking ykt6 farnesylation. 6A) GCase activity in FTI-treated A53T iPSn at d80 (LNK-754 5 nM, 5d). 6B) GCase activity in FTI-treated A53T iPSn expressing empty vector (vect) or ykt6-CS (n=4). 6C) Lysosomal GCase activity was assessed in FTI-treated SHSY5Y cells transfected with scrambled or ykt6 shRNA (KD) (n=3). 6D) Quantification of Triton X-100 soluble (T-sol) a-syn by western blot from FTI-treated A53T iPSn (5 nM, 7d). *, non-specific band. (n=3). 6E) Quantification of insoluble a-syn from A53T iPSn as in D (n=3). 6F) Insoluble a-syn in FTI-treated H4 cells (5 nM, 5 days) transfected with either scrambled or ykt6 shRNA (n=6). 6G) Neuron viability was assessed in FTI-treated A53T iPSn (5 nM, 14d from d86-d100) by quantification of neurofilament protein. Right, neuron viability in FTI-treated A53T iPSn expressing empty vector or ykt6-CS (n=4). Values are the mean+/−SEM, *p<0.05, p<0.01, *p<0.001.
Figure 6B:
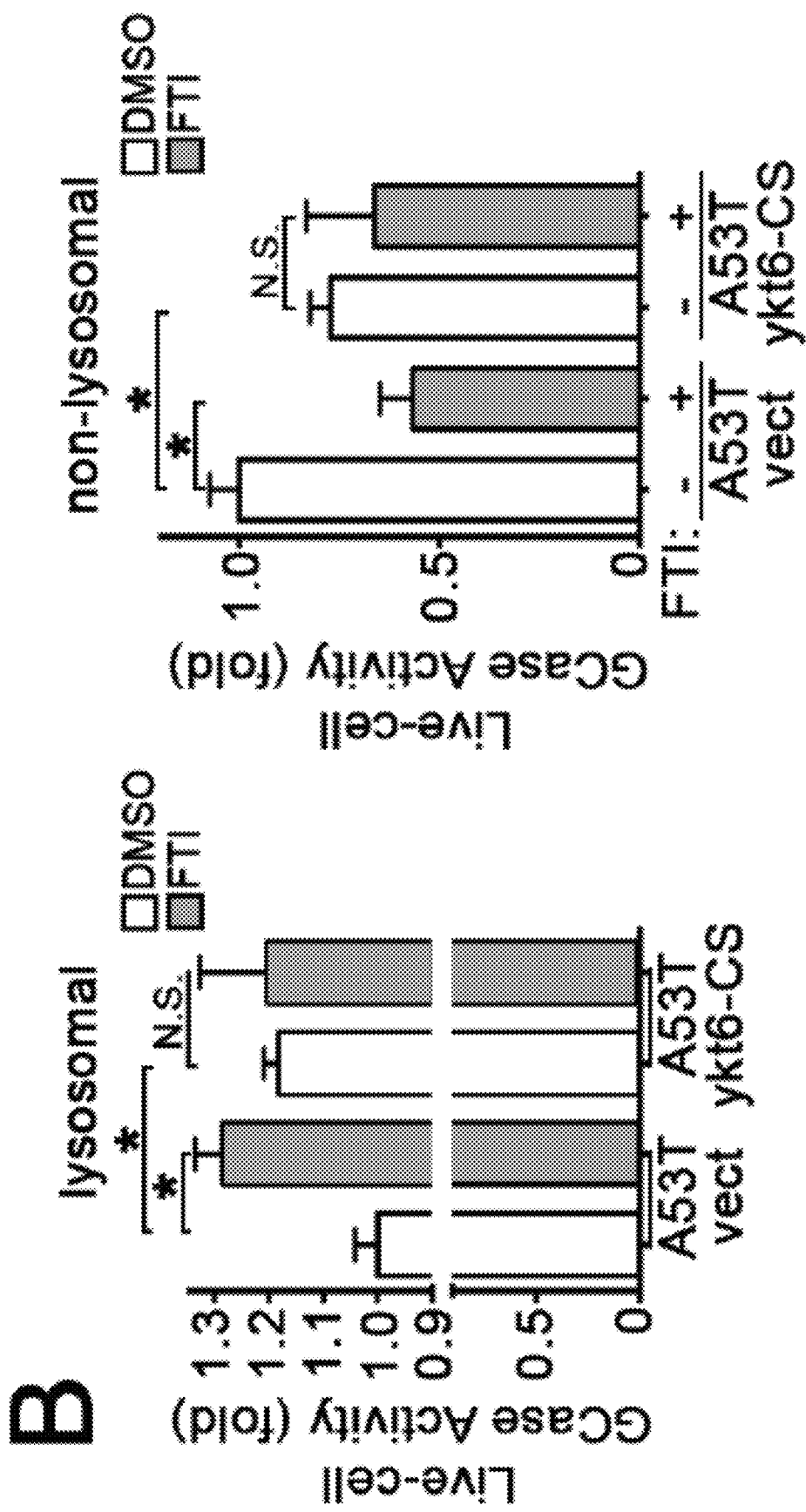
Figure 6C:
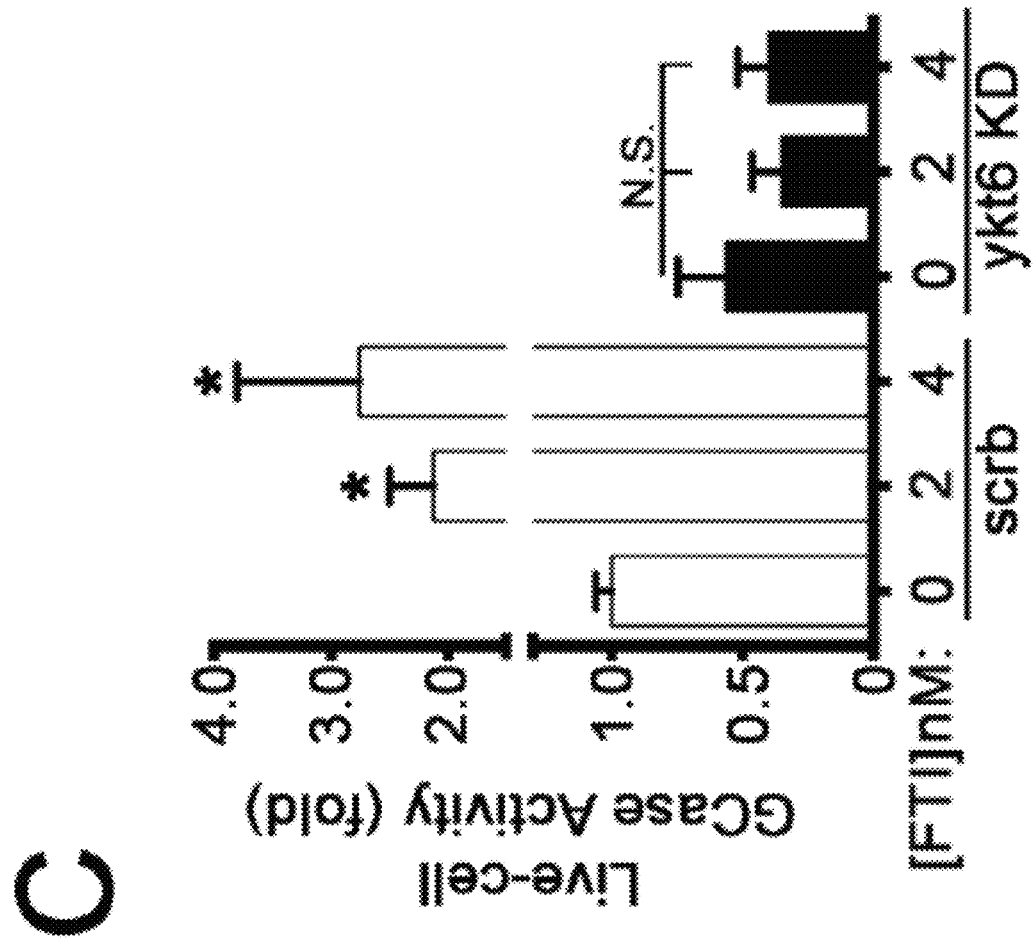
Figure 6D:
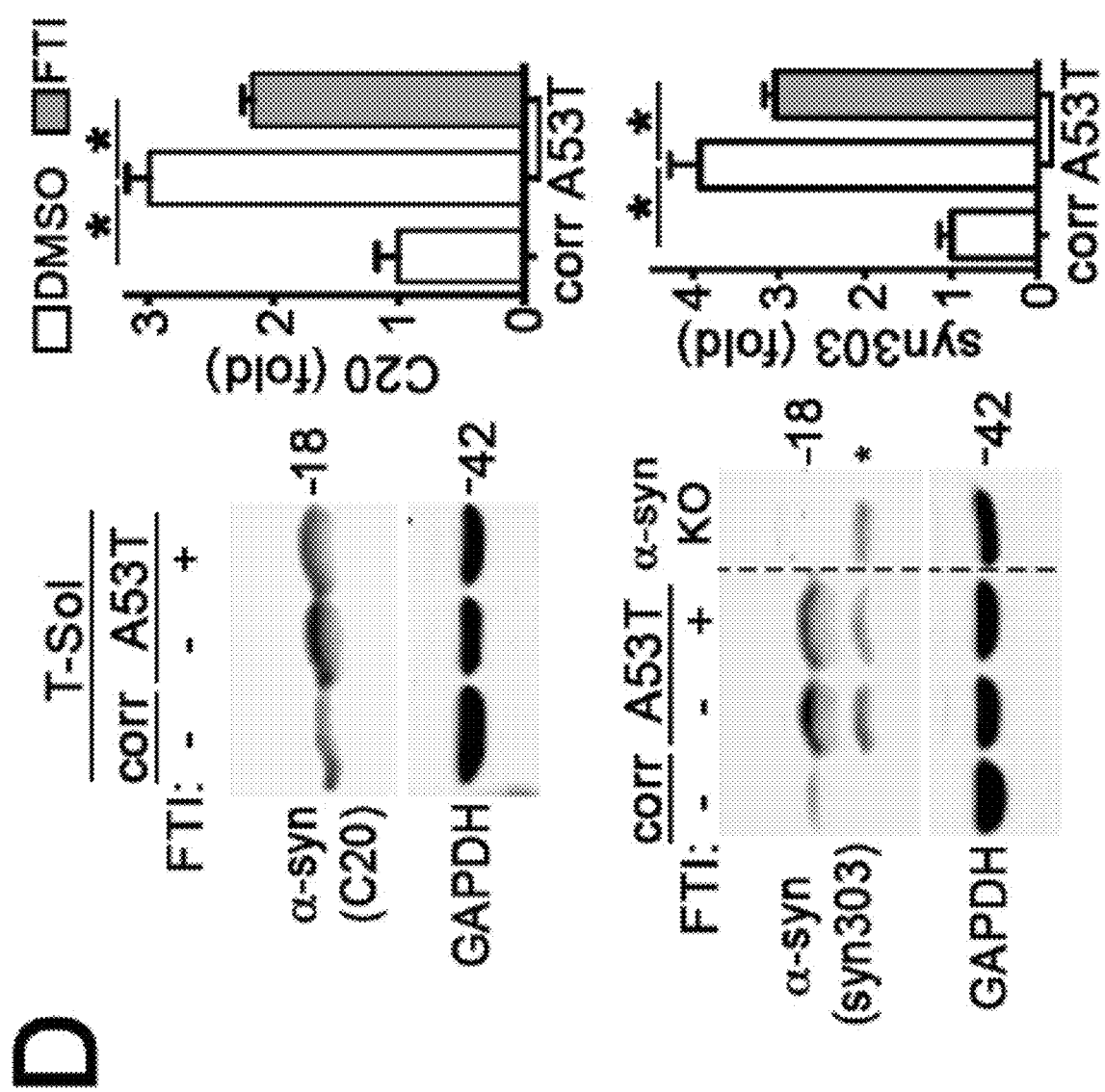
Figure 6E:
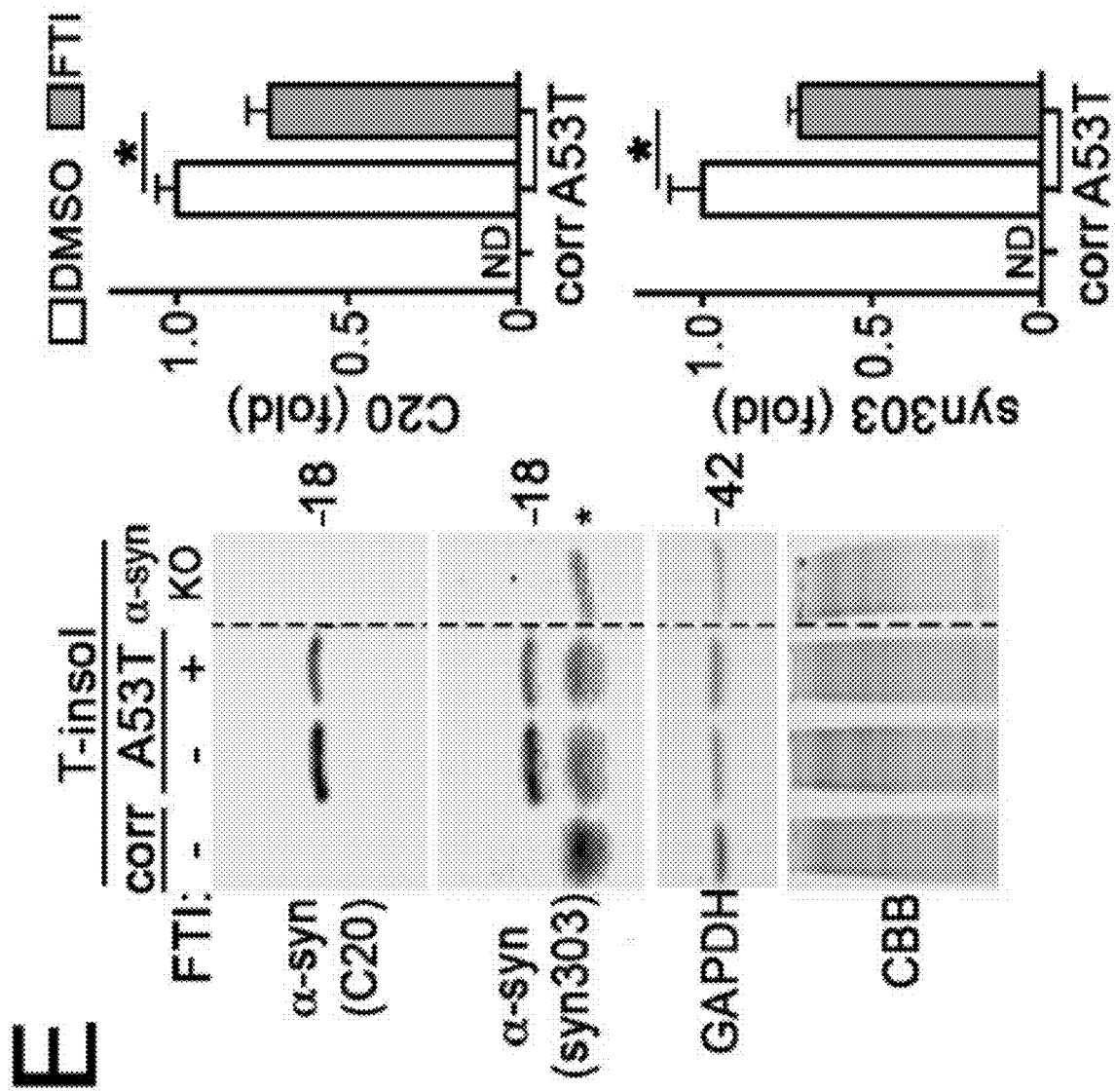
Figure 6F:
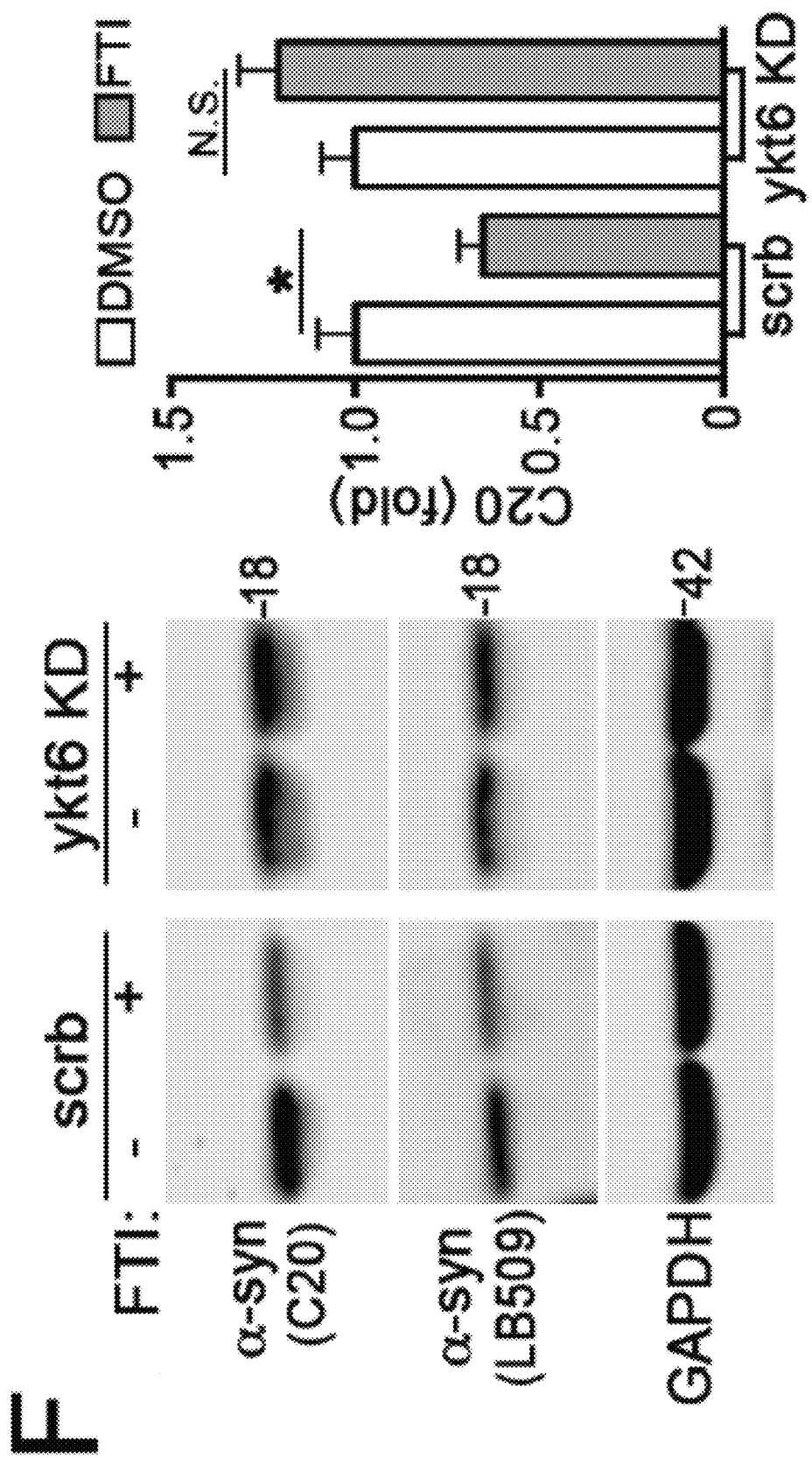
Figure 6G:
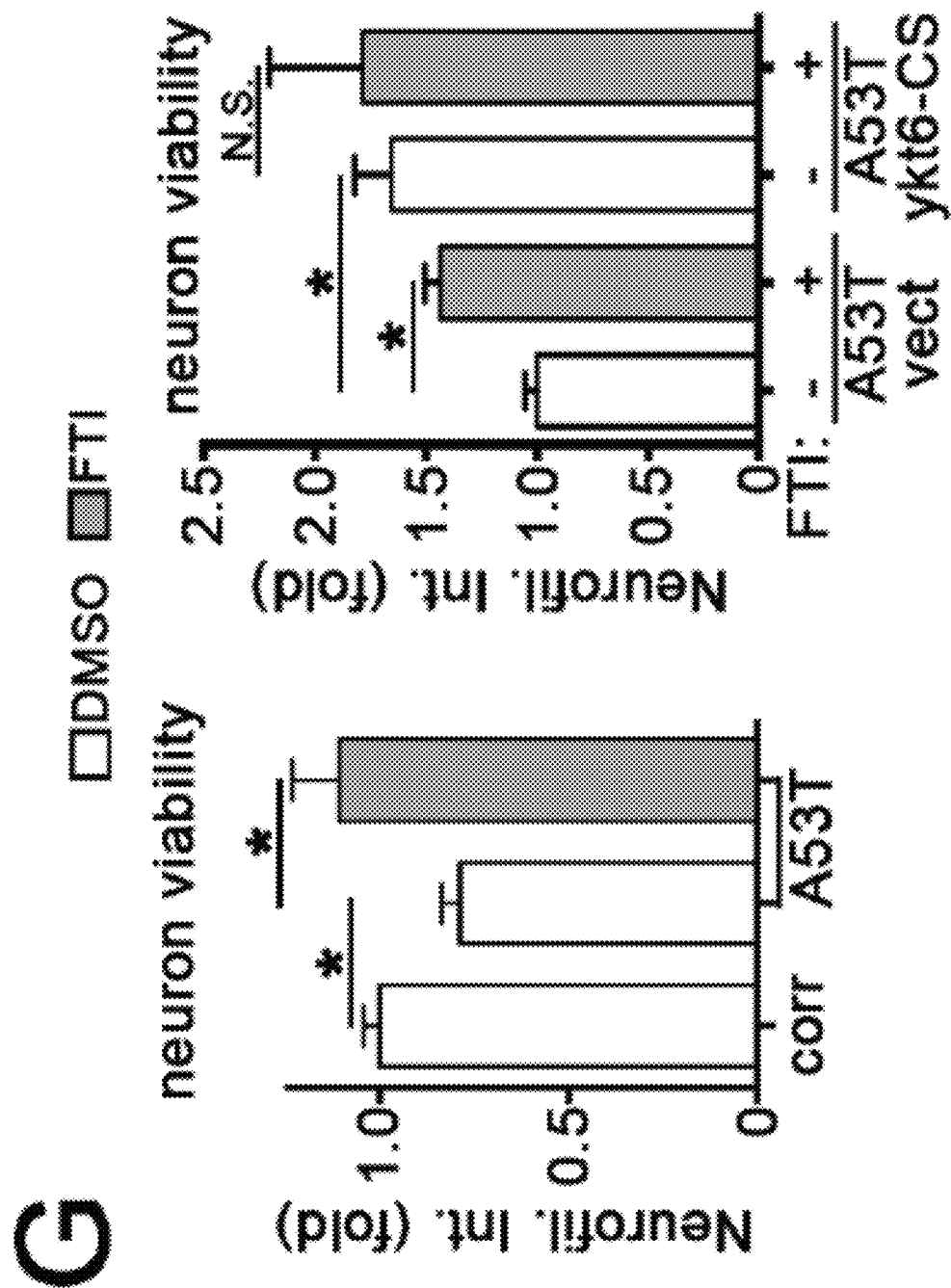
Figure 14G:
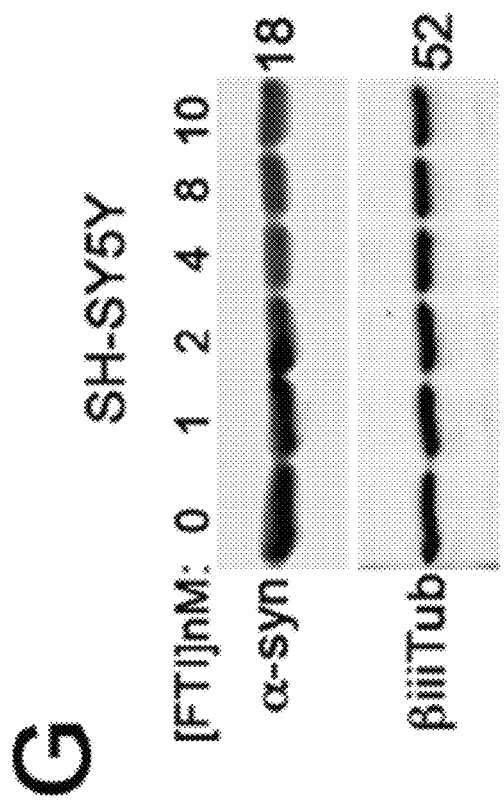

We next determined if FTI treatment could improve lysosomal GCase activity in PD iPSn. GCase activity was partially rescued with concentrations as low as 1 nM, and higher concentrations of 4 and 10 nM resulted in a near-complete rescue (FIG. 6A). This effect was likely due to reducing the farnesylation of ykt6, as opposed to other proteins, since FTIs could not further enhance lysosomal activity in ykt6-CS or ykt6 KD iPSn (FIG. 6B, C). We also found that 5 nM FTI treatment reduced soluble and insoluble levels of a-syn in A53T iPSn using the C20 antibody that detects total a-syn, as well as with syn303 that prominently reacts with pathological a-syn (Duda et al., 2002) (FIG. 6D-E, 14G). Importantly, a-syn reduction by the FTI was dependent on ykt6 (FIG. 6F). FTI treatment also improved neuron viability of A53T iPSn when analyzed at day 100, but had no effect on cells expressing ykt6-CS (FIG. 6G). Together, these data indicate that ykt6 can be activated by FTI, and can rescue cellular pathologies in PD patient neurons.

Figure 15A:
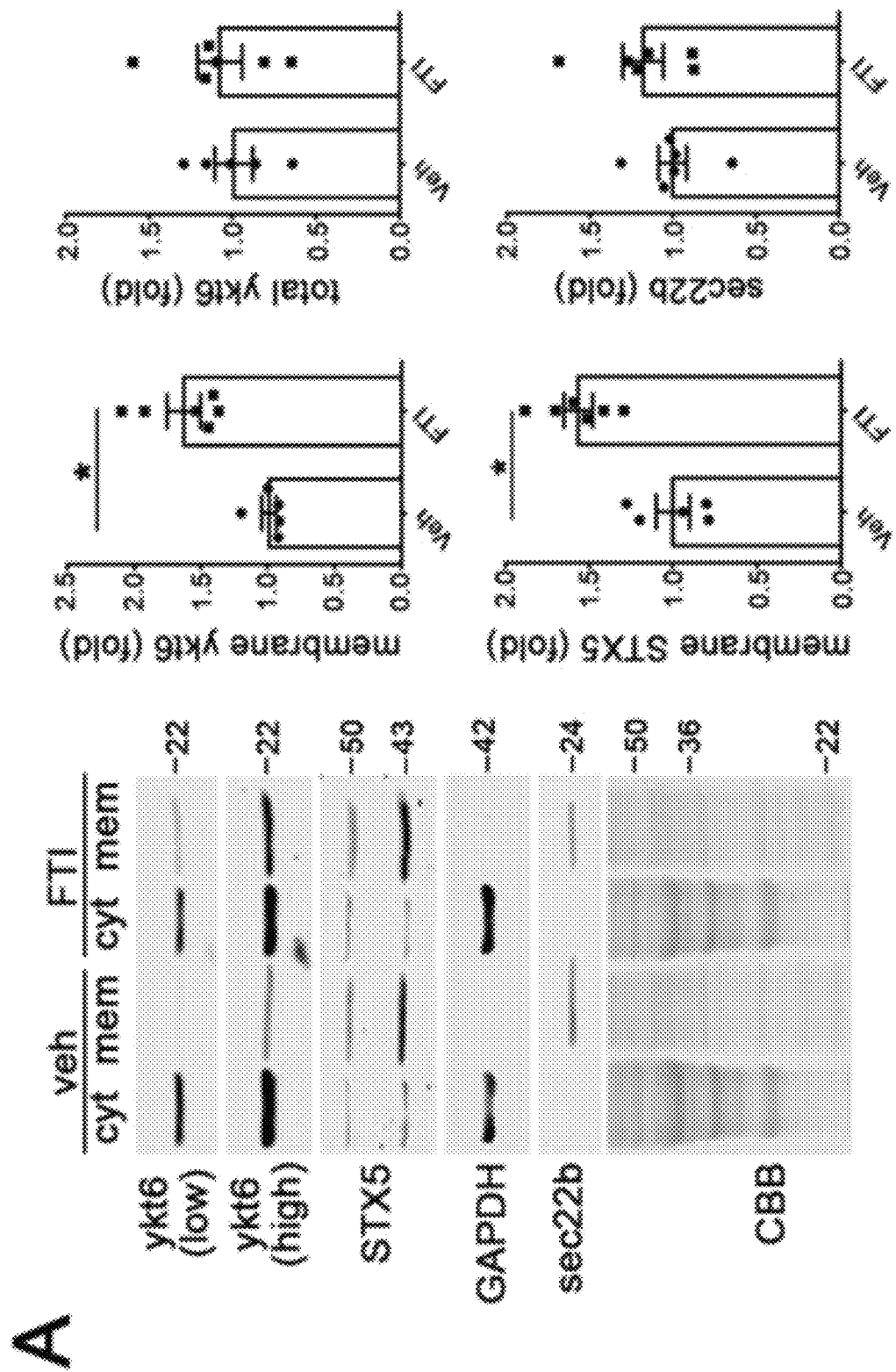
Figure 15B:
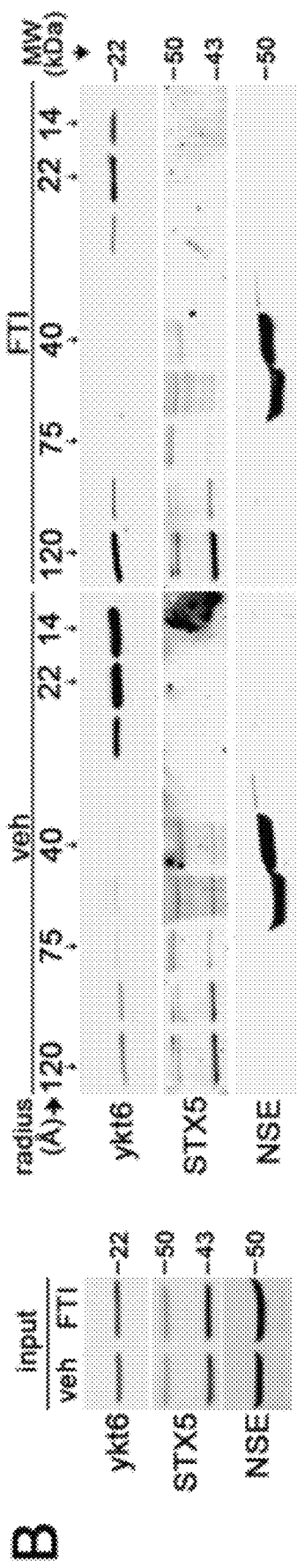
Figure 15C:
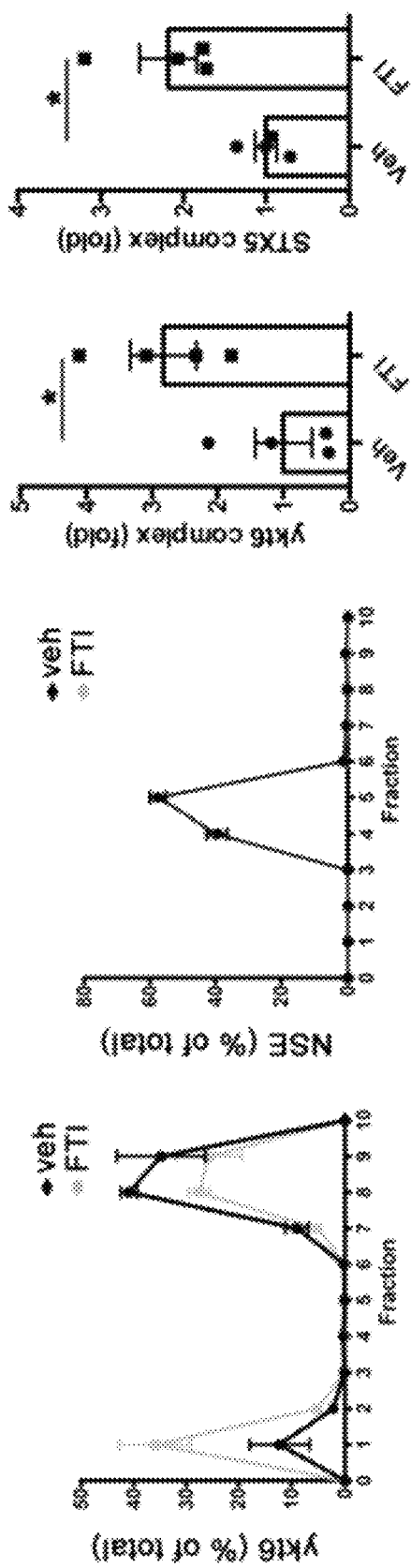
Figure 15D:
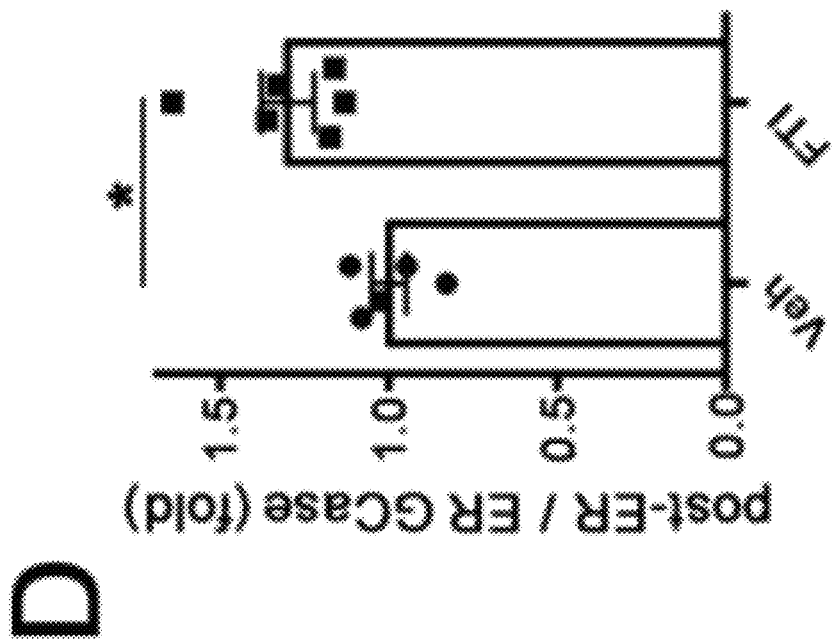
Figure 15E:
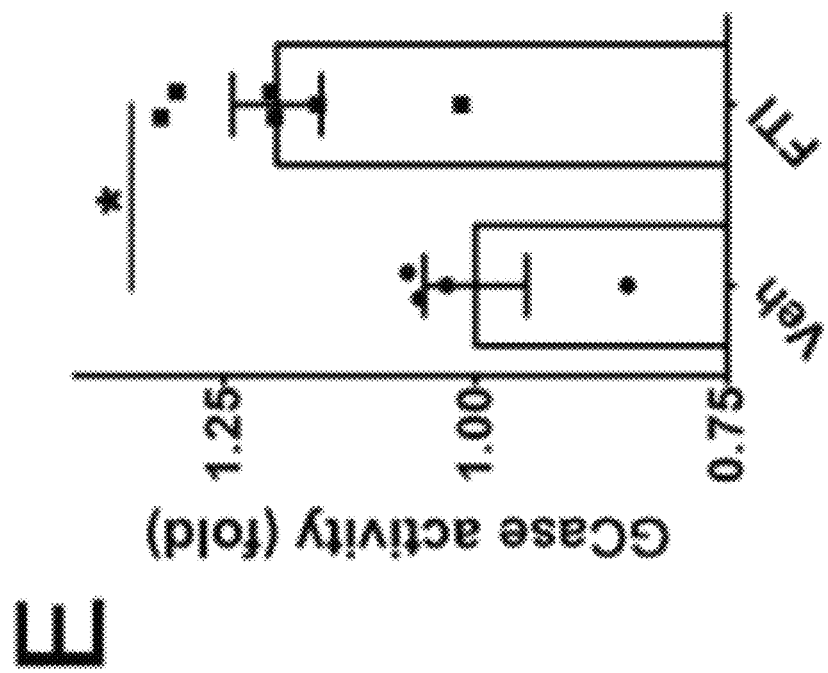
Figure 15F:
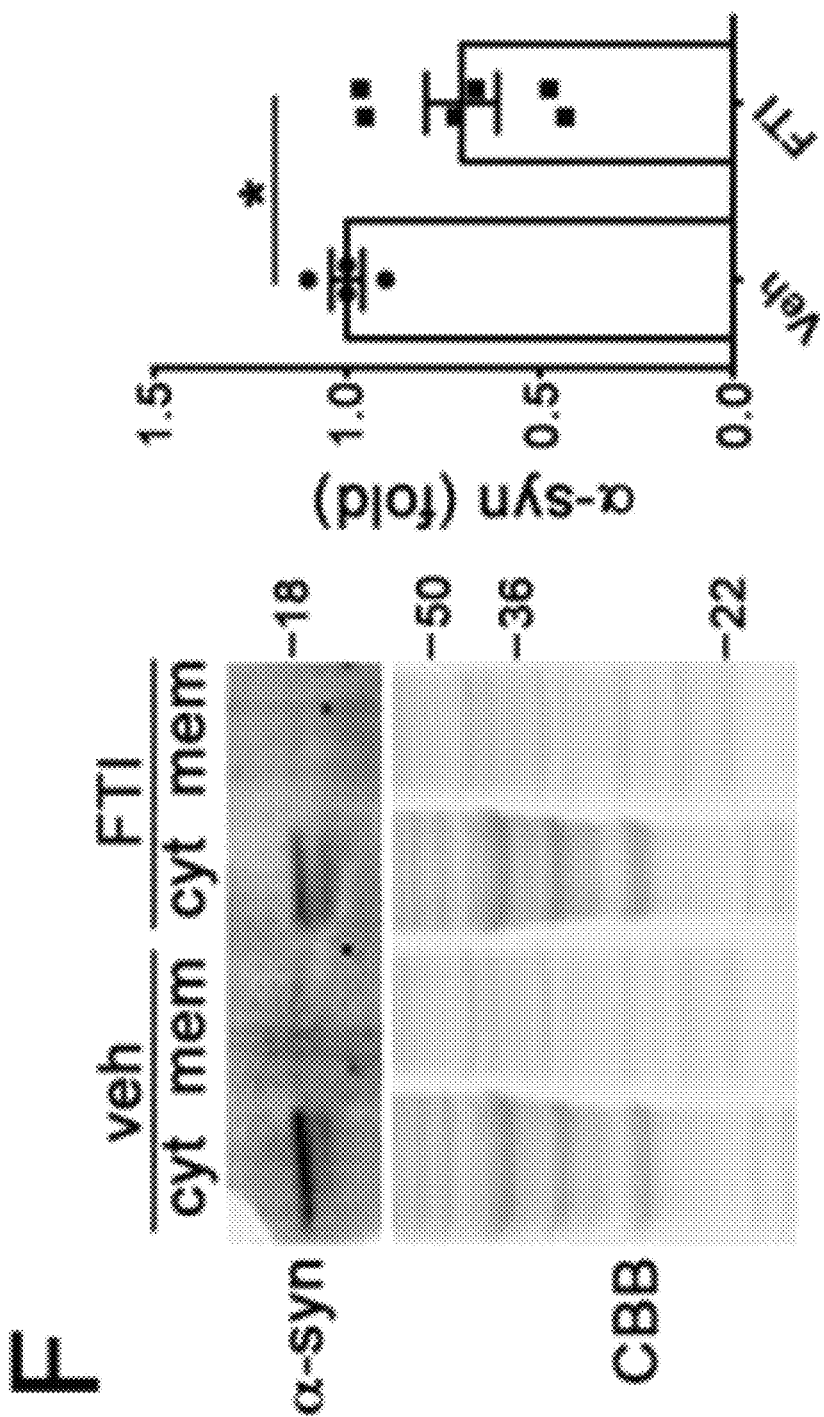

Farnesyltransferase inhibition activates ykt6 in vivo and reduces pathological aggregation in mice. We next sought to determine if FTIs could activate ykt6 in the brains of mice by first testing their effect in wild-type animals. Pharmacokinetic studies revealed that after a single oral dose, the FTI was cleared from plasma within 20 hours and could rapidly cross the blood-brain-barrier (data not shown). Daily intraperitoneal (i.p.) injection of wild-type mice showed that the FTI could increase the levels of membrane associated ykt6 and STX5, while no change was observed for sec22b (FIG. 15A). SEC indicated that FTI treatment did not change the total levels of ykt6, but shifted its distribution from monomers into high molecular weight complexes that co-eluted with STX5 (FIG. 15B, C). We also found elevated levels of mature, endo H resistant GCase and higher enzyme activity in the brain of FTI treated mice (FIG. 15D, E). Consistent with lysosomal activation, FTI treatment also reduced a-syn levels (FIG. 15F). Together, these data indicate that i.p. injection of FTIs can activate ykt6 in the brains of wild-type mice, resulting in lysosomal enhancement and a-syn reduction.

Figure 7A:
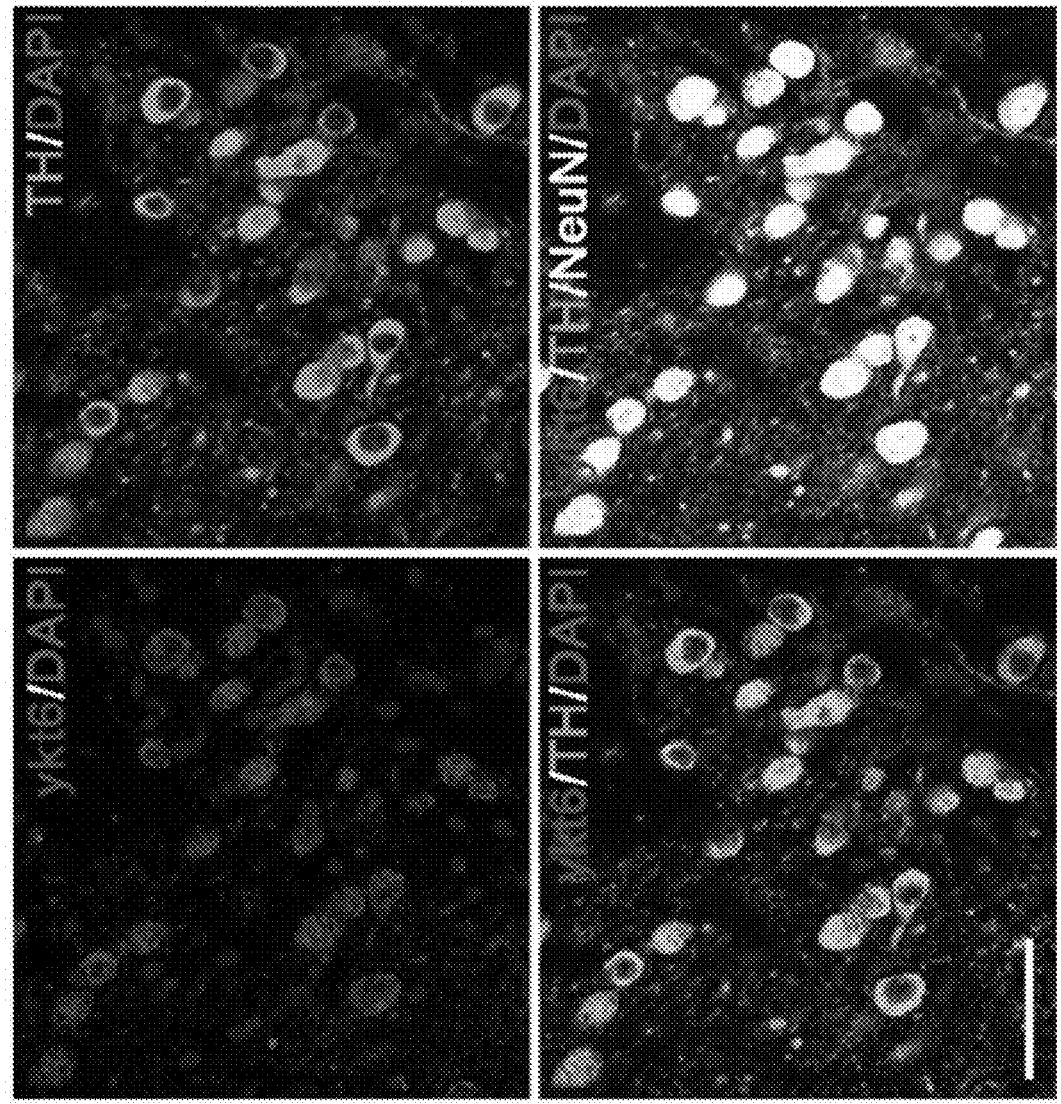
FIGS. 7A, 7B, 7C, 7D, and 7E. FTI treatment restores functional membrane-associated ykt6 complexes in DASYN53 mice. 7A) Immunohistochemistry in the midbrain of mice showing ykt6, tyrosine hydroxylase (TH), NeuN, and nuclei (DAPI). Scale bar, 50 µm. 7B) Ykt6 membrane shift analysis in olfactory bulbs of FTI (LNK-754)-injected DASYN53 mice (12-14 months, i.p. 26d, 0.9 mg/kg) (n=5, non-transgenic (nTg)+veh; n=4, DASYN53+veh; n=4 DASYN53+FTI). GAPDH and sec22b are loading controls. 7C) SEC/western blot analysis of midbrains of FTI-treated DASYN53 mice. Inputs are shown on the left. NSE is a loading control. Low exposure of ykt6 shows changes in monomers (22-14A); high exposures shows changes in complexes (120A). (n=3, nTg+veh; n=4, DASYN53+veh; n=4 DASYN53+FTI). 7D) Quantification of complexes from SEC in 7C. 7E) GCase maturation was assessed in midbrain lysates by endo H resistance (n=4, nTg+veh; n=4, DASYN53+veh; n=4 DASYN53+FTI). For all quantifications, each point represents a measurement from an individual animal. Values are the mean+/−SEM, *p<0.05; p<0.01, *p<0.001, ANOVA with Tukey's post-hoc test.
Figure 7B:
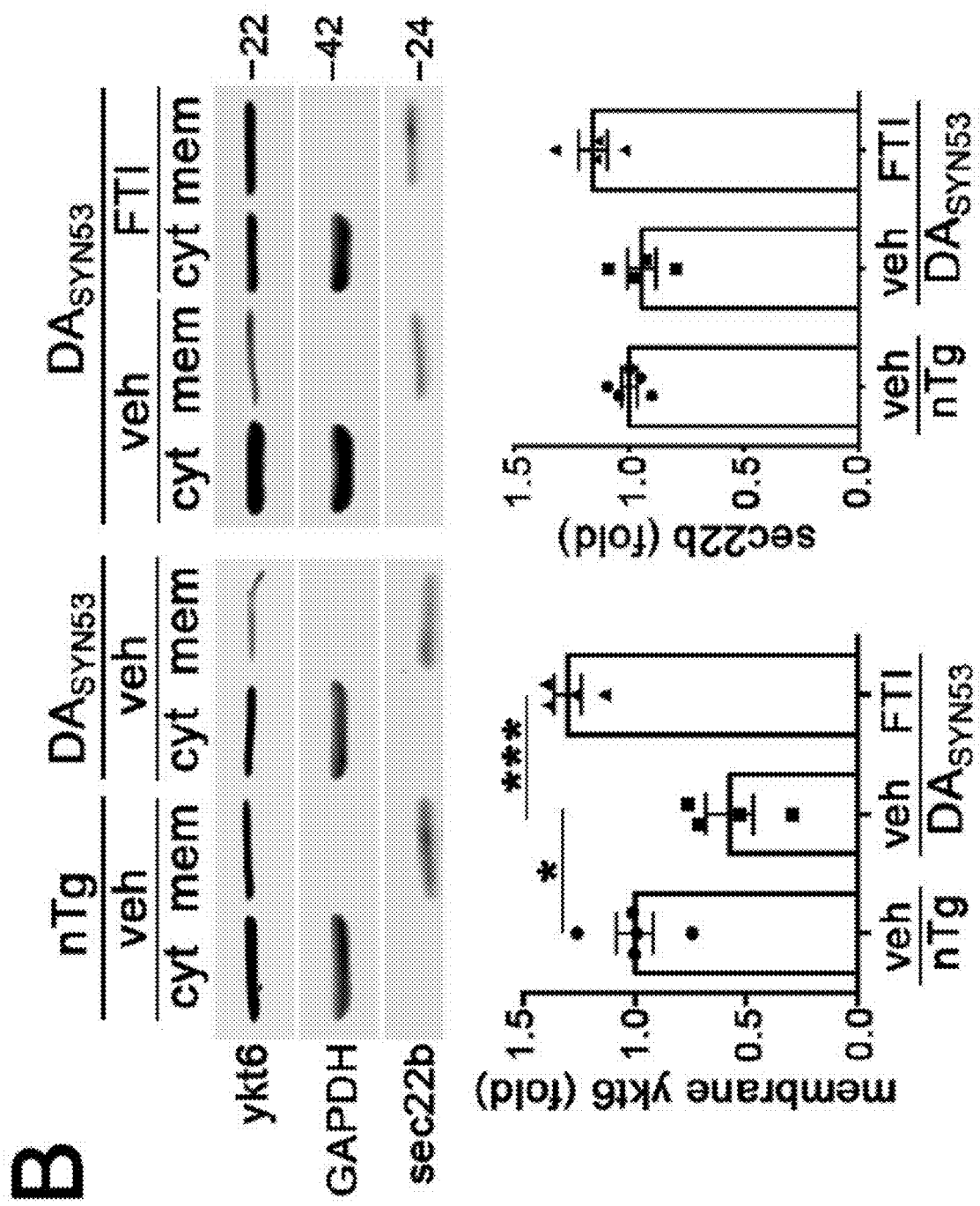
Figure 7C:
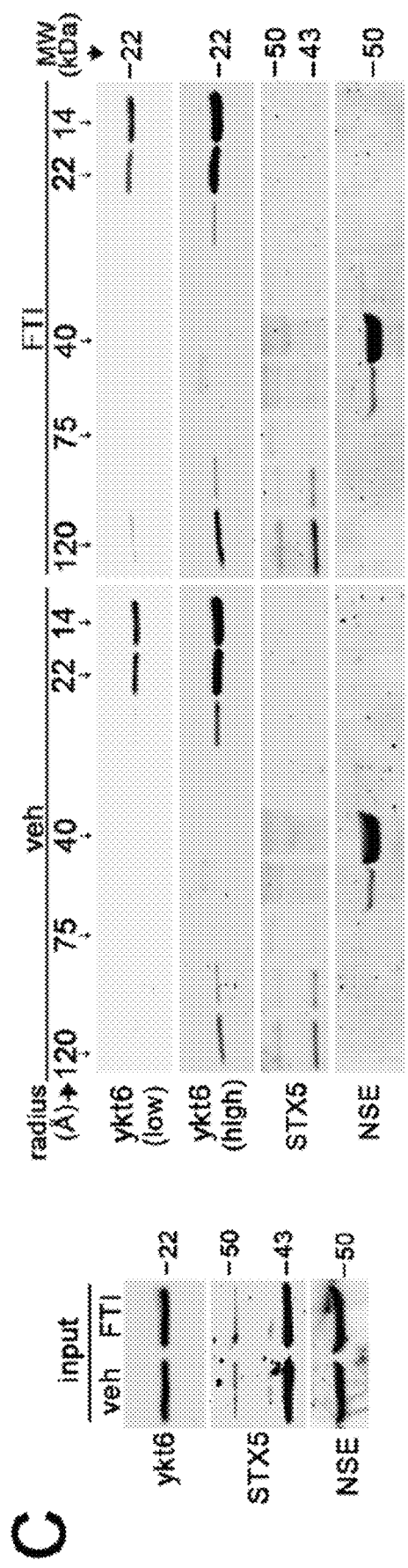
Figure 7D:
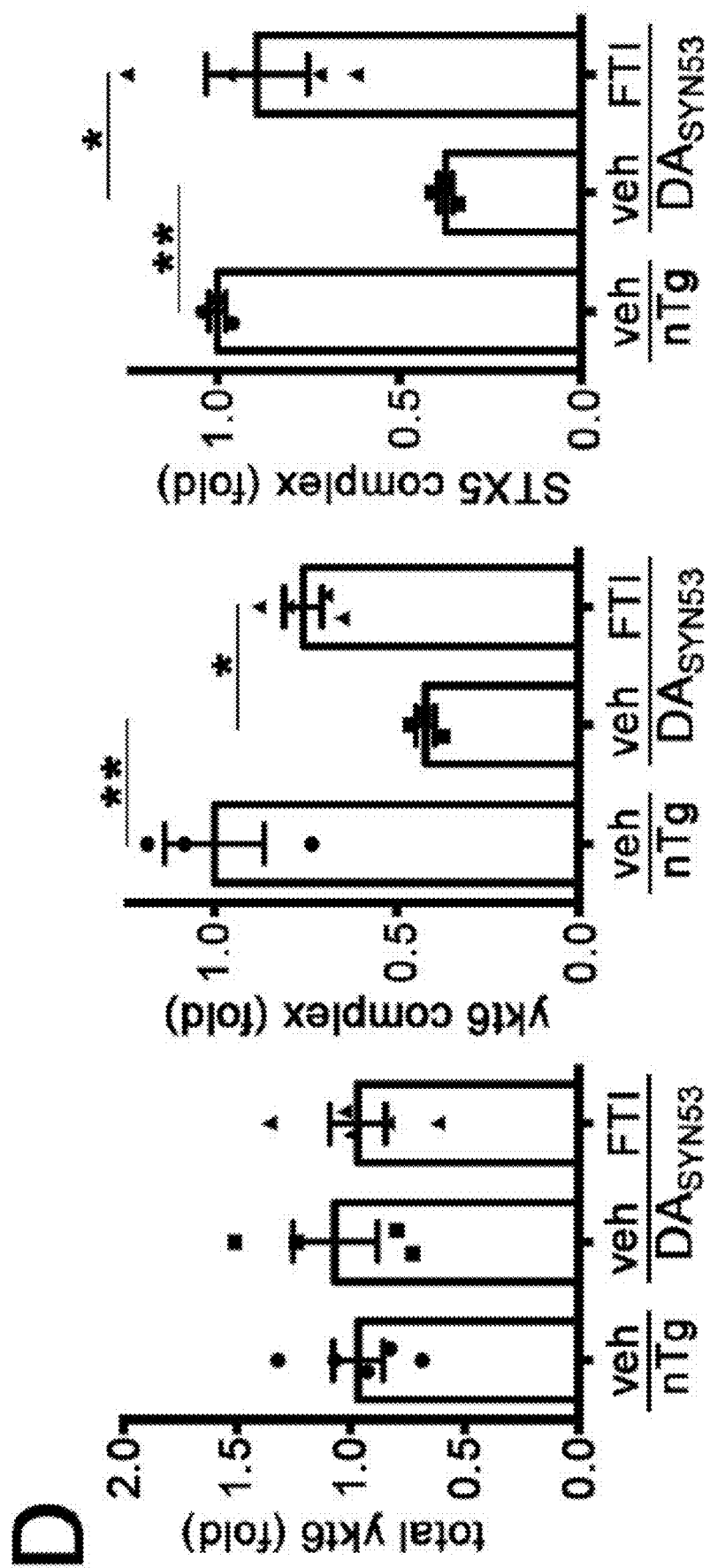
Figure 7E:
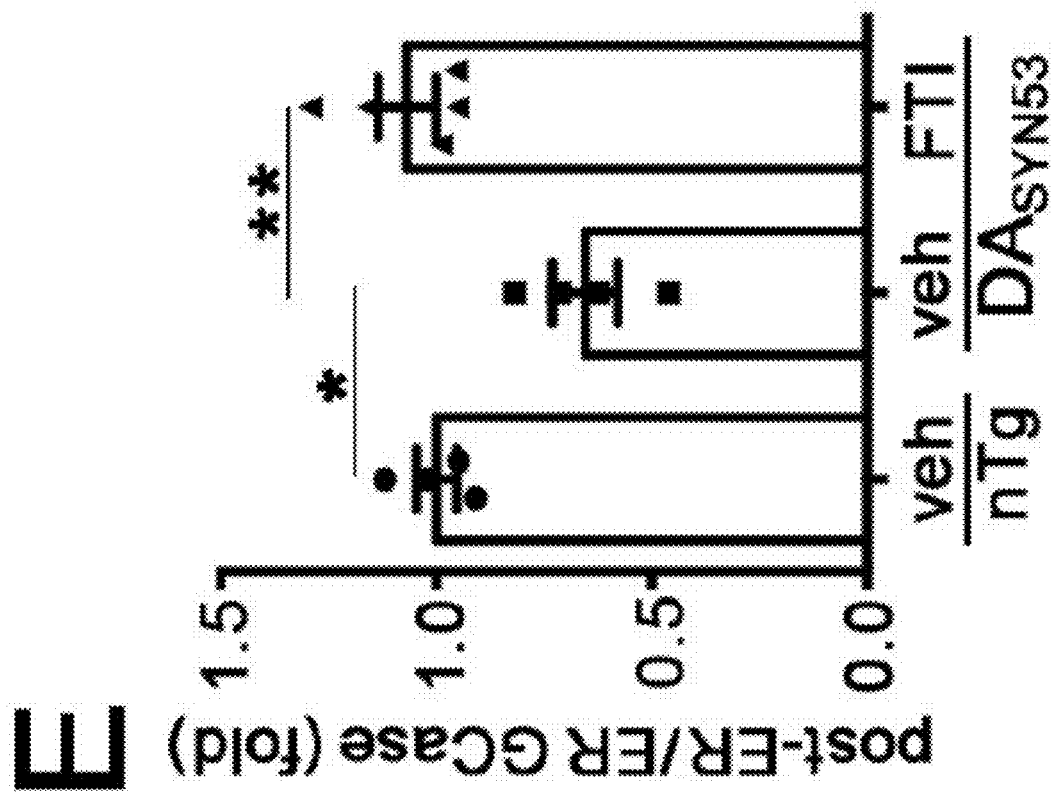
Figure 8A:
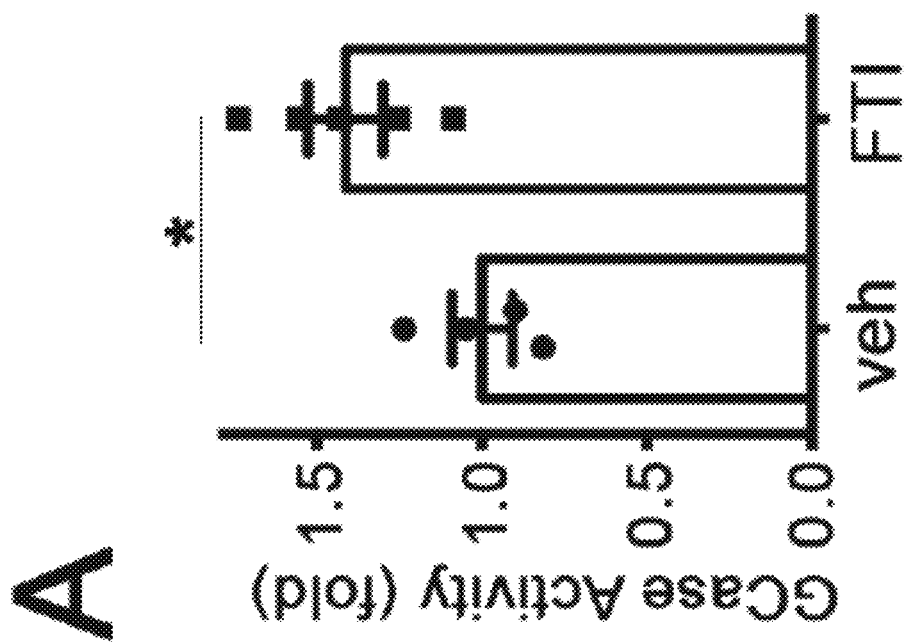
FIGS. 8A, 8B, 8C, 8D, 8E, and 8F. FTI treatment enhances GCase activity and reduces pathological a-syn in transgenic mice. 8A) GCase activity in the midbrain of FTI (LNK-754)-treated DASYN53 mice (treated as in FIG. 7) (n=4, veh; n=5, FTI). 8B & 8C) Quantification of soluble and insoluble a-syn from midbrains of FTI-treated DASYN53 mice normalized to total protein (CBB). Syn211 is selective for human (hu) a-syn; C20 and syn303 detect mouse (ms) and hu a-syn, (n=3, nTg+Veh; n=4 DASYN53+veh; n=5 DASYN53+FTI). 8D) Midbrain TH levels were quantified by western blot of FTI-treated DASYN53 mice (n=3). 8E) Body weight of FTI-treated DASYN53 mice (n=9, nTg+Veh; n=7, DASYN53+veh; n=7 DASYN53+FTI). 8F) Rotarod test of FTI-treated DASYN53 mice (n=12, nTg+Veh; n=7, DASYN53+veh; n=7 DASYN53+FTI). Values are the mean+/−SEM. *p<0.05, p<0.01, and * p<0.001. Student's t-test, panel A; ANOVA with Tukey's posthoc test, panels B-F.
Figure 8B:
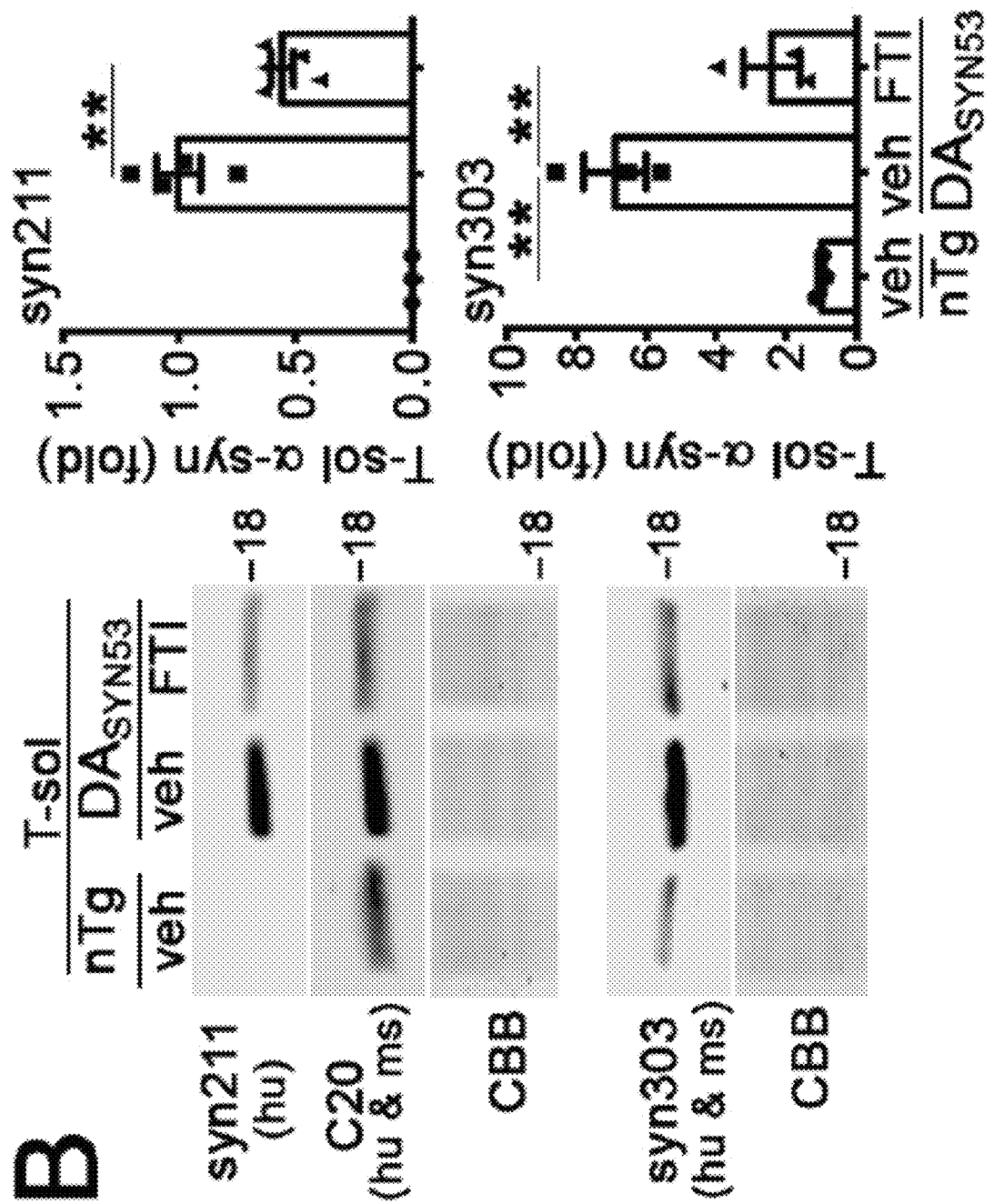
Figure 8C:
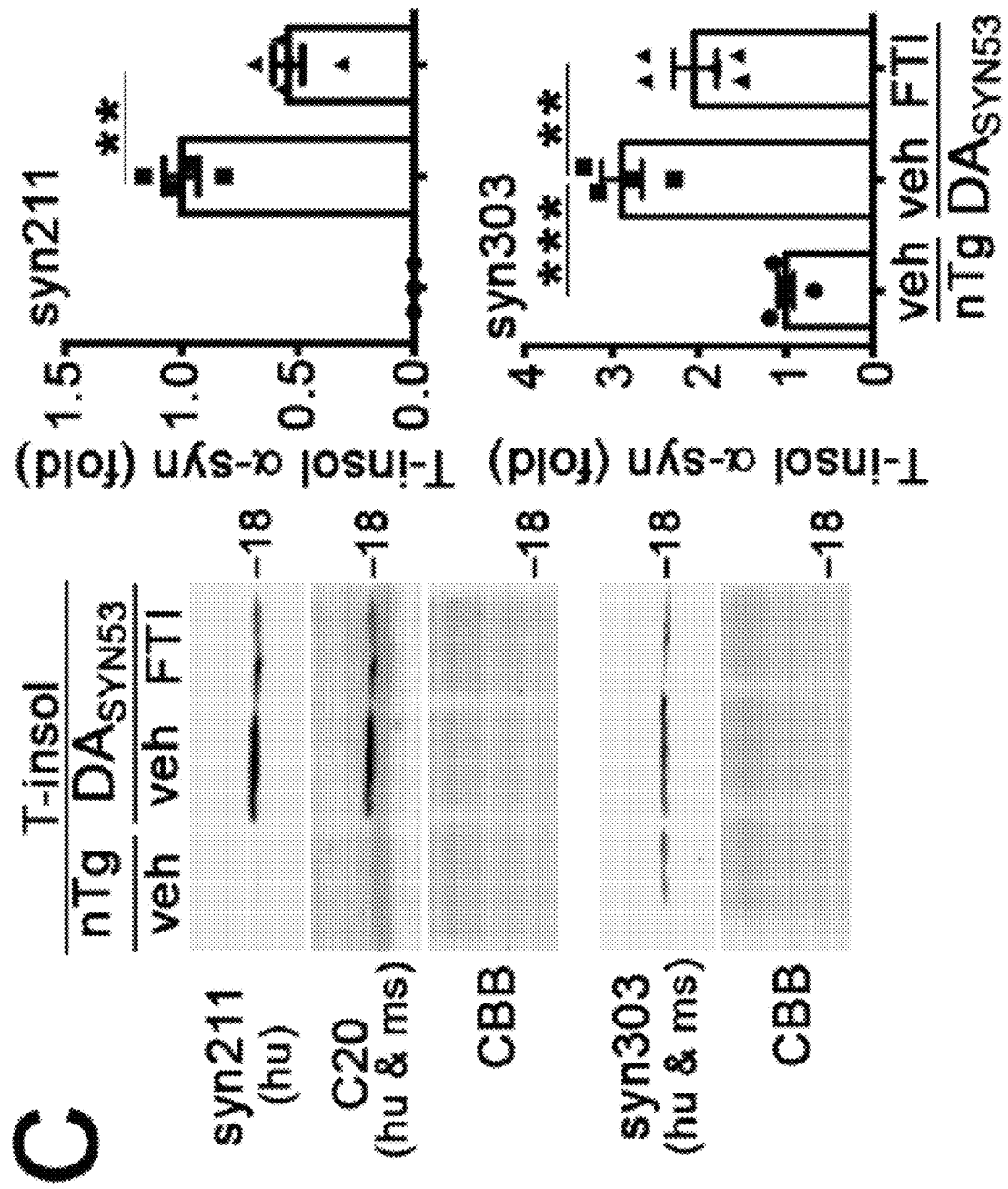
Figure 8D:
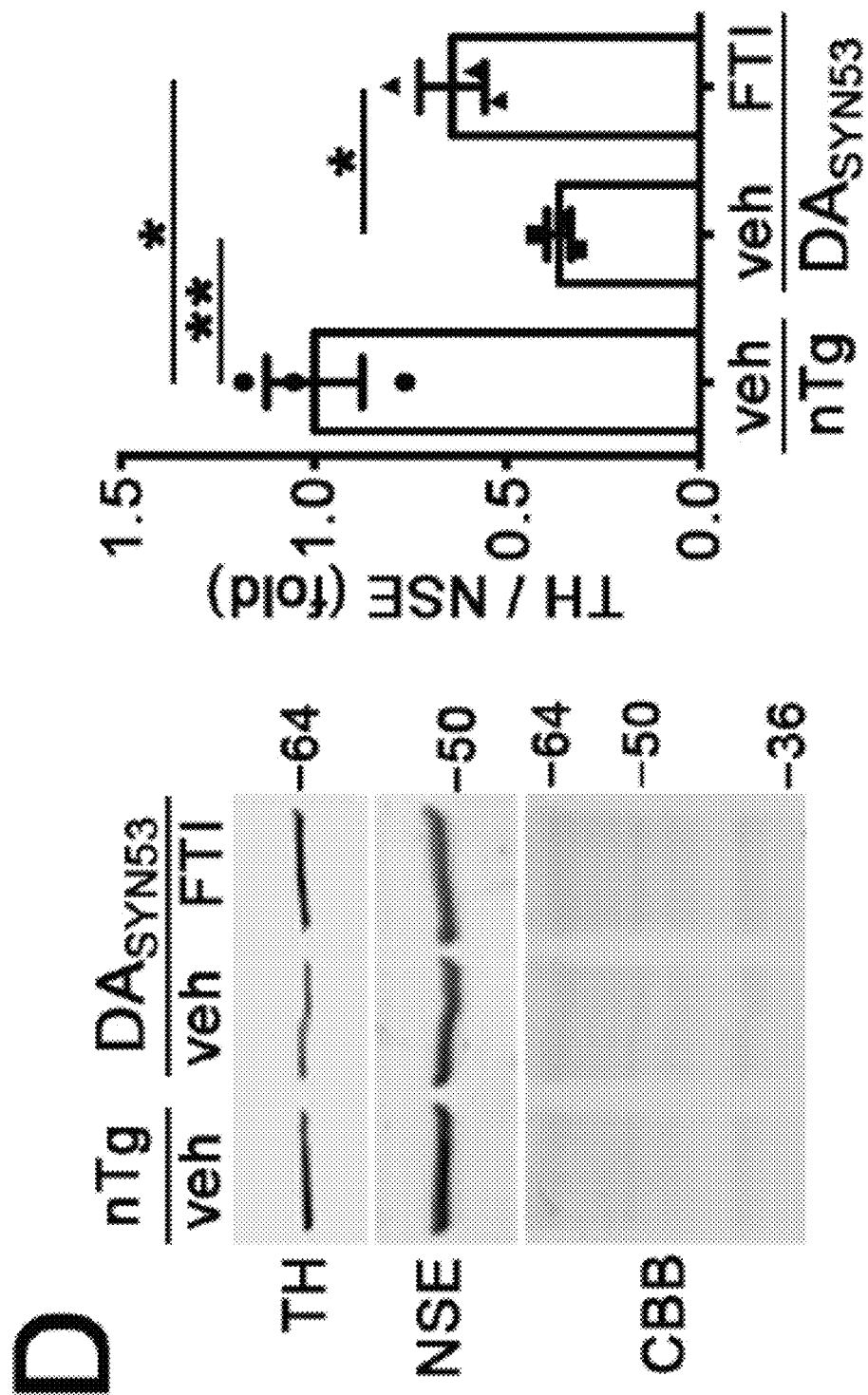
Figure 8E:
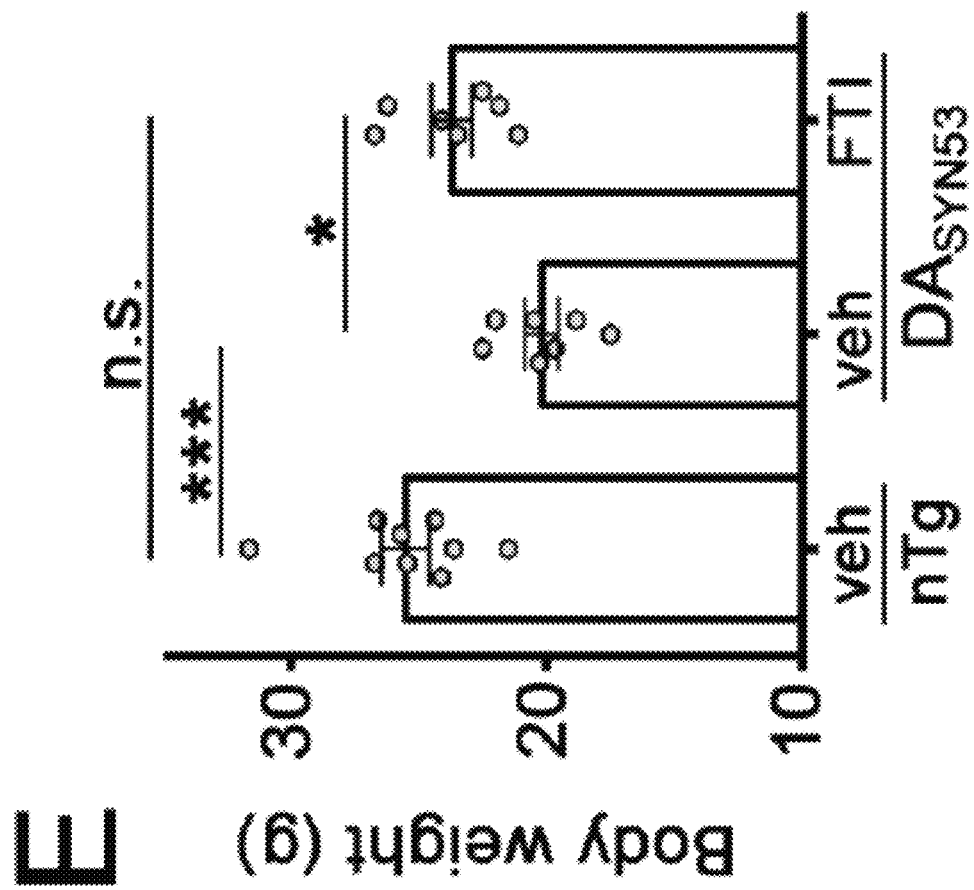
Figure 8F:
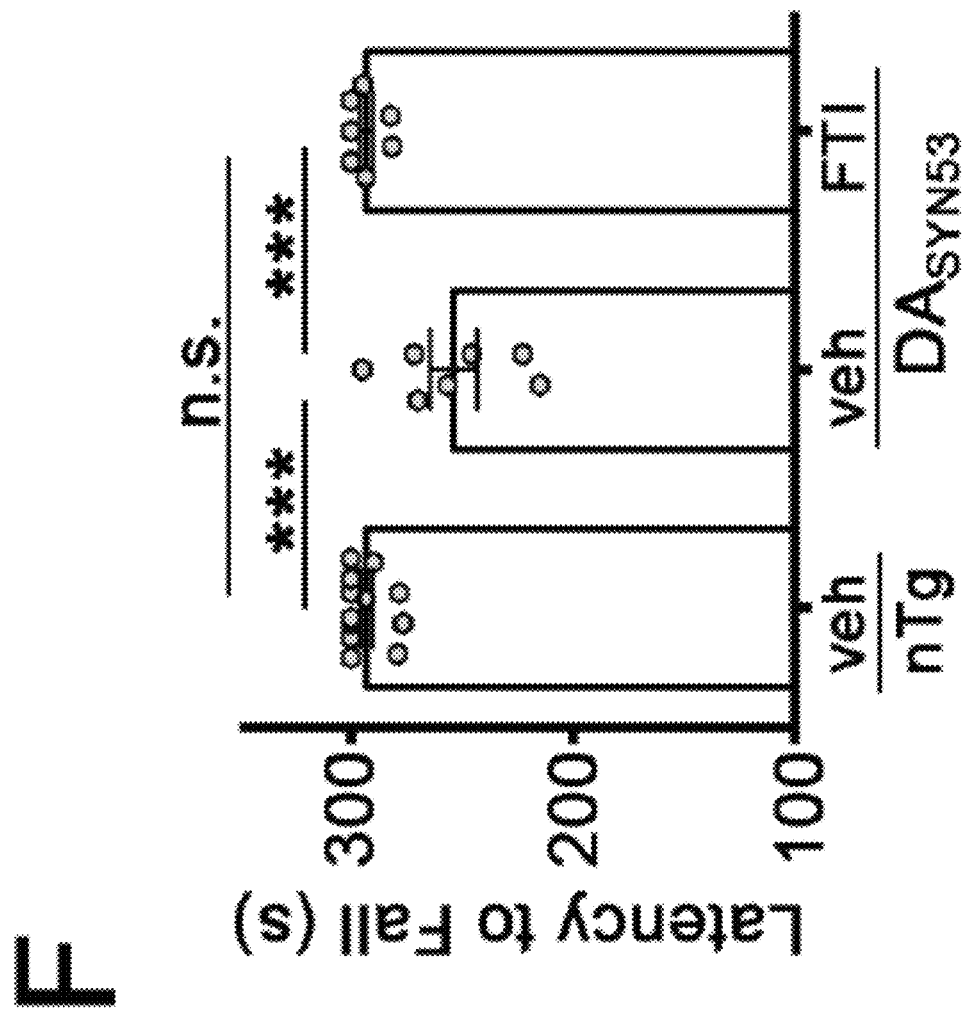

Having demonstrated that the FTI can activate ykt6 in vivo, we then tested its ability to rescue pathological phenotypes of an established mouse model that expresses human A53T a-syn within dopaminergic neurons (DASYN53) (Chen et al., 2015). We first examined the expression pattern of ykt6 within the midbrain and found that it was robustly expressed in TH+ neurons of the substantia nigra (FIG. 7A). DASYN53 mice demonstrated reduced membrane-associated ykt6 and SNARE complexes compared to non-transgenic (nTg) littermates, and FTI treatment by i.p. injection reversed these effects (FIG. 7B-D). FTI treatment enhanced GCase trafficking, as indicated by increased mature, endo H resistant forms of the protein (FIG. 7E). To determine the functional effects of FTIs on the lysosomal system, we measured GCase activity in midbrain of DASYN53 mice and found that the FTI enhanced activity by ca. 40% (FIG. 8A). Importantly, this level of activity enhancement was sufficient to reduce soluble and insoluble A53T a-syn in midbrain extracts (FIG. 8B, C). We then assessed the level of TH protein in the midbrains of DASYN53 mice, since previous studies have shown that reduction of TH is tightly associated with neurodegeneration and occurs subsequent to A53T a-syn accumulation (Chen et al., 2015). We confirmed that TH protein was reduced in the midbrain of DASYN53 mice compared to nTg mice, and found that FTI treatment could partially restore TH levels (FIG. 8D). We also documented a mild but significant reduction in body weight and motor performance of DASYN53 mice compared to nTg animals, which was rescued by FTI treatment (FIG. 8E, F). Together, these data indicate that the FTI activates ykt6 in the brains of mice to stimulate the lysosomal system and reduce pathological a-syn. FTI-mediated a-syn reduction in multiple iPSn and in vivo models indicates a strong therapeutic potential of this pathway for the treatment of synucleinopathies.

DISCUSSION

We have identified a novel regulatory trafficking pathway that senses and controls the physiological response to lysosomal stress. Previous studies have delineated regulatory gene networks that are required for the synthesis of lysosomal components upon metabolic stress (Sardiello et al., 2009; Settembre et al., 2011). Our studies indicate that ykt6 may be preferentially involved and synergistically interact with these networks by enhancing the transport of lysosomal machinery to promote cellular clearance. Interestingly, TFEB does not appear to regulate the transcription of ykt6 (Palmieri et al., 2011), and our data indicates that total ykt6 protein levels are unaffected by lysosomal stressors or TFEB overexpression (FIG. 3). Instead, our studies indicate that ykt6 responds to lysosomal stress by mechanisms that are mediated by post-translational prenylation, which may enable its rapid response to changing cellular environments. The non-functional cytosolic reserve pool of ykt6 likely acts as a buffer that senses metabolic stress and moves into membranes to promote hydrolase trafficking and lysosomal activity.

Our studies in human midbrain models indicate that lysosomal function is highly sensitive to ykt6 levels, since even partial KD could dramatically affect the transport and activity of lysosomal machinery, while constitutive protein secretion was not changed (FIG. 2, 12B). Previous studies have also noted a partial association of ykt6 with lysosomes (Hasegawa et al., 2003). Although this suggests that ykt6 may be preferentially involved in lysosomal clearance pathways, we were unable to achieve complete depletion of ykt6. It is possible that more efficient knock-down could affect the maturation of other proteins that are processed through the early secretory pathway. It is also possible that ykt6 may have a specialized role in trafficking lysosomal proteins within human iPSn, or its activity could be distributed at different cellular compartments depending on cellular metabolic requirements. For example, other studies have shown that ykt6 could affect constitutive protein secretion in non-neuronal cells or in Drosophila (Gordon et al., 2010; Gross et al., 2012). Ykt6 may have a more prominent secretory function in cells that exhibit high levels of basal constitutive secretion, such as rapidly dividing neuroendocrine or HEK cell lines. It is also important to note that previous studies have established redundancy in SNARE mediated trafficking pathways (Liu and Barlowe, 2002). Human iPSC-midbrain neurons may not possess a redundant SNARE pathway that can stimulate the trafficking of lysosomal proteins in the absence of ykt6, whereas secretory or plasma membrane protein trafficking may be compensated for by other SNARE complexes when ykt6 is depleted. Together, our data underscore the complexity of protein transport mechanisms utilized under basal vs. stressful conditions, and suggests that distinct SNARE complexes mediate different cargoes depending on the metabolic needs of the cell.

Previous studies have shown that the autophagic-lysosomal system is activated during periods of a-syn accumulation (Ebrahimi-Fakhari et al., 2011; Mak et al., 2010), and elevated expression of lysosomal proteins occurs in response to pathogenic protein accumulation in other neurodegenerative diseases (Cataldo et al., 1995). Consistent with this, we find that TFEB can translocate into the nucleus and elevate the mRNA and protein of lysosomal components in PD patient neurons that exhibit cellular inclusions (FIG. 10). This suggests that lysosomal dysfunction does not occur from reduced synthesis of lysosomal proteins, but instead occurs from impeded trafficking as suggested by previous studies (Chung et al., 2013; Cooper et al., 2006; Gitler et al., 2008; Mazzulli et al., 2016a). Our findings suggest that once a-syn accumulation is initiated, it can disable the physiological response to lysosomal stress by blocking vesicular trafficking pathways that are essential for lysosomal function (FIGS. 16 and 17). Since lysosomes are important for a-syn clearance (Cuervo et al., 2004), disabling this pathway could provide a permissive environment for aggregates to persist and continue to grow in the cell. This may also lead to favorable conditions for aggregate self-replication, by increasing opportunities for seed fibrils to interact and convert newly made, physiological a-syn into additional pathogenic species. Self-replication of amyloid fibrils by templated conformational conversion is a well established phenomenon (Jarrett and Lansbury, 1993), and early studies have shown that pathological a-syn fibrils can replicate by conversion of soluble monomers through a nucleation dependent mechanism (Wood et al., 1999). Similarly, more recent in vivo and culture studies have shown that a-syn fibrils can propagate within and between neurons (Luk et al., 2012; Volpicelli-Daley et al., 2011). Our studies are consistent with the notion that pathological a-syn possesses self-reproducing features by disabling clearance mechanisms that are meant to eliminate it from the cell (FIGS. 16 and 17).

Our data also have important implications for the development of novel therapies. We find that overexpression and activation of ykt6 alone is sufficient to restore lysosomal activity in PD patient neurons, leading to a reduction of pathological a-syn. Ykt6 overexpression preferentially rescues lysosomal function, and does not change the levels of plasma membrane proteins or constitutive secretion (FIG. 4). Our data indicates that ykt6 rescues lysosomal function by enhancing ER-Golgi transport and that blocking farnesylation of ykt6 could further enhance membrane association and binding of ER-Golgi SNAREs (FIG. 5A, B). Important for the development of ykt6 as a therapeutic target, we identify a druggable method to harness its fusogenic activity through the use of a validated FTI that exhibits drug-like properties. The FTI potently influences GCase activity by correcting its distribution into lysosomes at concentrations as low as 1 nM, resulting in reduced a-syn in PD patient neurons (FIG. 5C-G, FIG. 6). FTI treatment rescued phenotypes in DASYN53 mice, but also enhanced lysosomal activity in healthy wild-type mice (FIG. 15). This indicates the potential of this pathway for the clinical advancement of not only synucleinopathies, but possibly of other diseases characterized by protein aggregation such as Alzheimer's disease. Strategies centered on enhancing protein trafficking and lysosomal activity may provide the most effective disease-altering therapies for synucleinopathies, since they target two pathways that synergize and are considered critical for pathogenesis (Abeliovich and Gitler, 2016).

Experimental Model and Subject Details

Overview of models employed in this study. Inducible human H4 neuroglioma cells expressing a-syn under the control of a tetracycline-responsive promoter (tet-off) (Mazzulli et al., 2011) and iPS-derived dopaminergic neurons (iPSn; from control, PD and GD patients) were utilized as cell models to study a-syn aggregation and structure. iPS cells models have been previously authenticated (Mazzulli et al., 2016a). The authentication procedure is based on genotyping for common disease-causing mutations (published in (Mazzulli et al., 2011)), pluripotency analysis, karyotype analysis, efficient differentiation into midbrain dopamine neurons, and absence of *mycoplasma*. H4 cells have been previously authenticated (Mazzulli et al., 2011) by analyzing expression of a-synuclein (a-syn) and absence of *mycoplasma*. The gender of cell lines is listed in the "Key Resources Table" document. Randomization of samples or cell cultures during analysis of HPLC, cell toxicity assays, and biochemical assays was done to account for any technical variations as noted below. Blinding of the samples to the experimenter was done when possible and noted below. In some cases, obvious differences in culture behavior, morphology, solution turbidities, color, or other easily identifiable features made blinding difficult.

H4 cell culture. The culture of inducible human H4 neuroglioma cells express a-syn under the control of a tetracycline-responsive promoter (tet-off) were previously described (Mazzulli et al., 2011). Cells were grown in Optimem media containing 5% fetal bovine serum (FBS), 200 µg/ml Geneticin and Hygromycin, and 1% penicillin/streptomycin (from www.thermofisher.com). a-Syn expression was turned off by the addition of 1 µg/ml doxycycline (DOX) for 48 hours.

Generation of stable-transfected SH-SY5Y cell lines. Naïve SH-SY5Y cells (ATCC #CRL-2266, female origin) were cultured in a 10 cm dish in DMEM containing 10% FBS and 1% penicillin/streptomycin and transfected with pCDNA3.1, pCDNA3.1-wt-a-syn, pEGFP-wt-ykt6, pEGFP-ykt6-CS or pEGFP alone with lipofectamine 2000. After 48 hrs, cells were passaged into 10 ea 10 cm dishes G418 was added to the media gradually in 50 uM increments, starting at 50 uM and gradually increasing to 800 uM over 2 weeks. Remaining colonies (approx. 20 per line) were picked, expanded, and analyzed for a-syn expression, morphology, and the ability to differentiate with retinoic acid. The most stable clones were chosen for vector or wt-a-syn expressing cells and used for studies and cultured in the above media containing 200 uM G418. For each experiment, SH-SY5Y cells were differentiated with all trans retinoic acid (10 uM) for 5 days.

iPS cell culture and neuronal differentiation. iPS cell culture procedures and differentiation into midbrain dopaminergic neurons have been described in detail previously (Mazzulli et al., 2016a). Human iPSCs were maintained in mTeSR1 media (http://www.stemcell.com/en/Products/All-Products/mTeSR1.aspx) on matrigel (Thermofisher Scientific) coated dishes. Established iPSC lines from a healthy control was used (line "C3, 2135" from (Mazzulli et al., 2016a)). Parkinson's disease patient derived lines expressing A53T a-syn and matching isogenic corrected lines were generously provided by Dr. R. Jaenisch (Whitehead Institute of MIT) and characterized previously (Soldner et al., 2011). iPSC lines harboring the SNCA gene triplication were previously described and extensively characterized (Mazzulli et al., 2016a). iPSCs were differentiated into midbrain DA neurons using an established protocol (Kriks et al., 2011). Neurons were differentiated for 40 days in a cocktail of growth factors (Kriks et al., 2011) followed by withdrawal of growth factors from day 40-60. They were maintained in neurobasal media (Thermofisher Scientific, #21103-049) containing NeuroCult SM1 supplement (Stemcell Technologies #05711) and 1% penicillin/streptomycin until used for experiments. Maturation and quality control of iPSC-neurons was analyzed on each differentiation batch by the location of a-synuclein into synapse, by colocalization with synapsin, and the ratios of biii-Tubulin/GAPDH to assess the relative levels and efficiency of differentiation between batches. A full and extensive characterization of iPSCs and iPSC-derived midbrain neurons has previously been done in our recent study (Mazzulli et al., 2016a). iPSC lines were cultured for 60-130 days for each experiment, and each assay was done with at least 3 technical replicates as indicated in figure legends, and confirmed in 2 to 3 independent differentiation batches.

Control and transgenic alpha-synuclein mouse lines. Wild type C57Bl/6 mice were purchased at 3 months of age (equal male and female groups) from Charles River (Strain code 027) and housed in accordance with the US National Institutes of Health Guide to the Care and Use of Laboratory Animals and Society for Neuroscience guidelines. Mice were provided standard rodent chow and water ad libitum.

Transgenic mice expressing human A53T-a-syn under the control of the dopamine transporter promoter (DASYN53) were previously described (Chen et al., 2015). Single-transgenic mice between the ages of 12 and 14 months (equal male and female groups) were utilized for experiments. Mice were bred and housed according to the Institutional Animal Care and Use Committee at Northwestern University guides and handled in accordance with the US National Institutes of Health Guide to the Care and Use of Laboratory Animals and Society for Neuroscience guidelines. Mice were provided standard rodent chow and water ad libitum. Genotyping of animals was performed as a service provided by Transnetyx (https://www.transnetyx.com) by tail clipping and were numbered consecutively by ear tags. Non-transgenic control littermates were always compared to mice expressing A53T a-synuclein mice. These mice were employed for studies shown in FIGS. 7 and 8. The use of wild-type and transgenic mice were approved under Northwestern IACUC protocol number IS00011551.

Method Details

CRISPR/Cas9n of iPSCs

T7 Endonuclease I Assay for the analysis of off-target effects of alpha-syn knock-out iPSC. These procedures have been previously described (Zunke et al., 2018). Genomic regions of the top 9 homologous regions to SNCA were amplified using Q5 High Fidelity DNA polymerase (New England Biolabs). PCR amplicons were denatured and hybridized in a thermal cycler: 95° C. for 10 minutes, 95-85° C. (ramp rate −2C/sec), and 85-25° C. (ramp rate −0.2° C./sec). The hybridized PCR product was digested using T7 Endonuclease I (New England Biolabs) for 1 hour at 37° C. Equal volumes of undigested and digested PCR products were resolved on 1.5% agarose gel along with positive control (Genecopoeia).

Biochemistry and Cell Biology

Generation of plasmids. pENTR223-ykt6 containing cDNA plasmids were obtained from the Harvard plasmid ID repository (https://plasmid.med.harvard.edu/PLASMID/) and subcloned into either pCDNA3.1 for transfections or pER4 for lentiviral generation. GFP fusions were added by subcloning ykt6 into pEGFP-C1 (Clontech). Mutations in ykt6 were generated by site directed mutagenesis using the QuikChange kit from Agilent (www.agilent.com).

Co-immunoprecipitation analysis. To co-immunoprecipitate (co-IP) a-syn and ykt6, cultures were extracted in 0.3% CHAPS buffer (0.3% CHAPS, 40 mM HEPES pH 7.4, 120 mM NaCl, 1 mM EDTA, 10% v/v glycerol) by homogenization and incubation on ice/water slurry for 30 min. Lysates were cleared by centrifugation at 21,000×g for 20 min and pre-cleared by incubation with normal rabbit IgG (Santa Cruz)+pre-blocked protein A/G beads (Santa Cruz). 500 ug of lysate was incubated with 2 ug of anti a-syn antibody (C-20, Santa Cruz), ykt6 antibody (ab77150, abcam, www.abcam.com), or 2 ug of normal rabbit IgG to control for non-specific binding, plus 30 ul of preblocked protein A/G beads overnight at 4° C. with rotation. Beads were collected by centrifugation at 1000×g for 5 min, washed three times in 0.3% CHAPS lysis buffer, and complexes were eluted by boiling in 2× Laemmeli sample buffer. Samples were loaded onto 18% SDS-PAGE gels and analyzed by western blot using anti-a-syn (C-20), anti-sec22b (29-F7, SC-101267, Santa Cruz), anti-ykt6 (abcam), anti-bet1 (Santa Cruz, SC-136-390), anti-syntaxin 5 (Santa Cruz, SC-365124). Corresponding immunodepleted lysates were also analyzed by western blot to confirm interactions.

To co-IP ykt6 SNARE assemblies, approximately 106-107 cells expressing GFP-tagged YKT6, were harvested in 1 ml of PBS, scraped off the plate and transferred to centrifuge tubes. The cells were subjected to centrifugation 200×g for 5 m at 4° C. The cell pellet was resuspended in ~200 μl co-IP buffer (10 mM Tris-HCl pH 7.5, 150 mM NaCl, 0.5M EDTA and 0.5% NP-40 containing protease inhibitor cocktail, PMSF and NaF) and subjected homogenization (iPSC-neurons) or extensive pipetting (cell lines). The cells were incubated on ice water-slurry for 30 min on a rocker. The cell lysates were cleared by centrifugation at 21,000×g for 30 min, 4° C. and supernatants were subjected to protein assay. A total of 1 mg of protein was adjusted to 500-1000 μl with dilution buffer (Co-IP buffer without 0.5% NP-40). 25 μl of GFP-trap agarose beads (GTA-20, Chromotek, www.chromotek.com) were equilibrated by mixing beads with 500 μl dilution buffer followed by centrifugation at 2500×g for 2 min. The recovered beads were subjected to same procedure 2 more times. Equilibrated beads were mixed with the diluted lysate and incubated overnight at 4° C. under constant shaking. GFP trap beads were recovered by centrifugation and subjected to washing with dilution buffer 3 times. Proteins bound to GFP were eluted in 2× Laemmeli sample buffer and boiling the samples at 95° C. for 10 min. Eluates were analyzed by western blot as described below. The samples were not analyzed in a blinded manner.

Separation of lysates into cytosol and membrane fractions. Cell cultures from either a 10 cm dish (SH-SY5Y) or 6 well (iPSn) were scraped in cold PBS and pelleted by centrifugation at 400×g, 5 min, 4° C. The supernatant was discarded and cell pellets were homogenized in 200-400 ul of cold PBS containing protease inhibitor cocktail mix (1 mM phenylmethanesulfonyl fluoride (PMSF), 50 mM NaF, 2 mM Na orthovanadate, and a protease inhibitor cocktail (Roche diagnostics, http://www.roche.com, #11-836-170-001)) using a Teflon homogenizer in a conical glass vessel for 20-40 times, using a motor driven spindle at 4000 rpm (GlasCol, https://glascol.com/homogenizers). The extract was pelleted at 2,500×g, 4° C. for 10 min, the supernatant was saved, and the pellet was re-extracted as before. The supernatants were then centrifuged at 100,000×g, 4° C. for 30 min and saved as the cytosolic fractions. The remaining pellet was extracted in 1% Triton X-100 buffer (1% Triton X-100, 20 mM HEPES pH 7.4, 150 mM NaCl, 10% glycerol, 1 mM EDTA, 1.5 mM MgCl2, 1 mM phenylmethanesulfonyl fluoride (PMSF), 50 mM NaF, 2 mM Na orthovanadate, and a protease inhibitor cocktail (Roche diagnostics, http://www.roche.com, #11-836-170-001)) by pipetting and 3 freeze/thaw cycles, incubated on and ice-water slurry for 20 minutes and ultracentrifuged at 100,000×g, 4° C. for 30 minutes. The triton-soluble fraction was saved as the membrane containing fraction. Fractions were then analyzed by western blot analysis as described below. The samples were not analyzed in a blinded manner.

Size exclusion chromatography analysis. Cultures or PD brain (cingulate cortex, previously described (Mazzulli et al., 2011)) were homogenized as described above in 1% Triton buffer, centrifuged at 100,000×g for 30 min at 4° C. 1 mg of soluble lysate was injected on a Superdex 200 HR 10/300 gel filtration column (www.gelifesciences.com) using a mobile phase of phosphate buffered saline at pH 7.4

(PBS) (sample injection volume: 800 µg lysate into 250 flow rate at 0.3 ml/min; 0.5 ml sized fractions, sample loop maximum volume=400 ul), using an Agilent HPLC 1200 series pumps, autoinjector, UV/vis detector, and fraction collector. Samples were concentrated using 10,000 MWCO filters from Millipore, mixed with sample buffer, boiled, and loaded onto SDS-PAGE gels for western blot analysis. The sample identity was blinded for human samples and cell cultures.

Knock-down of ykt6 shRNA expressing constructs. MISSION shRNA sequences in pLKO.1 vectors targeting ykt6 were obtained from Sigma-Aldrich and tested for efficiency in transfected HEK cells by ykt6 western blot analysis. Clone #TRCN0000059765 was found to achieve the most efficient knock-down in the absence of toxicity and was used for further experiments. This construct was packaged into lentiviral particles by transfecting HEK293T cells with FuGENE HD (Promega) and virused was used at MOI 3, dpi 7 in iPSC-neurons or SH-SY5Y cells. Constructs were also transfected into SH-SY5Y cells and stable cell lines were selected with puromycin at 1-2 ug/ml.

Measurement of farnesyl-ykt6 in SH-SY5Y cells. The method used was based off of a previously published protocol (Kho et al., 2004). SH-SY5Y stable lines expressing GFP alone or GFP-ykt6 were cultured on 10 cm dishes until ~75% confluent. Media was replaced on all cultures with media containing 20 uM lovastatin and 20 uM farnesyl-alcohol azide (Cayman Chemical Company). Either 10 nM FTI (LNK-754) or an equivalent volume of DMSO was then added. After 48 hours of incubation, protein was extracted in 400 uL RIPA lysis buffer supplemented with fresh protease inhibitor cocktail, 50 mM NaF, 0.2 mM sodium orthovanadate, and 1 mM PMSF. 1 mg total protein in 1 mL Dilution/Wash buffer (10 mM Tris/Cl; 150 mM NaCl; 0.5 mM EDTA) was incubated with 20 uL GFP-Trap_A beads (Chromotek) for 1 hour at 4° C. rotating end over end. Beads were collected by centrifugation at 2500×g for 2 minutes at 4° C. following the provided protocol. Beads were washed 3× in Dilution/Wash buffer before resuspension in 500 uL Dilution/Wash buffer containing 50 uM phosphine-biotin (Cayman Chemical Company). Reactions were shaken horizontally overnight at room temperature. Beads were collected, washed 3×, and boiled for 10 minutes in 50 uL 2× sample buffer. The mixture was finally centrifuged at 2500×g for 2 minutes, and the supernatant was collected for western blot analysis using streptavidin-IRDye 800 conjugated detection reagent to detect farnesylykt6. Values were normalized to total amount of GFP-ykt6 precipitated using anti-GFP antibodies (Sigma) or anti-ykt6 antibodies. The sample identity was not blinded.

Measurement of Neuroserpin, LAMP1, GCase protein and activity from culture media. Media from cultures where ykt6 was depleted was conditioned for 3 days, collected and concentrated, and used for analysis. As a negative control, media not exposed to cultures was analyzed in parallel. For analysis of LAMP1, GCase, and total N-linked glycosylated proteins, 500 µl of conditioned media was mixed with 20 µg/ml biotinylated Concanavalin (CON-A) and the reaction mixture was incubated overnight at 4° C. with gentle rotation. CON-A bound proteins were recovered using neutrAvidin agarose beads (29204, ThermoFisher, Scientific). NeutrAvidin (25 µl) was added to the reaction mix and incubated at 4° C. for 1 h. Beads were collected by centrifugation at 2500×g for 2 min. This was followed by washing with PBS 3 times. N-glycosylated proteins were eluted in 2× Laemmeli sample buffer and boiling the samples at 95° C. for 10 min. Samples were analyzed by western blot for LAMP1, GCase, or total N-glycosylated proteins by Coomassie brilliant blue staining of the pulled-down samples.

Neuroserpin levels were measured in the conditioned media using LSBio Human neuroserpin ELISA development kit (LS-F31370). Conditioned media was collected and subjected to centrifugation at 200×g for 5 m at 4° C. to remove any dead cells. 1 ml media was concentrated to 20 ul using Amicon ultra centrifugal filter units (UFC50108K, Millipore). Concentrated media (10 µl) were subjected to neuroserpin ELISA following the manufacturer's protocol. The neuroserpin levels in the media were calculated using a standard curve and normalized to the total cellular protein levels.

Analysis of GCase activity was done in 100 ul of conditioned media that was concentrated to 20 ul using Amicon ultra centrifugal filter units (UFC50108K, Millipore) and buffer exchanged into GCase activity assay buffer ((0.25% (v/v) Triton X-100 (Sigma-Aldrich #T-8787), 0.25% (w/v) Taurocholic acid (Sigma-Aldrich, #T9034), 1 mM EDTA, in citrate/phosphate buffer, pH 5.4). 4-methylumbelliferyl β-D-glucopyranoside (4-MUGluc; Sigma-Aldrich) was added and incubated at 37° C. for 2 hours, followed by addition of an equal amount of stopping solution (1 M glycine, pH 12.5). 4-MU-Gluc fluorescence (ex=355 nm, em=460) was detected in a Molecular Devices i3 microplate reader using fluoro plates (Nunc, #475515). The sample identities were not blinded.

Measurement of mRNA. Total RNA was extracted and isolated from ykt6 shRNA infected iPSC neurons at 7 dpi using the PureLink RNA Mini Kit (Thermofisher Scientific). cDNA was synthesized using the RevertAid First Strand cDNA Synthesis Kit (Thermofisher Scientific). Real-time PCR was performed on a Applied Biostems 7500 Fast system using predesigned Taqman-primer probe sets: LAMP1 (Hs00174766_ml), GBA1 (Hs00164683_ml), YKT6 (Hs01127135_ml), and GAPDH (Hs02758991_gl). The quantification is represented as fold change of target mRNA expression normalized to GAPDH levels by delta-Ct method. The values are mean and s.e.m of three biological replicates (n=3) with three technical replicates for each. The sample identities were not blinded.

Analysis of post-ER GCase. 40 ug of lysates were digested with Endoglycosidase H (Endo H) according to the manufacturer's protocol (New England Biolabs, www.neb.com) for 2 hours. In parallel, samples without enzyme were incubated under the same conditions as a control. Laemmeli sample buffer was added and digests were run on 10% SDS-PAGE gels for 3-4 hours at 120V. Gels were subjected to western blot analysis by incubation with GCase (8E4) antibodies (Gift of J. Aerts, Leiden University). Endo H resistant bands migrating at 62-64 kDa were measured as post-ER forms of GCase, and normalized to GAPDH levels. The sample identities were not blinded.

Sequential biochemical extraction for the analysis of pathological a-synuclein. Cells were harvested in phosphate buffered saline (PBS), pH 7.4, and pelleted by centrifugation at 400×g for 5 minutes. Cell pellets were extracted in 1% Triton X-100 buffer (1% Triton X-100, 20 mM HEPES pH 7.4, 150 mM NaCl, 10% glycerol, 1 mM EDTA, 1.5 mM MgCl2, 1 mM phenylmethanesulfonyl fluoride (PMSF), 50 mM NaF, 2 mM Na orthovanadate, and a protease inhibitor cocktail (Roche diagnostics, http://www.roche.com, #11-836-170-001)) by homogenization, incubated on and ice-water slurry for 20 minutes and ultracentrifuged at 100,000× g, 4° C. for 30 minutes. Supernatant (Triton-soluble fraction) was used for Bradford or BCA (Pierce) protein assay. The Triton-insoluble pellets were dissolved in SDS-lysis buffer (2% SDS, 50 mM Tris, pH7.4 and a protease inhibitor cocktail (Roche diagnostics)). The samples were boiled for 10 min, sonicated three times for 3 seconds, boiled again for 10 min and centrifuged at 100,000×g for 30 min at 22° C. Protein concentration was measured by BCA assay (Pierce). The sample identities were not blinded.

Western blot analysis. 20-40 ug of total lysate or immunoprecipitated material was loaded into tris-glycine SDS-PAGE gels (10-15% acrylamide, depending on the assay) and run at 150V for 1.5 hrs for most assays, or for 3-4 hours for GCase post-ER/ER ratio analysis, using Thermofisher Scientific Mini Gel Tank module (#A25977). Gels were transferred onto Millipore immobilon-FL PVDF membranes with low-autofluorescence using Thermofisher Scientific Miniblot (#B1000) at 20V for 1 hour, post-fixed in 0.4% PFA (for a-syn) or 100% MeOH (all other applications), and blocked in Odyssey blocking buffer (Licor). Primary antibodies were incubated overnight at 4° C., washed 3 times with TBS-Tween (0.1%), and secondary antibodies (Alexa 680, Molecular Probes; or IRDye800, Licor) were added at 1:10,000 in blocking buffer for 1-2 hours. The blots were washed as before and scanned/analyzed using an Odyssey infrared imaging system with Image Studio Software. All blots were normalized to loading controls including GAPDH, biii-Tubulin, or total protein (Coomassie stain from the gel left over after the transfer). The sample identities were not blinded.

Measurement of neuron viability. iPSC-neurons were seeded on a PDL/laminin coated 96 well plate and analyzed and treated with lentivirus expressing ykt6 CS vs empty vector, or DMSO vs 5 nM FTI (LNK-754) for 14 days. Cells were fixed in 4% paraformaldehyde for 20 minutes and incubated with PBS containing 0.3% TritonX-100 for 20 minutes, then blocked with Odyssey blocking buffer (Li-cor) for 1 hour. Anti-neurofilament antibody (1:1000, mouse IgG 2H3, Developmental Studies Hybridoma Bank, University of Iowa, Iowa City, IA) was incubated overnight in blocking buffer at 4° C., followed by washing in PBS with 0.1% Tween for 20 minutes. IRdye 800-conjugated anti-mouse IgG antibodies (1:1000 dilution, Li-cor) was incubated in blocking buffer for 1 hour, and CellTag™ 700 (Li-cor) was added with the secondary antibody to use for cell normalization. Cells were washed four times in PBS– 0.1% Tween and scanned on an Odyssey infrared imaging system (Li-cor). Neurofilament intensity was determined using Image Studio software (version 2.1 Li-cor) and normalized to cell volume. Replicates represent values from four individual culture wells and were analyzed by Student's T-test using GraphPad Prism software V 6.0. The sample identities were not blinded.

Cell surface biotinylation assay. For biotinylation assays, cells were cultured on 10 cm dishes close to 90-100% confluency. Cells were then rinsed with cold PBS containing calcium (2.66 mM) two times. Cell surface proteins were subjected to biotinylation using EZ-Link™ NHS-Biotin (20217, Thermo-fisher scientific), 500 µg/ml in PBS containing calcium. The reaction was set up at 4° C. for half an hour on a rocker at low speed. Excess biotin was removed by washing cells with PBS containing calcium 3 times, 5 min each. This was followed by quenching excess biotin by washing cells with glycine 100 mM 20 min at 4° C. on a rocker. The cells were washed in PBS and harvested by centrifugation at 200×g for 5 min. The cell pellet was lysed in RIPA buffer (10 mM Tris/Cl pH 7.5, 150 mM NaCl, 5 mM EDTA, 0.1% SDS, 1% Triton-100 and 1% deoxycholate) and subjected to centrifugation at 21,000×g for 20 min at 4° C. The supernatants were subjected to a DCA protein assay (Biorad), and biotinylated proteins were precipitated with Pierce™ High Capacity NeutrAvidin™ Agarose beads (29204, ThermoFisher, Scientific). The desired amount of protein (500 µg) in a volume of 500 µl adjusted with lysis buffer was incubated with 50 µl of equilibrated NeutrAvidin beads, at 4° C. overnight rotating end over end. Beads were recovered by centrifugation at 2500×g, 5 min, 4° C., and subjected to washing with lysis buffer 3 times. Proteins bound to NeutrAvidin beads were eluted in 2× Laemmeli sample buffer and boiled 95° C. for 10 min. and analyzed by western blot using fluorescent labeled streptavidin antibody or anti-NCAM antibodies (Sigma, C9672). The sample identities were not blinded.

Live-Cell Assays

Live cell proteolysis assay and analysis of constitutive protein secretion. This assay was performed as described previously (Mazzulli et al., 2016a). iPSn were infected with either scrambled or shRNA sequences against ykt6, incubated for 7 days, then pulse-labeled with 3H-leucine for 48 hours. Half of the cultures were treated with leupeptin at 200 uM for 2 days added at the same time as 3H-leucine, and 1M NH4Cl was added for 16 hours (diluted from 20 mM stock made fresh in media) the night before the chase. After pulse-labeling for 48 hours, cells were washed and incubated with chasing medium (Neuralbasal media with SM1 neurocult, containing 2.8 mM cold leucine). Medium was changed one more time to exclude proteolysis that may occur through short-lived pathways (proteasome). Media aliquots of 70 ul were removed at each time point (0, 8, 24, and 30 hours) and added directly to tubes containing 2 mg/ml final BSA/20% final trichloroacetic acid, vortexed, and incubated overnight at 4° C. Samples were centrifuged at 21,000×g, 4° C. for 20 minutes to separate insoluble protein from soluble amino acids. Soluble fractions were analyze in a Perkin Elmer Scintillation counter for the presence 3H-Leucine, which represents degraded proteins. Labeled protein pellets were solubilized in 0.1N NaOH/ 0.1% Na Deoxycholate and quantified by scintillation as secreted proteins. The adherent cultures were extracted in 0.1N NaOH/0.1% Na Deoxycholate and quantified by scintillation as the total labeled protein pool. 3H leucine quantified in the media was normalized to total protein detected from adherent cultures, and the data were expressed as % proteolysis or secretion over time. Sample identities were blinded.

Live cell GCase activity assay. This assay was performed using the artificial GCase substrate 5-(pentafluoro-benzoylamino)fluorescein di-ß-D-glucopyranoside (PFB-FDGluc) from Thermofisher. Fluorescent signal was quantified over time and normalized to total cell volume using CellTag 700 (Licor) or lysosomal mass by using cascade dextran blue (#D-1976, Thermofisher). The procedure and analysis method has been described previously in detail, within the supplemental information of ref (Mazzulli et al., 2016a). The sample identities were not blinded.

Live cell ER-Golgi trafficking assay. H4 cells were transfected with an reporter protein that matures through the secretory pathway in an inducible manner. The reporter is retained in the ER by reversible dimerization of FM domains and release from the ER can be temporally controlled by addition of a D/D solubilizer (iDimerize system, Takara, www.takarabio.com) that binds to FM domains and solubilizes the reporter as previously described (Rivera et al., 2000). Cells were infected with CellLight Golgi marker (Thermofisher), and colocalization was analyzed using live cell time lapse imaging on a confocal microscope (approx. one image every 10-20 seconds). Images were analyzed my Image J software to obtain a Pearson's value at each time point and plotted against time to obtain kinetic values of transport. Initial Golgi entry was obtained by quantifying the area under kinetic curves between 0 and 200 seconds. The assay was repeated in 3 distinct culture wells per condition. The sample identities were not blinded.

Image Analyses

Immunofluorescence analysis of cell cultures. For LAMP1, GM130, and ykt6 staining, cultures were plated on PDL/laminin coated coverglasses and were fixed in 4% paraformaldehyde (PFA) in PBS for 20 minutes, washed 3 times in cold PBS, and permeabilized/blocked in blocking buffer (0.3% Triton X-100 buffer made in PBS with 2% BSA (fatty acid free) and 5% normal goat serum (NGS, Jackson immunofluorescence)) for 30 min. Primary antibodies were added at 1:100 dilutions in blocking buffer for LAMP1 (Santa Cruz, mouse monoclonal, #sc-20011), ykt6 (mouse monoclonal, Abcam #ab77150), and GM130 (rabbit polyclonal, Abcam, #ab52649) overnight at 4° C. Cells were washed 3 times for 20 min each in 0.3% Triton/PBS and secondary antibodies were added at 1:300 dilutions in blocking buffer for 2 hours, washed as before, mounted and examined by confocal microscopy on a Leica confocal microscope (Leica TCS SPE laser at 25-50% power; CTR4000/DMI4000B microscope) through a 10 um section (z-series at 1 um per section). Pearson's correlation values were used for colocalization and obtained with Image J software using the coloc 2 plugin. Individual cells were outlined as defined ROIs and calculated individually.

For ykt6/GM130 colocalization analysis after stress, it was found that brief detergent treatment was required to better reveal changes in ykt6 localization. Cells were treated with 200 nM bafilomycin A1 for 2 hours, washed one time with cold PBS, then permeabilized for 2 minutes with 50 ug/ml digitonin as described (Thayanidhi et al., 2012). Cells were then fixed in 4% PFA as described above, blocked for 30 minutes in PBS with 2% BSA and 5% NGS, and primary antibodies were incubated at 1:100 dilutions (ykt6, mouse monoclonal, Santa Cruz #sc-365732; GM130 rabbit polyclonal, Abcam, #ab52649) in PBS with 2% BSA and 5% NGS for 48 hours at 4° C. in a humidified chamber. Cells were then washed 3×20 minutes in PBS, and secondary antibodies were added in the same blocking buffer for 2 hours. Cells were mounted and analyzed by confocal microscopy as described above.

For GCase/LAMP2 colocalization, cultures were fixed in 4% PFA in PBS for 20 minutes, then permeabilized in 0.2% saponin in 0.2% glycine buffer as described previously (Mazzulli et al., 2016b). Primary antibodies (anti-GCase 8E4, gift of Johannes Aerts, University of Leiden, NL; anti-LAMP2, Invitrogen (#51-2210)) were diluted 1:100 in blocking buffer, incubated overnight at 4° C., washed and incubated with secondary antibodies (Alexa 568 conjugated anti-mouse, and Alexa 488-conjugated anti-rabbit, 1:400 dilution). Cells were mounted in DAPI-Fluoromount G (Southern Biotech) and analyzed by confocal microscopy as above. Colocalization was analyzed in individual cells as above using Pearson's correlation value. Images were analyzed by independent blinded observers.

Immunohistochemistry of DASYN53 mice. Mice were perfused and right hemibrains were collected and fixed in 10% formalin followed by preservation in 30% sucrose, 1×PBS solution. 30 μM sections were serially harvested into a 12-well plate from coronal or sagittal hemi-brain tissue using a freezing-sliding microtome and sections were stored in cryoprotective solution (1×PBS, 30% sucrose, 30% ethylene glycol) at −20° C. until use. Free-floating sections were then washed three times in tris-buffered saline (TBS) followed by incubation in 16 mM glycine in TBS for 1 hour at room temperature. Sections were then washed three additional times in TBS and blocked in 5% goat serum in 0.25% triton X-100 in TBS for 2 hours at room temperature. Sections were incubated overnight in primary antibodies (Anti-NeuN (Chicken EMD Millipore), 1:1000, Anti-ykt6 (Santa Cruz rabbit polyclonal (discontinued), 1:100, anti-tyrosine hydroxylase 1:1000 (Sigma mAb)) in 1% BSA, 0.25% triton X-100 and 1×TBS at 4° C. followed by immunostaining using donkey Alexafluor-labeled secondary antibodies (Thermo Fisher Scientific). Sections were mounted using ProLong Gold (#P36934, Thermo Fisher Scientific) and imaged on a Nikon A1 laser scanning confocal microscope at Northwestern University Center for Advanced Microscopy and Nikon Imaging Centre.

Lentivirus Treatment of Cultures

Lentiviral transduction of cell lines and iPSC-neurons. Lentivirus containing wild-type ykt6, ykt6-CS or GFP fusions were subcloned into the pER4 vector backbone driven by the PGK promoter (Deglon et al., 2000), packaged as described previously (Mazzulli et al., 2016a), and titered with a Zeptometrix HIV1-P24 ELISA kit. iPSC-neurons were infected at day 60 at a multiplicity of infection (MOI) of 2 to 3, depending on the batch, and harvested at either 6 or 8 weeks post infection. SH-SY5Y cells were similarly infected and analyzed at 7 days post infection (dpi).

FTI Treatment of Cultures and Mice

Treatment of cultures with farnesyltransferase inhibitors. Farnesyltransferase inhibitors LNK-754 and LNK-3248 were dissolved in DMSO and added to cultures between 1 and 10 nM, with equivalent volumes of DMSO used as vehicle controls. For cell lines, the compound was added every day for 5-7 days. For iPSC-neurons, the compound was replaced every 48 hrs. Cultures were harvested and analyzed as described in the above sections.

Treatment of C57Bl/6 and DASYN53 mice with farnesyltransferase inhibitors. 3 mo old C57BL6 mice were i.p. injected daily with 0.9 mg/kg LNK-754 that was formulated in a vehicle of 0.5% sodium carboxymethylcellulose and filtered before use for 14 days. DASYN53 mice were i.p. injected daily with 0.9 mg/kg LNK-754 as above. Mice were perfused with PBS and the brains (cortex) were rapidly dissected and frozen until analysis. DASYN53 mice were euthanized after 26 days of treatment, perfused with PBS, and the brain was rapidly dissected. The midbrain and olfactory bulbs were dissected and frozen for biochemical analysis.

Behavioral Analysis

Behavioral analysis of DASYN53 mice. These assays were done as previously described (Tsika et al., 2010). Body weight was taken daily before each injection of the FTI until the end of the injection protocol (nTg age-matched littermates+Vehicle, n=9; A53T+Vehicle, n=7; A53T+FTI, n=7). Reported body weights were from the end of the injection protocol (day 23-24). Each group had approximately equal male and female mice and no gender differences were noted. Balance and motor behavior testing was done at the end of the injection protocol (between days 24-26) and determined using a Rotarod apparatus (Ugo Basile) with acceleration from 4-40 rpm over a 300 second period. Latency to fall was recorded over 4 trials per mouse, and the data were presented as the average of 3 trials (excluding the first trial as a training session). For the rotorod study, mice were tested at in two separate groups from 4 different litters (nTg age-matched littermates+Vehicle, n=12; A53T+Vehicle, n=7; A53T+FTI, n=7). Each group had approximately equal male and female mice and no gender differences were noted. Animal numbers were obtained from pilot studies of rotorod performance by using the following equation: n number=2 (Za+Z1−b)2 (standard dev.)2/(Effect size)2, where Za is 1.96 (two tailed T-test with alpha=0.05) and Z1−b=1.2816 (power>80%), and incorporating a 10% drop out frequency. Animal genotype and treatments were not blinded.

Quantification and Statistical Analysis

Statistical tests were performed using GraphPad Prism software V6 (www.graphpad.com/scientificsoftware/prism.) . ANOVA with Tukey's post-hoc test was used when comparing more than two samples, while Student's t-test (two-sided) was when comparing two samples.

Data and Software Availability

Data supporting the conclusions of this study can be requested from lead contact at jmazzulli@northwestern.edu.

Example 3

We tested the activity of Compound #20 ((3R)-1-[(1-{[1-(4,5-dimethylthiophene-2-carbonyl)piperidin-4-yl]methyl}-1H-1,2,3-triazol-4-yl)methyl]pyrrolidin-3-amine) regarding activation of ykt6 in Hela cells. (See FIG. 19). Hela cells stably expressing GFP-ykt6 were treated with Compound #20 for 2 days at various concentrations, fixed, stained with Golgi marker GM130, and colocalization was quantified by Pearson's correlation. The results indicate that Compound #20 can activate ykt6 in Hela cells.

We next tested whether we could detect ykt6 in human and mouse blood and observed that we could detect both active and inactive forms of ykt6 in human and mouse blood. (See FIG. 20A). Next, using a Parkinson's disease mouse model we observed that inactive forms of ykt6 are more abundant in red blood cells (see FIG. 20B), suggesting that detection of inactive forms of ykt6 in red blood cells can be used as a biomarker for Parkinson's disease. Using a small farnesyl transferase inhibitor (FTI), we also observed activation of ykt6 in red blood cells after the mice were treated with the FTI. (See FIG. 20C). This suggests that detection of inactive and/or inactive forms of ykt6 in red blood cells can be utilized for target engagement in future clinical trials in Parkinson's patients.

REFERENCES

Abeliovich, A., and Gitler, A. D. (2016). Defects in trafficking bridge Parkinson's disease pathology and genetics. Nature 539, 207-216.

Aflaki, E., Borger, D. K., Moaven, N., Stubblefield, B. K., Rogers, S. A., Patnaik, S., Schoenen, F. J., Westbroek, W., Zheng, W., Sullivan, P., et al. (2016). A New Glucocerebrosidase Chaperone Reduces alpha-Synuclein and Glycolipid Levels in iPSC-Derived Dopaminergic Neurons from Patients with Gaucher Disease and Parkinsonism. J Neurosci 36, 7441-7452.

Amschl, D., Neddens, J., Havas, D., Flunkert, S., Rabl, R., Romer, H., Rockenstein, E., Masliah, E., Windisch, M., and Hutter-Paier, B. (2013). Time course and progression of wild type alpha-synuclein accumulation in a transgenic mouse model. BMC Neurosci 14, 6.

Bagshaw, R. D., Pasternak, S. H., Mahuran, D. J., and Callahan, J. W. (2003). Nicastrin is a resident lysosomal membrane protein. Biochemical and biophysical research communications 300, 615-618.

Bergmann, J. E., and Grabowski, G. A. (1989). Posttranslational processing of human lysosomal acid betaglucosidase: a continuum of defects in Gaucher disease type 1 and type 2 fibroblasts. Am J Hum Genet 44, 741-750.

Braak, H., Del Tredici, K., Rub, U., de Vos, R. A., Jansen Steur, E. N., and Braak, E. (2003). Staging of brain pathology related to sporadic Parkinson's disease. Neurobiol Aging 24, 197-211.

Burre, J., Sharma, M., Tsetsenis, T., Buchman, V., Etherton, M. R., and Sudhof, T. C. (2010). Alpha-synuclein promotes SNARE-complex assembly in vivo and in vitro. Science 329, 1663-1667.

Cataldo, A. M., Barnett, J. L., Berman, S. A., Li, J., Quarless, S., Bursztajn, S., Lippa, C., and Nixon, R. A. (1995). Gene expression and cellular content of cathepsin D in Alzheimer's disease brain: evidence for early up-regulation of the endosomal-lysosomal system. Neuron 14, 671-680.

Chen, L., Xie, Z., Turkson, S., and Zhuang, X. (2015). A53T human alpha-synuclein overexpression in transgenic mice induces pervasive mitochondria macroautophagy defects preceding dopamine neuron degeneration. J Neurosci 35, 890-905.

Chung, C. Y., Khurana, V., Auluck, P. K., Tardiff, D. F., Mazzulli, J. R., Soldner, F., Baru, V., Lou, Y., Freyzon, Y., Cho, S., et al. (2013). Identification and rescue of alpha-synuclein toxicity in Parkinson patient-derived neurons. Science 342, 983-987.

Conway, K. A., Harper, J. D., and Lansbury, P. T. (1998). Accelerated in vitro fibril formation by a mutant alphasynuclein linked to early-onset Parkinson disease. Nat Med 4, 1318-1320.

Cooper, A. A., Gitler, A. D., Cashikar, A., Haynes, C. M., Hill, K. J., Bhullar, B., Liu, K., Xu, K., Strathearn, K. E., Liu, F., et al. (2006). Alpha-synuclein blocks ER-Golgi traffic and Rab1 rescues neuron loss in Parkinson's models. Science (New York, NY) 313, 324-328.

Cuervo, A. M., Stefanis, L., Fredenburg, R., Lansbury, P. T., and Sulzer, D. (2004). Impaired Degradation of Mutant-Synuclein by Chaperone-Mediated Autophagy. Science 305, 1292-1295.

D'Souza, M. P., and August, J. T. (1986). A kinetic analysis of biosynthesis and localization of a lysosomeassociated membrane glycoprotein. Archives of biochemistry and biophysics 249, 522-532.

Daste, F., Galli, T., and Tareste, D. (2015). Structure and function of longin SNAREs. J Cell Sci 128, 4263-4272.

DeCourcy, K., and Storrie, B. (1991). Osmotic swelling of endocytic compartments induced by internalized sucrose is restricted to mature lysosomes in cultured mammalian cells. Exp Cell Res 192, 52-60.

Deglon, N., Tseng, J. L., Bensadoun, J. C., Zurn, A. D., Arsenijevic, Y., Pereira de Almeida, L., Zufferey, R., Trono, D., and Aebischer, P. (2000). Self-inactivating lentiviral vectors with enhanced transgene expression as potential gene transfer system in Parkinson's disease. Hum Gene Ther 11, 179-190.

Downward, J. (2003). Targeting RAS signalling pathways in cancer therapy. Nat Rev Cancer 3, 11-22.

Duda, J. E., Giasson, B. I., Mabon, M. E., Lee, V. M., and Trojanowski, J. Q. (2002). Novel antibodies to synuclein show abundant striatal pathology in Lewy body diseases. Ann Neurol 52, 205-210.

Ebrahimi-Fakhari, D., Cantuti-Castelvetri, I., Fan, Z., Rockenstein, E., Masliah, E., Hyman, B. T., McLean, P. J., and Unni, V. K. (2011). Distinct roles in vivo for the ubiquitin-proteasome system and the autophagy-lysosomal pathway in the degradation of alpha-synuclein. J Neurosci 31, 14508-14520.

Fukasawa, M., Varlamov, O., Eng, W. S., Söllner, T. H., and Rothman, J. E. (2004). Localization and activity of the SNARE Ykt6 determined by its regulatory domain and palmitoylation. Proceedings of the National Academy of Sciences of the United States of America 101, 4815-4820.

Gitler, A. D., Bevis, B. J., Shorter, J., Strathearn, K. E., Hamamichi, S., Su, L. J., Caldwell, K. A., Caldwell, G. A., Rochet, J. C., McCaffery, J. M., et al. (2008). The Parkinson's disease protein alpha-synuclein disrupts cellular Rab homeostasis. Proc Natl Acad Sci USA 105, 145-150.

Gordon, D. E., Bond, L. M., Sahlender, D. A., and Peden, A. A. (2010). A targeted siRNA screen to identify SNAREs required for constitutive secretion in mammalian cells. Traffic (Copenhagen, Denmark) 11, 1191-1204.

Gross, J. C., Chaudhary, V., Bartscherer, K., and Boutros, M. (2012). Active Wnt proteins are secreted on exosomes. Nature cell biology 14, 1036-1045.

Hasegawa, H., Zinsser, S., Rhee, Y., Vik-Mo, E. O., Davanger, S., and Hay, J. C. (2003). Mammalian ykt6 is a neuronal SNARE targeted to a specialized compartment by its profilin-like amino terminal domain. Molecular biology of the cell 14, 698-720.

Hay, J. C., Chao, D. S., Kuo, C. S., and Scheller, R. H. (1997). Protein interactions regulating vesicle transport between the endoplasmic reticulum and Golgi apparatus in mammalian cells. Cell 89, 149-158.

Jarrett, J. T., and Lansbury, P. T., Jr. (1993). Seeding "one-dimensional crystallization" of amyloid: a pathogenic mechanism in Alzheimer's disease and scrapie? Cell 73, 1055-1058.

Kho, Y., Kim, S. C., Jiang, C., Barma, D., Kwon, S. W., Cheng, J., Jaunbergs, J., Weinbaum, C., Tamanoi, F., Falck, J., et al. (2004). A tagging-via-substrate technology for detection and proteomics of farnesylated proteins. Proc Natl Acad Sci USA 101, 12479-12484.

Kriks, S., Shim, J. W., Piao, J., Ganat, Y. M., Wakeman, D. R., Xie, Z., Carrillo-Reid, L., Auyeung, G., Antonacci, C., Buch, A., et al. (2011). Dopamine neurons derived from human ES cells efficiently engraft in animal models of Parkinson's disease. Nature 480, 547-551.

Li, W., Lesuisse, C., Xu, Y., Troncoso, J. C., Price, D. L., and Lee, M. K. (2004). Stabilization of alpha-synuclein protein with aging and familial parkinson's disease-linked A53T mutation. J Neurosci 24, 7400-7409.

Liu, Y., and Barlowe, C. (2002). Analysis of Sec22p in endoplasmic reticulum/Golgi transport reveals cellular redundancy in SNARE protein function. Mol Biol Cell 13, 3314-3324.

Luk, K. C., Kehm, V., Carroll, J., Zhang, B., O'Brien, P., Trojanowski, J. Q., and Lee, V. M. (2012). Pathological alphasynuclein transmission initiates Parkinson-like neurodegeneration in nontransgenic mice. Science 338, 949-953.

Mak, S. K., McCormack, A. L., Manning-Bog, A. B., Cuervo, A. M., and Di Monte, D. A. (2010). Lysosomal-degradation of alpha-synuclein in vivo. J Biol Chem 285, 13621-13629.

Masliah, E., Rockenstein, E., Veinbergs, I., Mallory, M., Hashimoto, M., Takeda, A., Sagara, Y., Sisk, A., and Mucke, L. (2000). Dopaminergic loss and inclusion body formation in alpha-synuclein mice: implications for neurodegenerative disorders. Science 287, 1265-1269.

Matsui, T., Jiang, P., Nakano, S., Sakamaki, Y., Yamamoto, H., and Mizushima, N. (2018). Autophagosomal YKT6 is required for fusion with lysosomes independently of syntaxin 17. J Cell Biol 217, 2633-2645.

Mazzulli, J. R., Xu, Y. H., Sun, Y., Knight, A. L., McLean, P. J., Caldwell, G. A., Sidransky, E., Grabowski, G. A., and Krainc, D. (2011). Gaucher disease glucocerebrosidase and alpha-synuclein form a bidirectional pathogenic loop in synucleinopathies. Cell 146, 37-52.

Mazzulli, J. R., Zunke, F., Isacson, O., Studer, L., and Krainc, D. (2016a). alpha-Synuclein-induced lysosomal dysfunction occurs through disruptions in protein trafficking in human midbrain synucleinopathy models. Proc Natl Acad Sci USA 113, 1931-1936.

Mazzulli, J. R., Zunke, F., Tsunemi, T., Toker, N. J., Jeon, S., Burbulla, L. F., Patnaik, S., Sidransky, E., Marugan, J. J., Sue, C. M., et al. (2016b). Activation of beta-Glucocerebrosidase Reduces Pathological alpha-Synuclein and Restores Lysosomal Function in Parkinson's Patient Midbrain Neurons. J Neurosci 36, 7693-7706.

McNew, J. A., Sogaard, M., Lampen, N. M., Machida, S., Ye, R. R., Lacomis, L., Tempst, P., Rothman, J. E., and Sollner, T. H. (1997). Ykt6p, a prenylated SNARE essential for endoplasmic reticulum-Golgi transport. J Biol Chem 272, 17776-17783.

Moulder, S. L., Mahany, J. J., Lush, R., Rocha-Lima, C., Langevin, M., Ferrante, K. J., Bartkowski, L. M., Kajiji, S. M., Noe, D. A., Paillet, S., et al. (2004). A phase I open label study of the farnesyltransferase inhibitor CP-609, 754 in patients with advanced malignant tumors. Clin Cancer Res 10, 7127-7135.

Nair, U., Jotwani, A., Geng, J., Gammoh, N., Richerson, D., Yen, W.-L., Griffith, J., Nag, S., Wang, K., Moss, T., et al. (2011). SNARE Proteins Are Required for Macroautophagy. Cell 146, 290-302.

Nalls, M. A., Pankratz, N., Lill, C. M., Do, C. B., Hernandez, D. G., Saad, M., DeStefano, A. L., Kara, E., Bras, J., Sharma, M., et al. (2014). Large-scale meta-analysis of genome-wide association data identifies six new risk loci for Parkinson's disease. Nature Genetics 46, 989-993.

Nichols, B. J., and Pelham, H. R. (1998). SNAREs and membrane fusion in the Golgi apparatus. Biochim Biophys Acta 1404, 9-31.

Palmieri, M., Impey, S., Kang, H., di Ronza, A., Pelz, C., Sardiello, M., and Ballabio, A. (2011). Characterization of the CLEAR network reveals an integrated control of cellular clearance pathways. Hum Mol Genet 20, 3852-3866.

Polymeropoulos, M. H., Lavedan, C., Leroy, E., Ide, S. E., Dehejia, A., Dutra, A., Pike, B., Root, H., Rubenstein, J., Boyer, R., et al. (1997). Mutation in the alpha-synuclein gene identified in families with Parkinson's disease. Science 276, 2045-2047.

Pylypenko, O., Schonichen, A., Ludwig, D., Ungermann, C., Goody, R. S., Rak, A., and Geyer, M. (2008). Farnesylation of the SNARE protein Ykt6 increases its stability and helical folding. J Mol Biol 377, 1334-1345.

Rivera, V. M., Wang, X., Wardwell, S., Courage, N. L., Volchuk, A., Keenan, T., Holt, D. A., Gilman, M., Orci, L., Cerasoli, F., Jr., et al. (2000). Regulation of protein secretion through controlled aggregation in the endoplasmic reticulum. Science 287, 826-830.

Rocha, E. M., Smith, G. A., Park, E., Cao, H., Brown, E., Hayes, M. A., Beagan, J., McLean, J. R., Izen, S. C., Perez-Torres, E., et al. (2015). Glucocerebrosidase gene therapy prevents alpha-synucleinopathy of midbrain dopamine neurons. Neurobiol Dis 82, 495-503.

Sardi, S. P., Clarke, J., Viel, C., Chan, M., Tamsett, T. J., Treleaven, C. M., Bu, J., Sweet, L., Passini, M. A., Dodge, J. C., et al. (2013). Augmenting CNS glucocerebrosidase activity as a therapeutic strategy for parkinsonism and other Gaucher-related synucleinopathies. Proceedings of the National Academy of Sciences 110, 3537-3542.

Sardiello, M., Palmieri, M., di Ronza, A., Medina, D. L., Valenza, M., Gennarino, V. A., Di Malta, C., Donaudy, F., Embrione, V., Polishchuk, R. S., et al. (2009). A gene network regulating lysosomal biogenesis and function. Science 325, 473-477.

Settembre, C., Di Malta, C., Polito, V. A., Garcia Arencibia, M., Vetrini, F., Erdin, S., Erdin, S. U., Huynh, T., Medina, D., Colella, P., et al. (2011). TFEB links autophagy to lysosomal biogenesis. Science 332, 1429-1433.

Settembre, C., Fraldi, A., Medina, D. L., and Ballabio, A. (2013). Signals from the lysosome: a control centre for cellular clearance and energy metabolism. Nat Rev Mol Cell Biol 14, 283-296.

Singleton, A. B., Farrer, M., Johnson, J., Singleton, A., Hague, S., Kachergus, J., Hulihan, M., Peuralinna, T., Dutra, A., Nussbaum, R., et al. (2003). alpha-Synuclein locus triplication causes Parkinson's disease. Science 302, 841.

Soldner, F., Laganiere, J., Cheng, A. W., Hockemeyer, D., Gao, Q., Alagappan, R., Khurana, V., Golbe, L. I., Myers, R. H., Lindquist, S., et al. (2011). Generation of isogenic pluripotent stem cells differing exclusively at two early onset Parkinson point mutations. Cell 146, 318-331.

Soldner, F., Stelzer, Y., Shivalila, C. S., Abraham, B. J., Latourelle, J. C., Barrasa, M. I., Goldmann, J., Myers, R. H., Young, R. A., and Jaenisch, R. (2016). Parkinson-associated risk variant in distal enhancer of alpha-synuclein modulates target gene expression. Nature 533, 95-99.

Sollner, T., Whiteheart, S. W., Brunner, M., Erdjument-Bromage, H., Geromanos, S., Tempst, P., and Rothman, J. E. (1993). SNAP receptors implicated in vesicle targeting and fusion. Nature 362, 318-324.

Spillantini, M. G., Schmidt, M. L., Lee, V. M., Trojanowski, J. Q., Jakes, R., and Goedert, M. (1997). Alpha-synuclein in Lewy bodies. Nature 388, 839-840.

Stojkovska, I., Krainc, D., and Mazzulli, J. R. (2017). Molecular mechanisms of alpha-synuclein and GBA1 in Parkinson's disease. Cell Tissue Res.

Sun, J., Wang, L., Bao, H., Premi, S., Das, U., Chapman, E. R., and Roy, S. (2019). Functional cooperation of alphasynuclein and VAMP2 in synaptic vesicle recycling. Proc Natl Acad Sci USA.

Tai, G., Lu, L., Wang, T. L., Tang, B. L., Goud, B., Johannes, L., and Hong, W. (2004). Participation of the syntaxin 5/Ykt6/GS28/GS15 SNARE complex in transport from the early/recycling endosome to the trans-Golgi network. Mol Biol Cell 15, 4011-4022.

Takats, S., Glatz, G., Szenci, G., Boda, A., Horvath, G. V., Hegedus, K., Kovacs, A. L., and Juhasz, G. (2018). Noncanonical role of the SNARE protein Ykt6 in autophagosome-lysosome fusion. PLoS Genet 14, e1007359.

Tarentino, A. L., Plummer, T. H., Jr., and Maley, F. (1972). A re-evaluation of the oligosaccharide sequence associated with ovalbumin. J Biol Chem 247, 2629-2631.

Thayanidhi, N., Helm, J. R., Nycz, D. C., Bentley, M., Liang, Y., and Hay, J. C. (2010). Alpha-synuclein delays endoplasmic reticulum (ER)-to-Golgi transport in mammalian cells by antagonizing ER/Golgi SNAREs. Molecular biology of the cell 21, 1850-1863.

Thayanidhi, N., Liang, Y., Hasegawa, H., Nycz, D. C., Oorschot, V., Klumperman, J., and Hay, J. C. (2012). R-SNARE ykt6 resides in membrane-associated protease-resistant protein particles and modulates cell cycle progression when overexpressed. Biology of the Cell 104, 397-417.

Tochio, H., Tsui, M. M., Banfield, D. K., and Zhang, M. (2001). An autoinhibitory mechanism for nonsyntaxin SNARE proteins revealed by the structure of Ykt6p. Science 293, 698-702.

Tsika, E., Moysidou, M., Guo, J., Cushman, M., Gannon, P., Sandaltzopoulos, R., Giasson, B. I., Krainc, D., Ischiropoulos, H., and Mazzulli, J. R. (2010). Distinct region-specific alpha-synuclein oligomers in A53T transgenic mice: implications for neurodegeneration. J Neurosci 30, 3409-3418.

Volpicelli-Daley, L. A., Luk, K. C., Patel, T. P., Tanik, S. A., Riddle, D. M., Stieber, A., Meaney, D. F., Trojanowski, J. Q., and Lee, V. M. (2011). Exogenous alpha-synuclein fibrils induce Lewy body pathology leading to synaptic dysfunction and neuron death. Neuron 72, 57-71.

Wen, W., Yu, J., Pan, L., Wei, Z., Weng, J., Wang, W., Ong, Y. S., Tran, T. H., Hong, W., and Zhang, M. (2010). Lipid-Induced conformational switch controls fusion activity of longin domain SNARE Ykt6. Molecular cell 37, 383-395.

Wood, S. J., Wypych, J., Steavenson, S., Louis, J. C., Citron, M., and Biere, A. L. (1999). alpha-synuclein fibrillogenesis is nucleation-dependent. Implications for the pathogenesis of Parkinson's disease. J Biol Chem 274, 19509-19512.

Xu, D., Joglekar, A. P., Williams, A. L., and Hay, J. C. (2000). Subunit structure of a mammalian ER/Golgi SNARE complex. J Biol Chem 275, 39631-39639.

Xu, Y., Martin, S., James, D. E., and Hong, W. (2002). GS15 forms a SNARE complex with syntaxin 5, GS28, and Ykt6 and is implicated in traffic in the early cisternae of the Golgi apparatus. Mol Biol Cell 13, 3493-3507.

Yang, D. S., Tandon, A., Chen, F., Yu, G., Yu, H., Arawaka, S., Hasegawa, H., Duthie, M., Schmidt, S. D., Ramabhadran, T. V., et al. (2002). Mature glycosylation and trafficking of nicastrin modulate its binding to presenilins. J Biol Chem 277, 28135-28142.

Zhang, T., and Hong, W. (2001). Ykt6 forms a SNARE complex with syntaxin 5, GS28, and Bet1 and participates in a late stage in endoplasmic reticulum-Golgi transport. J Biol Chem 276, 27480-27487.

Zunke, F., Moise, A. C., Belur, N. R., Gelyana, E., Stojkovska, I., Dzaferbegovic, H., Toker, N. J., Jeon, S., Fredriksen, K., and Mazzulli, J. R. (2018). Reversible Conformational Conversion of alpha-Synuclein into Toxic Assemblies by Glucosylceramide. Neuron 97, 92-107 e110.

EP1827473A2.
U.S. Pat. No. 8,399,241B2.
US20060106060A1.
US20050277629A1.
WO2009151683A2.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating a disease or disorder associated with proteinopathy or cellular storage in a subject in need thereof, the method comprising administering to the subject an effective amount of a therapeutic agent that activates or augments activity of ykt6, wherein the therapeutic agent comprises a compound selected from the following compounds or a pharmaceutically acceptable salt thereof:

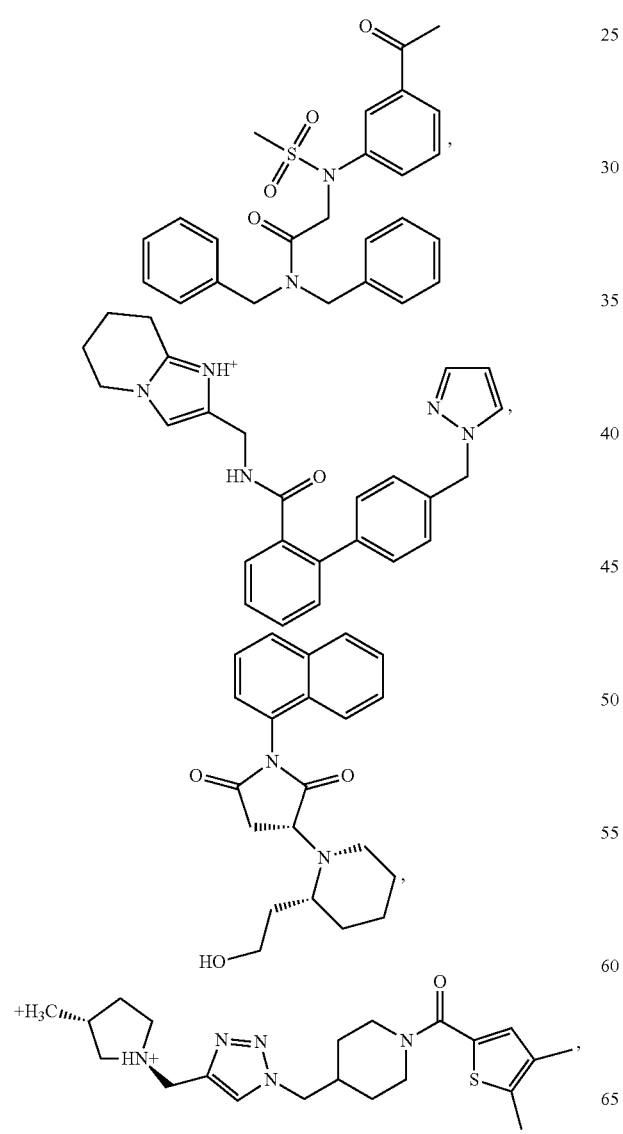

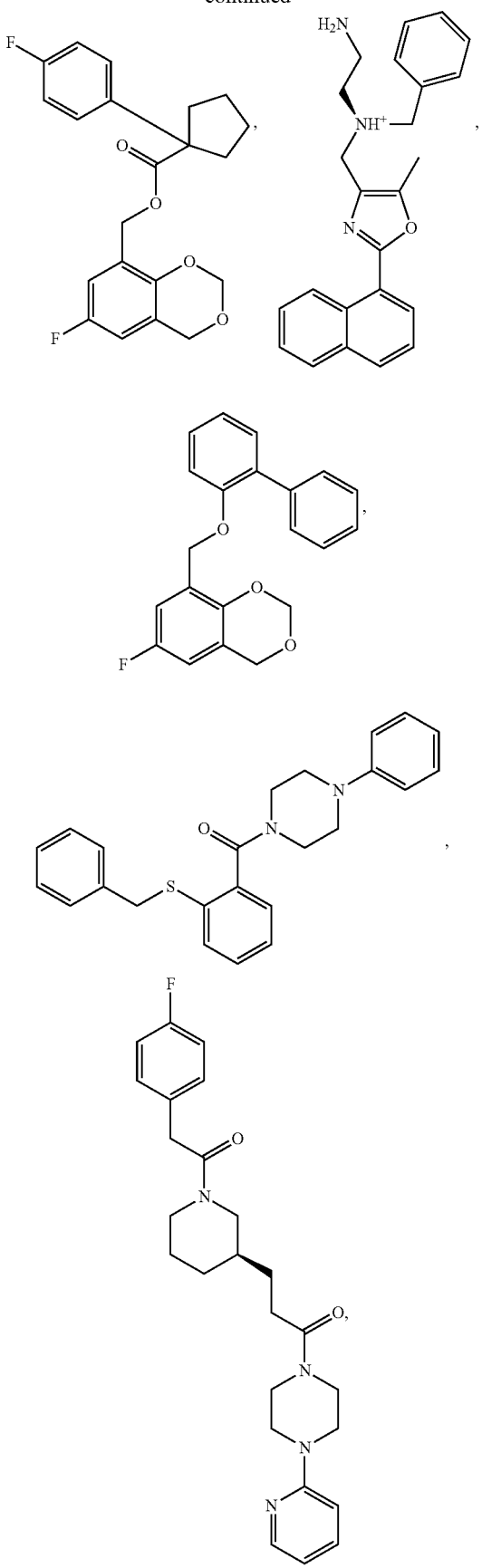

79
-continued
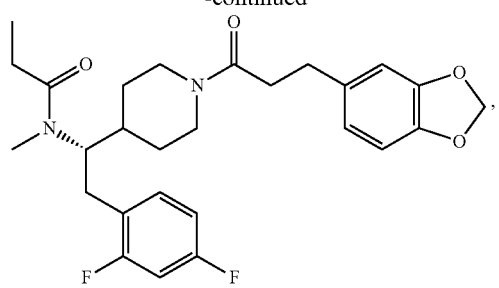
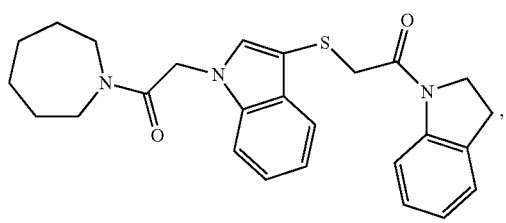
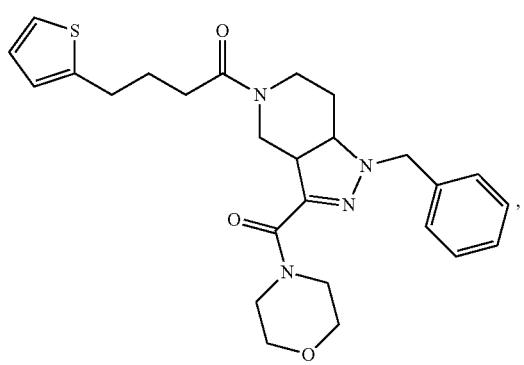
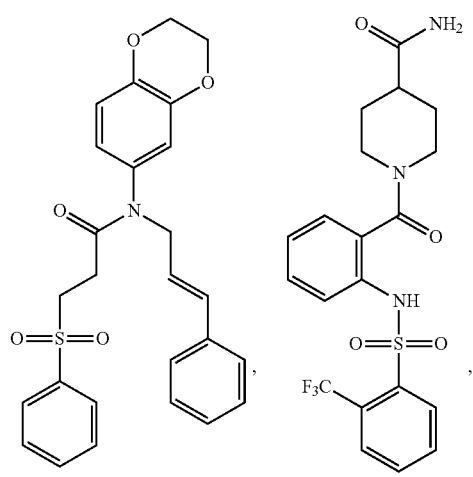
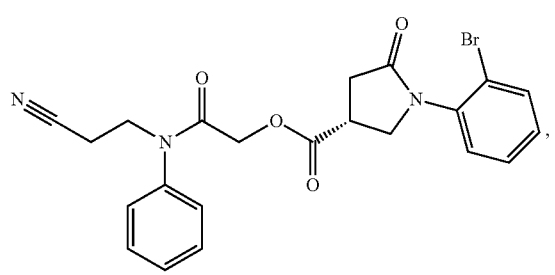
80
-continued
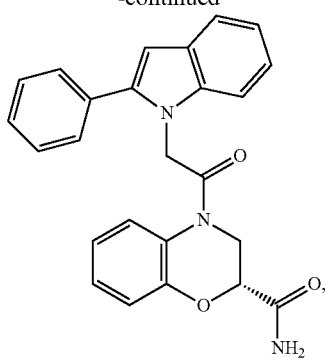
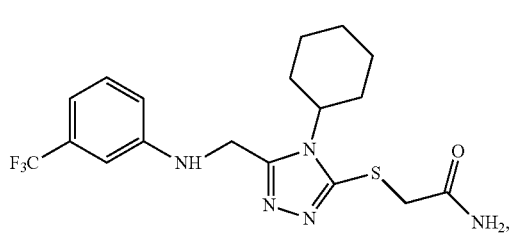
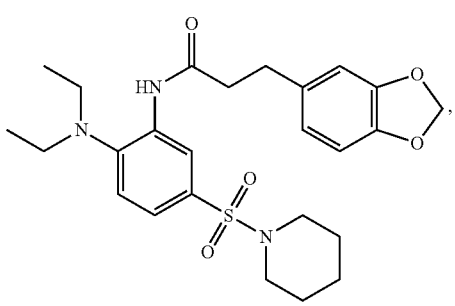
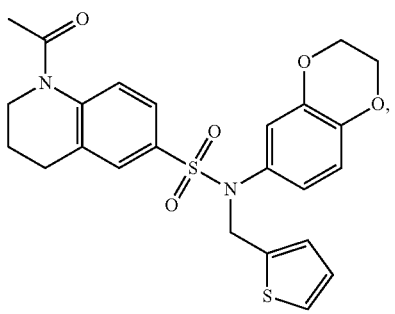
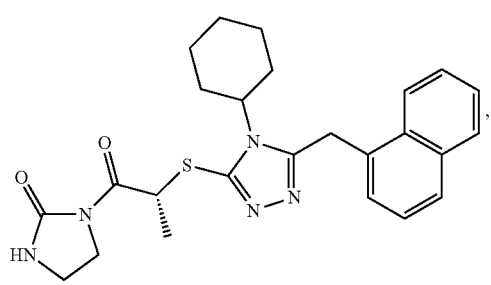

81
-continued
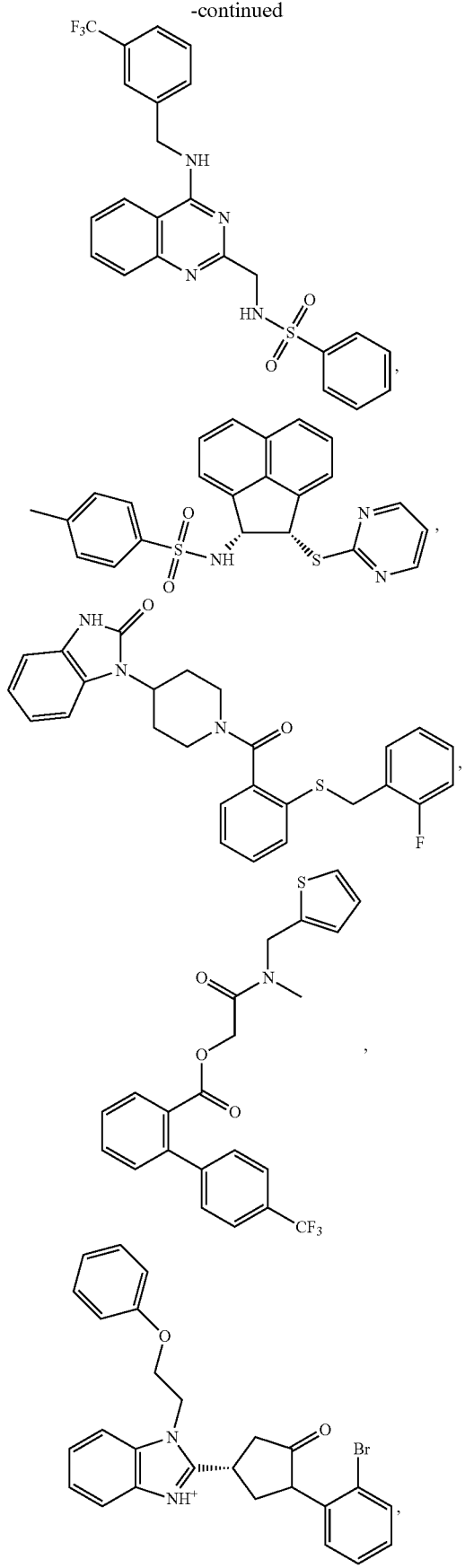
82
-continued
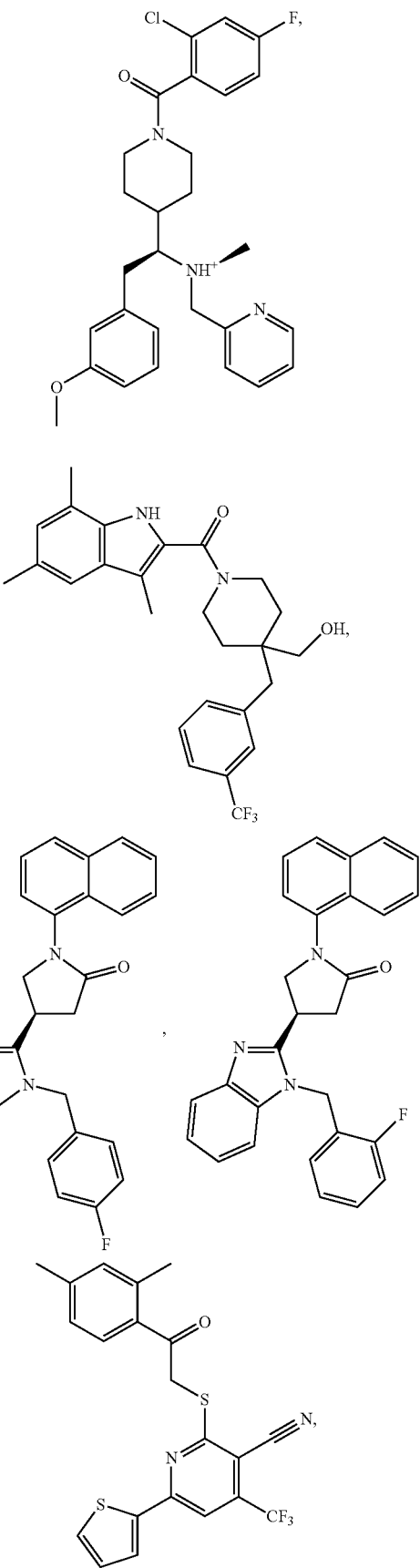

83
-continued
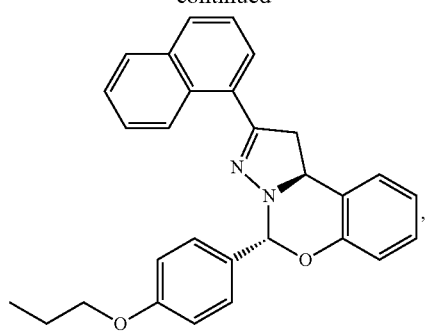
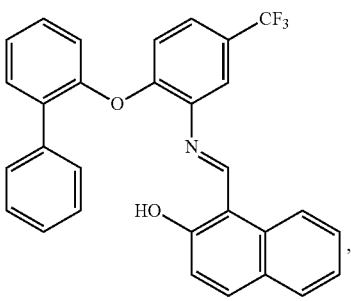
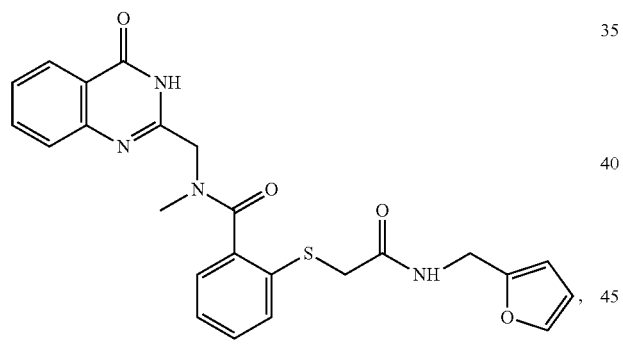
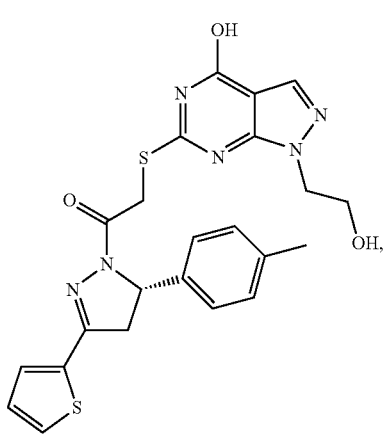
84
-continued
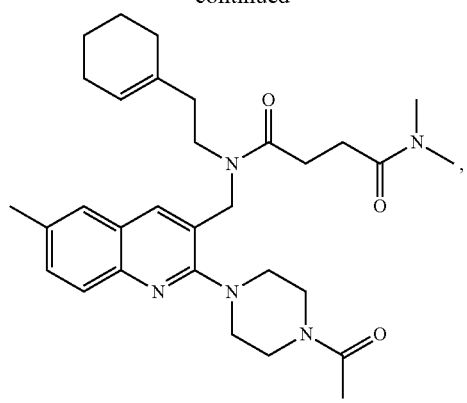
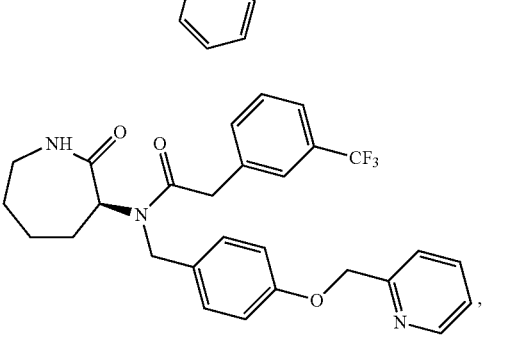
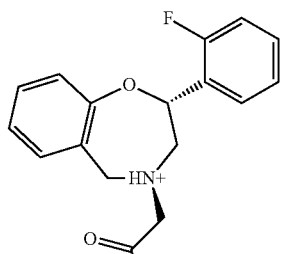
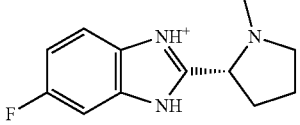
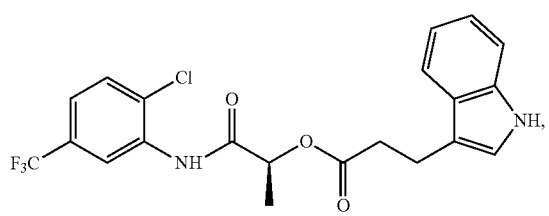

85
-continued
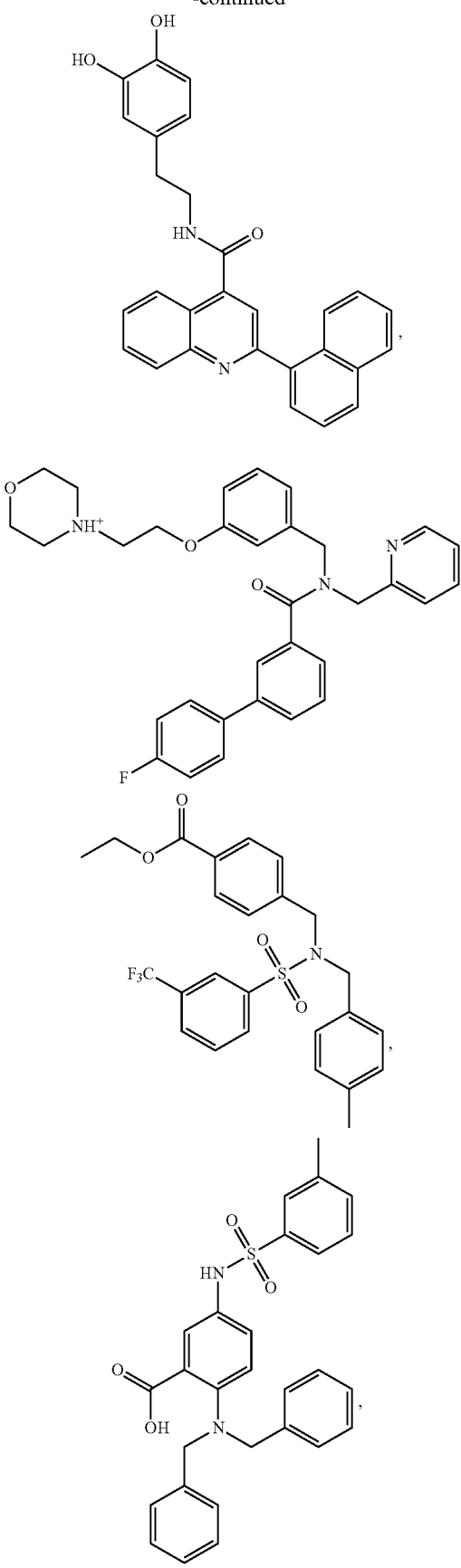
86
-continued
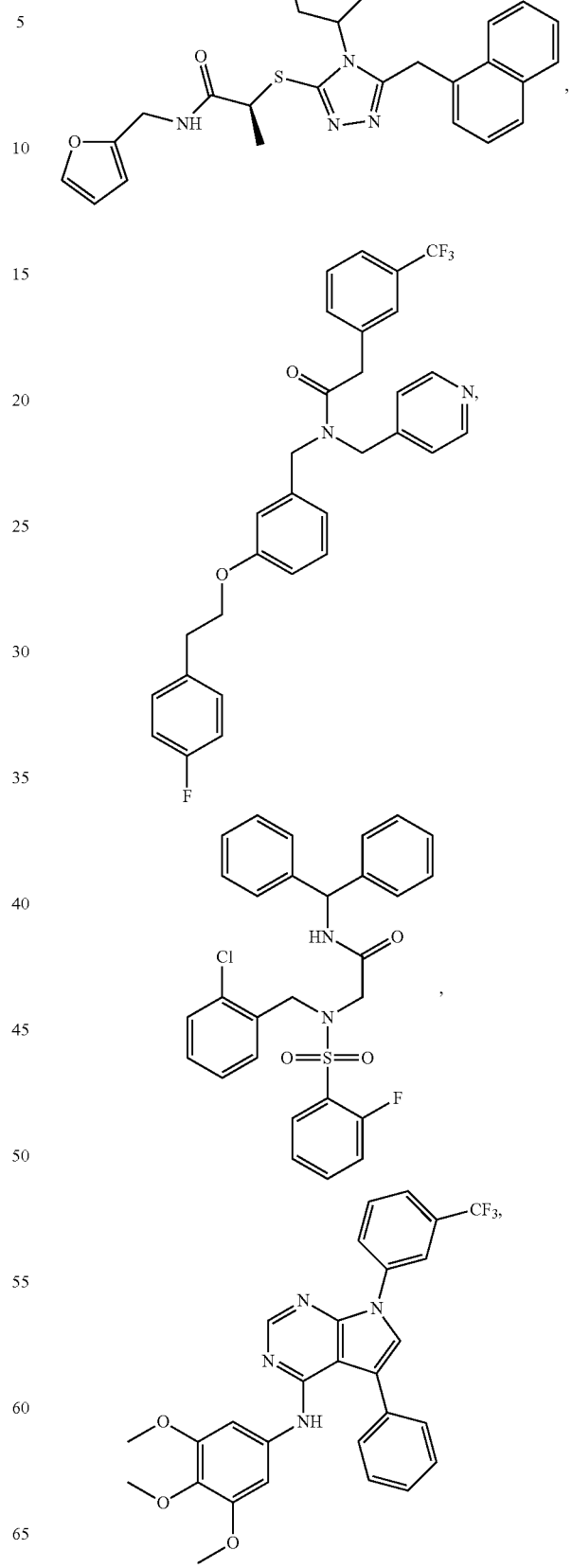

87
-continued
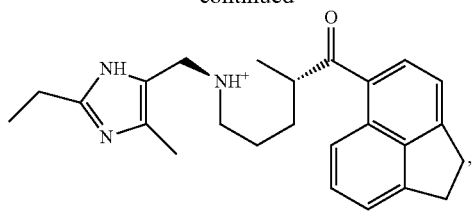
88
-continued
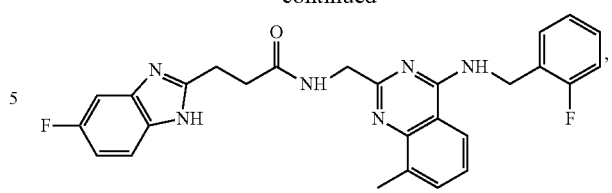
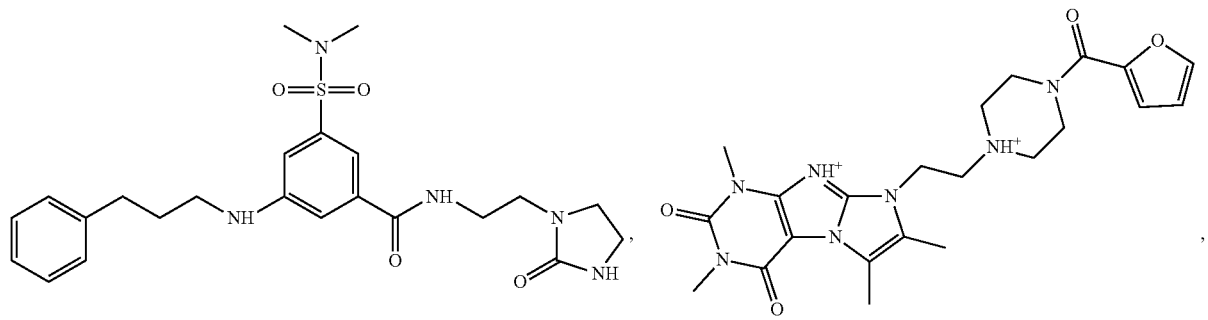
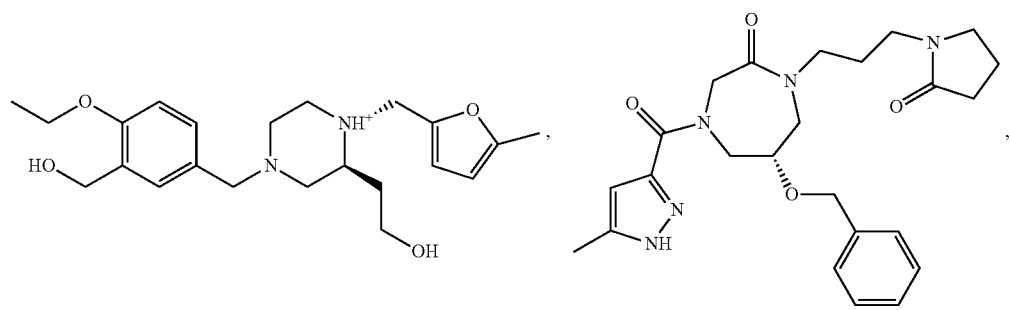
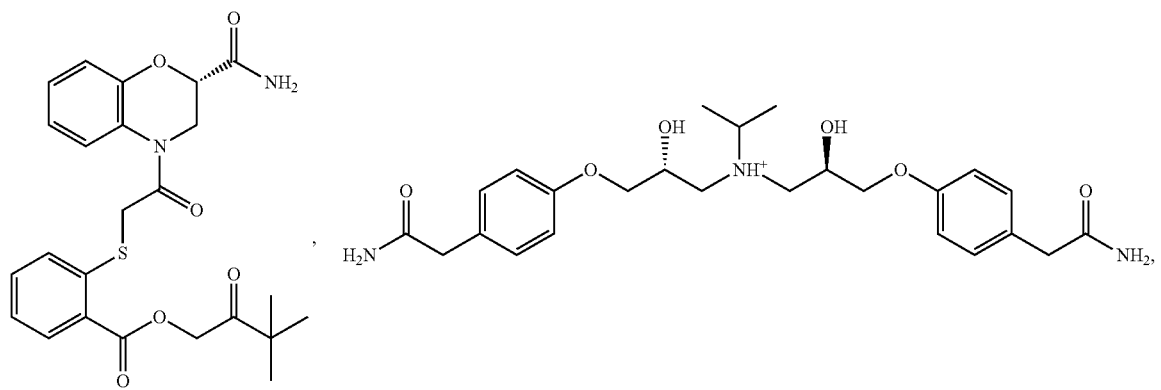
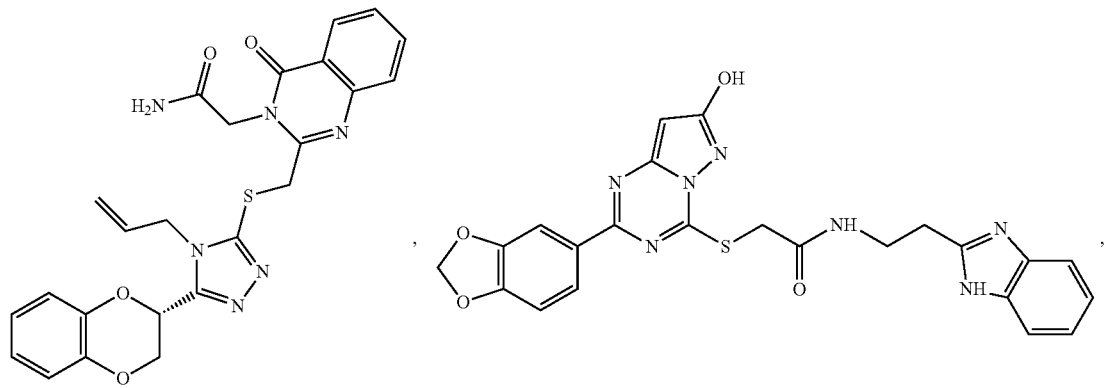

-continued
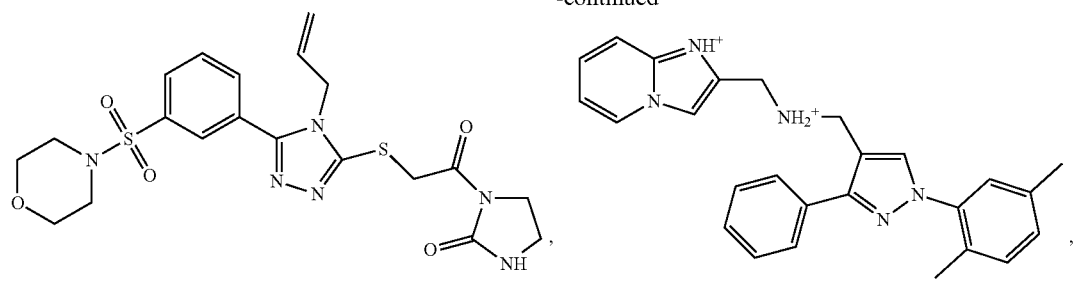
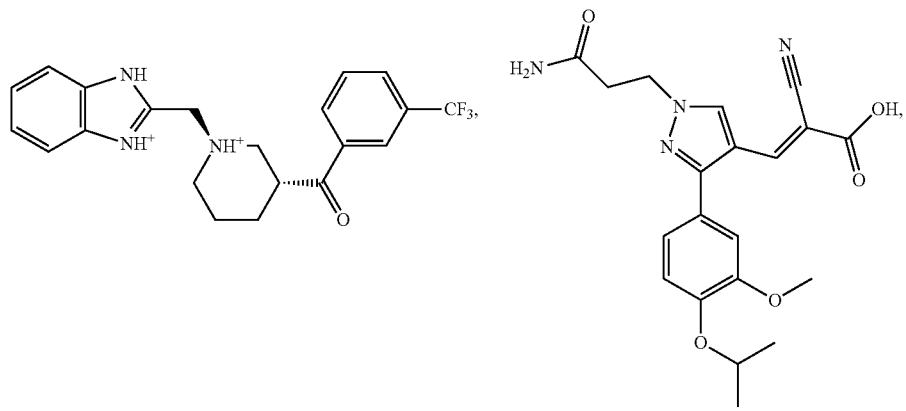
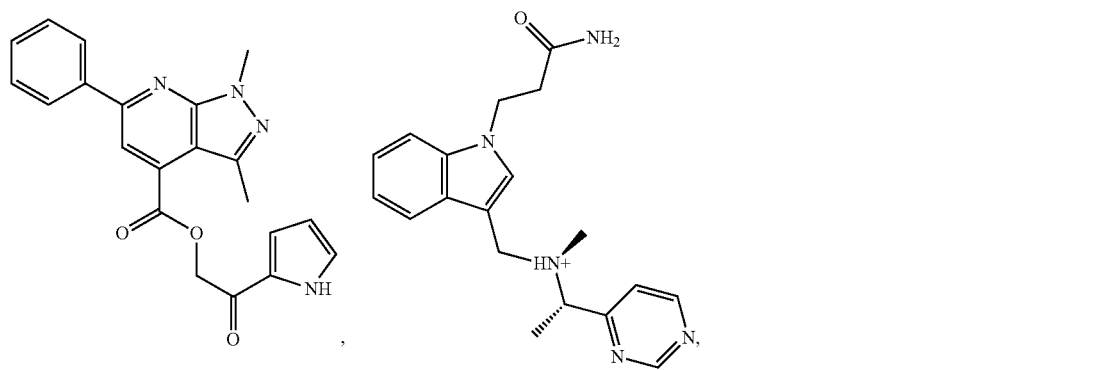
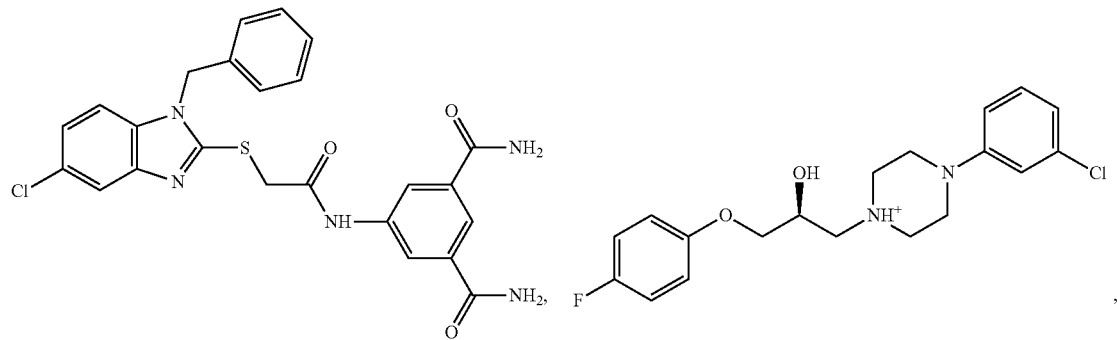
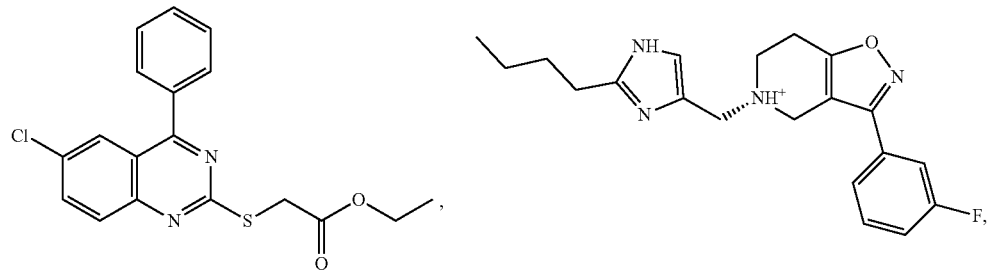

-continued

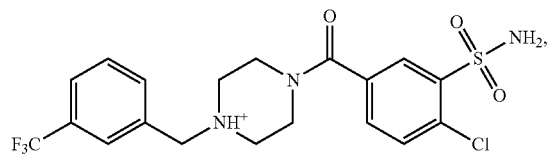
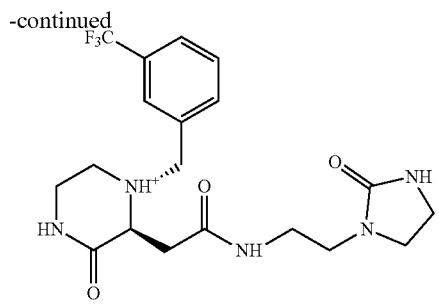
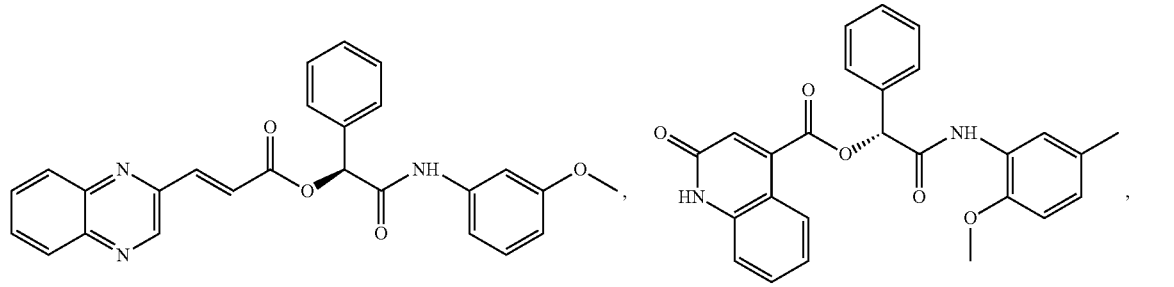
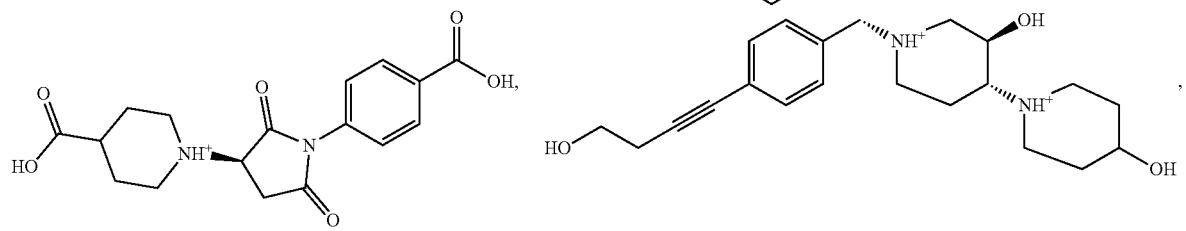
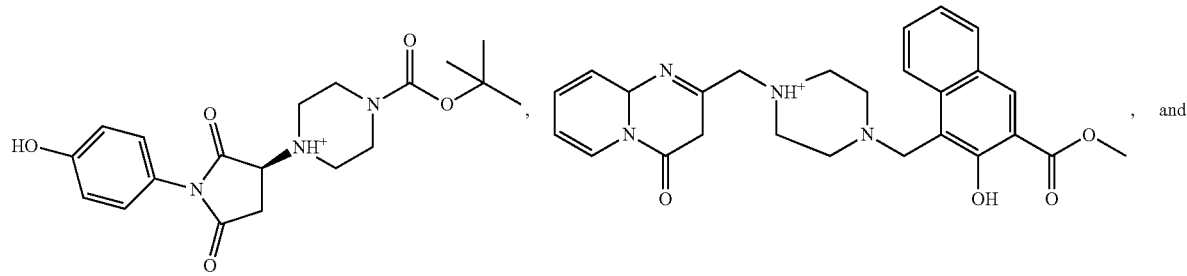
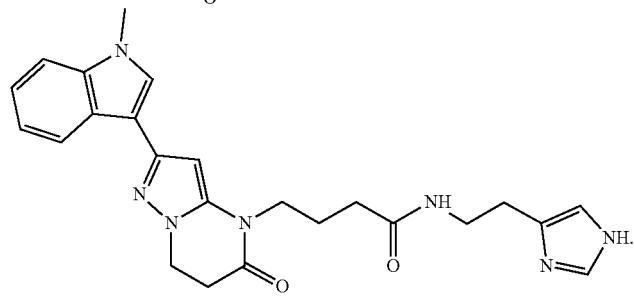

2. The method of claim 1, wherein the disease or disorder is a neurodegenerative disease or disorder and optionally an age-related neurodegenerative disease or disorder.

3. The method of claim 1, wherein the disease or disorder is selected from the group consisting of Parkinson's disease (PD), Lewy body Dementia (LBD), Alzheimer's disease (AD), amyotrophic lateral sclerosis (ALS), multiple system atrophy, Huntington's disease, Prion disease, frontotemporal dementia, Picks disease, progressive supranuclear palsy, and progeria.

4. The method of claim 1, wherein the therapeutic agent inhibits farnesylation or other type of prenylation of ykt6, including geranylgeranylation.

5. The method of claim 1, wherein the therapeutic agent is an inhibitor of farnesyltransferase or gernanyltransferase.

6. The method of claim 1, wherein the therapeutic inhibits and/or disrupts an interaction between farnesyltransferase and ykt6.

7. The method of claim 1, wherein the therapeutic agent promotes open, active conformation of ykt6 versus closed, inactive conformation of ykt6; and/or the therapeutic agent promotes organelle membrane association of ykt6 through enhancing protein palmitoylation or direct ykt6-membrane binding; influences other regulatory proteins that result in the activation of ykt6.

8. The method of claim 1, wherein the therapeutic agent comprises a compound selected from the following compounds or a pharmaceutically acceptable salt thereof:
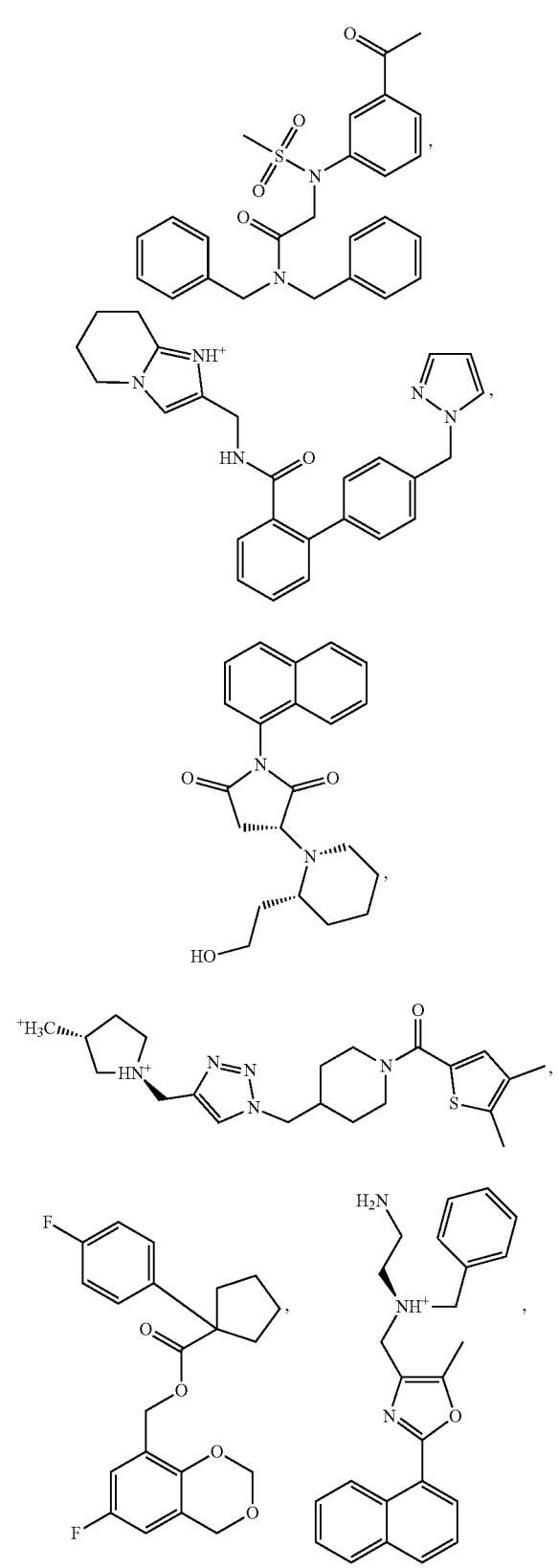
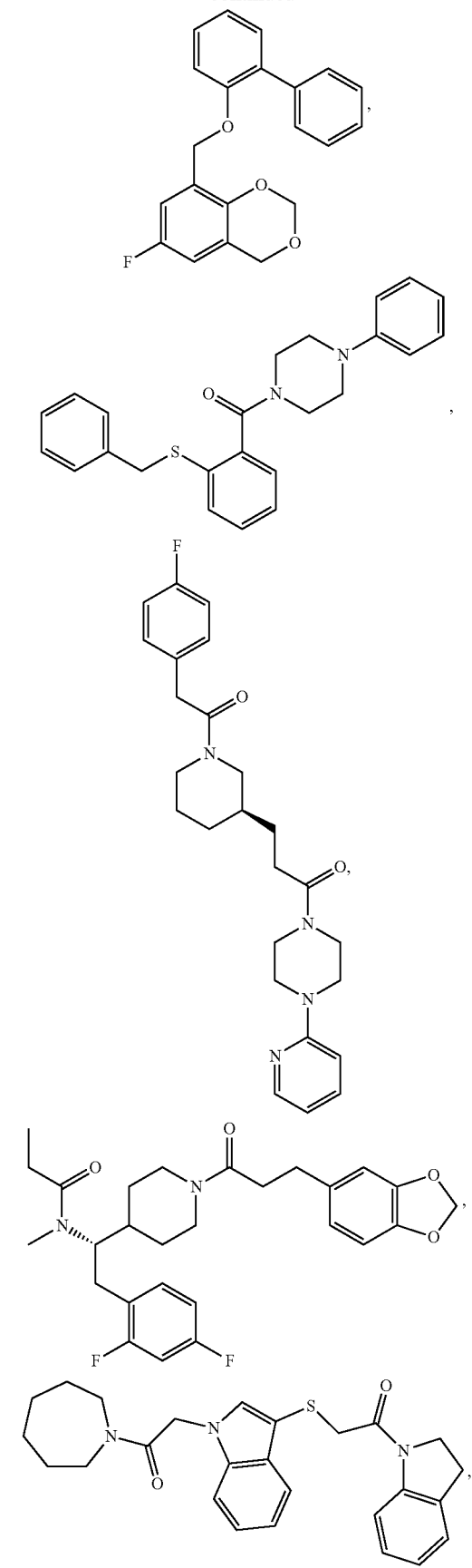

95
-continued
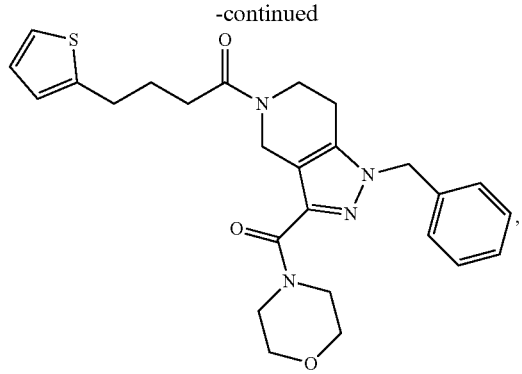
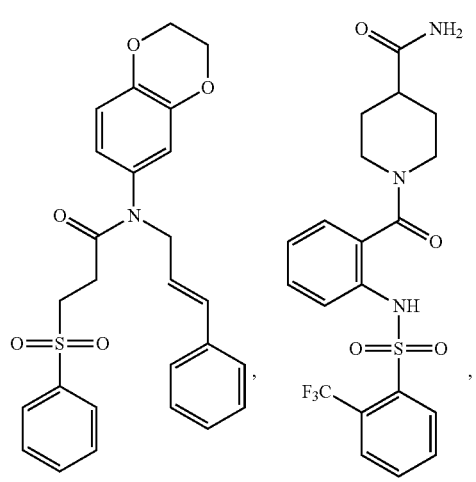
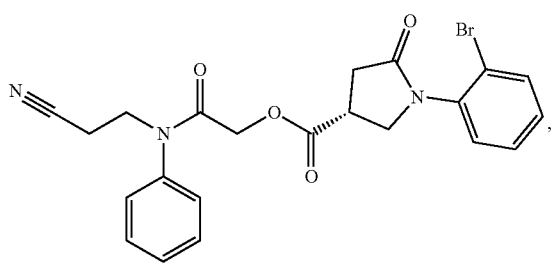
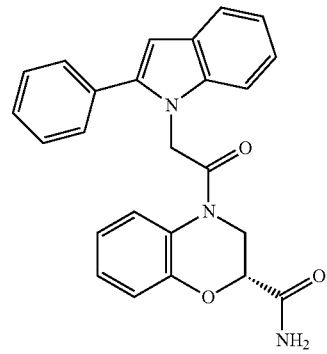
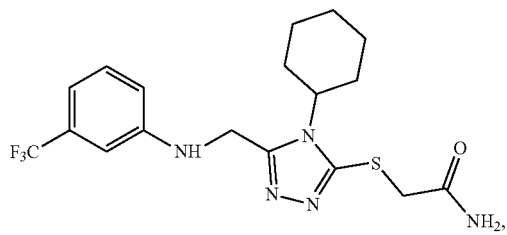
96
-continued
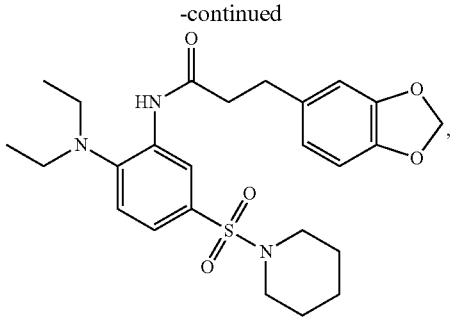
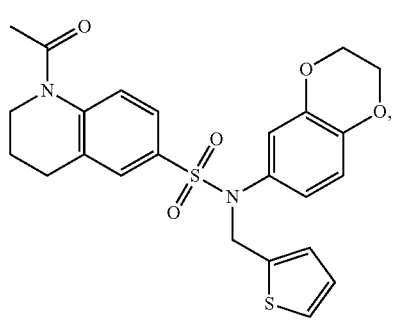
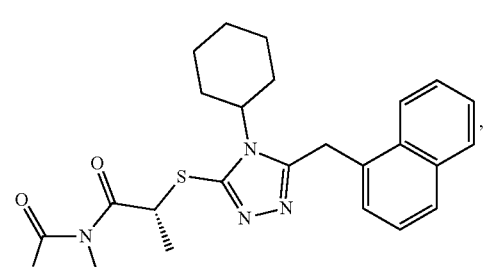
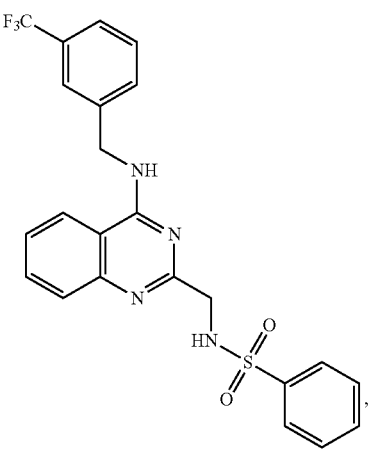
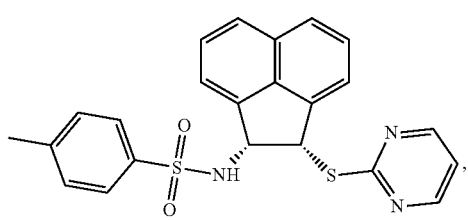

97
-continued
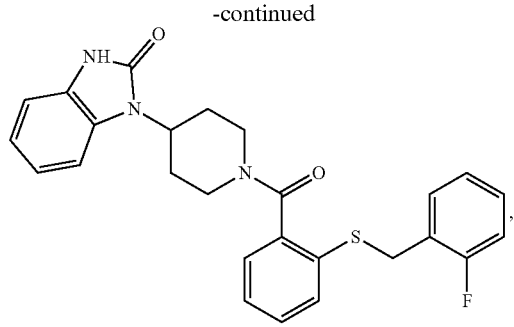
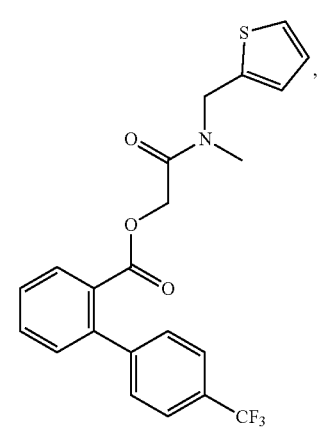
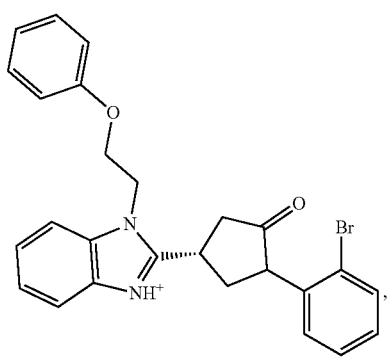
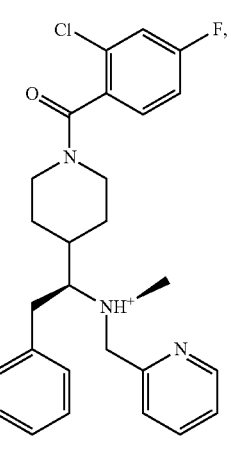
98
-continued
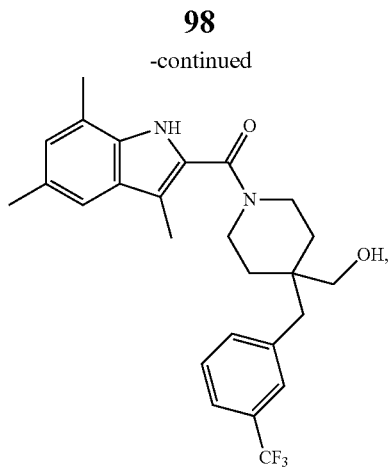
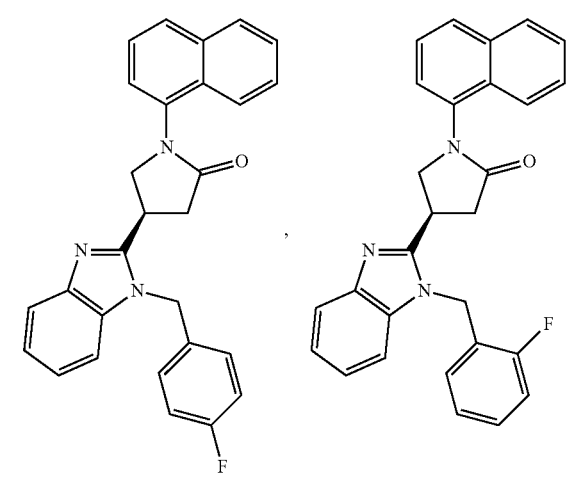
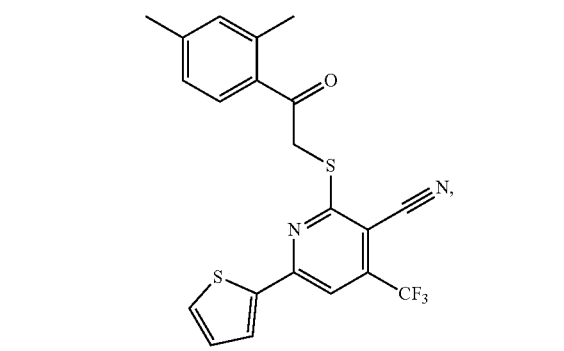
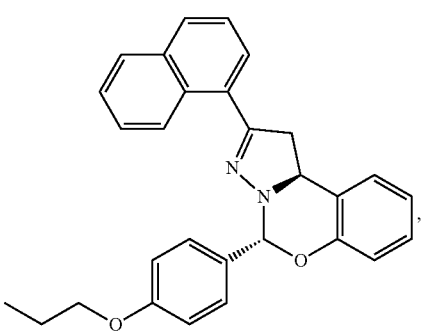

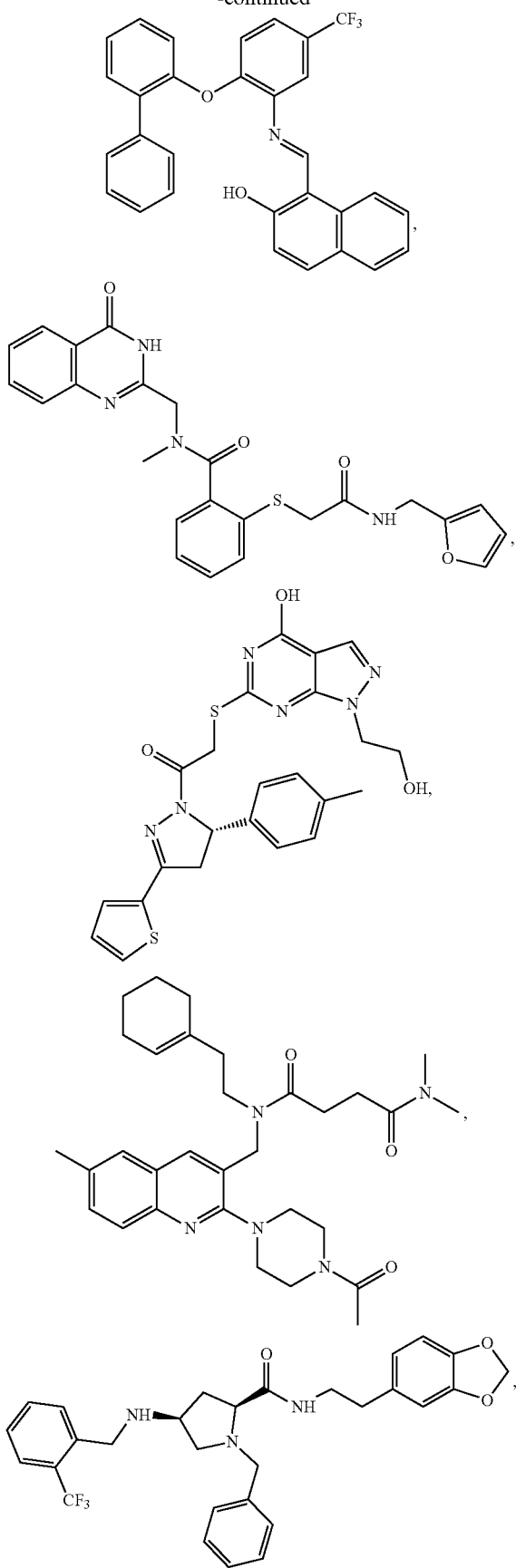
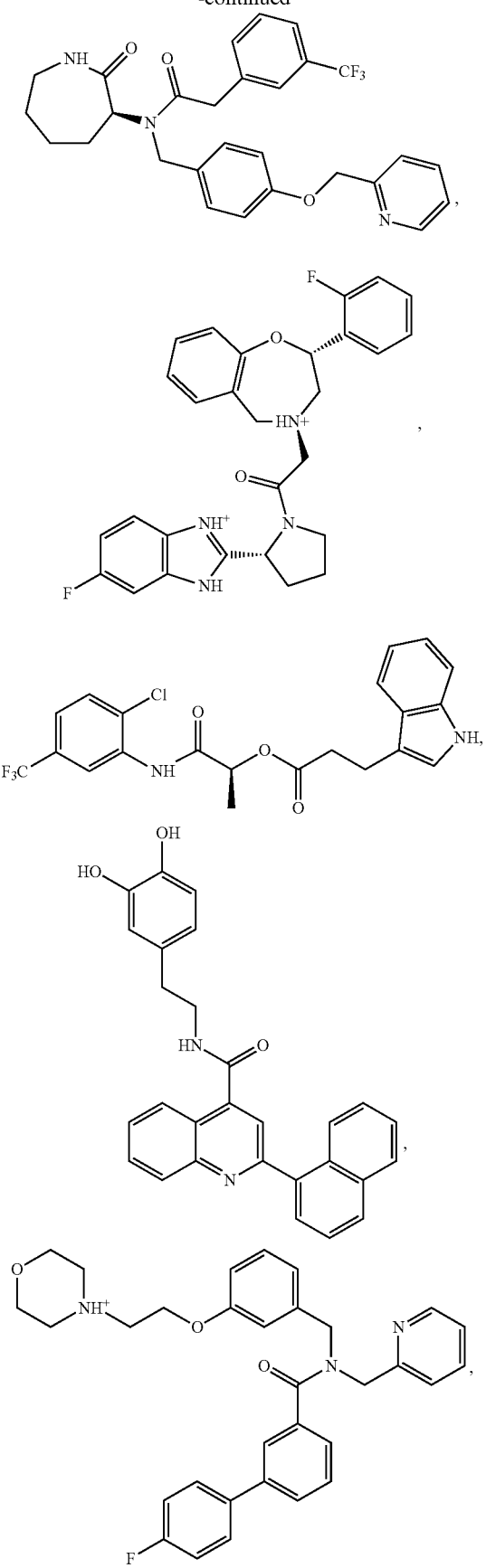

101
-continued
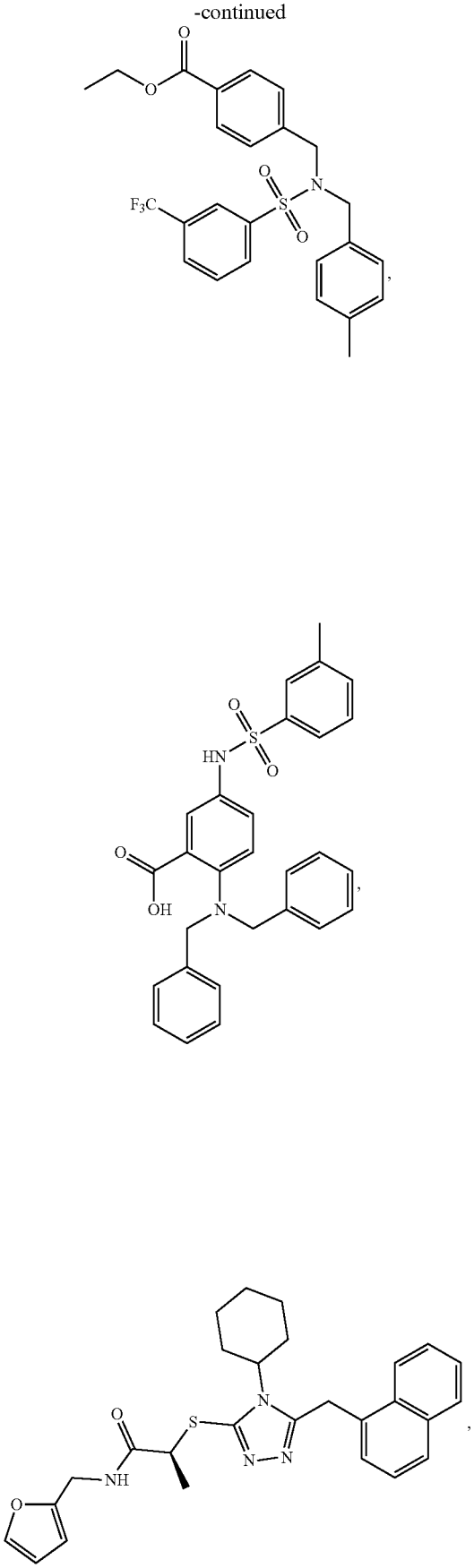
102
-continued
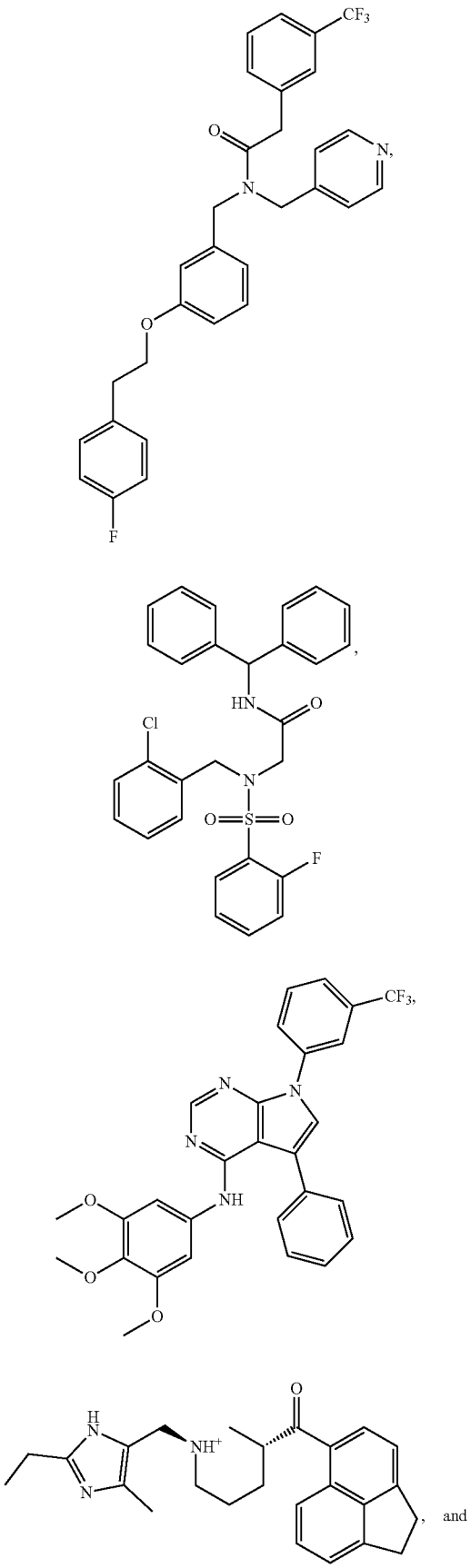
and

103
-continued
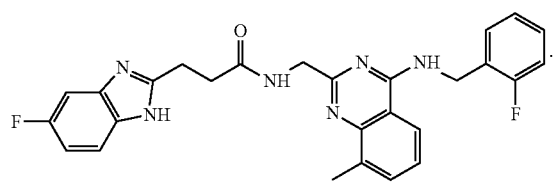
9. The method of claim 1, wherein the therapeutic agent comprises a compound selected from the following compounds or a pharmaceutically acceptable salt thereof:
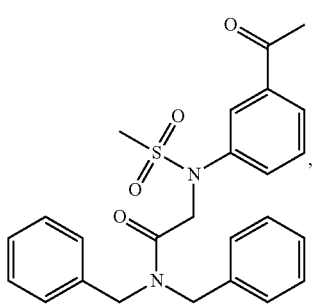
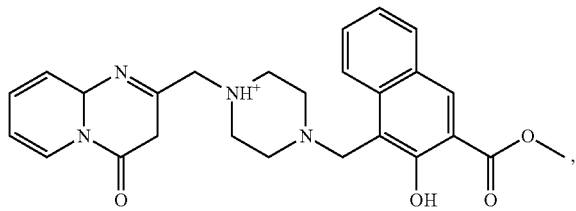
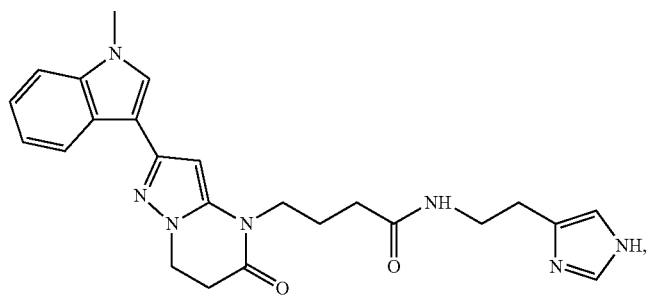
104
-continued
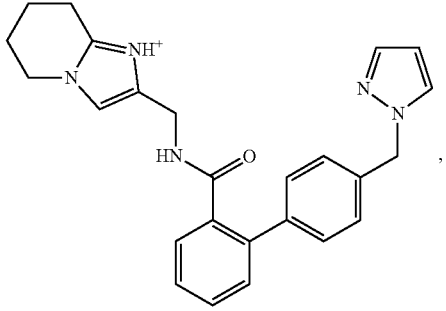
and
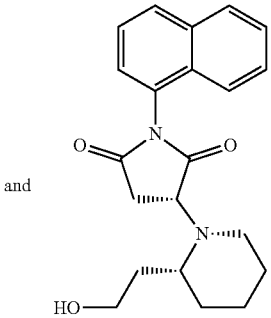
10. The method of claim 1, wherein the therapeutic agent comprises a compound selected from the following compounds or a pharmaceutically acceptable salt thereof:
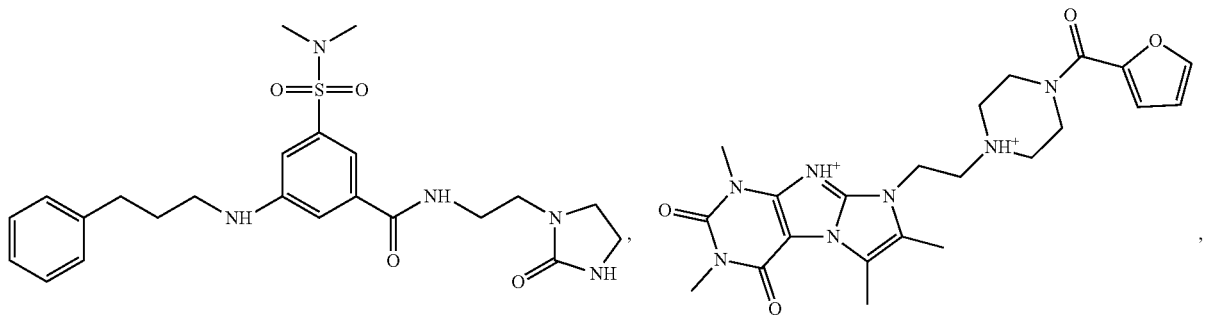

-continued
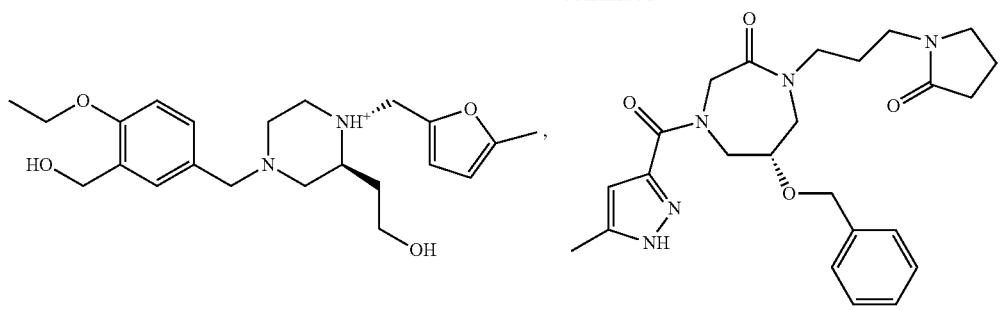
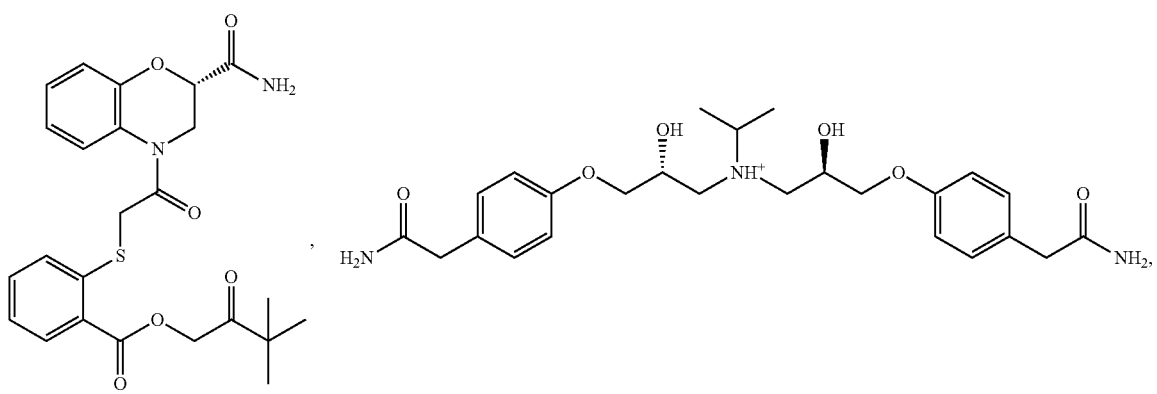
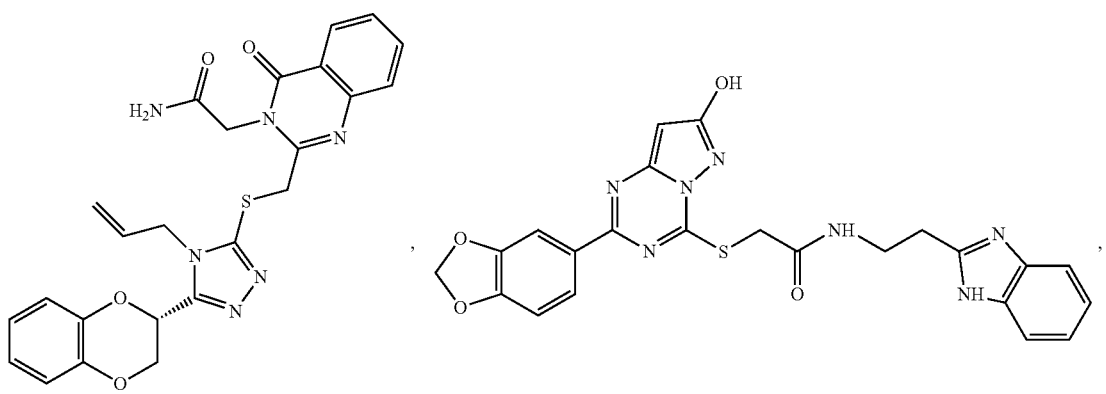
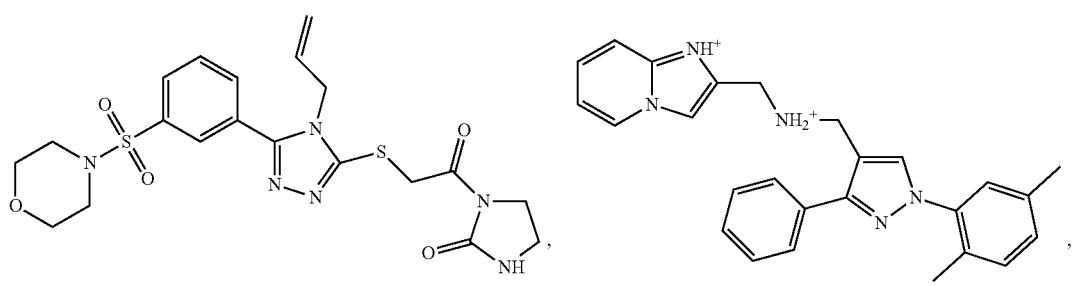

-continued
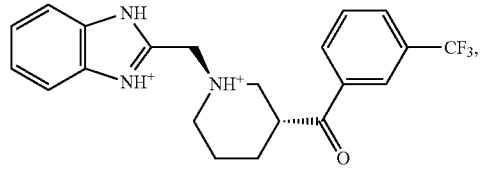
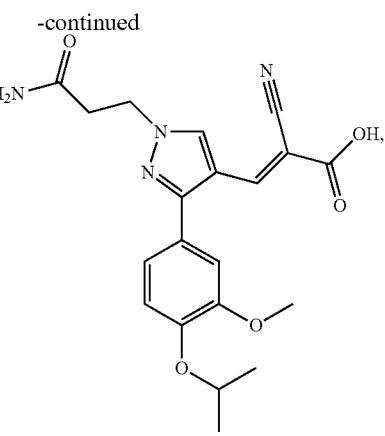
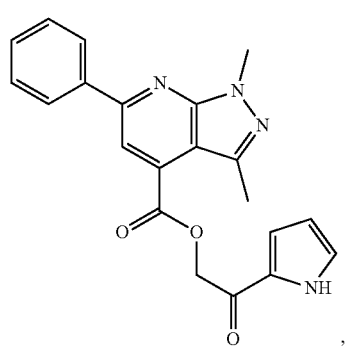
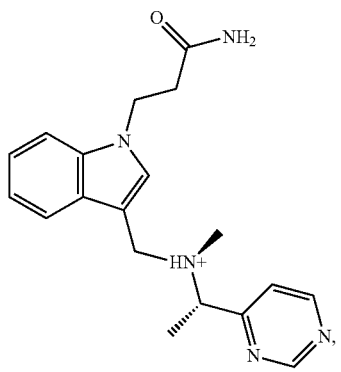
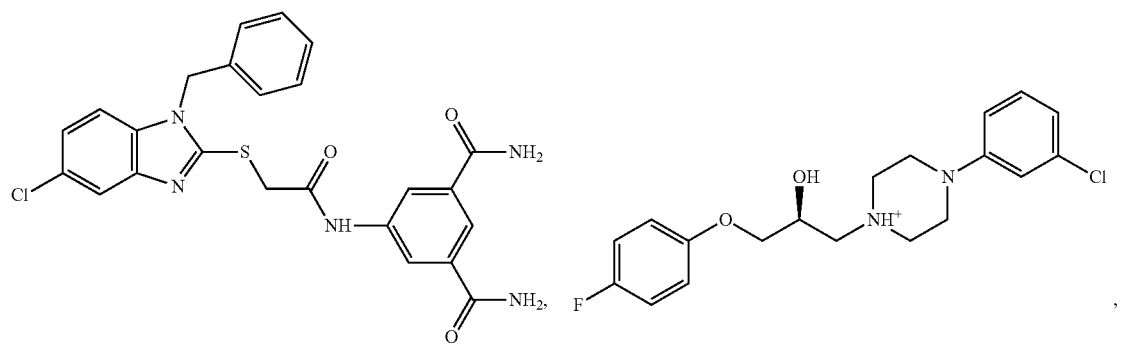
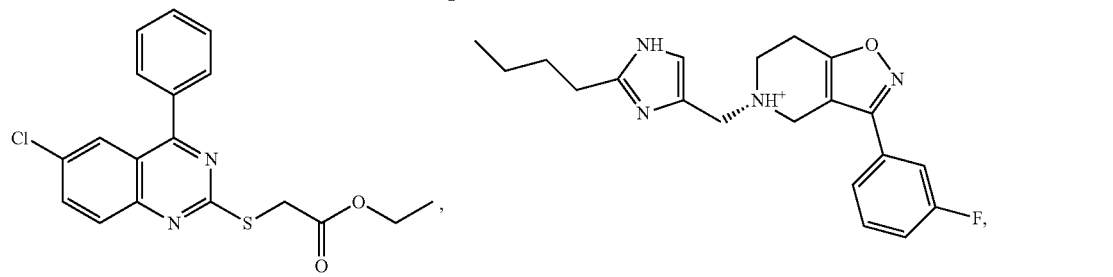
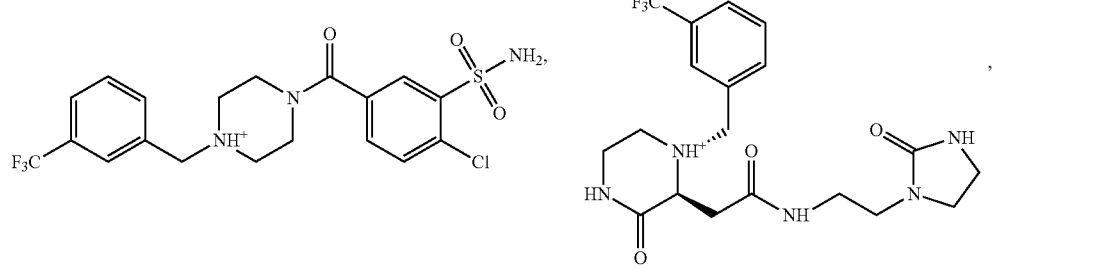

-continued
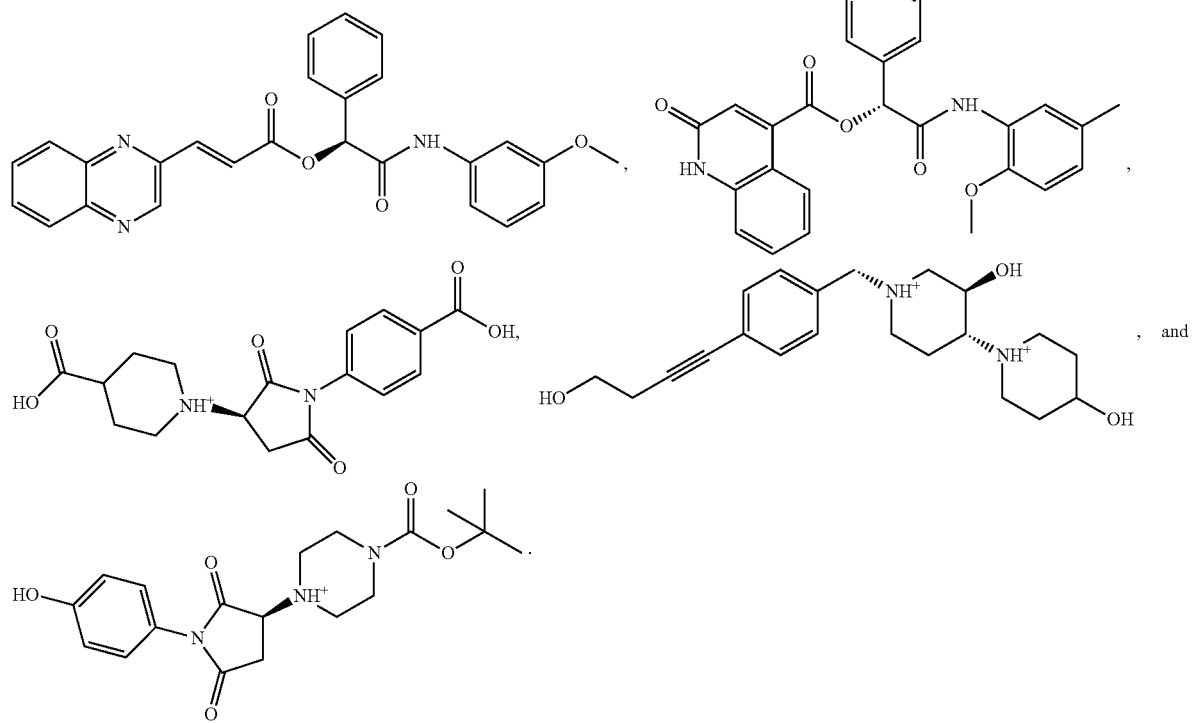
* * * * *